(12) United States Patent
Tomlins et al.

(10) Patent No.: US 8,969,527 B2
(45) Date of Patent: Mar. 3, 2015

(54) RECURRENT GENE FUSIONS IN PROSTATE CANCER

(75) Inventors: Scott Tomlins, Ann Arbor, MI (US); Daniel Rhodes, Ann Arbor, MI (US); Arul Chinnaiyan, Ann Arbor, MI (US); Rohit Mehra, Ann Arbor, MI (US); Mark A. Rubin, New York, NY (US); Xiao-Wei Sun, New York, NY (US); Sven Perner, Ellwaugen (DE); Charles Lee, Marlborough, MA (US); Francesca Demichelis, New York, NY (US)

(73) Assignees: The Regents of the University of Michigan, Ann Arbor, MI (US); The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 13/483,142

(22) Filed: May 30, 2012

(65) Prior Publication Data
US 2012/0296070 A1 Nov. 22, 2012

Related U.S. Application Data

(62) Division of application No. 12/650,164, filed on Dec. 30, 2009, now Pat. No. 8,211,645, which is a division of application No. 11/519,397, filed on Sep. 12, 2006, now Pat. No. 7,718,369.

(60) Provisional application No. 60/716,436, filed on Sep. 12, 2005, provisional application No. 60/779,041, filed on Mar. 3, 2006, provisional application No. 60/730,358, filed on Oct. 27, 2005, provisional application No. 60/795,590, filed on Apr. 28, 2006.

(51) Int. Cl.
| C07K 16/00 | (2006.01) |
| C12Q 1/68 | (2006.01) |
| C12N 15/113 | (2010.01) |
| G01N 33/574 | (2006.01) |

(52) U.S. Cl.
CPC ............ *C12Q 1/6886* (2013.01); *C12N 15/113* (2013.01); *G01N 33/57434* (2013.01); *C12N 2310/11* (2013.01); *C12N 2310/14* (2013.01); *C12Q 2600/112* (2013.01); *C12Q 2600/156* (2013.01); *Y10S 435/81* (2013.01)
USPC ........................................ 530/387.1; 435/810

(58) Field of Classification Search
None
See application file for complete search history.

(56) References Cited

U.S. PATENT DOCUMENTS

| 4,109,496 A | 8/1978 | Allemann et al. |
| 4,683,195 A | 7/1987 | Mullis et al. |
| 4,683,202 A | 7/1987 | Mullis et al. |
| 4,800,159 A | 1/1989 | Mullis et al. |
| 4,853,219 A * | 8/1989 | Alderman et al. ......... 424/139.1 |
| 4,873,191 A | 10/1989 | Wagner et al. |
| 4,965,188 A | 10/1990 | Mullis et al. |
| 4,968,103 A | 11/1990 | McNab et al. |
| 5,130,238 A | 7/1992 | Malek et al. |
| 5,225,326 A | 7/1993 | Bresser |
| 5,270,184 A | 12/1993 | Walker et al. |
| 5,283,174 A | 2/1994 | Arnold, Jr. et al. |
| 5,283,317 A | 2/1994 | Saifer et al. |
| 5,399,491 A | 3/1995 | Kacian et al. |
| 5,455,166 A | 10/1995 | Walker |
| 5,480,784 A | 1/1996 | Kacian et al. |
| 5,545,524 A | 8/1996 | Trent |
| 5,614,396 A | 3/1997 | Bradley et al. |
| 5,631,169 A | 5/1997 | Lakowicz et al. |
| 5,710,029 A | 1/1998 | Ryder et al. |
| 5,814,447 A | 9/1998 | Ishiguro et al. |
| 5,824,518 A | 10/1998 | Kacian et al. |
| 5,854,206 A | 12/1998 | Twardzik et al. |
| 5,856,125 A | 1/1999 | Mavrothalassitis et al. |
| 5,925,517 A | 7/1999 | Tyagi et al. |
| 5,928,862 A | 7/1999 | Morrison |
| 6,034,218 A | 3/2000 | Reed et al. |
| 6,043,033 A | 3/2000 | Bandman et al. |
| 6,080,912 A | 6/2000 | Bremel et al. |
| 6,121,489 A | 9/2000 | Dorner |
| 6,150,097 A | 11/2000 | Tyagi et al. |
| 6,166,194 A | 12/2000 | Wong et al. |
| 6,198,107 B1 | 3/2001 | Seville |
| 6,262,245 B1 | 7/2001 | Xu et al. |
| 6,303,305 B1 | 10/2001 | Wittwer et al. |
| 6,350,448 B1 | 2/2002 | Bandman et al. |
| 6,395,278 B1 | 5/2002 | Xu et al. |
| 6,444,419 B1 | 9/2002 | Wong et al. |
| 6,534,274 B2 | 3/2003 | Becker et al. |
| 6,541,205 B1 | 4/2003 | Yokoyama et al. |
| 6,573,043 B1 | 6/2003 | Cohen |

(Continued)

FOREIGN PATENT DOCUMENTS

| EP | 0684315 | 6/2002 |
| EP | 1409727 | 11/2005 |

(Continued)

OTHER PUBLICATIONS

Wang et al, Cancer Research 66:8347-8351, Sep. 2006.*
Duterque-Coquillaud, Oncogene 8:1865-1873, 1993.*
Wang, et al., "Gene-expression profiles to predict distant metastasis of lymph-node-negative primary breast cancer", The Lancet, vol. 365, No. 9460, Feb. 19-25, 2005, pp. 671-679.
Welsh, et al., "Analysis of gene expression identifies candidate markers and pharmacological targets in prostate cancer", Cancer Research, vol. 61, Aug. 15, 2001, pp. 5974-5978.
Wigle, et al., "Molecular profiling of non-small cell lung cancer and correlation with disease-free survival", Cancer Research, vol. 62, Jun. 1, 2002, pp. 3005-3008.

(Continued)

*Primary Examiner* — Lei Yao
(74) *Attorney, Agent, or Firm* — Thomas A. Isenbarger; Casimir Jones, S.C.

(57) ABSTRACT

Recurrent gene fusions of androgen regulated genes and ETS family member genes in prostate cancer are described. Compositions and methods having utility in prostate cancer diagnosis, research, and therapy are also provided.

11 Claims, 85 Drawing Sheets

(56) References Cited

U.S. PATENT DOCUMENTS

| | | | |
|---|---|---|---|
| 6,828,429 | B1 | 12/2004 | Srivastava et al. |
| 6,872,811 | B1 | 3/2005 | MacBeth et al. |
| 6,902,892 | B1 | 6/2005 | Salceda et al. |
| 7,008,765 | B1 | 3/2006 | Bussemakers et al. |
| 7,037,667 | B1 | 5/2006 | Afar et al. |
| 7,125,969 | B1 | 10/2006 | Benz et al. |
| 7,138,235 | B2 | 11/2006 | Bussemakers et al. |
| 7,374,885 | B2 | 5/2008 | Becker et al. |
| 7,718,369 | B2 | 5/2010 | Tomlins et al. |
| 2002/0119531 | A1 | 8/2002 | Bandman et al. |
| 2002/0182586 | A1 | 12/2002 | Morris |
| 2003/0103981 | A1 | 6/2003 | Spancake |
| 2003/0108963 | A1 | 6/2003 | Schlegel et al. |
| 2003/0170625 | A1 | 9/2003 | Rosenthal et al. |
| 2003/0175736 | A1 | 9/2003 | Chinnaiyan et al. |
| 2003/0185830 | A1 | 10/2003 | Xu et al. |
| 2004/0009481 | A1 | 1/2004 | Schlegel et al. |
| 2004/0259086 | A1 | 12/2004 | Schlegel et al. |
| 2005/0009086 | A1 | 1/2005 | Salceda et al. |
| 2005/0042638 | A1 | 2/2005 | Arnold, Jr. et al. |
| 2005/0112711 | A1 | 5/2005 | Romano et al. |
| 2005/0164223 | A1 | 7/2005 | Schalken et al. |
| 2005/0164379 | A1* | 7/2005 | Robertson et al. ............ 435/366 |
| 2005/0214309 | A1 | 9/2005 | Hinrichs et al. |
| 2006/0019256 | A1 | 1/2006 | Clarke et al. |
| 2006/0046265 | A1 | 3/2006 | Becker et al. |
| 2006/0068425 | A1 | 3/2006 | Monahan |
| 2006/0115821 | A1 | 6/2006 | Einstein et al. |
| 2006/0275794 | A1* | 12/2006 | Carrino et al. .................... 435/6 |
| 2007/0212702 | A1 | 9/2007 | Tomlins et al. |
| 2008/0269157 | A1* | 10/2008 | Srivastava et al. .............. 514/44 |
| 2009/0208937 | A1 | 8/2009 | Chinnaiyan |
| 2009/0239221 | A1 | 9/2009 | Chinnaiyan et al. |

FOREIGN PATENT DOCUMENTS

| | | |
|---|---|---|
| WO | 9410300 | 5/1994 |
| WO | 9845420 | 10/1998 |
| WO | 9962942 | 12/1999 |
| WO | 9965929 | 12/1999 |
| WO | 0000605 | 1/2000 |
| WO | 0004149 | 1/2000 |
| WO | 0012758 | 3/2000 |
| WO | 0018961 | 4/2000 |
| WO | 0023111 | 4/2000 |
| WO | 0065067 | 11/2000 |
| WO | 0070092 | 11/2000 |
| WO | 0153836 | 7/2001 |
| WO | 0157058 | 8/2001 |
| WO | 0160860 | 8/2001 |
| WO | 0188124 | 11/2001 |
| WO | 03009814 | 2/2003 |
| WO | 03053223 | 7/2003 |
| WO | 2004070056 A2 | 2/2004 |
| WO | 2004023973 | 3/2004 |
| WO | 2004074320 | 9/2004 |
| WO | 2004092397 | 10/2004 |
| WO | 2004097358 | 11/2004 |
| WO | 2004113571 | 12/2004 |
| WO | 2005007090 | 1/2005 |
| WO | 2005007830 A2 | 1/2005 |
| WO | WO2005007090 * | 1/2005 |
| WO | 2005007830 | 2/2005 |
| WO | 2005003387 | 3/2005 |
| WO | 2005113816 | 12/2005 |
| WO | 2009009432 | 1/2009 |
| WO | 2010096660 | 8/2010 |

OTHER PUBLICATIONS

Yoshimoto, et al., "Three-color FISH analysis of TMPRRSS2/ERG fusions in prostate cancer indicates that genomic microdeletion of chromosome 21 is associated with rearrangement", Neoplasia, vol. 8, No. 6, Jun. 2006, pp. 465-469.

Zhan, et al., "Global gene expression profiling of multiple myeloma, monoclonal gammopathy of undetermined significance, and normal bone marrow plasma cells", Blood, vol. 99, No. 5, Mar. 1, 2002, pp. 1745-1757.

Abdulkadir, Sarki A., "Conditional Loss of Nkx3.1 in Adult Mice Induces Prostatic Intraepithelial Neoplasia," Molecular and Cellular Biology, Mar. 2002, pp. 1495-1503.

Antoniou, Michael, et al., "Transgenes encompassing dual-promoter CpG islands from the human TBP and HNRPA2B1 loci are resistant to geterochromatin-mediated silencing", Genomics, vol. 82, 2003, pp. 269-279.

Attard, G., et al., "Duplication of the fusion of TMPRSS2 to ERG sequences identifies fatal human prostate cancer", Onogene vol. 27, 2008, pp. 253-263.

Beheshti, B., et al., "Identification of a high Frequency of Chromosomal Rearrangements in the Centromeric Regions of prostate Cancer Cell Lines by Sequential Giemsa Banding and Spectral Karyotyping", Molecular Diagnosis, vol. 5, No. 1,2000, pp. 23-32.

Beheshti, Ben, et al., "Evidence of Chromosomal Instability in Prostate Cancer Determined by Spectral Karyotyping (SKY) and Interphase FISH Analysis", Neoplasia, vol. 3, No. 1, 2001, pp. 62-69.

Cai, Changmeng, et al., "ETV1 is a Novel Androgen Receptor-Regulated Gene that Mediates Prostate Cancer Cell Invasion", Molecular Endocrinology 21 (8), pp. 1835-1846.

Seton-Rodgers, "Breast cancer: A striking resemblance" (Nature Reviews) Sep. 2007, vol. 7, p. 638.

Morris et al, (2008), "The discovery and application of gene fusions in prostate cancer," Bju International, vol. 102 p. 276-282.

Rickman et al., (2009) "SLC45A3-ELK4 is a novel and frequent erythroblast transformation-specific fusion transcript in prostate cancer," Cancer Research, 69, p. 2734-2738.

Han Bo et al., "A Fluoresence in SITU Hybridization Screen for E26 Transformation-Specific Aberrations: Identification of DDX5-ETV4 Fusion Protein in Prostate Cancer" Cancer Research Sep. 2008 68(18):7629-7637.

Hermans Karing G et al., "Truncated ETV1, Fused to Novel Tissued-Specific Gense, and Full Length ETV1 in Prostate Cancer" Cancer Research Sep. 2008 68:7541-7549.

Plueger Dorothee et al., "N-MYC Downstream Regulated Gene 1 (NDRG1) is fused to ERG in Prostate Cancer." Neoplasia (Aug. 2009) 11(8):804.

Singh, Jas et al., "Annotation of androgen dependence to human prostate cancer associated genes by microarray analysis of mouse prostate" Cancer Letters 2006, 237:298-304.

Singh, Jas et al., "RNA Reference mediated silencing of Spink reduces invasion and proliferation of prostate cancer cells." Proceedings of the Annual Meeting of the American Association for Cancer Research, American Association for Cancer Research, (Apr. 2006) 47(1):823 US.

Bjartell, A. et al., "Tumor-Associated Trypsin Inhibitor (TATI, PSTI, SPINK1) Expression in Prostate Cancer is Related to Tumor Grade" European Urology Supplements (Sep. 2006) 5(14):79.

Li Shijun et al., "Application of genomic technologies to human prostate cancer" OMICS A Journal of Integrative Biology (Sep. 2006) 10(3):261-275.

Laxman, Bharathi, et al., "A First-Generation Mulitplex Biomarker Analysis of Urine for the Early Detection of Prostate Cancer." Cancer Research (Feb. 2008) 68(3):645-649.

Rhodes et al., "Large-scale meta-analysis of cancer microarray data identifies common transcriptional profiles of neoplastic transformation and progression" Proc Natl Acad Sci USA (2004) 101:9309.

Haverback et al., "Trypsin, Trypsinogen and Trypsin Inhibitor in Human Pancreatic Juice." Am J. Med. (1960) 29:421-433.

Kazal et al., "Isolation of a Crystalline Trypsin Inhibitor-Anticoagulant Protein from Pancreas." Journal of the American Chemical Society (1948) 70:3034-3040.

Paju et al., "Biochemistry and Clinical Role of Trypsinogens and Pancreatic Secretory Trypsin Inhibitor." Crit. Rev. Clin. Lab Sci. (2006) 43:103-42.

Greene et al., "Human Pancreatic Secretory Trypsin Inhibitor." Methods Enzymol (1976) 45:813-25.

Stenman, "Tumor-associated Trypsin Inhibitor." Clin Chem (2002) 48:1206-9.

(56) References Cited

OTHER PUBLICATIONS

Schalken, "Molecular Diagnostics and Therapy of Prostate Cancer: New Avenues." Eur. Urol 1998 34 (Suppl.3):3-6.
Bussemakers et al, "DD3:A new Prostate-specific Gene, Highly Overexpressed in Prostate Cancer, " Cancer Res. (1999) 59:5975-5979.
Bussemakers et al, "Changes in Gene Expression and Targets for Therapy." Eur. Urol. (1999) 35:408-412.
De Kok et al., "DD3PCA3, a Very Sensitive and Specific Marker to Detect Prostate Tumors." Caner Res. (2002) 2695-8.
Block et al., "Use of targeted glycoroteomics to identify serum glycoproteins that correlate with liver cancer in woodchucks and humans." Proc Natl Acad Sci USA (2005) 102:779-784.
Kladney et al., "GP73, a novel Golgi-localized protein unregulated by viral infection." Gene 2000 249:53-65.
Yu et al., "Gene expression Alterations in Prostate Cancer Predicting Tumor Aggression and Preceding Development of Malignancy." J Clin Onc (Jul. 2004) 22(14):2790-2799.
Glinsky et al., "Gene expression profiling predicts clinical outcome of prostate cancer." J Clin Invest (2004) 113:913-23.
Vanaja et al., "Transcriptional Silencing of Zinc Finger Protein 185 Identified by Expressing Profiling in Associated with Prostate Cancer Progression." Cancer Res (2003) 63:3877-82.
Bittner et al., "A window on the dynamics of biological switches." Biotechnol. (2005) 23:183-4.
Su et al., "Molecular Classification of Human Carcinomas by Use of Gene Expression Signatures." Cancer Res (2201) 61:7388-93.
Andren et al., "How Well Does the Gleason Score Predict Prostate Cancer Death? A 20-Year Follow up of a Population Based Cohort in Sweden." J Urol (2006) 175:1337-40.
Johansson et al., "Natural History of Early, Localized Prostate Cancer." JAMA (2004) 291: 2713-9.
Han et al, "Long-term Biochemical Disease-Free and Cancerspecific Survival Following Anatomic Radical Retropubic Prostatectomy." Urol Clin North Am (2001) 28:555-65.
Hull et al., G.W. et al., "Cancer Control with Radical Prostatectomy Alone in 1,000 Consecutive Patients." J. Urol (2002) 167:528-34.
Kattan et al., "Postoperative Nomogram for Disease Recurrence After Radical Prostatectomy for Prostate Cancer." J. Clinical Oncol. (1999) 17:1499-507.
Kattan et al., "The Addition of Interleukin-6 Soluble Receptor and Transforming Growth Factor Beta1 Improves a Preoperative Nomogram for Predicting Biochemical Progression in Patients with Clinically Localized Prostate Cancer." J Clin Oncol (2003) 21:3537-9.
Paju et al., "Increased Expression of Tumor-Associated Trypsin Inhibitor, TATI, in Prostate Cancer and in Androgen-Independent 22Rv1 Cells." Eur Urol (2007) 52:1670-1681.
Sramkoski, R.M. et al., "A New Human Prostate Carcinoma Cell Line 22RV1." In Vitro Cell Dev Biol Anim (1999) 35:403-9.
Tomlins et al., "Whole Transcriptome Amplification for Gene Expression Profiling and Development of Molecular Archives." Neoplasia (2006) 8:153-62.
Vandesompele et al., "Accurate normalization of real-time quantitative RT-PCR data by geometric averaging of multiple internal control genes." Genome Biol 2002; 3 Research 0034.1-0034.11.
Kumar-Sinha et al., "Elevated Methylacyl-CoA Racemase Enzymatic Activity in Prostate Cancer." Am J. Path (2004) 164:787-93.
Specht et al., "Quantitative Gene Expression Analysis in Microdissected Archival Formalin-Fixed and Paraffin-Embedded Tumor Tissue." Am J. Pathol. 2001, 158:419-29.
Rubin et al., "Methylacyl Coenzyme A Racemase as a Tissue Biomarker for Prostate Cancer." JAMA (2002) 287:1662-70.
Faith et al., "Trefoil Factor 3 Overexpression in Prostate Carcinoma: Prognostic Importance Using Tissue Microarrays." Prostate (2004) 61:215-27.
Garraway et al., "Trefoil Factor 3 Is Overexpressed in Human Prostate Cancer." Prostate 2004 61:209-14.
Hessels et al., "DD3PCA3-based Molecular Urine Analysis for the Diagnosis of Prostate Cancer." Eur Urol (2003) 44:8-15 Discussion 6.
Fradet et al., "UPM3, A new molecular urine test for the detection of Prostate Cancer." Urology (2004) 64:311-5 Discussion 5-6.
Groskopf et al., "APTIMA PCA3 Molecular Urine Test: Development of a Method to Aid in the Diagnosis of Prostate Cancer." Clin Chem 2006 52:1089-95.
Marks et al., "PCA3 Molecular Urine Assay for Prostate Cancer in Men Undergoing Repeat Biopsy." Urology (2007) 69:532-5.
Delong et al., "Comparing the Areas Under Two or More Correlated Receiver Operating Characteristic Curves: A Nonparametric Approach." Biometrics (1988) 44:837-45.
Affymetrix NETAFXX Details for MG-U7AV2 Microarray Specifically Showing that EVT1 is present on the array accessed from www.affymetrix.com on May 1, 2009.
Affymetrix NETAFXX Details for MG-U7AV2 Microarray Specifically Showing that ERG is present on the array accessed from www.affymetrix.com on May 1, 2009.
Affymetrix NETAFXX Details for MG-U7AV2 Accessed from www.affymetrix.com on Aug. 18, 2008.
Database EMBL (Online) Mar. 2, 2007 "140298_1373_0575 3' ESTs from HeLa cell *Homo sapiens* Cdna 3', mRNA sequence." XP002597931 retrieved from EBI accession No. EMBL:EH3299833 Nucleotides 2-11.
Tognon Cristina et al., "Expression of the ETV6-NTRK3 gene fusion as a primary event in human secretory breast carcinoma" Cancer Cell (Nov. 2002) 2(5):367-376.
Maher, Christopher, et al., "Transcriptome sequencing to detect gene fusions in cancer." Nature (Mar. 2009) 458(7234):97-101.
Maher, Christopher, et al., "Chmimeric transcript discovery by paired-end transcriptome sequencing" Proceedings of the National Academy of Sciences of the United States of America (Jul. 2009) 106(30):12353-12358.
U.S. Office Action Mailed: Sep. 29, 2010, U.S. Appl. No. 12/272,865, filed Nov. 18, 2008 20 Pages.
International Search Report Mailed: May 25, 2010, Application No. PCT/US2009/064957; Filing Date: Nov. 18, 2009 WIPO Publication No. WO 2010/059702 (9 Pages).
Australian Further Office Action Mailed: Jan. 18, 2011, Application No. 2006291054; Filing Date: September 12, 2006 2 Pages.
Australian Office Action Mailed: Dec. 23, 2009, Application No. 2006291054; Filing Date: Sep. 12, 2006 3 Pages.
Canadian Office Action Mailed: Nov. 16, 2010, Application No. 2,662,295; Filing Date: Sep. 12, 2006 11 Pages.
Chinese Office Action Mailed: Dec. 31, 2010, Application No. 200680041826.6; Filing Date: Sep. 12, 2006 Publication No. 101341256 (8 Pages).
U.S. Final Office Action Mailed: Aug. 13, 2009, U.S. Appl. No. 11/519,397, filed Sep. 12, 2006 36 Pages.
U.S. Office Action Mailed: Feb. 23, 2009, U.S. Appl. No. 11/519,397, filed Sep. 12, 2006 50 Pages.
International Search Report Mailed: Dec. 4, 2007, Application No. PCT/US2006/035507; Filing Date: Sep. 12, 2006; WIPO Publication No. WO 2007/033187 (5 Pages).
European Office Action Mailed: May 5, 2010, Application No. 08826146.6; Filing Date: Jul. 3, 2008; Publication No. 2171094 (23 Pages).
International Search Report Mailed: Jan. 30, 2009, Application No. PCT/2008/069201; Filing Date: Jul. 3, 2008; WIPO Publication No. WO 20091009431 (5 Pages).
U.S. Office Action Mailed: Feb. 1, 2011, U.S. Appl. No. 11/825,552, filed Jul. 6, 2007; Publication No. 2009-0208937 (20 Pages).
U.S. Office Action Mailed: May 26, 2010, U.S. Appl. No. 11/825,552, filed Jul. 6, 2007; Publication No. 2009-0208937 (61 Pages).
International Search Report Mailed: Apr. 15, 2009; Application No. PCT/US2008/069204; Filing Date: Jul. 3, 2008; WIPO Publication No. WO 2009/009432 (8 Pages).
Australian Office Action Mailed: Nov. 5, 2010; Application No. 2007317306; Filing Date: Nov. 8, 2007 2 Pages.
Canadian Office Action Mailed: Jan. 6, 2011; Application No. 2,668,961; Filing Date: Nov. 8, 2007 5 Pages.
European Office Action Mailed: Aug. 17, 2010; Application No. 07864115.6; Filing Date: Nov. 8, 2007 Publication No. 2079851 (9 Pages).

(56) References Cited

OTHER PUBLICATIONS

International Search Report Mailed: Jul. 28, 2009; Application No. PCT/US2007/084090; Filing Date: Nov. 8, 2007 WIPO Publication No. WO 2008/058239 (5 Pages).
International Search Report Mailed: Nov. 5, 2010; Application No. PCT/US2010/020501; Filing Date: Jan. 8, 2010; WIPO Publication No. WO 2010/081001 (9 Pages).
Goodsell DS (1999), "The Molecular Perspective: The ras Oncogene," Oncologist 4(3): 263-4.
Downward J, (2003), "Targeting RAS signalling pathways in cancer therapy," Nat Rev Cancer 3(1): 11-22.
Wennerberg et al., 2005, "The Ras superfamily at a glance," J. Cell Sci, 118 (Pt 5): 843-6.
Munemitsu et al., 1990, "Molecular Cloning and Expression of a G25K cDNA, the Human Homolog of the Yeast Cell Cycle Gene CDC42," Mol Cell Biol 10(11): 5977-82.
Sithanandam et al, "Complete coding sequence of a human B-raf cDNA and detection of B-raf protein kinase with isozyme specific antibodies," (1990) Oncogene 5(12): 1775-80.
Sithanandam et al, (1992), "B-raf and a B-raf pseudogene are located on 7q in man," Oncogene, 7 (4) 795-9.
Davies et al, 2002, " Mutations of the BRAF gene in human cancer," Nature 417, (6892): 949-54.
Mark et al, (Apr. 1984), "Primary structure of v-raf: relatedness to the src family of oncogenes," Science 224 (4646) 285-9.
Shimizu et al, (1986), "Structure of the activated c-raf-1 gene from human stomach cancer," Princess Takamatsu Symp, 17: 85-91.
Sridhar et al, (2005), "Raf kinase as a target for anticancer therapeutics," Mol Cancer Ther 4(4): 677-85.
Burns Ed., Immunochemical Protocols, 3RD Ed., Humana Press, 2005.
Harlow and Lane, Antibodies: A Laboratory Manual Cold Spring Harbor Laboratory (1988).
Kozbor et al, "The production of monoclonal antibodies from human lymphocytes," Immunology Today 4: 72-79 (1983).
Kohler and Milstein, (1975), "Continuous cultures of fused cells secreting antibody of predefined specificity," Nature 256: 495-497.
Mullis et al, (1987), Specific synthesis of DNA in vitro via a polymerase-catalyzed chain reaction, Meth Enzymol. 155: 335-350.
Murakawa et al, (1988), "Direct detection of HIV-1 RNA from AIDS and ARC patient samples," DNA 7: 287-295.
Weiss, (1991), "Hot prospect for new gene amplifier," Science 254: 1292-1293.
Walker G. et al, (1992), "Isothermal in vitro amplification of DNA by a restriction enzyme/DNA polymerase system," Proc Natl Acad Sci USA, 89: 392-396.
Lizardi et al, "Exponential Amplification of Recombinant-RNA Hybridization Probes," Biotechnol 6: 1197-1202 (1988).
Kwoh et al, (1989), "Transcription-based amplification system and detection of amplified human immunodeficiency virus type 1 with a bead-based sandwich hybridization format," Proc Natl Acad Sci USA 86: 1173-1177.
Guatelli et al, (1990), "Isothermal, in vitro amplification of nucleic acids by a multienzyme reaction modeled after retroviral replication," Proc Natl Acad Sci USA 87: 1874-1878.
Nelson, Norman C., et al., (1995) "Detection of Acridinium Esters by Chemiluminescence" Nonisotopic Probing, Blotting, and Sequencing, 2nd Edition, edited by Larry J. Kricka, Ch. 17, pp. 391-428.
Sumerdon et al, "An Optimized Antibody-Chelator Conjugate for Imaging of Carcinoembryonic Antigen with Indium-111," Nucl Med Biol 17: 247-254 (1990).
Griffin et al, (1991), "Initial clinical study of indium-111-labeled clone 110 anticarcinoembryonic antigen antibody in patients with colorectal cancer, " J Clin Oncol, 9: 631-640.
Lauffer, (1991), "Targeted relaxation enhancement agents for MRI," Magnetic Resonance in Medicine 22: 339-342 (1991).
Zervos et al, "Mxi1, a protein that specifically interacts with Max to bind Myc-Max recognition sites," Cell 72: 223-232 (1993).
Madura et al "N-recognin/Ubc2 interactions in the N-end rule pathway," J Biol Chem 2668. 12046-12054 (1993).

Bartel et al, "Elimination of false positives that arise in using the two-hybrid system," Biotechniques 14: 920-924 (1993).
Iwabuchi et al, "Use of the two-hybrid system to identify the domain of p53 involved in oligomerization," Oncogene 8: 1693-1696 (1993).
Karnoub et al, " Ras oncogenes: split personalities," Nat Rev Mol Cell Biol, 9, 517-531 (2008).
Rodriguez-Viciana et al, "Cancer targets in the Ras pathway," Cold Spring Harb Symp Quant Biol 70, 461-467 (2005).
Moul et al, "Infrequent RAS oncogene mutations in human prostate cancer," Prostate 20, 327-338 (1992).
Seeburg et al, "Biological properties of human c-Ha-ras1 genes mutated at codon 12," Nature 312, 71-75 (1984).
Schubbert et al., "Hyperactive Ras in developmental disorders and cancer," Nat Rev Cancer 7, 295-308, (2007.
Mullighan et al, " BCR-ABL1 lymphoblastic leukaemia is characterized by the deletion of Ikaros," Nature 453, 110-114 (2008).
Graux et al, "Fusion of NUP214 to ABL1 on amplified episomes in T-cell acute lymphoblastic leukemia," Nat Genet 36, 1084-1089 (2004).
Ferreira et al, "Array CGH and gene-expression profiling reveals distinct genomic instability patterns associated with DNA repair and cell-cycle checkpoint pathways in Ewing's sarcoma," Oncogene 27, 2084-2090 (2008).
Koivunen et al, "EML4-ALK fusion gene and efficacy of an ALK kinase inhibitor in lung cancer," Clin Cancer Res 14, 4275-4283 (2008).
Stergianou et al, " Fusion of NUP214 to ABL1 on amplified episomes in T-ALL—implications for treatment," Leukemia 19, 1680-1681 (2005).
Graff et al, "Increased AKT activity contributes to prostate cancer progression by dramatically accelerating prostate tumor growth and diminishing p27Kip1 expression," J. Biol Chem 275, 24500-24505 (2000).
Xu et al, "MAPKAPK2 and HSP27 are downstream effectors of p38 MAP kinase-mediated matrix metalloproteinase type 2 activation and cell invasion in human prostate cancer," Oncogene 25, 2987-2998 (2006).
Wang et al, "A neoplastic gene fusion mimics trans-splicing of RNAs in normal human cells," Science 321, 1357-1361 (2008).
Der et al, "Transforming genes of human bladder and lung carcinoma cell lines are homologous to the ras genes of Harvey and Kirsten sarcoma viruses," Proc Natl Acad Sci USA 79, 3637-3640 (1982).
Zhu et al, "Transformation potential of Ras isoforms correlates with activation of phosphatidylinositol 3-kinase but not ERK," J Biol Chem 279, 37398-37406 (2004).
Moynihan et al, " Fine-mapping, genomic organization, and transcript analysis of the human ubiquitin-conjugating enzyme gene UBE2L3," Genomics 51, 124-127 (1998).
Hoeller et al., "Targeting the ubiquitin system in cancer therapy," Nature 458, 438-444 (2009).
CA Office Action Issued Mar. 29, 2011 (Application No. 2692441) Our File: UM-14512/CA-1/PCT.
Barr et al. 1996, "In Vivo Amplification of the PAX3-FKHR and PAX7-FKHR Fusion Genes in Alveolar Rhabdomyosarcoma" Hum. Mol. Genet., 5; 15-21.
Ciampi, R. et al., "BRAF kinase activation via chromosomal rearrangment in radiation-induced and sporadic thyroid cancer." Cell Cycle 2005 4(4): 547-548.
Jones, D.T. et al., "Tandem duplication producing a novel oncogenic BRAF fusion gene defines the majority of pilocytic astrocytomas." Cancer Research 2008 68(21):8673-8677.
Esgueva, R. et al., "Prevalence of TMPRSS2-ERG and SLC45A3-ERG gene fusions in a large prostatectomy cohort." Modern Pathology 2010 23(4):539-546.
Palanisamy, N. "Rearrangments of the RAF kinase pathway in prostate cancer, gastric cancer and melanoma." Nature Medicine 2010 16(7):793-798.
Fradet et al., "APTIMA® PCA3 Molecular Urine Test: Development of Prostate Cancer" European Urology Supplements 2006, 5(2): 275.
Kong et al. Blood 1997, 90:1192.
International Search Report Mailed May 20, 2011 Application No. PCT/US2010/048915; 13 Pages.

(56) References Cited

OTHER PUBLICATIONS

US Final Office Action Mailed Jun. 22, 2011, U.S. Appl. No. 12/272,865.
Australian Office Action Mailed Jun. 27, 2011 Application No. 2008275304, 2 Pages.
Persing, David H. "In Vitro Nucleic Acid Amplification Techniques" Diagnostic Medical Microbiology: Principles and Applications 1993, 51-87.
US Final Office Action Mailed Aug. 23, 2011, U.S. Appl. No. 11/825,552, 42 Pages.
European Office Action Issued Jun. 28, 2011, U.S. Appl. No. 08772418.3, 4 Pages.
European Office Action Issued Jun. 27, 2011, Application No. 07864115.6, 6 Pages.
EP Search Report Dated Jul. 8, 2011; Application No. 06814528.3.
Li J. et al., "PTEN, A Putative Protein Tyrosene Phosphatase Gene Mutated in Human Brain, Breast, and Prostate Cancer." Science, American Association for the Advancement of Science 1997, 275:1943-1947.
Jarrard D.F. et al., "Deltional, Mutational, and Methylation Analyses of CDKN2 (P16/MTS1) in Primary and Metastatic Prostate Cancer." Genes, Chromosomes & Cancer 1997, 19(2)P90-96.
Asatiani E. et al., "Deletion, methylation, and expression of the NKX3.1 suppressor gene in primary human prostate cancer." Cancer Research 2005, 65(4):1164-1173.
Jeon In-Sang et al., "A variant Ewing's sarcoma translocation (7;22) fuses the EWS gene to the ETS gene ETV1." Oncogene 1995, 10(6):1229-1234.
Oikawa T. et al., "Molecular biology of the ETS family of transcription factors." Gene 2003, 303(16):11-34.
Sorenson Poul H B et al., "A Second Ewing's sarcoma translocation, t (21; 22), fuses the EWS gene to anther ETS-family transcription factor, ERG." Nature Genetics 1994, 6(2):146-151.
Au Office Action dated Jul. 5, 2011; Application No. 2009316693; 3 pages.
Cheung et al., "Integration of cytogenetic landmarks into the draft sequence of the human genome." Nature 2001, 409:953-958.
Kuo et al., "Detection of aneuploidy involving chromosomes 13, 18, or 21, by fluorescence in situ hybridization (FISH) to interphase and metaphase amniocytes." Am. J. Human Genet. 1991, 49:112-119.
Klinger et al., "Rapid detection of chromosome aneuploidies in uncultured amniocytes by using fluorescence in situ hybridization (FISH)." Am. J. Hum. Gen. 1993, 52:854-865.
Liu et al., "Lineage Relationship between LNCaP and LNCaP-Derived Prostate Cancer Cell Lines." The Prostate 2004, 60:98-108.
Pettus et al., "Multiple abnormalities detected by dye reversal genomic microarrays in prostate cancer: A much greater sensitivity than conventional cytogenetics." Cancer Genet. Cytogent. 2004, 154(2):110-118.
Jayarman et al., "p300/Capm-responsive Element-binding Protein Interactions with Ets-1 and Ets-2 in the Transcriptional Activation of the Human Stromelysin Promoter." J Biol Chem 1999, 274:17342-17352.
Zou et al, "The Oncogenic TLS-ERG Fusion Protein Exerts Different Effects in Hematopeoitic Cells and Fibroblasts." Molecular and Cellular Biology 2005, 25(14): 6235-6246.
Yang et al., "EWS-Ffli-1 Fushion Protein Interacts with Hyperphosphylated RNA Polymerase II and Interfaces with Serine-Arginine Protein-mediated Rna Splicing." J Biol. Chem. 2009, 275(48):37612-37618.
Lukkonen et al., "Tumor-associated trypsin inhibitor in normal and malignant renal tissue and in serum of renal-cell carcinoma patients." International J of Cancer 1999, 83(4):486-490.
Solakidi et al., "Co-expression of trypsin and tumour-associated trypsin inhibitor (TATI) in colorectal adenocarcinomas." Histology and Histopathology 2003, 18(4):1181-1188.
Fukayama et al., "immunohistochemical localization of pancreatic secretory trypsin inhibitor in fetal and adult pancreatic and extrapancreatic tissues." J Histochemistry and Cytochemistry. 1986 34(2): 227-235.

Wu et al., "Regulation of the ETS transcription factor ER81 by the 90-kDa ribosomal S6 kinase and protein kinase A." The J Biology Chem. 2002, 277(45): 42669-42679.
Brahmajothi et al., "Regional localization of ERG, the channel protein responsible for the rapid component of the delayed rectifier, K+ current in the ferret heart." Circulation Research 1997, 81(1):128-135.
Iftikhar et al., "Disease-and cell-specific expression of GP73 in human liver disease." Am. J Gastrenterology 2004, 99(6):1087-1095.
Harbigs et al., "A sequence identification of the genes detected by probesets on the Affymetrix U133 plus 2.0 array." Nucleic Acids Research. Feb. 2005, 33(3): e31.
Whitehead et al., "Variation induces different gense in the lungs of rates compared with mice." Genome Biology 2005, 6(2), Article R13.
Hoshikawa et al., "Hypoxia induces different genes in the lungs of rats compared with mice." Physical Genomics 2003, 12:209-219.
Affymetrix HG_U95Av2 array showing SPINK1 https://www.affymetrix.com/analysis/netaffx/fullrecord.affx?pk=HG-U95AV2:38582_AT accesses online Jun. 1, 2012.
Affymetrix HG_U95Av2 array showing ERG https://www.affymetrix.com/analysis/netaffx/fullrecord.affx?pk=HG-U95AV2:36383_AT accesses online Jun. 1, 2012.
Afar, et al., "Catalytic cleavage of the Androgen-regulated TMPRSS2 Protease Results in Its Secretion by Prostate and Prostate Cancer Epithelial," Cancer Research, 2001, pp. 1686-1692 vol. 61.
Ahlers and Figg. "ETS-MPRSS2 Fusion Gene Products in Prostate Cancer." Cancer Biology & Therapy, (2006) 5:3 pp. 254-255.
Cerveira, et al. "TMPRSS2-ERG Gene Fusion Causing ERG Overexpression Precedes Chromosome Copy Number Changes in Prostate Carcinomas and Paired HGPIN Lesions." Neoplasia, (2006) pp. 826-832 vol. 8 (10).
Demichelis, et al. "TMPRSS2: ERG gene fusion associated with lethal prostate cancer in a watchful waiting cohort." Oncogene, (2007) 26(31):4596-4599.
Hendriksen, et al. "Evolution of the Androgen Receptor Pathway during Progression of Prostate Cancer." Cancer Research, (2006) 66(10):5012-5020.
Hermans, et al. "TMPRSS2:ERG Fusion by Translocation or Interstitial Deletion Is Highly Relevant in Androgen-Dependent Prostate Cancer, But Is Bypassed in Late-Stage Androgen Receptor-Negative Prostate Cancer." Cancer D Research (2006) pp. 10658-10663, vol. 66:22.
Iljin, et al. "TMPRSS2 Fusions with Oncogenic ETS Factors in Prostate Cancer Involve Unbalanced Genomic Rearrangements and Are Associated with HDAC1 and Epigenetic Reprogramming." Cancer Research (2006) pp. 10242-10246, vol. 66:21.
Jacquinet, et al. "Cloning and characterization of the cDNA and gene for human epitheliasin." European Journal of Biochemistry (2001) pp. 2687-2699, vol. 268.
Rowley, J.D., "Chromosome translocations: dangerous liaisons revisted", Nature Reviews, Cancer; vol. 1, Dec. 2001, pp. 245-250.
Dhanasekaran et al, "Delineation of prognostic biomarkers in prostate cancer." Nature (2001) 412:822-6.
Mosquera, et al. "Morphological Features of TMPRSS2-ERG gene fusion prostate cancer." Journal of Pathology, (2007) pp. 91-101, vol. 212.
Oettgen, et al. "PDEF, a Novel Prostate Epithelium-specific Ets Transcription Factor, Interacts with the AndrogenReceptor and Activates Prostate-specific Antigen Gene Expression." Journal of Biological Chemistry, (2000) pp. 1216-1225, vol. 275:2.
Owczarek et al. "Detailed mapping of the ERG-ETS2 interval of human chromosome 21 and comparison with the region of conserved synteny on mouse chromosome 16." Gene, (2004) pp. 65-77, vol. 324.
Perner, et al. "TMPRSS2:ERG Fusion-Associated Deletions Provide Insight into the Heterogeneity of Prostate Cancer." Cancer Res, (2006) pp. 8337-8341, vol. 66:17.
Petrovics et al. "Frequent overexpression of ETS-related gene-1 (ERG1) in prostate cancer transcriptome." Oncogene (2005) pp. 3847-3852, vol. 24.
Reddy, et al. "The erg gene: A human gene related to the ets oncogene." Proc. Natl. Acad. Sci. (1987) pp. 6131-6135, vol. 84, USA.

(56) References Cited

OTHER PUBLICATIONS

Rubin and Chinnaiyan. "Bioinformatics approach leads to the discovery of the TMPRSS2:ETS gene fusion in prostate cancer." Laboratory Investigation (2006) pp. 1099-1102, vol. 86.
Vaarala, et al. "The TMPRSS2 Gene Encoding Transmembrane Serine Protease Is Overexpressed in a Majority of Prostate Cancer Patients: Detection of Mutated TMPRSS2 Form in a Case of Aggressive Disease." International Journal of Cancer, (2001) pp. 705-710, vol. 94.
Rao, et al. "erg, a Human ets-Related Gene on Chromosome 21: Alternative Splicing, Polyadenylation, and Translation." Science (1987) pp. 635-639, vol. 237:4815.
Wang, et al. "Expression of Variant TMPRSS2/ERG Fusion Messenger RNAs Is Associated with Aggressive Prostate Cancer," Cancer Res. (2006) pp. 8347-8351, vol. 66: 17.
Bittner et al, "Molecular classification of cutaneous malignant melanoma by gene expression profiling," Nature, vol. 406, Apr. 2000, pp. 536-540.
Chen, et al., "Variation in gene expression patterns in human gastric cancers", Mol Biol of the Cell , vol. 14, Aug. 2003, pp. 3208-3215.
Cheok, et al., Treatment-specific changes in gene expression discriminate in vivo drug response in human leukemia cells, Nature Genetics, vol. 34, May 2003, pp. 85-90, 231.
Deininger, The development of imatinib as a therapeutic agent for chronic myeloid leukemia, Blood, vol. 105, No. 7, Apr. 1, 2005, pp. 2640-2653.
deKlein, "A cellular oncogene is translocated to the Philadelphia chromosome in chronic myelocytic leukaemia", Nature, vol. 300, Dec. 1982, pp. 765-767.
Dhanasekaran, et al., "Molecular profiling of human prostate tissues: insights into gene expression patterns of prostate development during puberty", The FASEB Journal, vol. 19, No. 2, Feb. 2005, pp. 243-245.
Eisen, et al., "Cluster analysis and display of genome-wide expression patterns", PNAS, vol. 95, No. 25, Dec. 8, 1998, pp. 14863-14868.
Ferrando, et al., "Gene expression signatures define novel oncogenic pathways in T cell acute lymphoblastic leukemia", Cancer Cell, vol. 1, Feb. 2002, pp. 75-87.
Fonseca, et al., "Genetics and Cytogenetics of Multiple Myeloma: A Workshop Report", Cancer Research, vol. 64, Feb. 15, 2004, pp. 1546-1558.
Garraway, et al., "Integrative genomic analyses identify MITF as a lineage survival oncogene amplified in malignant melanoma", Nature, vol. 436, Jul. 7, 2005, pp. 117-122.
Golub, et al., "Molecular classification of cancer: class discovery and class prediction by gene expression monitoring", Science, vol. 286, Oct. 15, 1999, pp. 531-537.
Huang, et al., "Gene expression predictors of breast cancer outcomes", The Lancet, vol. 361, May 10, 2003, pp. 1590-1596.
Jain, et al., "Expression profiles provide insights into early malignant potential and skeletal abnormalities in multiple endocrine neoplasia type 2B syndrome tumors", Cancer Research 64, Jun. 1, 2004, pp. 3907-3913.
Keats, et al., "Overexpression of transcripts originating from the MMSET locus characterizes all (t;14)(p16;q32)—positive multiple myeloma patients", Blood, vol. 105, No. 10, May 15, 2005, pp. 4060-4069.
Lapointe, et al., "Gene expression profiling identifies clinically relevant subtypes of prostate cancer", PNAS, Jan. 20, 2004, vol. 101, No. 3, pp. 811-816.
Latulippe, et al., "Comprehensive gene expression analysts of prostate cancer reveals distinct transcriptional programs associated with metastatic disease", Cancer Research 62, Aug. 1, 2002, pp. 4499-4506.
Lin, et al., "Prostate-localized and Androgen-regulated Expression of the Membrane-bound Serine Protease TMPRSS21", Cancer Research 59, Sep. 1, 1999, pp. 4180-4184.
Mitelman, F., "Recurrent chromosome aberrations in cancer", Mutation Research 462 (2000), pp. 247-253.
Paoloni-Giacobino, et al., "Cloning of the TMPRSS2 gene, which encodes a novel serine protease with transmembrane, LDLRA, and SRCR domains and maps to 21q22.3", Genomics, vol. 44, No. 3, Sep. 15, 1997, pp. 309-320.
Paris, et al., "Whole genome scanning identifies genotypes associated with recurrence and metastasis in prostate tumors", Human Molecular Genetics, 2004, vol. 13, No. 13, pp. 1303-1313.
Rabbits, T.H., "Chromosomal translocations in human cancer", Nature, vol. 372, Nov. 10, 1994, pp. 143-149.
Rhodes, et al., "ONCOMINE: A cancer microarray database and integrated data-mining platform", Neoplasia, vol. 6, No. 1, Jan./Feb. 2004, pp. 1-6.
Rosenwald et al. "The proliferation gene expression signature is a quantitative integrator of oncogenic events that predicts survival in mantle cell lymphoma," Cancer Cell., vol. 3, Feb. 2003, pp. 185-197.
Rowley, "A new Consistent Chromosomal Abnormality in Chronic Myelogenous Leukaemia Identified by Quinacrine Fluorescence and Giemsa Staining", Nature, vol. 243, Jun. 1, 1973, pp. 290-293.
Rubin, et al., "Overexpression, amplification, and androgen regulation of TPD52 in prostate cancer", Cancer Research 64, Jun. 1, 2004, pp. 3814-3822.
Schwartz, et al., "Gene expression in ovarian cancer reflects both morphology and biological behavior, distinguishing clear cell from other poor-prognosis ovarian carcinomas", Cancer Research 62, Aug. 15, 2002, pp. 4722-4729.
Slamon, et al., "Human breast cancer: correlation of relapse and survival with amplification of the HER-2/neuoncogene", Science, vol. 235, No. 4785, Jan. 9, 1987, pp. 177-182.
Sollar et al., "Confirmation of the High Frequency of the IMPRSS2/ERG Fusion Gene in Prostate Cancer", Genes, Chromosomes & Cancer, vol. 45 (2006), pp. 717-719.
Sotiriou, et al., "Breast cancer classification and prognosis based on gene expression profiles from a population-based study", PNAS, vol. 100, No. 18, Sep. 2, 2003, pp. 10393-10398.
Tian, et al., The role of the Wnt-signaling antagonist DKK1 in the development of osteolytic lesions in multiple myeloma, The New England Journal of Medicine, vol. 349, No. 26, Dec. 25, 2003, pp. 2483-2494.
Wallace, James C. et al., "High-density rhesus macaque Oligonucleotide Microarray design using early-stage rhesus genome sequence information and human genome annotations." BMC Genomics (Jan. 2007) v.8.
Tusher et al., "Significance analysis of microarrays applied to the ionizing radiation response," PNAS vol. 98, No. 9, Apr. 24, 2001, pp. 5116-5121.
Vasselli, et al., "Predicting survival in patients with metastatic kidney cancer by gene-expression profiling in the primary tumor", PNAS, vol. 100, No. 12, Jun. 10, 2003, pp. 6858-6963.
Velasco, et al., "Identification and validation of novel androgen-regulated genes in prostate cancer", Endocrinology vol. 145(8), 2004, pp. 3913-3924.
Di Cristofano, Antonio, et al., "Pten and p27KIP1 cooperate in prostate cancer tumor suppression in the mouse", Nature Genetics, vol. 27, Feb. 2001, pp. 222-224.
Eisenberg, Eli and Levanon, Erez Y., "Human housekeeping genes are compact", Trends in Genetics, vol. 19, No. 7, Jul. 2003, pp. 362-365.
Fingleon, Barbara, "Matrix metalloproteinases: roles in cancer and metastasis", Frontiers in Bioscience, vol. 11, Jan. 1, 2006, pp. 479-491.
Gibas, Zenon, "A high-Resolution Study of Chromosome Changes in a Human Prostatic Carcinoma Cell Line (LNCaP)", Cancer Genetics and Cytogenetics 1984, vol. 11, pp. 399-404.
Guasch, Geraldine, et al., "Endogenous retroviral sequence is fused to FGFR1 kinase in the 8p12 stem-cell myeloproliferative disorder with t(8;19)(p12;q13.3)", Blood, vol. 10, No. Jan. 1, 2003, pp. 286-288.
Kalos, Michael, et al, "Profile Expression is highly Restricted to Normal and Malignant Prostate Tissues", The Prostate 60:246-256 (2004).
Kim, Minjung, et al., "Cooperativity of Nkx3.1 and Pten loss of function in a mouse model of prostate carcinogenesis", PNAS, Mar. 5, 2002, vol. 99, No. 5, pp. 2884-2778.

(56) References Cited

OTHER PUBLICATIONS

Mirosevich, Janni, et al., "Expression and role of Foxa proteins in Prostate Cancer", the Prostate 66:1013-1028 (2006).
Mirosevich, Janni, et al., "Expression of Foxa Transcription Factors in the Developing and Adult Murine Prostate", The Prostate 62:339-352 (2005).
Murillo, Horacio, et al., "Prostate Cancer Cells use Genetic an Epigenetic mechanisms for Progression to Androgen Independence", Genes, Chromosomes 7 Cancer, 2006, pp. 702-716.
Ono, Masao, et al., "Stimulation of Expression of the Human Endogenous retrovirus Genome by Female Steroid Hormones in Human Breast Cancer Cell Line T47D", Journal of Virology, Jun. 1987, pp. 2059-2062.
Pang, See-Tong, et al., "Cytogenetic and Expression profiles Associated with Transformation to Androgen-Resistant Prostate Cancer", the Prostate 66: 157-172 (2006).
Patience, Clive, et al., "Human Endogenous Retrovirus Expression and Reverse Transcriptase Activity in the T47D Mammary Carcinoma Cell Line", Journal of Virology, Apr. 1996, pp. 2654-2657.
Weigle, Bernd, et al., "D-PCa-2: A Novel Transript Highly Overexpressed in Human prostate and Prostate Cancer", International Journal of Cancer, vol. 109, 2004, pp. 882-892.
Shai, Xu-Bao, et al., "Molecular Alterations Associated With LNCaP Cell Progression to Androgen Indpendence", The Prostate 60:257-271 (2004).
Smith, Richard, et al., "Expression profiling of EWS/FLI identifies NKX2.2 as a critical target gene in Ewing's sarcoma", Cancer Cell, vol. 9, May 2006, pp. 405-416.
Stauffer, Yves, et al, Digital Expression profiles of human endogenous retroviral families in normal and cancerous tissues, Cancer Immunity 4:2 (2004).
Stavenhagen, Jeffrey B. and Robins, Diane M., "An Ancient Provirus Has Imposed Androgen Regulation on the Adjacent Mouse Sex-Limited Protein Gene", Cell, vol. 55, No. 2, Oct. 21, 1988, pp. 247-254.
Stefford, Jon C., The use of multicolor fluorescence technologies in the characterization of prostate carcinoma cell lines: a comparison of multiplex fluorescence in situ hybridization and spectral karyotyping data, Cancer Genetics and Cytogenetics, vol. 124, 2001, pp. 112-121.
Suzukawa, Kazumi, et al., "Identification of a Breakpoint Cluster Region 3' of the Ribophorin I Gene at 3q21 Associated With the Transcriptional Activation of the EVil Gene in Actue Myelogenous Leukemias With inv(3) (q21q26)", Blood, vol. 84, No. 8, Oct. 15, 1994, pp. 2681-2688.
Takaha, Natsuki, et al., "High Mobility Group Protein I(Y): A Candidate Architectural protein for Chromosomal Rearrangements in Prostate Cancer Cells", Cancer Research vol. 62, Feb. 1, 2002, pp. 647-651.
Thalmann, George N., "Androgen-independent Cancer Progression and Bone Metastasis in the LNCaP Model of Human Prostate Cancer", Cancer Research, vol. 54, May 15, 1994, pp. 2577-2581.
Tomlins, Scott A., et al., "Integrative Biology of Prostate Cancer Progression", Annual Review of pathology: Mechanisms of Disease, vol. 1, 2006, pp. 243-271.
Van Bokhoven, Adrie, et al., "Spectral Karyotype (SKY) Analysis of Human Prostate Carcinoma Cell Lines", The Prostate 57:226-244 (2003).
Wang-Johanning, Feng, et al., "Quantitation of HERV-K env gene expression and splicing in human breast", Onogene(2003)22,pp. 1528-1535.
Watson, Spencer K., et al., "Cytogenetically balanced translocations are associated with focal copy numbers alterations", Hum Genet (2007) 120, pp. 795-805.
Wieser, "Rearrangements of Chromosome Band 3q21 in Myeloid Leukemia." Leukemia & Lymphoma Jan. 2002, 43(1): 59-65.
Williams, Steven, et al., "CpG-island fragments from the HNRPA2B1/CBX3 genomic locus reduce silencing and enhance transgene expression from the hCMV promoter/enhancer in mammalian cells", BMC Biotechnology, 2005, 5:17,9 pages.

Xu, Jiangchun, et al., "Identification and Characterization of Prostein, a Novel Prostate-specific Protein", Cancer Research, vol. 61, Feb. 15, 2001, pp. 1563-1568.
Tomlins, Scott A., et al., "Integrative molecular concept modeling of prostate cancer progression", Nature Genetics, vol. 39, No. 1, Jan. 2007, pp. 41-51.
Hartel, et al., "Characterisation of steroid receptor expression in the human prostate carcinoma cell line 22RV1 and quantification of androgen effects on mRNA regulation of prostate-specific genes," The Journal of Steroid Biochemistry & Molecular Biology 2004, vol. 92(3): pp. 187-197.
Schroeder (2007) European Urology 2247-1-4 Comments on Attard et al. (2007), "Duplication of the Fusion of TMPRSS2 to ERG sequences identifies Fatal Human Prostate Cancer", Onogene 2007; 1-11.
Walker Michael G. et al., "Prediction of gene function by genome-scale expression analysis: Prostate cancer-associated genes" vol. 9, pp. 1198-1203, Dec. 1, 1999.
Helgeson Beth et al., "Characterization of TMPRSS2: ETV5 and SLC45A3: ETV5 gene fusions in prostate cancer," Cancer Research Jan. 1, 2008, vol. 68, pp. 73-80.
Lynch et al., "Activating mutations in the epidermal growth factor receptor underlying responsiveness of non-small-cell lung cancer to gefitinib." N Engl J Med. May 20, 2004;350(21):2129-39.
Slamon et al., "Use of chemotherapy plus a monoclonal antibody against HER2 for metastatic breast cancer that overexpresses HER2." N Engl J Med. Mar. 15, 2001;344(11):783-92.
Demetri et al., "Efficacy and safety of imatinib mesylate in advanced gastrointestinal stromal tumors." N Engl J Med. Aug. 15, 2002;347(7):472-80.
Druker et al., "Five-year follow-up of patients receiving imatinib for chronic myeloid leukemia." N Engl J Med. Dec. 7, 2006;355(23):2408-17.
Greenman et al., "Patterns of somatic mutation in human cancer genomes." Nature. Mar. 8, 2007;446(7132):153-8.
Weir et al., "Characterizing the cancer genome in lung adenocarcinoma." Nature. Dec. 6, 2007;450(7171):893-8.
Wood et al., "The genomic landscapes of human breast and colorectal cancers." Science. Nov. 16, 2007;318 (5853):1108-13.
Barber et al., "Somatic mutations of EGFR in colorectal cancers and glioblastomas." N Engl J Med. Dec. 30, 2004;351(27):2883.
Futreal et al., "A census of human cancer genes." Nat Rev Cancer. Mar. 2004;4(3):177-83.
Choi et al., "Identification of novel isoforms of the EML4-ALK transforming gene in non-small cell lung cancer." Cancer Res. Jul. 1, 2008;68(13):4971-6.
Perner et al., "EML4-ALK fusion lung cancer: a rare acquired event." Neoplasia. Mar. 2008; 10(3):298-302.
Rikova et al., "Global survey of phosphotyrosine signaling identifies oncogenic kinases in lung cancer." Cell. Dec. 14, 2007;131(6):1190-203.
Soda et al., "Identification of the transforming EML4-ALK fusion gene in non-small-cell lung cancer." Nature. Aug. 2, 2007;448(7153):561-6.
Campbell et al., "Identification of somatically acquired rearrangements in cancer using genome-wide massively parallel paired-end sequencing." Nat Genet. Jun. 2008;40(6):722-9.
Parsons et al., "An integrated genomic analysis of human glioblastoma multiforme." Science. Sep. 26, 2008;321 (5897):1807-12.
Strausberg et al., "The cancer genome anatomy project: building an annotated gene index." Trends Genet. Mar. 2000;16(3):103-6.
Lin et al., "Prostate-localized and androgen-regulated expression of the membrane-bound serine protease TMPRSS2." Cancer Res. Sep. 1, 1999;59(17):4180-4.
GenBank: AAC51784.1, serine protease [*Homo sapiens*], 2 pages, Oct. 10, 1997.
GenBank: U75329.1, Human serine protease mRNA, complete cds, 2 pages, Oct. 10, 1997.
Ota et al., "Complete sequencing and characterization of 21,243 full-length human cDNAs." Nat Genet. Jan. 2004;36 (1):40-5.

(56) References Cited

OTHER PUBLICATIONS

Smith et al., "Cloning, expression, and characterization of a soluble calcium-activated nucleotidase, a human enzyme belonging to a new family of extracellular nucleotidases." Arch Biochem Biophys. Oct. 1, 2002;406(1):105-15.
Genbank Accession NM_014685.3, *Homo sapiens* homocysteine-inducible, endoplasmic reticulum stress-inducible, ubiquitin-like domain member 1 (HERPUD1), transcript variant 1, mRNA, 4 pages, Mar. 27, 2013.
Genbank Accession NM_004449.4, *Homo sapiens* v-ets erythroblastosis virus E26 oncogene homolog (avian) (ERG), transcript variant 2, mRNA, 6 pages, Mar. 24, 2013.
Genbank Accession M17254.1, Human erg2 gene encoding erg2 protein, complete cds, 2 pages, Nov. 8, 1994.
Swiss Protein Acc. No. P11308.2, RecName: Full=Transcriptional regulator ERG; AltName: Full=Transforming protein ERG, 6 pages, Mar. 6, 2013.
Genbank Accession No. NC_000007.11, *Homo sapiens* chromosome 7, complete sequence, 1 page, Oct. 25, 2004.
Genbank Accession No. NT_007819.15, *Homo sapiens* chromosome 7 genomic contig, 4 pages, Aug. 20, 2004.
Genbank Accession No. NM_004956.4, *Homo sapiens* ets variant 1 (ETV1), transcript variant 1, mRNA, 6 pages, Mar. 24, 2013.
Genbank Accession No. NP_004947.2, ETS translocation variant 1 isoform a [*Homo sapiens*], 5 pages, Mar. 24, 2013.
Genbank Accession No. NC_000017.9, *Homo sapiens* chromosome 17, reference assembly, complete sequence, Mar. 3, 2008.
Genbank Accession No. NT_010783.14, *Homo sapiens* chromosome 17 genomic contig, reference assembly, 3 pages, Feb. 29, 2008.
Genbank Accession No. NT_086880.1, 3 pages, Aug. 20, 2004.
Genbank Accession No. NM_001986.2, *Homo sapiens* ets variant 4 (ETV4), transcript variant 1, mRNA, 4 pages, Mar. 17, 2013.
UniProtKB/Swiss-Prot: P43268.3, RecName: Full=Adenovirus E1A enhancer-binding protein; AltName: Full=E1A-F; AltName: Full=Polyomavirus enhancer activator 3 homolog; Short=Protein PEA3, 6 pages, Mar. 6, 2013.
NC_000003.10, *Homo sapiens* chromosome 3, reference assembly, complete sequence, 1 page, Mar. 3, 2008.
NM_004454.2, *Homo sapiens* ets variant 5 (ETV5), mRNA, 5 pages, Mar. 31, 2013.
Klinger et al., "Rapid detection of chromosome aneuploidies in uncultured amniocytes by using fluorescence in situ hybridization (FISH)." Am J Hum Genet. Jul. 1992;51(1):55-65.
McConnell et al, "The cytosensor microphysiometer: biological applications of silicon technology." Science. Sep. 25, 1992;257(5078)1 906-12.
Sjolander et al., "Integrated fluid handling system for biomolecular interaction analysis." Anal Chem. Oct. 15, 1991;63(20):2338-45.
Szabo et al., "Surface plasmon resonance and its use in biomolecular interaction analysis (BIA)." Curr Opin Struct Biol. Oct. 1995;5(5):699-705.
Rubin et al.,Rapid ("warm") autopsy study for procurement of metastatic prostate cancer. Clin Cancer Res. Mar. 2000;6(3):1038-45.
Karolchik et al., "The UCSC Table Browser data retrieval tool." Nucleic Acids Res. Jan. 1, 2004;32(Database issue):D493-6.
GenBank: DQ204772.1, *Homo sapiens* TMPRSS2/ERGa fusion transcript, 1 page, Nov. 2, 2005.
GenBank: M30829.1, Human bcr/abl fusion protein mRNA, partial cds, clone K28, 1 page, Feb. 14, 1996.
Communi et al., "Cotranscription and intergenic splicing of human P2Y11 and SSF1 genes." J Biol Chem. May 11, 2001;276(19):16561-6.
Shtivelman et al., "Fused transcript of abl and bcr genes in chronic myelogenous leukaemia." Nature. Jun. 13, 1985;315(6020):550-4.
Kato et al., "Activation of Holliday junction-recognizing protein involved in the chromosomal stability and immortality of cancer cells." Cancer Res. Sep. 15, 2007;67(18):8544-53.

Bashir et al., "Evaluation of paired-end sequencing strategies for detection of genome rearrangements in cancer." PLoS Comput Biol. Apr. 25, 2008;4(4):e1000051.
Yu et al., "Integrative genomics analysis reveals silencing of beta-adrenergic signaling by polycomb in prostate cancer." Cancer Cell. Nov. 2007;12(5):419-31.
Mitelman et al., "Fusion genes and rearranged genes as a linear function of chromosome aberrations in cancer." Nat. Genet. Apr. 2004; 36(4):331-4.
Volik et al, "End-sequence profiling: sequence-based analysis of aberrant genomes." Proc Natl Acad Sci U S A. Jun. 24, 2003;100(13):7696-701.
Tuzun et al., "Fine-scale structural variation of the human genome" Nat Genet. Jul. 2005;37(7):727-32.
Ruan et al., "Fusion transcripts and transcribed retrotransposed loci discovered through comprehensive transcriptome analysis using Paired-End diTags (PETs)." Genome Res. Jun. 2007;17(6):828-38.
Barlund et al., "Cloning of BCAS3 (17q23) and BCAS4 (20q13) genes that undergo amplification, overexpression, and fusion in breast cancer" Genes Chromosomes Cancer. Dec. 2002;35(4):311-7.
Hampton et al., "A sequence-level map of chromosomal breakpoints in the MCF-7 breast cancer cell line yields insights into nto the evolution of a cancer genome." Genome Res. Feb. 2009;19(2):167-77.
Hahn et al., "Finding fusion genes resulting from chromosome rearrangement by analyzing the expressed sequence databases." Proc Natl Acad Sci U S A. Sep. 7, 2004;101(36):13257-61.
Shadeo & Lam. "Comprehensive copy number profiles of breast cancer cell model genomes." Breast Cancer Res. 2006;8(1):R9.
Huang et al., "Whole genome DNA copy number changes identified by high density oligonucleotide arrays." Hum Genomics. May 2004;1(4):287-99.
Neve et al., "A collection of breast cancer cell lines for the study of functionally distinct cancer subtypes." Cancer Cell. Dec. 2006;10(6):515-27.
Bodmer et al., "Disruption of a novel MFS transporter gene, DIRC2, by a familial renal cell carcinoma-associated t(2;3)(q35;q21)." Hum Mol Genet. Mar. 15, 2002;11(6):641-9.
Montagut et al., "Targeting the RAF-MEK-ERK pathway in cancer therapy." Cancer Letters Feb. 2009, 283 (2):125-134.
Wang et al., "Identification and characterization of AGTRAP, a human homolog of murine Angiotensin II Receptor-Associated Protein (Agtrap)" Intl. J Biochem. & Cell Biology 2002, 34:93-102.
Joosten et al., "The production of antibody fragments and anitbody fusion proteins by yeasts and filamentous fungi." Microbial Cell Factories 2003, 2:1-15.
RAF Family Antibody Sampler Kit #2330, Cell Signaling Technology, downloaded from: http://www.cellsignal.com/products/2330.html on May 16, 2013.
Sun et al, "TMPRSS2-ERG fusion, a common genomic alteration in prostate cancer activates C-MYC and abrogates prostate epithelial differentiation." Oncogene Jun. 9, 2008, 27(40):5348-5353.
Makkonen et al., "Identification of ETS-like transcriptome factor 4 as a novel androgen receptor target in prostate cancer cells." Oncogene May 12, 2008, 27(36):4865-4876.
Illum & Jones, "Attachment of Monoclonal Antibodies to Microspheres." Methods in Enzymology 1985, 112: 67-84.
Zucman et al., "Combinatorial generation of variable fusion proteins in the Ewing family of tumours." EMBO Journal 1993, 12(12): 4481-4487.
Park et al., "Antibody-Based Detection of ERG Rearrangement-Positive Prostate Cancer." Neoplasia Jul. 2010, 12(7): 590-598.
Schmidt et al., "Quantitative Multi-Gene Expression Profiling of Primary Prostate Cancer." The Prostate 2006, 66:1521-1534.
Wilson et al., "The membrane-anchored serine protease, TMPRSS2, activates PAR-2 in prostate cancer cells" Biochem. J. (2005) 388: 967-972.
Mitelman et al., "Prevalence estimates of recurrent balanced cytogenetic aberrations and gene fusions in unselected patients with neoplastic disorders." Genes Chromosomes Cancer. Aug. 2005;43(4):350-66.

* cited by examiner

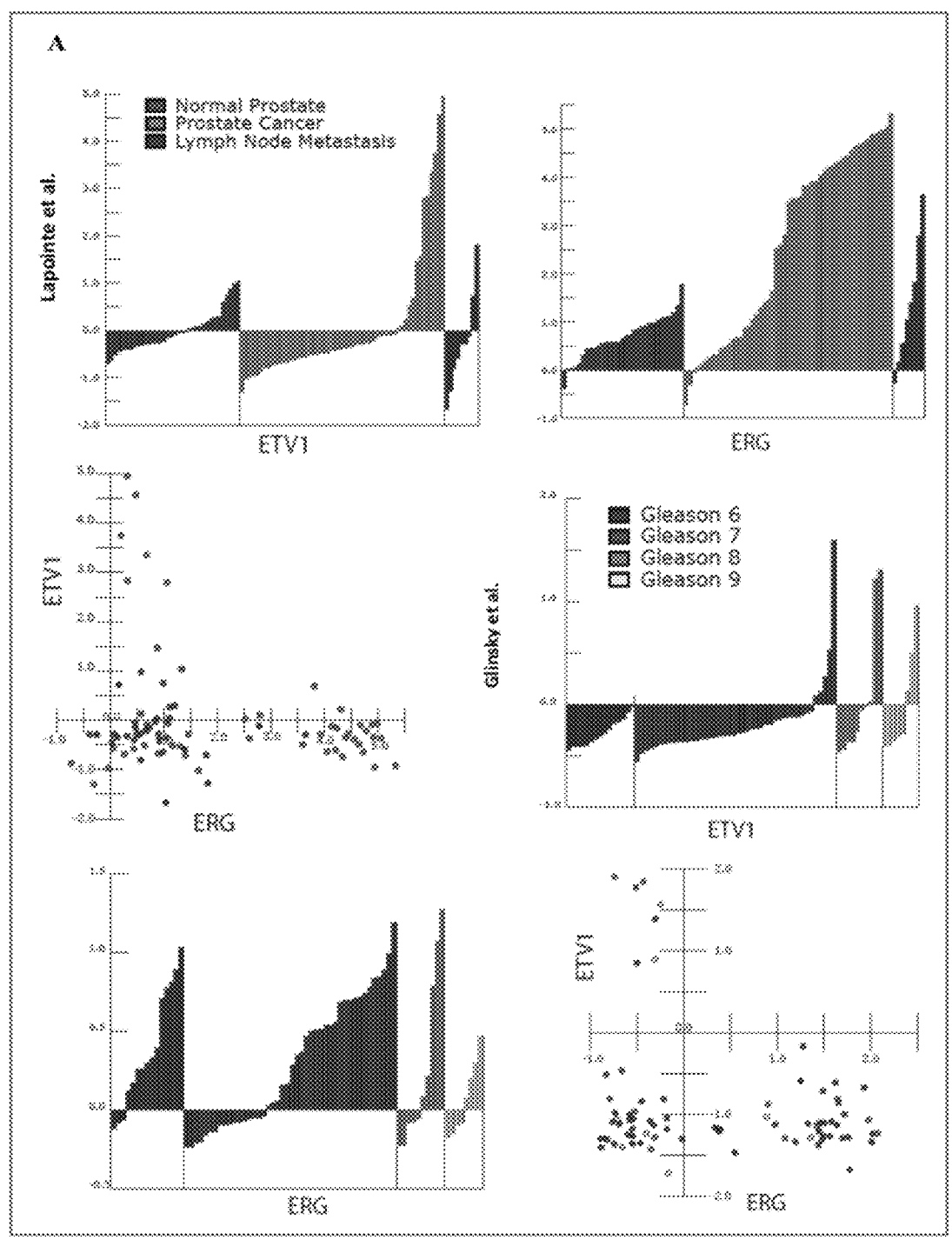

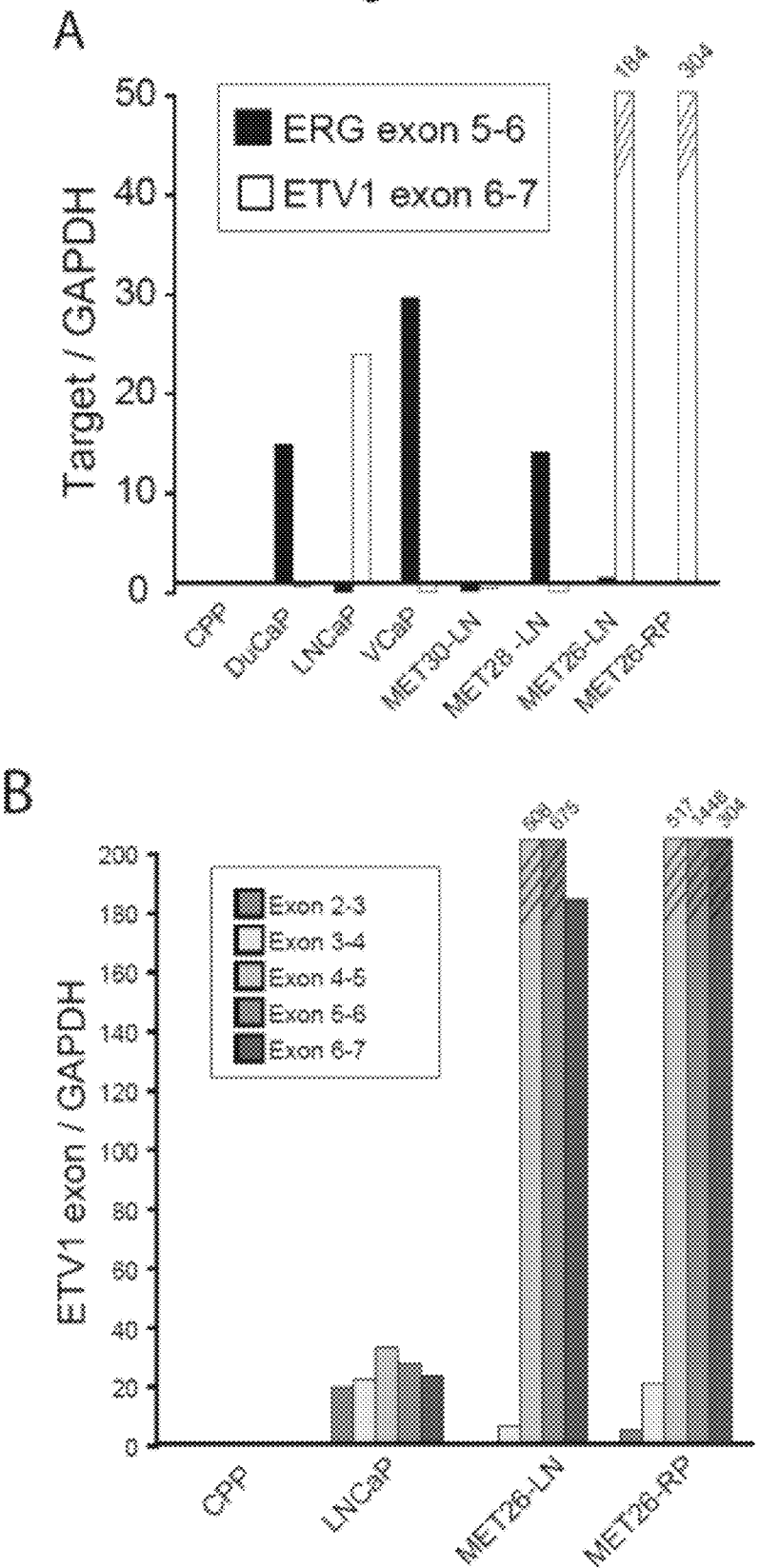

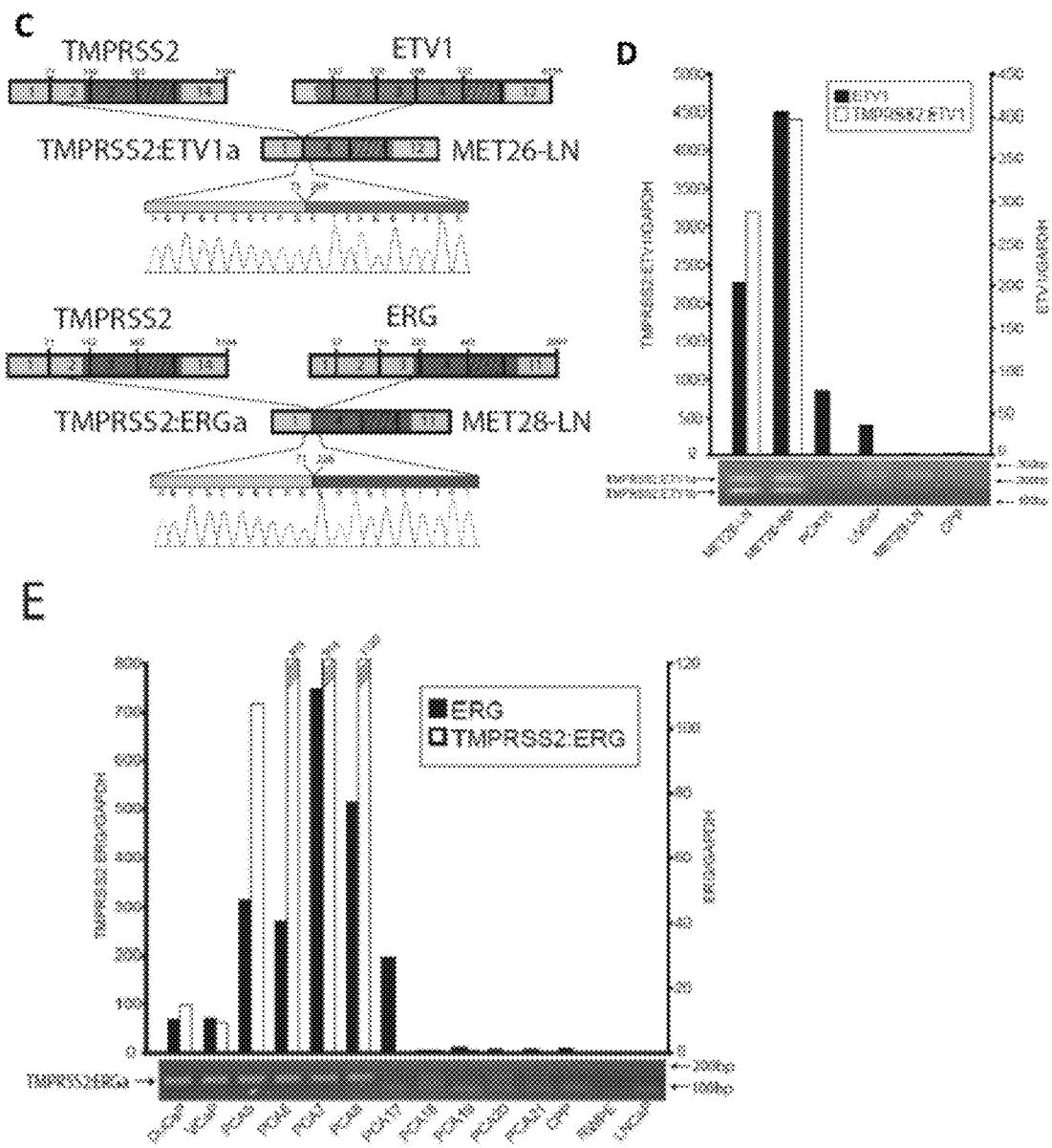

Figure 5
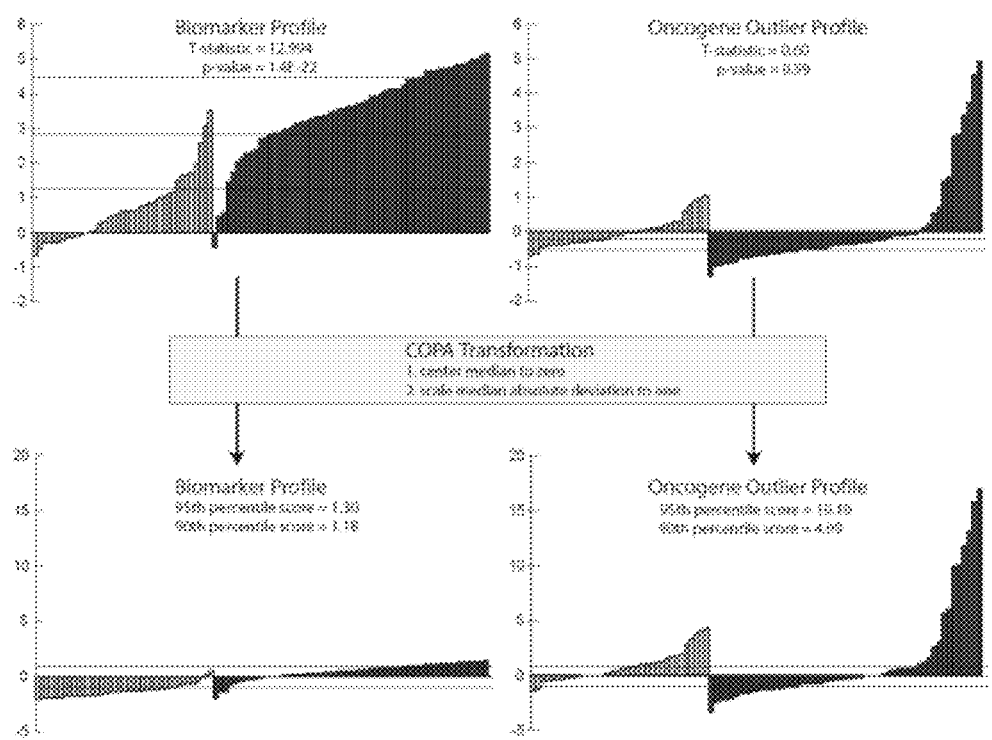
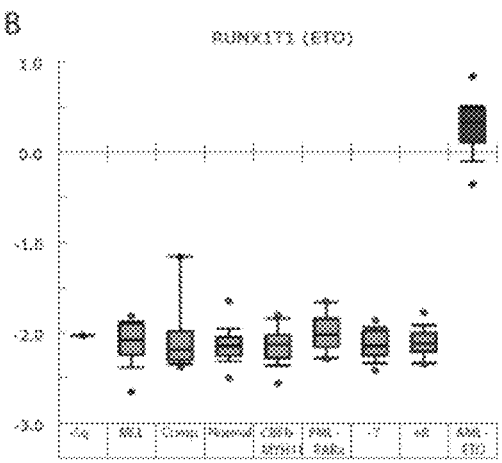
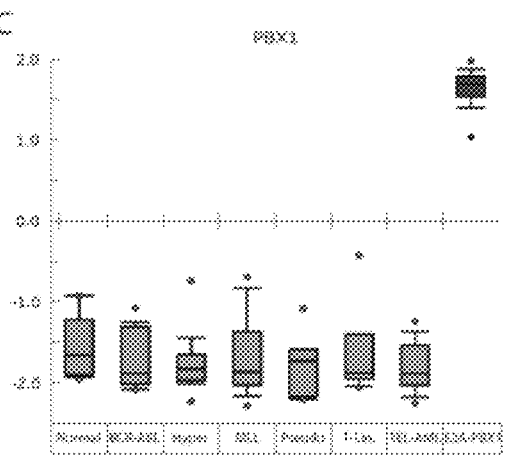

Figure 7
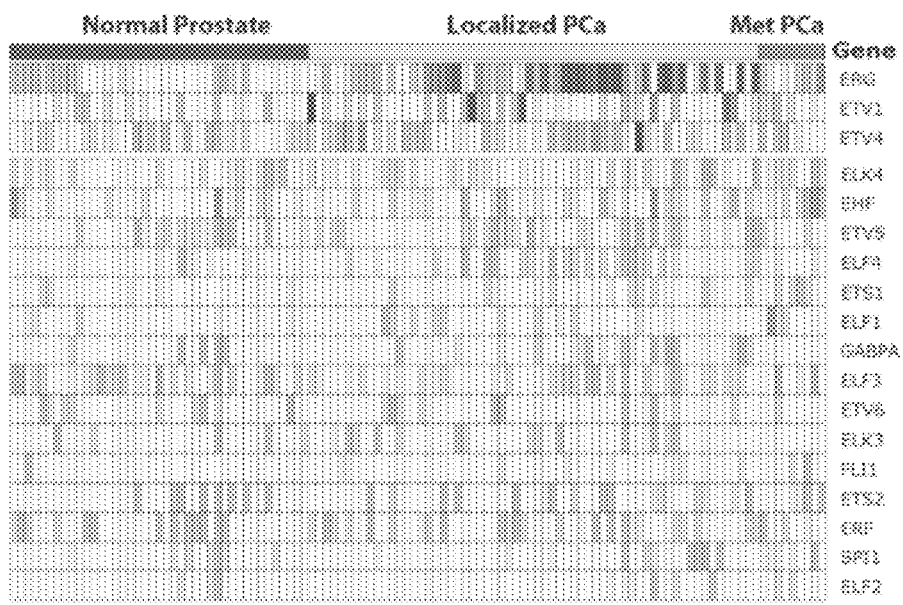
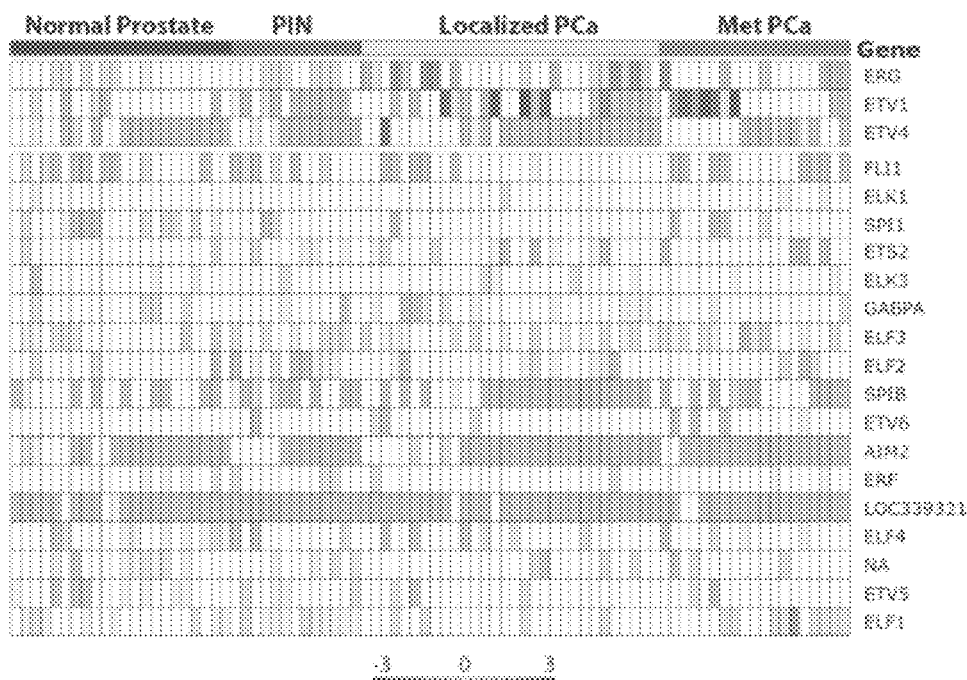

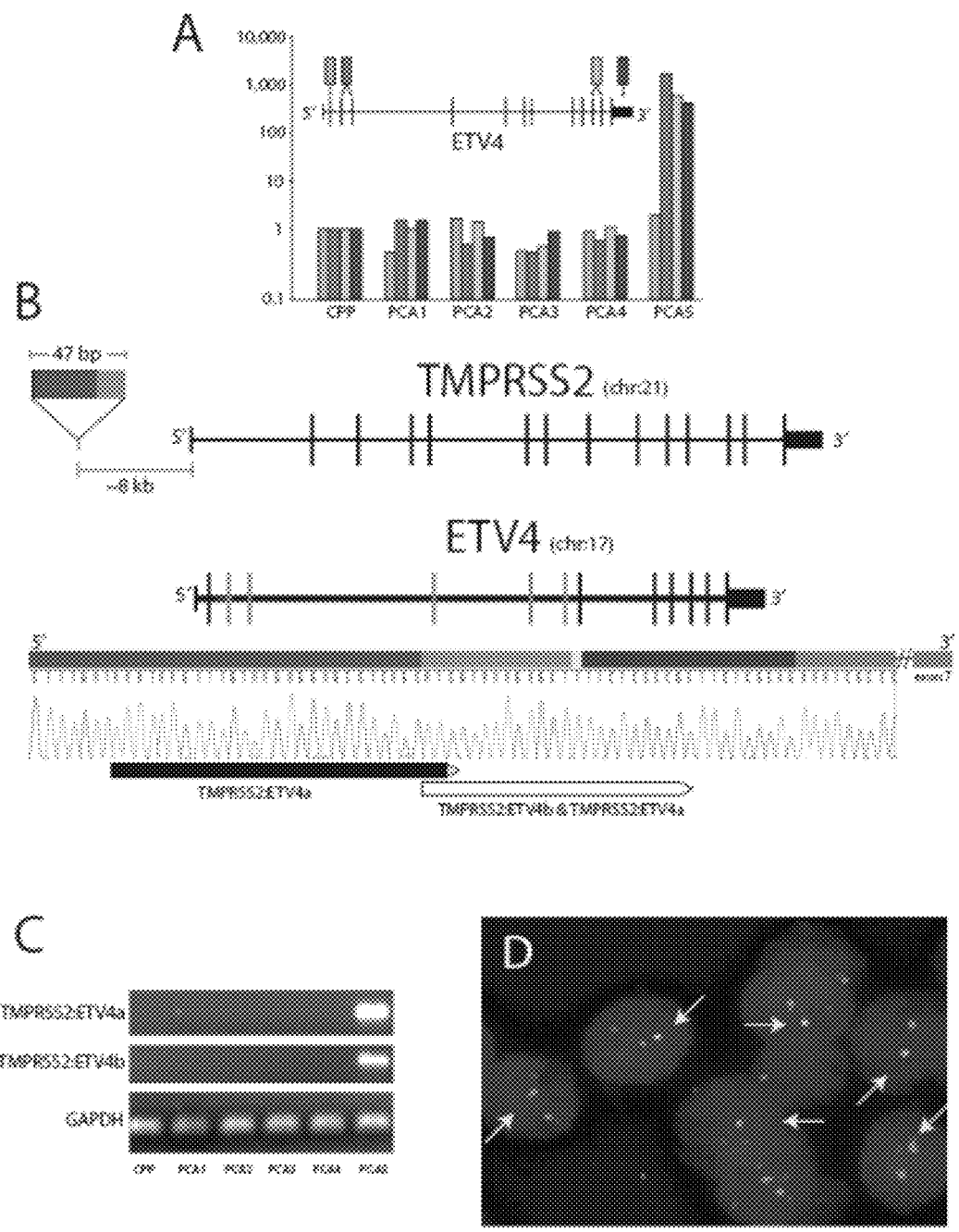

Figure 9

AF001732 (ERG mRNA) SEQ ID NO:32

1 ccgtcggcgc cgagggagtt agtgcgaccc ggctcggcgc gcacggccaa ggcacgcgcg
     61 ctggcacacg cgggcgcgga cacgcgcgga cacacacgtg cgggacacgc ctcccccga
    121 cggcggcgct aacctctcgg ttattccagg atcttggag accgaggaa agccgtgttg
    181 accaaaagca agacaaatga ctcacagaga aaaagatgg cagaaccaag ggcaactaaa
    241 gccgtcaggt tctgaacagc tggtagatgg gctggcttac tgaaggacat gattcagact
    301 gtcccggacc cagcagctca tatcaag RM_004956 (ETV1 mRNA) SEQ ID NO:33

1 gttgatagaa gtccagatcc tgaggaaatc tccagctaaa tgctcaaaat ataaaatact
     61 gagctgagat ttgcgaagag cagcagcatg gatggatttt atgaccagca
agtgccttac
    121 atggtcacca atagtcagcg tgggagaaat tgtaacgaga accaacaaa
tgtcaggaaa
    181 agaaaattca ttaacagaga tctggctcat gattcagaag agctcttca
agatctaagt
    241 caattacagg aaacatggct tgcagaagct caggtacctg acaatgatga
gcagtttgta
    301 ccagactatc aggctgaaag tttggctttt catggcctgc cactgaaaat
caagaaagaa
    361 ccccacagtc catgttcaga aatcagctct gcctgcagtc aagaacagcc
ctttaaattc
    421 agctatggag aaaagtgcct gtaaaagtc agtgcctatg atcagaagcc
acaagtggga
    481 atgaggccct ccaaccccc cacaccatcc agcacgccag tgtccccact
gcatcatgca
    541 tctccaaact caactcatac accgaaacct gacggggct tccagctca
cctccctcca
    601 tcgcagtcca taccagatag cagctacccc atggaccaca gatttcgccg
ccagctttct
    661 gaaccctgta atccttcc tccttcgccg acgatgccaa gggaaggacg
tcctatgtac
    721 caacgccaga tgtctgagcc aaacatcccc ttcccaccac aaggctttaa
gcaggagtac
    781 caagacccag tgtatgaaca caaccactg gttggcagtg cggccagcca
aagctttccc
    841 cctcctctga tgattaaaca ggaacccaga gattttgcat atgactcaga
agtgcctagc
    901 tgccactcca tttatatgag gcaagaaggc ttcctggtc atccagcag
aacagaaggc
    961 tgtatgtttg aaaagggcca caggcagttt tatgatgaca cctgtgttgt
cccagaaaaa
   1021 ttcgatggag acatcaaaca agagccagga atgtatcgg aaggacccac
ataccaacgg

Figure 9 (Cont.)

```
1081 cgaggatcac ttcagctctg gcagttttg gtagtcttc tggatgacc
ttcaaattct
1141 cattttattg cctggactgg tcgaggcatg gaatttaaac tgattgagcc
tgaagaggtg
1201 gcccgacgtt gggcattca gaaaaacagg ccagctatga actatgataa
acttagccgt
1261 tcactccgct attactatga gaaggaatt atgcaaaagg tggctggaga
gagatatgtc
1321 tacaagtttg tgtgtgatcc agagccctt ttctccatgg cctttccaga
taatcagcgt
1381 ccactgctga agacagacat ggaacgtcac atcaacgagg aggacacagt
gcctctttct
1441 cactttgatg agagcatggc ctacatgccg gaaggggct gctgcaaccc
ccaccctac
1501 aacgaaggct acgtgtatta acacaagtga cagtcaagca gggcgttttt
gcgcttttcc
1561 tttttctgc aagatacaga gaattgctga atcttgttt tattctgtt
gtttgtattt
1621 tattttaaa taataataca caaaaagggg ctttttcctgt tgcattattc
tatggtctgc
1681 catggactgt gcacttatt tgagggtggg tgggagtaat ctaaacattt
attctgtgta
1741 acaggaagct aatgggtgaa tggcagagg gattggggga ttacttttta
cttaggcttg
1801 ggatgggtc ctacaagttt tgagtatgat gaaactatat catgtctgtt
tgattccata
1861 acaacataag ataatgtta ttttatcggg gtatctatgg tacagttaat
ttcacgttgt
1921 gtaaatatcc actggagac tatttgcctt gggcattttc cctgtcatt
tatgagtctc
1981 tgcaggtgta caaaaaacc ccaatctact gtaaatggca gtttaattgt
tagaaatgac
2041 tgttttgca ccacttgtaa aaggtattt agcgattgca ttgctgttt
gttgttttat
2101 tttgcttat atatgacttg cagaggataa ccataaaatg ggtaattctc
tctgaagttg
2161 aataatcacc atgactgtaa atgaggggca caatttggga ctcggcgcc
aaactgagtc
2221 ataggccagt agcattacgt gtatctggtg ccaccttgct gtttagatac
aaatcatacc
2281 gtcttttaaa tattttgaag cccatttcag ttaaataatg acatgtcatg
gtccttggaa
2341 atcttcattt aaagttaaa tctggaatca aatgaagca aaaatatct
gtctccttt
2401 cactttcttc agtacataaa tacattattt aatcaataag aattaactgt
actaaatcat
2461 gtattatgct gttctagtta cagcaaacac tctttaagaa aaatatccaa
tacactaaat
2521 aggtactata gtaattttta gacatggtac ccattgatat gcatttaaac
cttttactgc
2581 tgtgttatgt tgataacata tataaatatt agataatgct aatgcttctg
ctgctgtctt
```

Figure 9 (Cont.)

```
2641 ttctgtaata ttctctttca tgctgaattt actatgacca tttataagca
gtgcagttaa
2701 ctacagatag catttcagga caaaatagat gactcaaacc atttattgct
taaaaatag
2761 cttacgccat gctatgctat aagcagcttt tatgcacatt gacaaatgaa
gagtaagctt
2821 cagcttgcta aaggaaactg tggaaccttt tgtaactttt ggtgatatgg
aaaattattt
2881 acaaaccgtc aaagaatatg aggaagttgc tgtatgacat agtgctggca
ctgatattat
2941 ccatcatctc tttttggaca cttctgtaaa tgtgattgga ttgtttgaaa
gaagatttaa
3001 agtttcaaag ttttttgttc tgtttttgct ttgcatttgg agaaatatt
gaaagcaggg
3061 tatgttgttt cattcacctt gaaaaaacca tgagtaaatg gggatataga
atctctgaat
3121 agctcgctaa aagattcaag caagggacat gaattttgtt ccatctatca
ataatatcca
3181 gaagaacaac ttttttaaag agtctatagc aaaagcaaa aaaaaaaaa
aattctaaac
3241 acaaagtcaa aataaaccta ttgtaaaagc atttcgtgat gagcatgaaa
aagattgttt
3301 aaagatgatc ccccagcta cccatttttcc aaaactacac agatcacagc
tcatttctct
3361 aagtggagca gttatcaaga aaccccaaaca ccaaaattgc tactcttcac
attaatcct
3421 acaaaaagta ctccaatttc aaaatatgta tgtaacctgc gatttcaatg
attgttgttc
3481 atatacatca tgtattattt tggcccattt tgggcctaaa aaagaaaact
atgccttaaa
3541 aatcagaacc ttttctcccc actatgctta tgtggccatc tacagcactt
agaataaaaa
3601 cagatgttaa aatattcagt gaaagttta ttggaaaaag gaattgagat
atataattga
3661 gatttggtga aattgaagga gaaaatttaa gtgagtcttt aaaatatatt
ctgaatgaaa
3721 actgtattga ggattcattt ttgttccttt ttttctttt tctcttttct
ccttttttctt
3781 cttttaata gtctagtttt agtcagtcag tgaggaagaa ttgggccatg
ctaacgttat
3841 cacaagagaa caatggcaga aatggtatta gttatataat atttaaggac
aaactatatg
3901 ttttgctgtt ttaacgtagt gactcactga actaaataca taattgacca
acattaagtg
3961 tatttccaat acagaagggt tgaaaatatt acattataaa ctcttttgaa
aaatgtatct
4021 aaaattcttt aagttctgtt ttgattccac ttttggttg agttttatg
ttttgttt
4081 caggtagatt aataaatctg gcagctgatt tctgcaagat tcttgtgttt
tgaatttctc
4141 attgaattgg ctactcaaac atagaaatca tttgttaatg atgtaatgtc
ttctctagc
4201 tttatcttc actgctgttt tgtgtctctt gatgatgaca tgttaatacc
caatagatta
```

Figure 9 (Cont.)

```
     4261 attgcaacaa acacttatac tcaaataact aagtaaaaat aattttttt
gttatgtcca
     4321 tgaaaagtgc ttcagaataa aaatccacaa gactgacagt gcagaacatt
ttttcaaat
     4381 catgggcgga tcttggaggt ctagtttccc gtagatgctg taaccaatta
ccacaacttc
     4441 agtaatttac acaaatttat cttatagttc tggaggcaga agttcaaaag
aagcttaag
     4501 agactaaaac caagatgtcc ttaggtctgg ttccttctgg aggctccagg
ggagatttct
     4561 ccagctttca cttctagagt ctgctgacat tccttggctc ctggctacat
cacttcaatc
     4621 tctgcttcca tggtcacata ctcttctact atagtcaaat ttccttcctg
cctcttataa
     4681 ggatgcttgt gattacattt aggggatgct cagataatcc aggacaatct
ctccatctca
     4741 agatccttaa cttaatgacg tgtgccaagt ccctttggct agataattat
tcataggtcc
     4801 cagggattag gacatggatg taagggtga gggcagggct gttattcaga
acaccgcacg
     4861 gaggaggaag actgtgtagc aaagactcta attgatttac tcaggaacag
tggagttctg
     4921 ctgagggatc taggatttga aagtactaga gtttgttttt attaccact
gagatatttt
     4981 ccccttattc tgcataaata attttgaaaa ctttctatat taaatttcaa
ctattccact
     5041 aaaatgtctg gtaatcacat caagccttta gattattcaa atccttcccc
agccccagg
     5101 aaacactaa gtcatgaaac agaaaacag aaggtatgat aataatagta
ataacagtta
     5161 aatcagtggt ctaatccaga ttttatttt taatacattc ctttggtgt
taatatgggt
     5221 tactatgtga tcttatcatt tgctagtgat tattacttat taggtaagaa
caatgtgtaa
     5281 aatatgtcta ttactcaaaa gaacaattgc aaaatgagtc aacttatctt
tatataacca
     5341 ggaaagaaat atattgccag aagctacaga attttgccag atgatagga
ttttctaaaat
     5401 gagccacttt gtctatcatg cagccttttc agagcttgta atgagaaaac
attacagagg
     5461 agaaggtcat tggatgttt gttacttgga atcctagaaa acaaaaacta
aaatttaaaa
     5521 ataagaagtg agtaagctat ttccatttg cgatttggta tggagaagag
agaaatagaa
     5581 attattaaaa aaatacaaat tgggtaaaag tgatggtgga aaaaatataa
agaaggcaaa
     5641 tgtacatatt aagcaattct actaagaatt ggaaaaatca agtttcaaaa
agatggtaat
     5701 agttgggcat gatactagaa aatttcaccc agtttattca gagctcaact
agtacttta
     5761 ggacttcttt tttatatac atgagactca ctttgacata cttaaaaaaa
aaacagttta
     5821 tggaaagtac agtttaagag gagaatttga ttagactaag tggatatctt
tatagaaata
```

Figure 9 (Cont.)

5881 ttaatgattt cagaattttc agttacaagt gtatataccg tggctattgt
ttatggattc 5941 atatgtaagg tagggtcttt tttgcatata gactccagta ttagttactt
tcattctaaa 6001 attatattta tgcttctatg gggaagaaaa ttttaattc actggttgt
attaaaatta 6061 tacttacggt ttgagaaaac atgctatgaa aatcatgatt atagcaaatt
aaatatgctc 6121 aaaatttaaa tctaaaataa aagcccagaa actgaaaa NM_005238 (ETS1 mRNA) SEQ ID NO:34

1 cgggcgaggg ccgggcagga ggagcgggcg cggcgcgggc gaggctggga cccgagcgcg 61 ctcacttcgc cgcaaagtgc caacttcccc tggagtgccg ggcgcgcacc
gtccgggcgc 121 gggggaaaga aaggcagcgg gaatttgaga tttttgggaa gaaagtcgga
tttccccgt 181 cccctcccc ctgttactaa tcctcattaa aagaaaaac aacagtaact
gcaaacttgc 241 taccatcccg tacgtccccc actcctggca ccatgaaggc ggccgtcgat
ctcaagccga 301 ctctcaccat catcaagacg gaaaaagtcg atcggagct tttccctcc
cggatatgg 361 aatgtgcaga tgtcccacta ttaactccaa gcagcaaaga aatgatgtct
caagcattaa 421 aagctacttt cagtggtttc actaaagaac agcaacgact ggggatccca
aaagacccc 481 ggcagtggac agaaacccat gttcgggact gggtgatgtg ggcgtgaat
gaattcagcc 541 tgaaaggtgt agacttccag aagttctgta tgaatggagc agccctctgc
gcctgggta 601 aagactgctt tctcgagctg gcccagact ttgttgggga catcttatgg
gaacatctag 661 agatcctgca gaaagaggat gtgaaaccat atcaagttaa tggagtcaac
ccagctatc 721 cagaatcccg ctatacctcg gattacttca ttagctatgg tattgagcat
gcccagtgtg 781 ttccaccatc ggagttctca gagcccagct tcatcacaga gtcctatcag
acgctccatc 841 ccatcagctc ggaagagctc ctctcctca gtatgagaa tgactaccc
tggtcattc 901 tccgagaccc tctccagaca gacaccttgc agaatgacta ctttgctatc
aaacaagaag 961 tcgtcacccc agacaacatg tgcatgggga ggaccagtcg tggtaaactc
ggggccagg 1021 actcttttga aagcatagag agctacgata gttgtgatcg cctcacccag
tcctggagca 1081 gccagtcatc tttcaacagc ctgcagcgtg tccctcta tgacagttc
gactcagagg 1141 actatccggc tgcctgccc aaccacaagc ccaaggcac cttcaaggac
tatgtgcggg

Figure 9 (Cont.)

```
1201 acggtgctga cctcaataag gacaagcctg tcattcctgc tgctgcccta
gctggctaca
1261 caggcagtgg accaatccag ctatggcagt ttcttctgga attactcact
gataaatcct
1321 gtcagtcttt tatcagctgg acaggagatg gctgggaatt caaactttct
gacccagatg
1381 aggtggccag gagatgggga aagaggaaaa acaaacctaa gatgaattat
gagaaactga
1441 gccgtggcct acgctactat tacgacaaaa acatcatcca caagacagcg
gggaaacgct
1501 acgtgtaccg ctttgtgtgt gacctgcaga gcctgctggg gtacacccct
gaggagctgc
1561 acgccatgct ggacgtcaag ccagatgccg acgagtgatg gcactgaagg
ggctggggaa
1621 accctgctga gaccttccaa ggacagccgt gttggttgga ctctgaattt
tgaattgtta
1681 ttctatttt tatttcca g aactcattt ttaccttcag gggtgggagc
taagtcagtt
1741 gcagctgtaa tcaattgtgc gcagttggga aaggaaagcc aggacttgtg
gggtgggtgg
1801 gaccagaaat tcttgagcaa attttcagga gagggagaag ggccttctca
gaagcttgaa
1861 ggctctggct taacagagaa agagactaat gtgtccaatc attttaaaa
atcatccatg
1921 aaaaagtgtc ttgagttgtg gacccattag caagtgacat tgtcacatca
gaactcatga
1981 aactgatgta aggcaattaa tttgcttctg ttttaggtc tgggagggca
aaaagaggt
2041 gggtgggatg aaacatgttt tggggggga tgcactgaaa atctgagaac
tattaccta
2101 tcactctagt ttgaagcaa agatggactt cagtggggag gggccaaaac
cgttgttgtg
2161 ttaaaattta tttt attaaa ttttgtgcca gtatttttt tctaaaaat
cgtcttaagc
2221 tctaaggtgg tctcagtatt gcaatatcat gtaagtttgt ttttatttgc
cggctgagga
2281 ttctgtcaca atgaaagaaa actgtttata tagaccccat tggaaaagca
aaacgctctc
2341 actgagatca gggatcccaa attcatggga cttatataag aaggacaatt
aatgctgatt
2401 tgggtacagg ggaattatgt gtgtgaatgt catctacaat taaaaaaaat
tagcacatcc
2461 cttacttac ttgttatcag tggattctcg gggtttggac ttaatgttga
gctaagaagc
2521 attaagtctt tgaactgaat gtattttgca tccctggttt tggacgacag
taaacgtagg
2581 agcactgttg aagtcctgga aggagatcg aaggaggaag attgacttgg
ttcttttctta
2641 gtcctatatc tgtagcatag atgacttgga ataaaagctg tatgcatggg
cattaccct
2701 caggtcctaa gaaataagtc ctgaatgcat gtcgttccaa actaacactc
tgtaatttt
2761 cttttatgtc ttatttcca agagtcctcc atttttgca ccccctcacc
gccaactctg
```

Figure 9 (Cont.)

```
2821 ttattcagta gagagaagtg tacggcttc tgattggtga gtgaaaaagt
aacttgagac
2881 acgacctaag ttgaagagtt tagacttgct gagttttaga agtgatggaa
attaagagag
2941 cattcaata aaatgtgact tggctgtctt tggaagagaa gtgcaaggct
ttcctttgaa
3001 gaattaaat tagtccggta ggatgtcagg tgagactgtg tatgcaaaat
gaatgcaca
3061 ggtgatgcca gggcctcttg cttggtctg atgtcttggc acagggtaag
tgaaggttaa
3121 ttccagaaga gaggaatgac ttgaaggcaa aggaaactaa ggaaggaggt
tcagtgagga
3181 aaataaggtt gtccatgaga tttgaataga ttttagttc cccaaggtt
taaatacaaa
3241 catagtcaag caaggtagtc atctttctgc tggttgtgag gggaatctg
aaaatggagt
3301 tttagaggaa aagtcaacat ctaactagtg aggaaaagtg cctaatacaa
ttagaatctc
3361 cctcactcta tagttgccca gttgaaagga taaggaggag gggtggcttt
tatggacttc
3421 catgagagaa ggaaagaaat atttcaggta agcttctcag ggctggcct
ttttgggatt
3481 tggatgagaa attggaagta ctaactactt tctagcatat ctttaagaaa
attgattgtt
3541 atttactccc agatcctctt gcagaccag aattatcagg aacatagctc
tgtgattcat
3601 gagtgtcccc atactgatga attggagcat ccatatggaa agcaaaggca
gaattatccc
3661 agctgtatta ttttgatctt ttggatgcag gtgccttaat gaagctctca
aaatatttta
3721 ggagctgctc agggagtgtt gggtggaact gtttggacta cattgttttc
tcttagatta
3781 tgtgattttt gttgggaact ggcaaaaggt gtgtgtgtga atgtgtcat
gtgtgtgaat
3841 gttgtgtgtg tgtgtgtgtg tgtgtgtgtg tgtgtgtgtg tttgcagaca
tgcaaaactg
3901 cagctgaaat aataccttag atttctaggt aagtctttcc acattctaat
aatgggtaag
3961 agtagaacca gggccgggta tcaattattg cttgctgttt gcaaccaggc
ataaaatcac
4021 ttttctcaaat catccaccgt tcctattaaa tttatgccgg aaactctcct
tctgtgagta
4081 taactcctgc agttcctata gcagataaga tataagaaag tgcctcctag
ggctcctccg
4141 cccgcttgtt tgctaaaatt ccctttctct ataagtccac cattttcaag
attgtagat
4201 agtgtattag ttaagacagc tttgtcgatc tggccagatg ttttttctcc
tttgtccaaa
4261 ggccagagac catccagga agagtggtgg gtggtttata cactggaaat
gttgcgttta
4321 tgcttttaa aaacacacgt taacttcaga ggaaggatgg gcaaatctgg
tctagctggg
4381 tgaaaccctt attttcccag agatgcctta accttgttg gttttggctt
tagggttcag
```

Figure 9 (Cont.)

```
   4441 agtcacttt  gttccttct  ccattctgga  gagggactt c  cctacatag
agccctgatt
   4501 tttgtggctg  tgggattgg  aggtagcatt  caaagatcag  atgtgcttt
cctcacttt g
   4561 gagatgaaca  ctctgggttt  tacagcatta  acctgctaa  ccttcatggt
gagaaataca
   4621 ccatctctct  tctagtcatg  ctgtgcatgc  cgcttactct  gttgggtct
atataattt
   4681 gttgaactct  tacctacatt  ccaagaagt  ttcaaggaac  cataaatata
tgtatacata
   4741 tacatata  aatatatat  attaaataa  aattatcagg  atactgcct
cagttatga
   4801 actttttttt  ttaagaatac  ttttttttta  agctgagaag  tataggatg
aaaagatgt
   4861 tatattgtgt  ttgactattt  tccaacttgt  attttcatat  aatttatatt
ttttaaaagc
   4921 tgaaaattta  gaagcaagat  gaaaaaaagg  aaaagcaggt  gcttttaaa
aatcagaact
   4981 gaggtagctt  agagatgtag  cgatgtaagt  gtcgatgttt  tttaaaaaa
aatgcaaaa
   5041 aattctat  ggggagttt  ttgtttgtt  tattttagta  gctgatgctg
gcacatcatt
   5101 ttgctggaga  gtttttata  tactgtagcc  tgatttcata  ttgtatttta
aactgtgtga
   5161 aattaaaaac  aaagaattc  attcataaaa  aaaaaaaaaa  aaaaaaaaa
aaaaaaaaa
   5221 aaaaaaaa
```

NM_005239 (ETS2 mRNA) SEQ ID NO:35

```
   1 gcccggttac  ttcctccaga  gactgacgag  tgcggtgtcg  ctccagctca  gagctcccgg
  61 agccgcccgg  ccagcgtccg  gcctccctga  tcgtctctgg  ccggcgccct
cgccctcgcc
 121 cggcgcgcac  cgagcagccg  cggcgccga  gcagccaccg  tcccgaccaa
gcgccggccc
 181 tgcccgcagc  ggcaggatga  atgatttcgg  aatcaagaat  atggaccagg
tagcccctgt
 241 ggcaacagt  tacagaggga  cactcaagcg  ccagccagcc  ttgacacct
ttgatgggtc
 301 cctgttgct  gttttcctt  ctctaaatga  agagcaaaca  ctgcaagaag
tgccaacagg
 361 cttggattcc  attctcatg  actccgccaa  ctgtgaattg  cctttgttaa
cccgtgcag
 421 caaggctgtg  atgatccaag  cctaaaagc  tacttcagt  ggcttcaaaa
aggaacagcg
 481 cgcctgggc  attccaaaga  accctggct  gtggagtgag  caacaggtat
gccagtggct
 541 tctctgggcc  accaatgagt  tcagtctggt  gaacgtgaat  ctgcagaggt
tcggcatgaa
 601 tggccagatg  ctgtgtaacc  ttgcaagga  acgtttctg  gagctggcac
ctgacttga
 661 gggtgacatt  ctctgggaac  atctggagca  aatgatcaaa  gaaaaccaag
aaagacaga
```

Figure 9 (Cont.)

```
 721 agatcaatat gaagaaaatt cacacctcac ctccgttcct catcggatta
acagcaatac
 781 attaggtttt ggcacagagc aggcgccta tggaatgcag acacagaatt
accccaaagg
 841 cggcctcctg gacagcatgt gtccggcctc cacacccagc gtacccagct
ctgagcagga
 901 gtttcagatg ttccccaagt ctcggctcag ctccgtcagc gtcacctact
gctctgtcag
 961 tcaggacttc ccaggcagca acttgaattt gctcaccaac aattctggga
ctcccaaaga
1021 ccacgactcc cctgagaacg gtgcggacag cttcgagagc tcagactccc
tcctccagtc
1081 ctggaacagc cagtcgtcct tgctggatgt gcaacgggtt cctccttcg
agagcttcga
1141 agatgactgc agccagtctc tctgcctcaa taagccaacc atgtctttca
aggattacat
1201 ccaagagagg agtgacccag tggagcaagg caaaccagtt ataccctgcag
ctgtgctggc
1261 cggctcaca ggaagtggac ctattcagct gtggcagttt ctcctggagc
tgctatcaga
1321 caaatcctgc cagtcattca tcagctggac tggagacgga tgggagttta
agctcgccga
1381 ccccgatgag gtggccgcc ggtggggaaa gaggaaaaat aagcccaaga
tgaactacga
1441 gaagctgagc cggggcttac gctactatta cgacaagaac atcatccaca
agacgtcggg
1501 gaagcgctac gtgtaccgct tcgtgtgcga cctccagaac ttgctggggt
tcacgcccga
1561 ggaactgcac gccatcctgg gcgtccagcc cgacacggag gactgaggtc
gccggacca
1621 ccctgagccg gccccaggct cgtggactga gtgggaagcc catcctgacc
agctgctccg
1681 aggacccagg aaaggcagga ttgaaaatgt ccaggaaagt ggccaagaag
cagtggcctt
1741 attgcatccc aaaccacgcc tcttgaccag gctgcctccc ttgtggcagc
aacggcacag
1801 ctaattctac tcacagtgct tttaagtgaa aatggtcgag aaagaggcac
caggaagccg
1861 tcctggcgcc tggcagtccg tggacggga tggttctggc tgtttgagat
tctcaaagga
1921 gcgagcatgt cgtggacaca cacagactat tttagatt tcttttgcct
tttgcaacca
1981 ggaacagcca atgcaaaaac tctttgagag ggtaggaggg tgggaaggaa
acaaccatgt
2041 catttcagaa gttagtttgt atatattatt ataatcttat aattgttctc
agaatccctt
2101 aacagttgta tttaacagaa attgtatatt gtaatttaaa ataattatat
aactgtattt
2161 gaaataagaa ttcagacatc tgaggtttta tttcattttt caatagcaca
tatggaattt
2221 tgcaaagatt taatctgcca agggccgact aagagaagtt gtaaagtatg
tattatttac
2281 atttaataga cttacaggga taaggcctgc gggggtaat ccctgctttt
tgtgttttt
```

Figure 9 (Cont.)

```
     2341 tgttgtttg tttgttgtt ttgggggt tttcttgcct tggttgtctg
gcaaggactt
     2401 tgtacatttg ggagttttta tgagaaactt aaatgttatt atctgggctt
atatctggcc
     2461 tctgcttct cctttaattg taaagtaaaa gctataaagc agtattttc
ttgacaaatg
     2521 gcatatgttt tccacttctt tgcatgcgtt taagtcagtt tatacacaaa
atggattta
     2581 tttttagtt taactgtgtt tctccgacag ctcacctctc tctgaccacc
cagccattc
     2641 cttcctgtgc tccacgttct tctgtgtgat taaaataaga atattatttt
tgaaatatg
     2701 caactcctt tcagagatca ggaggatttt atgtagcagc tatttttact
gcaaaagtaa
     2761 tccactggaa aaaaatgta atttgtaaga aagctttatt tttatctcag
ctctatgtaa
     2821 agttaaagtt actgtacaga gctgaaggac gggggcggt aggggtcttg
atgaaactc
     2881 ttgaacgaag cacagtttgt cccatctttg ttcactgtg tgtctcaacc
atcttaatag
     2941 catgctgctc ctttttgctc agtgtccaca gcaagatgac gtgattctta
ttttcttgga
     3001 cacagactat tctgaggcac agagcgggga cttaagatgg gaaagagaaa
gcatcggagc
     3061 cattcattcg gagaaaacgt tttgatcaaa atggagactt ttgtagtcgt
ttcaaaagag
     3121 cacctgagtc atgtgtattc ccggccttta taaatgaccc ggtcaagttg
gtttcaaagt
     3181 ccgacaggct tgtctgttta ctagctgcgt ggccttggac gggtggctga
catctgtaaa
     3241 gaatcctcct gtgatgaaac tgaggaatcg ggtggccggg caagctggga
agagcaaagc
     3301 cagagctgcg ctgcctcaat acccacaaaa gaccattccc agtatacata
agcacaggat
     3361 gttttttctca agaggatgt attataact tggacatctg tttataatat
aaacagacat
     3421 gtgactggga acatcttgct gccaaaagaa tcctaggcag tggctcattg
tatgtgaggt
     3481 tgaaccacgt gaaattgcca atattaggct ggctttato tacaaagaag
gagttttcatg
     3541 gggttcagcc taacagttat ggaaactaca gtccttataa accattggca
tggtaataaa
     3601 cagatcttaa gtataaaaat ttgtaattg ggcttact ctctcaataa
taaagtattt
     3661 tgtttatata aa
//
BC058150 (ELK1 mRNA) SEQ ID NO:36

1 cgctacacac aggtacccct gggatggcgt gagcactccc ccagcgatgg acccatctgt
   61 gacgctgtgg cagtttctgc tgcagctgct gagagagcaa ggcaatggcc
acatcatctc
  121 ctggactca cgggatggtg gtgaattcaa gctggtggat gcagaggagg
tggccgggct
```

Figure 9 (Cont.)

```
    181 gtggggcta cgcaagaaca agaccaacat gaattacgac aagctcagcc
ggccttgcg
    241 gtactactat gacaagaaca tcatccgcaa ggtgagcggc cagaagttcg
tctacaagtt
    301 tgtgtcctac cctgaggtcg cagggtgctc cactgaggac tgccgccca
agccagaggt
    361 gtctgttacc tccaccatgc caaatgtggc ccctgctgct atacatgccg
cccagggga
    421 cactgtctct ggaaagccag gcacaccaa gggtgcagga atggcaggcc
caggcggttt
    481 ggcacgcagc agccggaacg agtacatgcg ctcgggcctc tattccacct
tcaccatcca
    541 gtctctgcag ccgcagccac ccctcatcc tcggcctgct gtggtgctcc
ccagtgcagc
    601 tcctgcaggg gcagcagcgc cccctcggg gagcaggagc accagtccaa
gccccttgga
    661 ggcctgtctg gaggctgaag aggccggctt gctctgcag gtcatcctga
cccgcccga
    721 ggcccaaac ctgaaatcgg aagagcttaa tgtggagccg ggtttgggcc
gggctttgcc
    781 cccagaagtg aaagtagaag ggcccaagga agagttggaa gttgcggggg
agagagggtt
    841 tgtgccagaa accaccaagg ccgagccaga agtccctcca caggagggcg
tgccagcccg
    901 gctgcccgcg gttgttatgg acacgcagg gcaggcggc ggccatgcgg
cttccagccc
    961 tgagatctcc cagccgcaga agggccggaa gccccgggac ctagagcttc
cactcagccc
   1021 gagctgcta ggtgggcgg gacccgaacg gacccagga tcgggaagtg
gctccggcct
   1081 ccaggctccg gggcgggcgc tgacccatc cctgcttcct acgcatacat
tgaccccggt
   1141 gctgctgaca cccagctgc tgcctcctag cattcacttc tggagcaccc
tgagtcccat
   1201 tgccccggt agcccggcca agctctcctt ccagtttcca tccagtggca
gcgccaggt
   1261 gcacatccct tctatcagcg tggatggcct ctgaccccc gtggtgctct
cccagggcc
   1321 ccagaagcca tgactactac caccaccacc accaccctt ctggggtcac
tcatccatg
   1381 ctctctccag ccagccatct caaggagaaa catagttcaa ctgaaagact
catgctctga
   1441 ttgtggtggg gtgggatcc ttgggaagaa ttactcccaa gagtaactct
catatatctcc
   1501 tccacagaaa acacacagct tccacaactt ctctgtttc tgtcagtccc
ccagtgccg
   1561 cccttacacg tctcctactt caatggtagg ggcggtttat ttatttatt
ttgaaggcc
   1621 actgggagga gcctgaccta accttttagg gtggttagga catctccccc
acctcccac
   1681 tttttttccc aagacaagac aatgaggtc tggcttgaga aagacctttc
tttctttatt
   1741 tctcagccg cccttgggga gatgagggag ccctgtctgc gtttttggat
gtgagtagaa
```

Figure 9 (Cont.)

```
1801 gagttagttt gttttgtttt attattcctg gccatactca ggggtccagg aagaatttgt
1861 accatttaat gggttgggag tcttggccaa ggaagaatca caccctggaa atagaaattt
1921 ccacctcccc aacctttctc tcagacagct tatccttttc aaccaactttt tggccaggg
1981 aggaatgtcc cttttgttct tccccctgag aagccattcc tttgtctgcc aacctccctg
2041 gggtcctgcc tgtttcctcc caatggaggg ttttttttggg gggtggtccc cgtctggggg
2101 gccccctccag ccagtactcc aggtctccct gtctctcccc cgctgccatt ttgatagtat
2161 aatctatttt taaatggggc ttttcaatag gggagaggga gtcatctctt cctatatttg
2221 gtgggtggg tggaaggaa gggatttggg ggggaatctt cctgccgcct ccccactcc
2281 aagtgtttat ttttgatacc aaacatgaat tttcagttcc ctccctccca gccccccaat
2341 ttcctgcggg cgggtacaaa ggacccttc aatgtccctg gagttgggag ggaggaatgg
2401 gggacataaa gcctgtcctg tctctattct aggcaagaga gagtgggttc aaaagactcc
2481 tgggctcacc tgttagcgct ggcccagccc aggccttggg acctgggggt tggtgatttg
2521 ggggacagtg ctacactcgt ctccactgtt tgtttact ccccaaaatg gacctttttt
2581 ttttctaaag agtcccagag aatggggaat tgttcctgta aatatatatt tttcaaagtg
2641 aaaaaaaaaa aaaaaaaaa aaaaaaa
```

NM_001987 (TEL (ETV6) mRNA) SEQ ID NO:37

```
1 gcgtcccggg tcccgcgcc gcgccgcgac ctgcagacc cgccgccgcg ctcgggcccg
61 tctcccacgc cccgccgcc ccgcgcgccc aactccgccg gccgcccgcc ccgccccgc
121 gcgctccaga ccccggggc ggctgccggg agagatgctg gaagaaactt cttaaatgac
181 cgcgtctggc tggccgtgga gcctttctgg gttggggaga ggaaaggaaa gtggaaaaaa
241 cctgagaact tcctgatctc tctcgctgtg agacatgtct gagactcctg ctcagtgtag
301 cattaagcag gaacgaattt catatacacc tccagagagc ccagtgccga gttacgcttc
381 ctcgacgcca ttcatgttc cagtgcctcg agcgctcagg atggaggaag actcgatccg
421 cctgcctgcg cacctgcgct tgcagccaat ttactggagc agggatgacg tagcccagtg
481 gctcaagtgg gctgaaaatg agttttcttt aagccaatt gacagcaaca cgtttgaaat
541 gaatggcaaa gctctcctgc tgctgaccaa agaggacttt cgctatcgat ctccttcattc
601 aggtgatgtg ctctatgaac tccttcagca tattctgaag cagaggaaac ctcggatttct
```

Figure 9 (Cont.)

```
  661 tttttcacca ttcttccacc ctggaaactc tatacacaca cagccggagg
tcatactgca
  721 tcagaaccat gaagaagata actgtgtcca gaggacccc aggccatccg
tggataatgt
  781 gcaccataac cctccaacca ttgaactgtt gcaccgctcc aggtcaccta
tcacgacaaa
  841 tcaccggcct tctcctgacc ccgagcagcg gccctccgg tccccctgg
acaacatgat
  901 ccgccgcctc tccccggctg agagagctca gggacccagg ccgcaccagg
agaacaacca
  961 ccaggagtcc taccctctgt cagtgtctcc catggagaat aatcactgcc
cagcgtcctc
 1021 cgagtcccac ccgaagccat ccagccccg gcaggagagc acacggtga
tccagctgat
 1081 gcccagcccc atcatgcacc ctctgatcct gaaccccgg cactccgtgg
attcaaaca
 1141 gtccaggctc tccgaggacg ggctgcatag ggaagggaag cccatcaacc
tctctcatcg
 1201 ggaagaccct gcttacatga accacatcat ggtctctgtc tccccgcctg
aagagcagc
 1261 catgcccatt gggagaatag cagactgtag actgctttgg gattacgtct
atcagttgct
 1321 ttctgacagc cggtacgaaa acttcatccg atgggaggac aaagaatcca
aaatattccg
 1381 gatagtggat cccaacggac tggctcgact gtggggaaac cataagaaca
gaacaaacat
 1441 gacctatgag aaaatgtcca gagccctgcg ccactactac aaactaaaca
ttatcaggaa
 1501 ggagccagga caaaggcttt tgttcaggtt tatgaaaacc ccagatgaaa
tcatgagtgg
 1561 ccgaacagac cgtctggagc acctagagtc ccaggagctg gatgaacaaa
tataccaaga
 1621 agatgaatgc tgaaggaacc aacagtccac ctcagcgggc cagcagcca
gggaaccct
 1681 gcccaccagg atgctggaa gtgtgacgga gcaggcgggc tgaggagagt
ggaaaaggaa
 1741 gggagcccaga aatggcaggg acacttctct tgcagaccaa gagggaccct
ggagcacctt
 1801 agacaaacta cccagcacag gcggggctgg aattctggcg gagggcatga
gcctgggact
 1861 ccatgtcacg tttccttctg attggaatc tctccatctg taattcctca
ccctcaccct
 1921 tccaccgttg ttagtatcat ggtgttttg ttttgtttt tgtttaaga
acctgcagtt
 1981 tgactcttca tcgttcatct aggggaagac atatgatgtt gttttcctat
ggaaatatat
 2041 atctattata tatatatttt ttgcaaatct cacaaagtgc ggcaagccca
gctggtcagg
 2101 aaagagaata cttgcagagg ggttcaggtt cctcttttc ctgccacgtg
gatcaggtct
 2161 gttcctgtta ctgttgggtc ttggctgaaa aaaaaaatg cttttaaaaa
agataaaatg
 2221 aaaaggagag ctctcttttt ctctctcttg ctctgttctt cccttggtcc
cctctgtcct
```

Figure 9 (Cont.)

```
2281 cccgccctgc ctgcagttga gattcagatg ccttctgaca gagttcagcc
tcttggagag
2341 tcttgggat tgttggcacc taaacagaat cagtgacccg ggtgcttgt
ggccagcagc
2401 acagaatcaa acccgatcc cagcattggg ccacccatct gagggaggcc
aaaatcatca
2461 cagatgctgc tgtgctgcag acagatacat gctagtccag agagccgccc
ctgagatggc
2521 tgtgagaacc atgtgtctaa gggctaagat aaggatggaa ggctgtccaa
gttatttgga
2581 aggcctcggc agcttgggat tagcttggga gcgcagcgct gcaaagtgga
aaatatgaaa
2641 agaccacaca ggccagcag tccagaaact gggcaaaaat attctgcagt
gggatttat
2701 ttttccaaag cagtaacag aggctagtga gaaagaaaag ctcctctctg
ctccattcca
2761 aaggccatct tgtggtcagt ttcatgccct cacctgattt ttttctttt
tttttttt
2821 caattcctaa cctttttaa agtttcctgg tctccactgg acacagagct
ttggagacgg
2881 aggatcccag agggcagtct cagttgcaat cagtgtgtgc ccagcctggg
cagacaggaa
2941 attcctagga tacattattt tttcttctt tcatagctgt gtctcagaaa
ggacccattt
3001 gtggctcttt ttcagctcaa aataagatcg atggtatctt gtaaaatgag
ggtagtgcca
3061 cttcttagta tttttgaaag ctgtttaga tttttttttt ttttccttt
ctagccatct
3121 aaattgactc ttccaatata ggtctcagaa atccaatatt tggagtacaa
tttctttaa
3181 tccagattac acctgcctta caaagcaccc cctccttgtt cccctctgtt
tccctactc
3241 agttggggga gaaactcaca gctcctcgg gatacatatg tgccctcagc
agcagctccc
3301 aggtgaagtt accagacccc tgggcttctc cccagcttt tctgagttga
gtcagacatg
3361 tagagtttgg gtcacacagg caagaggaat tttccctggg ccttactgac
aaggacacca
3421 acctagggtg caaacagatg gactatggtt caaggacact ggaattgagg
agctgatcaa
3481 ggctctattc agccttgctc tgtccctgcc tcttatcaga gcacaggtag
acacacgggc
3541 atagccagcc cactcctact gtcacaggcg cccaccatt caaccttccg
ggaggtcagg
3601 gaccttctat atgaggcgag tgggtctcag tctgcttgaa tggtgatgag
attctgctgg
3661 atctcagcac gctgcaggtg tcttttgaga gcattcagta ggacatggtg
atccctattt
3721 cagcctctaa gatgactggt attctatctg aaatgcagag attaagccaa
atacctgatg
3781 tattgtgaaa gccactgatt ttaagaatgg agagaaaggg attttttact
gcatccctct
3841 gtatgaatat gaaatcagag accagggcat gatgttgcta ggattagagc
ctctcagtct
```

Figure 9 (Cont.)

```
3901 ggcctcttca cccaagtgca agaactcagt ctcttactgt tcaaagaatc
ttaacagttg
3961 aattatggag ggaaattccc ttttgcccca agcatttcta tatttaaagc
aatatcccag
4021 gagaatatgt tgacttagg atgatacctt cagccacttg aagaagaat
agaaggcgct
4081 cattccaata tagtctttat ttcccattca gatacaggtc gagcatcct
aatctgaaca
4141 gttaaaaccc ccaatgccc caaaatccaa accttcctga acgctatgac
accatgagtg
4201 gaaaattcca cacctaacaa acacatttgc tttcttatgg ttcaatgtac
acaaactgtt
4261 ttatatagaa aatgatttca aatatcataa aattaccttc aggctatgtg
tataaagtat
4321 atatgagcca taaatgaatt ttgtgtttag acttgtgtc catcccaag
atctctcatt
4381 ttatatatat atatatatat atatatatat atatatatat atatatatac
acacacacac
4441 acatacacaa atattccagg atacaaaaaa aaacatttaa aaatccgaga
cccagaacac
4501 ttctggtccc aagcatttca gataagggat atcaatctgt actaccaata
aggatttcgt
4561 aattccccta actgcaaatg tcctcttcat ttgttctttta tgagaaaacc
cgggtagtgc
4621 cagcacctgg atacagtatt tacacctgc agaccctaaa gatttcagat
tcagttagca
4681 aaacttgatg aagcacctgc tggacactga gggacccaaa gctcaatcag
ccataatccc
4741 tgcttcaga gtttatattg tacctgccta atccaccgg cgtgactcat
ttcaacacta
4801 agtactaggg gtgttgtcag gagacaaatc tgaagtcagg agaggaaaat
gcaaaggagc
4861 cctgccgtgt gatggatgtg cattctcact tgggtcttga agttctcatt
cctacatctc
4921 aagctagcca ggcagtctcc tctctatcag aagaaagcac tggtaattgg
ctagctggc
4981 tatgttgaag gtaacatgaa ctctaagatc ttgacccagg gcgacttggt
tttgcttaag
5041 gtggcatcac caatgttcca aatcctttag ggagatgagg gtatcccac
agaaaagag
5101 gaataataga ccaatggatt ttctccttttc accagtatgt ttggaacct
ctgatccaat
5161 gtcctttgat actgatctct tgtccaaatg agaatgtcgc tttagctgaa
attcaaatgg
5221 ctgtgacaat ttaccgaaat gatgaagtaa ccaccattcc cacctttcac
tgcctaggct
5281 ccaagtctga atacattttt gaaataggaa ctccctttttg caaaaaagaa
acctgggtgt
5341 caggaggtg aagtgacttg ccctaggagc agacagcatg ccaagaatgg
aattaggctc
5401 aggatccagc ctgggctcac cctgtgtggc tcattcccac ccaggaaact
gaagataaaa
5461 gatttgggaa aacacaccaa gaaaaagggg cagttttctt tgcccaagca
ttggtgcta
```

Figure 9 (Cont.)

```
5521 gttagaggct gttcactctc tcctgctcct cttcggagta gaaataaagg
ctgtgacaca
5581 aggaagccag tggggtggga gggaggcacc ataatccctc cctaaaaccc
acagaagact
5641 aacctgatac tcttttgacc caactgcatc aacactaaac agctgcagac
ccctgaatc
5701 tttcacacat gccaagtgaa cattcttgat gatttctctt tgtgaccgca
accacctgca
5761 aaccagaacg actctagaat ttccttcccc gccccctttt ttgtttagtt
tctaatctct
5821 tgtttatgag gtgtggggtt tataaggac tgaatcaaat gaatgtaaca
aaaagaaaa
5881 aaaaaacaaa aaaaaatgcc ttttctcagg gccagtgagt tgcaaataat
ttttaaagaa
5941 aagcctataa ttacatcatc tcaataaatt tttataaaa aaaaaaaaa aa
```

NM_016135 (TEL2 (ETV7) mRNA) SEQ ID NO:38

```
   1 gattcctcc caagcgacct tccagttctc ggagccaggt tagggtttg
gcggaggagg
  61 actgcgggc gcgggcctag ggcccagca gccacggcca gggagcgct
caagacagaa
 121 agccggtggc ttcctcacct ccacctgtaa tgcaggaggg agaattggct
atttctccta
 181 taagcctgt ggcagccatg cctccctag gcaccacgt gcagccaga
tgtgaagctc
 241 aaattaacct gctgggtgaa gggggatct gcaagctgcc aggaagactc
cgcatccagc
 301 ccgcactgtg gagcagggag gacgtgctgc actggctgcg ctgggcagag
caggagtact
 361 ctctgccatg cacgcggag cacgggttcg agatgaacgg accgccctc
tgcatcctca
 421 ccaaggacga cttccggac cgtgcgccca gtcaggtga cgtcctgtat
gagctgctcc
 481 agtacatcaa gacccagcgg cgagccctgg tgtgtggacc cttttttgga
gggatcttca
 541 ggctgaagac gccaaccag cactctacag tccccccgga agaggtgact
ggccccctc
 601 agatggacac ccgaagggc cacctgctgc agccaccaga cccagggctt
accagcaact
 661 tcggccacct ggatgaccct ggcctggcaa ggtggacccc tgcaaggag
gagtccctca
 721 acttatgtca ctgtgcagag ctggctgca ggacccaggg ggtctgttcc
ttcccggga
 781 tgccgcaggc cccattgac ggcaggatcg ctgactgccg cctgctgtgg
gattacgtgt
 841 atcagctgct cctgatacc cgatatgagc cctacatcaa gtgggaagac
aaggacgca
 901 agatcttccg agtgtggat ccaaggggc tgccagact ctgggaaat
cacaagaacc
 961 gggtgaacat gacctacgag aagatgctc gtgccctgcg ccactattat
aagcttaata
```

Figure 9 (Cont.)

```
1021 tcattaagaa ggaaccgggg cagaaactcc tgttcagatt tctaaagact
ccgggaaaga
1081 tggtccagga caagcacagc cacctggagc cgctggagag ccaggagcag
gacagaatag
1141 agttcaagga caagaggcca gaaatctctc cgtgagggc aggtggactc
caggcaccg
1201 gtaccgatgg ggcagggacc gagtctccca tgaaggcaga ctcctcctcc
cagcagagca
1261 gcaggatccc cagccagact ctgtacccac aggattacag ccattgcttg
ggaaggctgg
1321 gaggcctccc atccaggaca ctggggcag gagtgtcatc ttttgggcag
ggcaatcctg
1381 gggctaaatg aggtacaggg gaatggactc tccctactg cacccctggg
agaggaagcc
1441 aggcaccgat agagcaccca gccccacccc tgtaaatgga atttaccaga
tgaagggaat
1501 gaagtccctc actgagcctc agatttcctc acctgtgaaa tgggctgagg
caggaaatgg
1561 gaaaaagtgt tagtgcttcc aggcggcact gacagcctca gtaacaataa
aaacaatggt
1621 agctgaaaaa aaaaaaaaaa aaaaaaaaaa aaaaaaaaa aaaaaaaaaa
```

NM_004454 ERM (ETV5) mRNA SEQ ID NO:39

```
1 gagtccagcc gctggtgcgc ggagcggttc accgtcttcg gagcggttcg gccagcctt
61 tcgccagga gccaggccc gctgcgcg tgcgtgagcg cgcctgcgcc
gccagggccg
121 ctgcaagggg aggagagcgg ccgcctcagg aggatccctt ttccccaga
aattactcaa
181 tgctgaaacc tctcaaagtg gtattagaga cgctgaaagc accatggacg
ggttttatga
241 tcagcaagtc cctttatgg tcccaggaa atctcgatct gaggaatgca
gaggggggcc
301 tgtgattgac agaaagagga agttttgga cacagatctg gctcacgatt
ctgaagagct
361 atttcaggat ctcagtcaac ttcaagaggc ttggttagct gaagcacaag
ttcctgatga
421 tgaacagttt gtcccagatt ttcagtctga taactggtg cttcatgccc
cacctccaac
481 caagatcaaa cgggagctgc acagccctc ctctgagctg tcgtcttgta
gccatgagca
541 ggtcttggt gctaactatg gagaaaagtg cctctacaac tattgtcct
atgataggaa
601 gcctccctct gggtccagc cattaaccc tcctacaacc ccctctcac
ccacccatca
661 gaatccccta tttccccac ctcaggcaac tctgcccacc tcagggcatg
ccctgcaga
721 tggcccagtt caaggtgtgg gccccgccc cgccccccat tcgcttccag
agcctggacc
781 acagcagcaa acattgcggg tccccgacc accacatcag ccctgcaga
tgccaaagat
841 gatgcctgaa aaccagtatc catcagaaca gagatttcag agacaactgt
ctgaacctg
```

Figure 9 (Cont.)

```
 901 ctacccctto cotcctcago caggagttcc tggagataat cgcccagtt
accatcggca
 961 aatgtcagaa cctattgtcc ctgcagctcc cccgccccct cagggattca
aacaagaata
1021 ccatgaccca ctctatgaac atggggtccc gggcatgcca gggcccccag
cacacgggtt
1081 ccagtcacca atgggaatca agcaggagcc tcgggattac tgcgtcgatt
cagaagtgcc
1141 taactgccag tcatcctaca tgagagqggg ttatttctcc agcagccatg
aaggttttto
1201 atatgaaaaa gatccccgat tatactttga cgacacttgt gtgtgcccg
agagctgga
1261 aggcaaagtc aaacaggagc ctaccatgta tgagagggg cccccttacc
agaggcgagg
1321 ttccttcag ctgtggcagt tcctggtcac cettcttgat gacccagcca
atgccacctt
1381 cattgcctgg acaggtcgag gcatggagtt caagctgata gaaccggaag
aggttgctcg
1441 gcgctggggc atccagaaga accggccagc catgaactat gacaagctga
gccgctctct
1501 ccgctattac tatgaaaagg gcatcatgca gaaggtggct ggagagcgat
acgtctacaa
1561 atttgtctgt gacccagatg ccctcttctc catggctttc ccggataacc
agcgtccgtt
1621 cctgaaggca gagtccgagt gccacctcag cgaggaggac accctgccgc
tgacccactt
1681 tgaagacagc cccgcttacc tcctggacat ggactgctgc agcagcctcc
cctatgccga
1741 aggctttgct tactaagttt ctgagtggcg gagtggccaa acctagagc
tagcagttcc
1801 cattcaggca acaagggca gtggttttgt ttgtgttttt ggttgttcct
aaagcttgcc
1861 ctttgagtat tatctggaga accaagctg tctctggatt ggcacccttc
aagacagata
1921 cattggctgg ggagtgggaa cagggagggg cagaaaacca ccaaaaggcc
agtgcctcaa
1981 ctcttgattc tgatgaggtt tctgggaaga gatcaaaatg gagtctcctt
accatggaca
2041 atacatgcaa agcaatatct tgttcaggtt agtacccgca aaacgggaca
tgatgtgaca
2101 atctcgatcg atcatggact actaaatggc cttacatag aagggctctg
atttgcacaa
2161 tttgttgaaa aatcacaaac ccatagaaaa gtgagtaggc taagttgggg
aggctcaaac
2221 cattaagggt caaaaataca tcttaaacat tggaaagctc ttctagctga
atctgaaata
2281 ttaccccttg tctagaaaaa gggggcagt cagaacagct gttccccact
ccgtgttctc
2341 aaaatcataa accatggcta ctcttgggaa ccacccggcc atgtggtcgc
caagtagagc
2401 aagccccctt tctcttccca atcaacgtggc tgagtgtgga tgactttat
tttaggagaa
2461 gggcgattaa cacttttgac agtattttgt tttgccctga tttggggat
tgtttttgttt
```

Figure 9 (Cont.)

```
2521 tggtggttgt ttggaaaaa cagtttataa actgatttt gtagtttgg
tattaaagc
2581 aaaaaacga aaacaaaaa acaaaaacaa acctttggt aatgtgact
ggtcttag
2641 ccagggcgt gcaattatg aagaactgc agcttgagag gggctttgt
gaggcttcc
2701 cttggcatg tgaaagccg cctgttgcc tgctttgtgc ttcctgcacc
agacaactg
2761 atggaacatt tgcactgag ttgtacattt ttgaagtgtg cagggcagcc
tggacacaag
2821 cttagattct ctatgtatag ttccccgtgt tcactaacat gccctctctg
gaaagcatat
2881 gtatataaca tgtgtcatgt cctttggaaa cctggtcacc tggtgaaaac
ccttgggatt
2941 cttcctggg catgactgat gacaatttcc attcatcag tttgttttgt
ttttctttt
3001 ctttaaatct tggactttaa accctacctg tgtgattcag tagggtttga
gacttagctg
3061 tgatactgac aggtaagcaa cagtgctagc attctagatt cctgcttt
tttaaaaga
3121 aattattctc attgctgtat tatattggaa aagttttaaa caaccaagct
aaagctatgt
3181 gaaagttgag ctcaaagtag aggaaaagtt actggtggta cctgctgcc
tgctctgctg
3241 gtagaattct gtgctccccg tgacacttag tacattaaga atgactacac
tgttcctcgt
3301 atgtgaagga ggcagtgctg actccgtgag tgtgagacac gtgctttgaa
ctgcttttct
3361 attcatggag cactccatag tctcaaactg tccccttat gaccaacagc
acattgtga
3421 agaggttgc agggataagg ggtgcacttt atagctatgg aaacatgaga
ttctcctcta
3481 ttggaagcta attagccac aaaggtggta aacctgtaga ttgggcctta
attagcattg
3541 tactctaatc aaaggactct ttctaaacca tattatago tttcttaacc
tacacatagt
3601 ctatacatag atgcatattt tacccccagc tggctagaga tttattgtt
gtaaatgctg
3661 tatagattg gtttcctt cttacttac cctggttgg atcttttt
tttttcttt
3721 tgaatggatt tatgtgtct tagcaatatg acaataatcc tctgtagctt
gagctacccc
3781 tccctgctg taacttacgt gactgtgct gtcactggc ataggacaga
ggcatcacgg
3841 ttgcattccc attggactca tgcactcc ggatggtttc tgttttttc
gggttctt
3901 tgggttgt ttgttgctc cttttccaga gtgtggaaag tgtacagtgc
agaaaggctt
3961 gaacctgcca gctgattga aatactttca cactgcgcag ggccgtatgc
atccgccaa
4021 gctgcgttat attctgtact gtgtacaata aagaagtttg cttttcgttt a
```

BC030507 (ELF1) SEQ ID NO:40

Figure 9 (Cont.)

```
1 gccaagaagc ttgagagaag aaaaatttca gaaaaattgt ctcaatttga ctagaatatc
   61 aatgaaccag gaaaactgaa gcaccttccc taaagaaaac ttgggtatac aattactcca
  121 cagacagagc tgagggtttt ttaccaaat cagtcactgg atttgctgc ctgatacgtg
  181 aatcttcttg gaattttctt catgtggatc taaggggaat gctttattat ggctgctgtt
  241 gtccaacaga acgacctagt atttgaattt gctagtaacg tcatggagga tgaacgacag
  301 cttggtgatc cagctatttt tcctgccgta aatgtggaac atgttccngg tgctgatatt
  361 ctcaatagtt atgcccggtct agcctgtgtg gaagagccca atgacatgat tactgagagt
  421 tcactggatg ttgctgaaga agaaatcata gacgatgatg atgatgacat cacccttaca
  481 gttgaagctt cttgtcatga cggggatgaa acaattgaaa ctattgaggc tgctgaggca
  541 ctcctcaata tggattcccc tggcccatg ctggatgaaa aacgaataaa taataatata
  601 tttagttcac ctgaagatga caggttgtt gccccagtca cccatgtgtc cgtcacatta
  661 gatgggattc ctgaagtgat ggaaacacag caggtgcaag aaaaatatgc agactcaccg
  721 ggagcctcat caccagaaca gcctaagagg aaaaaaggaa gaaaaactaa accaccacga
  781 ccagattccc cagccactac gccaaatata tctgtgaaga agaaaaacaa agatggaaag
  841 ggaaacacaa tttatcttg ggagtttta ctggcactgc tccaggacaa ggctacttgt
  901 cctaaataca tcaagtggac ccagcgagag aaaggcattt ttaaattggt ggattctaaa
  961 gcagtgtcca ggttgtgggg gaagcacaaa aacaaacctg atatgaatta tgagaccatg
 1021 ggaagagcac tcaggtacta ttaccaaagg ggtattctgg caaagtgga aggtcagcgc
 1081 ttggtgtatc agtttaaaga aagccaaaa gatcttatat atataatga tgaggatcca
 1141 agttccagca tagagtcttc agatccatca ctatcttcat cagccacttc aaataggaat
 1201 aaaccagcc ggtcgagagt atcttcaagt ccagggtaa aaggaggagc cactacagtt
 1261 ctaaaccag ggaattctaa agctgcaaaa cccaaagatc ctgtggaagt tgcacaacca
 1321 tcagaagttt tgaggacagt gcagccacg cagtctccat atcctaccca gtcttccgg
 1381 actgttcatg tagtacagcc agtacaggct gtccagaggg gagaagcagc tagaaccagt
 1441 accatgcagg atgaaacatt aaattcttcc gttcagagta ttaggactat acaggctcca
 1501 acccaagttc cagtggttgt gtctcctagg aatcagcagt tgcatacagt aacactccaa
 1561 acagtgccac tcaacagt tatagccagc acagatccat cagcaggtac tggatctcag
```

Figure 9 (Cont.)

```
1621 aagtttattt tacaagccat tccatcatca cagcccatga cagtactgaa
agaaaatgtc
1681 atgctgcagt cacaaaaggc gggctctcct ccttcaattg tcttgggccc
tgcccaggtt
1741 cagcaggtcc ttactagcaa tgttcagacc atttgcaatg gaaccgtcag
tgtggcttcc
1801 tctccatcct tcagtgctac tgcacctgtg gtgaccttt ctcctgcag
ttcacagctg
1861 gttgctcacc cacctggcac tgtaatcact tcagttatca aaactcaaga
aacaaaaact
1921 cttacacagg aagtagagaa aaaggaatct gaagatcatt tgaaagagaa
cactgagaaa
1981 acggagcagc agccacagcc ttatgtgatg gtagtgtcca gttccaatgg
attcacttct
2041 caggtagcta tgaaacaaaa cgaacgctg gaacccaact cttttttagtt
aatataccaa
2101 agcttatgaa taattgtttg ttaattgaac attttcaatt atatgcagac
tgactgattc
2161 taagataaat tctaaggagg tttctaattt tgtaattgtt aaaaatagag
taaattttga
2221 ctttgttaga tgagggagga aaactcaact gtttctcttt gttatctaaa
tgtttcagaa
2281 ttcaatcgtg aaggaacagg catttacac tatgaagaca ttcttttgag
attttatt
2341 cagttgctat atcataagca tttttaaagt ttctttttcta attttacatt
gtattagatt
2401 ttctgattct tttgtaaata cagaacttaa atagaaggca acaggaaatt
tatataggaa
2461 ctattttcat tccactgtg taagtaagt cttgactctt tcaaatgcaa
aaaacctatt
2521 ttatgctttg ttaaaattat ggtgtcactt agattgactt tagttgactg
cactatataa
2581 tatagaacta tgaatatgta gaataacatg aaaaattgga ggtgctggtg
gtatggctga
2641 ccctgtttca gaagcaggat agtataaaag catcagccta agaatggcac
tcccactaac
2701 tagctatgta atcttgacct ctttgggctt tagttcctct cataaaagga
agagatgtat
2761 tggattagac tagattatca ccactttctc ttctagttct aattttttta
attctaatac
2821 ctatattttc aagttatgtc aattaaatca ttatcaggtt atttcctaat
gtaagaatag
2881 ctaaaatgtt gcagagaaat aagtgaccca acaaaattta ttcatctgtt
atgggtaaga
2941 tctgccataa attcttccta aataatttgt ttactaactc tttaggccac
tgtgctttgc
3001 ggtccattag taaactgtg ttgctaagtg ctaaacagaa tactgctatt
ttgagagagt
3061 caagactctt tcttaagggc caagaaagca actgagcct tgggctaatc
tggctgagta
3121 gtcagttata aaagcataat tgcttatat tttggatcat tttttactgg
gggcggactt
3181 ggggggggtt gcatacaaag ataacatata tatccaactt tctgaaatga
aatgttttta
```

Figure 9 (Cont.)

```
3241 gattactttc tcaactgtaa atastgtaca tttaatgtca caagaaaaaa
atgtcttctg
3301 caaattttct agtataacag aaattttgt agatgaaaaa aatcattatg
tttagaggtc
3361 taatgctatg tttcatatt acagagtgaa tttgtattta aacaaaatt
taaattttgg
3421 aatcctctaa acattttgt atctttaatt ggtttattat taaataaatc
atataaaat
3481 tctcaaaaaa aaaaaaaa
```

NM_001986 (ETV4 (E1AF)) SEQ ID NO:41

```
1 gccaggctcc tggagcagg tctggcccc agcttgggc ccggccgtg cggccggagg
61 gagcggccgg atggagcgga ggatgaaagc cggatacttg gaccagcaag
tgccctacac
121 cttcagcagc aaatcgcccg gaaatggag cttgcgcgaa gcgctgatcg
gccgctggg
181 gaagctcatg gacccgggct cctgccgcc cctcgactct gaagatctct
tccaggatct
241 aagtcactc caggagacgt ggctcgctga agctcaggta ccagacagtg
atgagcagtt
301 tgttcctgat ttccattcag aaaacctagc tttccacagc cccaccacca
ggatcaagaa
361 ggagcccag agtccccgca cagacccggc cctgtcctgc agcaggaagc
cgcaactccc
421 ctaccaccat ggcgagcagt gcctttactc cagtgcctat gacccccca
gacaaatcgc
481 catcaagtcc cctgccctg gtgccttgg acagtcgcc ctacagcct
ttccccgggc
541 agagcaacgg aatttcctga gatcctctgg cacctccag cccaccctg
gccatgggta
601 cctcgggaa catagctccg tcttccagca gccctgac atttgccact
ccttcacatc
661 tcagggaggg ggccgggaac ccctcccagc ccctaccaa caccagctgt
cggagccctg
721 cccaccctat cccagcaga gcttaagca agaataccat gatcccctgt
atgaacaggc
781 ggcccagcca gccgtggacc agggtgtggt caatgggcac aggtaccag
gggcgggggt
841 ggtgatcaaa caggaacaga cggacttcgc ctacgactca gatgtcaccg
gtgcgcatc
901 aatgtacctc cacacagagg gcttctctgg gcctctcca ggtgacggg
ccatgggcta
961 tggctatgag aaacctctgc gaccaatccc agatgatgtc tgcgttgtcc
ctgagaaatt
1021 tgaaggagac atcaagcagg aagggtcgg tcatttcga gagggccgc
cctaccagcg
1081 ccggggtgcc ctgcagctgt ggcaatttct ggtggcttg ctggatgacc
caacaaatgc
1141 ccattccatt gcctggacgg gcggggaat ggagttcaag ctcattgagc
ctgaagaggt
1201 cgccaggctc tggggcatcc agaagaaccg gccagccatg aattacgaca
agctgagccg
```

Figure 9 (Cont.)

```
   1261 ctcgctccga tactattatg agaaaggcat catgcagaag gtggctggtg
agggttacgt
   1321 gtacaagttt gtgrgtgagc ccgaggccct cttctcttctg gcttcccgg
acastcagcg
   1381 tccagctctc aaggctgagt ttgaccggcc tgtcagtgag gaggacacag
tccctttgtc
   1441 ccacttggat gagagcccg cctacctccc agagctggct ggccccgccc
agccatttgg
   1501 ccccaagggt ggctactctt actagccccc agggctgtt ccccctgccg
caggtgggtg
   1561 ctgcctgtg tacatataaa tgaatctggt gtcgggaaa ccttcatctg
aaacccacag
   1621 atgtctctgg ggcagatccc cactgtccta ccagttgccc tagcccagac
tctgagctgc
   1681 tcaccggagt cattggaag aaaagtgga gaaatggcaa gtctagagtc
tcagaaactc
   1741 ccctgggggt ttcacctggg cctggagga attcagctca gcttcttcct
aggtccaagc
   1801 ccccacacc tttccccaa ccacagagaa caagagttg ttctgttctg
ggggacagag
   1861 aaggcgcttc ccaactrcat actggcagga gggtgaggag gttcactgag
ccccccagat
   1921 ctcccactgc ggggagacag aagcctggac tctgcccac gctgtggccc
tggagggtac
   1981 cggtttgtca gttcttggtg ctctgtgttc ccagaggcag ggggaggttg
aagaaggaa
   2041 cctggatga gggtgctgg gtataagcag agagggatgg gttcctgctc
caagggaccc
   2101 tttgccttcc ttcrgccctt cctaggccc aggcctgggt tttgtacttcc
accttccacca
   2161 catctgccag accttaataa aggccccac ttctcccaaa aaaaaaaaa aa
```

NM_006494 (ERF) SEQ ID NO:42

```
      1 tctgagaggc gaggccgggt gaggcggcga gggcggcccg acggcgcgg gacgggacgg
     61 ggcagcgagg gcgccgggag ccgggccccg gaatcgggc gcttcgcccc
ggcccccca
    121 gcatgaagac ccggccggac acagggtttg cctcccgga ttgggcctac
aagccagagt
    181 cgtccctgg ctcaaggcag atccagctgt ggcactttat cctgagctg
ctgcggaagg
    241 aggagtacca gggcgtcatt gcctggcagg gggactacgg ggaattcgtc
atcaaagacc
    301 ctgatgaggt ggccggctg tggggcgttc gcaagtgcaa gccccagatg
aattacgaca
    361 agctgagccg ggccctgcgc tattactata tacaagcgcat tctgcacaag
accaaggga
    421 aacggttcac ctacaagttc aatttcaaca actggtgct ggtcaattac
ccattcattg
    481 atgtggggtt ggcgggggt gcagtgccc agagtgccc gccagtgccg
tcggggggta
    541 gccacttccg cttccctccc tcaacgccct ccgaggtgct gtccccacc
ggggacccc
```

Figure 9 (Cont.)

```
 601 gctcaccacc agcctgctct tcatcttcat cttccctctt ctgggtgtg
gtggcccgcc
 661 gcctgggccg aggctcagtc agtgactgta gtgatggcac gtcagagctg
gaggaaccgc
 721 tgggagagga tccccgcgcc cgaccaccg gccctcggga tctgggtgcc
ttccgagggc
 781 cccgctggc cggctgccc catgacctg gtgtcttccg agtctatccc
cggctcggg
 841 gtggccctga accctcagc cccttccctg tgtcgctct ggcggtcct
ggatccctgc
 901 tgccctca gctctcccg gctctgccca tgacgccac ccacctggcc
tacactccct
 961 cgcccacgct gagcccgatg tacccagtg gtgcggggg gcccagcggc
tcaggggag
1021 gctcccactt ctccttcagc cctgaggaca tgaaacggta cctgcaggcc
cacacccaaa
1081 gcgtctacaa ctaccacctc agccccgcg ccttcctgca ctaccctggg
ctggtggtgc
1141 cccagcccca gcgccctgac aagtgcccgc tgcagccat ggcaccgag
accccaccgg
1201 tccctcctc ggcctgtca tctcttctt ctctcctc cccattcaag
tttaagctcc
1261 agcggccc actggacgc cggcagcggg cagctgggga gaaggccgta
gccgctgctg
1321 acaagagcgg tggcagtgca ggcgggctgg ctgaggggc agggcgcta
gcccaccgc
1381 cccgccacc acagatcaag gtggagccca tctcggaagg cgagtcggag
gaggtagagg
1441 tgactgacat cagtgatgag gatgaggaag acggggaggt gttcaagacg
cccgtgccc
1501 cacctgcacc ccctaagcct gagcccggcg aggcacccgg ggcatcccag
tgcatgcccc
1561 tcaagctacg ctttaagcgg cgctggagtg aagactgtcg cctcgaaggg
ggtggggcc
1621 ccgcggggg cttgaggat gagggtgagg acaagaaggt gcgtgggggag
gggcctgggg
1681 aggctggggg gcccctcacc ccaaggcggg tgagctctga cctccagcat
gccacggccc
1741 agctctccct ggagcacgga gactcctgag ggctgtggc aggggacctg
tgtgccccgc
1801 accccccatg cttctcttgc tgccttaagc ccctatgcc ctggaggtga
gggcagctct
1861 cttgtctctt ccctgcctcc tcccttttcc ctcccacat tttgtataaa
actttaattt
1921 cttttttta aaatggtgg gggtgggtgg gtgcccaggg ctagggcta
ttcctgtct
1981 ctgtgggttt ctaagctctg ggcaaattgg tggtaggggg agggaggggg
aagttaaggg
2041 ggtcacctcc attctgggga attatattt gaattgaggc tttggcctta
acacccagga
2101 actttctat tacaatgct taggaagtaa agcctgtct ccctccctgt
tctctgcctc
2161 tgtaccccc ctgacccacc cgctctgccc cactccagc cctcctcagc
cccagccctg
```

Figure 9 (Cont.)

```
   2221 cctgcctgc cctccaggg ggccatgagt gcctaggttt ctcatcccc
acaaggtcac
   2281 agcaggggag ggaggaaca ttttataatg aaccaaaaat tccatgtgtt
gggggtggg
   2341 ggacggagga gggtgagggg tgccgccat gggcacaaa tctctacaag
tgcctgctat
   2401 ccctctccca ctcccaccc cagcaccggt ccaaccctt catcccagc
tgctcctagg
   2461 actgcccat gggcaggag gtggggat gggaggggg tgcctgaaa
caaactgga
   2521 agccccctct gcctcccagc tggggcctct gggtgggt ggggctgt
ggtcaagcct
   2581 cattctgcat tggggactga gggtggggg agtagagggg ccgctggaga
atgtattcaa
   2641 aacaataaac tttggacctt tggaaaa

NM_083120 (P0.1) SEQ ID NO:43

1 aaaatcagga acttgtgctg gcctgcaat gtcaagggag ggggctcacc cagggctcct
  61 gtagctcagg gggcaggcct gagcctgca ccgcccac gaccgtccag
ccctgacgg
 121 gcaccccatc ctgagggt ctgcattggc cccaccgag gcagggatc
tgaccgactc
 181 ggagcccggc tggatgttac aggcgtgcaa aatggaaggg tttccctcg
tccccastcc
 241 atcagaagac ctggtgcct atgacacgga tctataccaa cgccaaacgc
acgagtatta
 301 ccctatctc agcagtgatg gggagagcca tagcgaccat tactgggact
tcccacccca
 361 ccacgtgcac agcgagttcg agagcttcgc cgagaacaac ttcacggagc
tcagagcgt
 421 gcagccccg cagctgcaga agctctaccg ccacatggag ctggagcaga
tgcacgtcct
 481 cgataccccc atggtgccac cccatccag tcttggccac caggtctct
acctgccccg
 541 gatgtgcctc cagtacccat ccctgtccca agcccagcc agctcagatg
aggaggagg
 601 cgagcggcag agcccccac tggaggtgtc tgacggcgag gggatggcc
tggagccgg
 661 gcctgggctc ctgcctgggg agacaggcag caagaagaag atcgcctgt
accagttcct
 721 gttggactg ctccgcagcg gcgacatgaa ggacagcatc tggtgggtgg
acaaggacaa
 781 gggcacctc cagttctgt ccagcacaa ggagcgctg gcgcaccgct
ggggcatcca
 841 gaaggcaac cgcaagaaga tgacctacca gaagatggcg cgcgcgctgc
gcaactacgg
 901 caagacgggc gaggtcaaga aggtgaagaa gaagctcacc tacagttca
gggcgaagt
 961 gctgggcgc gggggctgg ccgagcggcg ccacccgcc cactgagccc
gcagccccg
1021 ccggcccga caggcctccc cgctggccat agcattaagc cctcgccgg
ccggacaca
```

Figure 9 (Cont.)

```
     1081 gggaggacgc tcccggggcc cagaggcagg actgtggcgg gcgggctcc
gtcacccgcc
     1141 cctccccca ctccaggccc cctccacatc ccgcttcgcc tccctccagg
acccacccc
     1201 ggctcccgac gccagtgggg cgtcagccc acggcaacc ttgcagagga
cgacccgggg
     1261 tactgccttg ggagtctcaa gtccgtatgt aaatcagatc tcccctctca
ccctcccac
     1321 ccattaacct cctcccaaaa aacaagtaaa gttattctca atcc NM_001973 (ELK4, transcript variant a, mRNA) SEQ ID NO:44

1 tttcttgtta aacaaacacc taatttattt cttggaggtt ttgttcagct gtcctaattt
      61 atgacttac attccttctg gtgctaaact gctcaagtag cctcttgtat
caagtgtgac
     121 ctgattcctt aagaattta cttaatgaga acctctaagc tagaaacct
tgctaggtgt
     181 ttcatgcacc ttattttctt taatcattac aacaactca agattgggtt
ctctccacct
     241 tataaatgat gactgtttta gagaggttaa ggttgcttaa aattggtgag
ttagtgaggg
     301 gtagagccac gaatggattt ctggtcgctg cctccatcgt cagggcaagc
ttttcccacg
     361 actccagcgc ttccattgt cagtcccag gctagaaagc cacagtgcta
attagtatt
     421 tatcaagcgt ttgtagtgtc ctgggatctg gcacttcgat gagaaagctg
tgacggcccc
     481 aacttctaac agcgagtggt aagaggacg agggacacag gagggaggag
actctcccca
     541 aagcttagca ccaacagaag tggtcccccg caggttgctc tgcgagcgcc
acctcttccc
     601 tccaaccgag gagaaagtgg cgcgcctttg aggagtccga ggtcccggcc
caggcggcag
     661 cttgggtcct ggcgggttcc ggacgggcgc ctcagggacc tggaagcaac
cggaccgaac
     721 gcgacggaga gcggcgagac gactccagga ggcgccgag ctacatcccc
cggccacacc
     781 aaaccgggt ttgctggcag acgggctca cgacaccct taggtcgca
gcccctcccc
     841 cggaagtgac gtgtagcgac tacggcgtct ggagggacc caggagcagt
cggggggttt
     901 gagagtggcg gcggccgcgg agggctggc aggccccgcc gctgcaagga
acgcccgaa
     961 cgcgcgcgcc cggcgtgtag cggcccaag accgcgcg ccgctgccgc
gtgcggggc
    1021 ggggaggcg gggcgccagg agccgcggcg cgggagatg cgggcggctg
cgggcacccg
    1081 gcgggctcgg cttggccgcc gcggccttct acggctccga cgcggggtc
gcgcggcgtg
    1141 ccggccgtc ctcgagtttc cagcgtgagg aggaggctga gggcggagag
gcgcatcgtg
    1201 ttcgaggcgg agaccgaggg ggagcccgc gcgcggcgtc gtcattgct
atggacagtg
```

Figure 9 (Cont.)

```
1261 ctatcaccct gtggcagttc cttcttcagc tcctgcagaa gcctcagaac
aagcacatga
1321 tctgttggac ctctaatgat gggcagttta agcttttgca ggcagaagag
gtggctcgtc
1381 tctggggat tcgcagaac aagcctacca tgaattatga caaactcagc
cgagccctca
1441 gatactatta tgtaaagaat atcatcaaaa aagtgaatgg tcagaagttt
gtgtacaagt
1501 ttgtctctta tccagagatt tgaacatgg atccaatgac agtgggcagg
actgagggtg
1561 actgtgaaag tttaaacttc agtgaagtca gcagcagttc caagatgtg
gagaatggag
1621 ggaaagataa accacctcag cctggtgcca agacctctag ccgcaatgac
tacatacact
1681 ctggcttata ttcttcattt actctcaact cttgaactc ctccaatgta
aagcttttca
1741 aattgataaa gactgagaat ccagccgaga aactggcaga gaaaaaatct
cctcaggagc
1801 ccacaccatc tgtcatcaaa tttgtcacga cacttccaa aaagccaccg
gttgaactg
1861 ttgctgccac catttcaatt ggcccaagta tttctccatc ttcagaagaa
actatccaag
1921 ctttggagac atggttttcc ccaaaactgc cttccctgga agcccaacc
tctgcctcta
1981 acgtaatgac tgcttttgcc accacaccac ccatttcgtc catcccct
tcgcaggaac
2041 ctcccagaac acctcacca ccactgagtt ctcaccaga catcgacaca
gacattgatt
2101 cagtggcttc tcagccaatg gaacttccag agaatttgtc actggagcct
aaagaccagg
2161 attcagtctt gctagaaaag gacaaagtaa ataattcatc aagatccaag
aaacccaaag
2221 ggttagaact ggcaccacc cttgtgatca cgagcagtga accaagccca
ctgggaatac
2281 tgagcccatc tctccctaca gcttctctta caccagcatt ttttcacag
acacccatca
2341 aactgactcc aagccccttg ctatccagta tccacttctg gagtactctc
agtcctgttg
2401 ctccctaag tccagccaga ctgcaaggtg ctaacacact tttccagttt
acttctgtac
2461 tgaacagtca tgggccattc actctgtctg ggctgaatgg acttccacc
ccggcccat
2521 tttcccccaga cctacagaag acataaccta tgcacttgtg gaatgagaga
accgaggaac
2581 gaagaaacag acattcaaca tgattgcatt tgaagtgagc aattgatagt
tctacaatgc
2641 tgataataga ctattgtgat ttttgccatt ccccattgaa aacatctttt
taggattctc
2701 tttgaatagg actcaagttg gactatatgt ataaaaatgc cttaattgga
gtctaaactc
2761 cacctcccta tgtctttttcc tttatttt cattcctcc ttcctttttct
tttctccttt
2821 aaaatatttt tgagcttagt gctgaagaag ttttggtgg gcttagtga
ctgtgcttg
```

Figure 9 (Cont.)

```
2881 caaaagcaat taagaacaaa gttactcctt ctggctattg ggaccttttg
gccaggaaaa
2941 attatgctta gaatctatta tttaaagaaa tatttgtgaa atgaaaaaaa
aaaaaaaaa
3001 aaaaaaaaaa aaaaaaaaaa aaaaaaaaaa aaaa
```

NM_021795 (ELK4, transcript variant b, mRNA) SEQ ID NO:45

```
   1 tttcttgtta aacaaaaacc taattattc cttggaggtt ttgttcagct gtcctaattt
  61 atgacttttac attccttctg gtgctaaact gctcaagtag cctcttgtat
caagtgtgac
 121 ctgattcctt aagaatttta cttaaagaga acctctaagc tagaaactct
tgctaggtgt
 181 ttcagcacc ttattttctt taatcattac aacaactcta agattgggtt
ctctccacct
 241 tataaatgat gactgcttta gagaggtaaa ggtgcttaa aattggtgag
tagtgaggg
 301 gtagagccac gaatggattt ctggtcgctg cctccatcgt caggggcaagc
ttttcccacg
 361 actccagcgc ttccattgt cagtcccag gctagaaagc cacagtgcta
attagtatt
 421 tatcaagcgt ttgtagtgtc ctgggatctg gcacttcgat gagaaagctg
tgaaggcccc
 481 aacttctcaac agcgagtggt aaggaggacg agggacacag gaggggaggag
actctcccca
 541 aagcttagca ccaacagaag tggtccccg caggttgctc ttgcgagcgcc
acctcttccc
 601 tccaccgag gagaaagtgg cgcgcctttg aggagtccga ggtcccggcc
caggcggcag
 661 cttgggtcct gcgggttcc ggacgggcgc ctcagggacc tggaagcaac
cgcaccgaac
 721 gcgacggaga gcggcgagac gactccagga ggcgcccgag ctacatcccc
cggccacacc
 781 aaaccgggt ttgctggcag acgcggctca cgacacccct tagggtcgca
gcccctcccc
 841 cggaagtgac gtgtagcgac tacggcgtct ggagggacc caggagcagt
cgggggtttt
 901 gagagtggcg gcgggccgcgg aggcctggc aggcccgcc gctgcaagga
accctccgaa
 961 agcgcgccc cggcgtgtag cggccccaag accggcgcg ccgctgccgc
gtcgagggc
1021 ggggaggcg gggccaggg agccgcggcg gcggagatg cgggccggctg
cgggcacccg
1081 gcgggctgg cttgccgcc gcgcctcct acggtccgc cgcagggtc
gcagcggctg
1141 ccgcgccgtc ctcgagtttc cagcgtgagg aggagctga gggcggagag
gggcatcgtg
1201 ttcgaggcgg agaccgaggg ggagcccgc gcgcggcgtc gccattgct
atggacagtg
```

Figure 9 (Cont.)

```
1261 ctatcacct gtggcagttc cttcttcagc tcctgcagaa gcctcagaac
aagcacatga
1321 tctgttggac ctctaatgat gggcagttta agcttttgca ggcagaagag
gtggctcgtc
1381 tctggggat tcgcaagaac aagcctaaca tgaattatga caaactcagc
cgagccctca
1441 gatactatta tgtaaagaat atcatcaaaa aagtgaatgg tcagaagttt
gtgtacaagt
1501 ttgtctctta tccagagatt ttgaacatgg atccaatgac agtgggcagg
attgagggtg
1561 acgtgaaag tttaaacttc agtgaagtca gcagcagttc caaagatgtg
gagaatggag
1621 ggaaagataa accacctcag cctggtgcca agacctctag ccgcaatgac
tacatacact
1681 ctggcttata ttcttcattt actctcaact ctttgaactc ctccaatgta
aagcttttca
1741 aattgataaa gactgagaat ccagccgaga aactggcaga gaaaaatct
cctcaggagc
1801 ccacaccatc tgtcatcaaa tttgtcacga cacttccaa aaagccacgg
gttgaacctg
1861 ttgctgcac catttcaatt ggcccaagta tttctccatc ttcagaagaa
actatccaag
1921 ctttggagac attggtttcc ccaaaactgc cttcctgga agccccaacc
tctgcctcta
1981 acgtaatgac tgcttttgcc accacaccac ccatttcgtc catacccct
ttgcaggaac
2041 ctccagaac accttcacca ccactgagtt ctcacccaga catcgacaca
gacattgatt
2101 cagtggcttc tcagccaatg gaacttccag agaatttgtc actggagcct
aaagaccagg
2161 attcagtctt gctagaaaag gacaaagtaa ataatccatc aagatccaag
aaacccaaag
2221 ggttagaact ggcacccacc cttgtgatca cgagcagtga tccaagccca
ctgggaatac
2261 tgagcccatc tctcctaca gcttctctta ccaccagcat tttttcacag
gtagcttgct
2341 cgctctttat ggtgtcacca ttgcttcat ttatttgcc ttttaagcaa
atccagaatt
2401 tatacactca agttgctt ctgttactta ggtttgtctt agaaaggtta
tgtgtgactg
2461 tcatgtgaaa gttaccccat ttctcatctt aattaggatt gctaaaatag
aaagtttgga
2521 gtattttctt aaaaaattca ttgttctaca agtaaataaa tattttgatt
tttctatttc
2581 ctcctaaaga aagtacaac actctctcgc tctctctcgg tcttataaaa
ctcgttggtg
2641 tcttataaaa caaacagtga taatctcaag ttagaaaaca gtaggtcctg
agaaccataa
2701 gaaaatgac tggtgtgatg ttgagtaaca agttggtaca gttactttag
ctatttatta
2761 actgctcat ctcaagaac attttagtag attttttcaca cacctcatta
ttaaaaaaaa
2821 acaaacatgc tggtgtcttg gttaccatt attcctctgt acctgaattc
aggtaggttt
```

Figure 9 (Cont.)

```
2881 ttctatttgg aaaagacttt ataaatgttg ggtaaaaag aggttgagca
ccagaatctc
2941 agaatttacc accaaagaac tcatccatgt aaccaaaaac cacttgtacc
cccaaaaact
3001 attgaataa aaatttaaaa aattttaaaa aaaaaaaaaa aaaaaaaaa
aaaaaaaaaa
3061 aaaaaaaaa aaaaaaa
```

NM_005240 (NETS(ETV3)) SEQ ID NO:46

```
   1 gggggggtg gatgaggagg agccggagac gccgcggagg agaccggacc gaagacggac
  61 cgtgccggga agagcaggcg ggtgaaaatg aaagccggct gtagcatcgt
ggaaaagcca
 121 gaaggaggtg gagggtatca gtttcctgac tgggcctaca aaacagagtc
atcccaggc
 181 tcccggcaga tccagctgtg gcacttcatc ctggagctgc tgcagaagga
agagttccgc
 241 catgtcatcg cctggcagca gggagagtac gggggaatttg tcatcaagga
tccagatgag
 301 gtggcccgcc tctgggccg caggaaatgc aaaccacaga tgaattatga
caagctgagc
 361 cgggccctca gatactatta caacaagagg atccttcata aacaaaagg
gaaaagattt
 421 acctataaat ttaacttcaa caagctggtg atgcccaact accattcat
caacattcgg
 481 tcaagtggta agatacaaac tctttttggta gggaattaat tttgaattga
aaagaatttt
 541 taaaaatcca aatctaagac atggcatgtt tagaagatt ttagaaacac
taaataatg
 601 tgatcctttg gattgcctca atgttcttac tcaagtcatc tcacttataa
gagaggtat
 661 aggctattca gtatcaagat agattctttt ggtttattg gttggttccc
ttttctgcat
 721 attgttgta atctcctaga tactattacg ctatcttgtt tggaatgat
gtttcatagg
 781 ttgtgatga tcttttacgtt caggactcag ttttaacacc cagcccagtg
gttcttcat
 841 agatgggaac ctgttctac aaacacttcc gattttcgt gaaactacca
agctctcct
 901 tatccagtga atatcatcaa aaccacagca tccttgatca gagaagggg
aggttcacat
 961 gttgcagtg aaaagcagtg tctttgatct gcaacagcaa atcctcagag
aaaaagattc
1021 tggggttact tgaccttctc tcctgttaag tgcagtaggg cttccctct
tgactttcct
1081 ggttatagct ttccatcaca gctcccaca ttctctcttg atgtgaaag
cagtctctca
1141 aaagactttg tgttgtgtg gtttttgtt tgtgattttt ttcttatgc
aaatcatact
1201 cctgcccaag aaaatacagt agttcccctt atgtgagcag tatatgttct
aagcccta
1261 gtagattcgc aaaccacaga tagtaccaaa ctccattcat atatatgatg
tttttcttc
```

Figure 9 (Cont.)

1321 ccttaacccc actcatatgt aactgtgata aagtttaatt tataaattag
gcaaagtaag
    1381 agattaatga caatactaaa atagaaaaat tataaaaaaa aaaaaaaaa
aaaaaaaaa
    1441 aaa

S72620 (ERS/P111) SEQ ID NO:47

1 cccactagtt acccacccca aactggatcc tacagccaag ctccaagtca atatagccaa
     61 cagagcagca gctacgggca gcagaatccg tatcagatcc tgggcccgac
cagcagtcgc
    121 ctagccaacc ctggaagcgg gcagtccag ctgtggcaat tcctcctgga
gctgctctcc
    181 gacagcgcca acgccagctg tatcacctgg gagggacca acgggagt

BC029743 (ESE2 (ELF5)) SEQ ID NO:48

1 cacaaggcta caggtgtctt tatttccact gcagctggt gctggagcg cctgccttct
     61 ctgccttga aagcctcctc tttggaccta gccaccgctg ccctcacggt
aatgttggac
    121 tcggtgacac acagcacctt cctgcctaat gcatccttct gcgatcccct
gatgtcgtgg
    181 actgatctgt tcagcaatga agagtactac cctgcctttg agcatcagac
agcctgtgac
    241 tcatactgga catcagtcca ccctgaatac tggactaagc gccatgtgtg
ggagtggctc
    301 cagttctgct gcgaccagta caagtggac accaattgca tctccttctg
caactttcaac
    361 atcagtggcc tgcagctgtg cagcatgaca caggaggagt tcgtcgaggc
agctggcctc
    421 tgggcgagt acctgtactt catcctcag aacatccgca cacaaggtta
ctccttttct
    481 aatgacgctg aagaagcaa ggccaccatc aaagactatg ctgattccaa
ctgcttgaaa
    541 acaagtggca tcaaagtca agctgtcac agtcatagta gaaccagcct
ccaaagttct
    601 catctatggg aatttgtacg agcctgctt ctatctcctg aagaaactg
tggcattctg
    661 gaagggaag atagggaaca aggaattttt cgggtggtta aacggaagc
cctggcaaag
    721 atgtggggac aaggaagaa aatgacaga atgacatatg aaaagttgag
cagagcctg
    781 agatactact ataaaacagg aattttggag cgggttgacc gaaggttagt
gtacaaattt
    841 ggaaaaaatg cacacgggtg gcaggaagac aagctatgat ctgctccagg
catcaagctc
    901 atttatgga tttctgtctt taaaacaat cagattgcaa tagacattcg
aaaggcttca
    961 tttcttctc tttttttt aacctgcaaa catgctgata aaattcctcc
acatctcaga
    1021 ttacatttgg attcagagtt gttgtctacg gagggtgaga gcagaaactc
ttaagaaatc

Figure 9 (Cont.)

```
     1081 ctttcttctc cctaagggga tgaggggatg atcttttgtg gtgtcttgat
caaactttat
     1141 ttcctagag ttgtggaatg acaacagccc atgccattga tgctgatcag
agaaaaacta
     1201 ttcaattctg ccattagaga cacatccaat gctcccatcc caaaggttca
aaagttttca
     1261 aataactgtg gcagctacc aaaggtgggg gaaagcaaga ttagtttgca
ggttatggta
     1321 ggagagggtg agatataaga catacatact ttagatttta aattattaaa
gtcaaaaatc
     1381 catagaaaag tatccctttt ttttttttt gagacgggt ctcactatgt
tgcccagggc
     1441 tggtcttgaa ctcctatgct caagtgatcc tcccaccctcg gctcccaaa
gtactgtgat
     1501 tacaagcgtg agccacggca cctggcaga aagtatctt aattaatgaa
agagctaagc
     1561 catcaagctg ggacttaatt ggatttaaca taggttcaca gaaagtttcc
taaccagagc
     1621 atcttttga ccactcagca aaacttccac agacatcctt ctggacttaa
acacttaaca
     1681 ttaaccacat tattaattgt tgctgagttt attccccctt ctaactgatg
gctggcatct
     1741 gatatgcaga gttagtcaac agacactggc atcaattaca aaatcactgc
tgtttctgtg
     1801 attcaagctg tcaacacaat aaaatcgaaa ttcattgatt ccatctctgg
tccagatgtt
     1861 aaagtttat aaaaccggaa atgcctaac aactctgtaa tggcaaatta
aattgtgtgt
     1921 cttttttgtt ttgtcttcct acccgatgtg tatccaagtg ctataacacg
tatttccctg
     1981 acaaaaatag tgacagtgaa ttcacactaa taaatgtca taggttaaag
tctgcacgga
     2041 cattttctca tcaatcactg gtaagtaagt tatcagtgac tgacagctag
gtggactgcc
     2101 cctaggactt ctgtttcacc agagcaggaa tcaagtggtg aggcactgaa
tcgctgtaca
     2161 ggctgaagac ctccttatta gagttgaact tcaaagtaac ttgtttaaa
aaatgtgaat
     2221 tactgtaaaa taatctattt tggattcatg tgttttccag gtggatatag
ttgtaaaca
     2281 atgtgaataa agtattaac atgtaaaaaa aaaaaaaa

NM_012153 (EHF3) SEQ ID NO:49

1 accogtggtg ccccatccct ataggagctg gtgagattgc agcctgctgc ctccctcca
  61 tcagccacag ctattggatt tcccaccag aatcttagg taaatgagat
catgattccg
 121 gaaggaggtg gtgtaatgaa tctcaacccc ggcaacaacc tccttcacca
gccgccagcc
 181 tggacagaca gctactccac gtgcaatgtt tccagtgggt tttttgaggg
ccagtggcat
 241 gaaattcatc ctcagtactg gaccaagtac caggtgggg agtggctaaa
gcacctccgg
```

Figure 9 (Cont.)

```
 301 gacaccaacc agctggatgc caattgtatc cctttccaag agttcgacat caaggcgag
 361 cacctctgca ggatgagttt gcaggagttc acccgggcgg caggacggc gggcagctc
 421 ctctacagca acttgcagca tctgaagtgg aacggccagt gcagtagtga cctgttccag
 481 tccacacaca atgtcattgt caagactgaa caaactgagc cttccatcat gaacacctgg
 541 aaagacgaga actatttata tgacaccaac tatggtagca cagtagattt gttggacagc
 601 aaaactttct gccgggctca gatctccatg acaaccacca gtcaccttcc tgttgcagag
 661 tcacctgata tgaaaaagga gcaagacccc cctgccaagt gccacaccaa aaagcacaac
 721 ccgagaggga ctcacttatg ggaattcatc cgcgacatcc tcttgaaccc agacaagaac
 781 ccaggattaa taaaatggga agaccgatct gaggcgtct tcaggttctt gaaatcagag
 841 gcagtggctc agctatgggg taaaaagaag aacaacagca gcatgaccta tgaaaagctc
 901 agccgagcta tgagatatta ctacaaaaga gaaattctgg agcgtgtgga tggacgaaga
 961 ctggtatata aatttgggaa gaatgcccga ggatggagag aaaatgaaaa ctgaagctgc
1021 caatactttg gacacaaacc aaaacacaca ccaaataatc agaaacaaag aactcctgga
1081 cgtaaatatt tcaaagacta cttttctctg atatttatgt accatgaggg gaacaagaaa
1141 ctacttctaa cgggaagaag aaacactaca gtcgattaaa aaaattattt tgttacttcg
1201 aagtatgtcc tatatgggga aaaaacgtac acagttttct gtgaaatatg atgctgtatg
1261 tggttgtgat ttttttttcac ctctattgtg aattcttttt cactgcaaga gtaacaggat
1321 ttgtagcctt gtgcttcttg ctaagagaaa gaaaaacaaa atcagagggc attaaatgtt
1381 ttgtatgtga catgatttag aaaaaggtga tgcatcctcc tcacataagc atccatatgg
1441 cttcgtcaag ggaggtgaac attgttgctg agttaaattc cagggtctca gatggttagg
1501 acaaagtgga tgatgccgg gaagtttaac ctgagcctta ggatccaatg agtggagaat
1561 ggggacttcc aaaacccaag gttggctata atctctgcat aaccacatga cttggaatgc
1621 ttaaatcagc aagaagaata atggtggggt ctttatactc attcaggaat ggtttatctg
1681 atgccagggc tgtcttcctt tctcccttt ggatggtggg tgaaatactt taattgccct
1741 gtctgctcac ttctagctat ttaagagaga acccagcttg gttcttttt gtccaagtg
1801 cttaaaaata agttggaaaa aggagacggt ggtgtggaaa tggctgaaga gttgctctt
1861 gtatccctat agtccaaggt ttctcaatct gcacaattga cattttggc cggagtgttc
```

Figure 9 (Cont.)

```
1921 tttgtggtga gggctttcct gtgcattgta agatgttcag cagtatccac
tcatgtctc
1981 taaccacttg acaccagaaa cccccoagct gtgataacgc aaaatgtctc
tagacatcac
2041 caaatgttcc ctggggtgg caaatttgcc cttgattgag aaccaccagt
ttagctagtc
2101 aatatgagga tggtggttta ttctcagaag aaaaagatat gtaaggtctt
ttagctcctt
2161 agagtgaagc aaaagcaaga cttcaacctc aacctatctt tatgttttaa
atgttaggga
2221 caataagttg aaatagctag aggagcttct tttcagaacc ccagatgaga
gccaatgtca
2281 gataaagtaa gcatagtaat gtagcaggaa ctacaataga agacattttc
actggaatta
2341 caaagcagaa ttaaaattat attgtagaag gaaacaccaa gaaagaatt
tccagggaaa
2401 atcctctttg caggtattaa ttcttataat ttttttgtctt tggattatc
tgttttactgt
2461 ctcatctgaa ctgatcccag gtgaacggtt tattgcctag atttgtactc
agaggaattt
2521 tttttgtttt gttttgtctt ttaagaaagg aagaaagga tgaaaaaaat
aaacagaaaa
2581 ctcagctcag gcacaattgt caccaaggag ttaaaagctt cttcttcaat
agaggaattg
2641 ttctgggggt cctggagact taccattgag ccatgcaatc tgggaagcac
aggaataagt
2701 agacactttg aaaatggatt tgaatgttct catcccttt gcagcttttc
ttttggctc
2761 tctcatgtcc ttggcttgct cctctattct acctctcttt ctccagcaat
aatatgcaaa
2821 tgaagacatg tatccataag aaggagtgct cttcatcaac taatagagca
cctaccacag
2881 tgtcatacct ggtagaggtg agcaattcat attcaaaggt tgcaaagtgt
ttgtaatata
2941 ttcatgaggc tggaagtaag aagaattaaa aatttgtcct aattacaatg
agaaccattc
3001 taggtagtga tcttggagca cacatgaata actttctgaa ggtgcaacca
aatccatttt
3061 tattttctgcc tggcttggtc acctctgtaa aggtttaact tagtgttgtc
aagtaacagt
3121 tactgaaaga gctgagaaaa agaacaatga acagcaacga tcttgactgt
gcaactcaga
3181 cattctgca gaaaagacat atgttgcttt acaagaaggc caaagaacta
tgggccttc
3241 ccagcatttg actgttcatt gcatagaatg aattaaatat ccagttactt
gaatgggtat
3301 aacgcatgaa tatttgtgtg tctgtgtgtg tgtctgagtt gtgtgatttt
attaggggca
3361 tctgccaatt ctctcaactgt ggttccttct ctgactttgc ctgttcatca
tctaaggagg
3421 ctagatcctt cgctgacttc accattccta aaacctgtaa gtttctcact
tcttccaaat
3481 tggctttggc tctttctgca accttccat tcaagagcaa tctttgctaa
ggagtaagtg
```

Figure 9 (Cont.)

```
3541 aatgtgaaga gtaccaacta caacaattct acagataatt agtggattgt gctgtttgtt
3601 gagagtgaag gtttctt

AP071538 (PDSP) SEQ ID NO:50

1 gtctgacttc ctcccagcac attcctgcac tctgccgtgt ccacactgcc ccacagaccc
  61 agtcctccaa gcctgctgcc agctccctgc aagccctca ggttgggcct tgccacggtg
 121 ccagcaggca gccctgggct gtgggtaggg gactccctac aggcacgcag ccctgagacc
 181 tcagagggcc acccttgag ggtgccagg ccccagtgg ccaacctgag tgctgcctct
 241 gccaccagcc atgctggccc ctggttccgc tggccccca gatgcctggc tgagacacgc
 301 cagtggcctc agctgcccac acctcttccc ggccctgaa gttggcactg cagcagacag
 361 ctccctgggc accaggcagc taacagacac agccgccagc ccaaacagca gcggcatggg
 421 cagcgccagc ccgggtctga gcagcgtatc cccagccac ctcctgctgc ccccgacac
 481 ggtgtcgcgg acaggcttgg agaaggcggc agcggggggca gtgggtctcg agagacggga
 541 ctggagtccc agtccacccg ccacgcccga gcagggcctg tccgccttct acctctccta
 601 ctttgacatg ctgtaccctg aggacagcag ctgggcagcc aaggcccctg gggccagcag
 661 tcgggaggag ccacctgagg agcctgagca gtgcccggtc attgacagcc aagcccagc
 721 gggcagcctg gacttggtgc caggcgggct gaccttggag gagcactcgc tggagcaggt
 781 gcagtccatg gtggtgggcg aagtgctcaa ggacatcgag acggcctgca agctgctcaa
 841 catcaccgca gatcccatgg actggagccc cagcaatgtg cagaagtggc tcctgtggac
 901 agagcaccaa tacggctgc ccccatggg caaggccttc caggagctgg cgggcaagga
 961 gctgtgcgcc atgtcggagg agcagttccg ccagcgctcg ccctggggtg gggatgtgct
1021 gcaagcccac ctggacatct ggaagtcagc ggcctggatg aaagagcgga cttcacctgg
1081 ggcgattcac tactgtgcct cgaccagtga ggagagctgg accgacagcg aggtggactc
1141 atcatgctcc gggcagccca tccacctgtg gcagttcctc aaggagttgc cactcaagcc
1201 ccacagctat ggccgcttca ttaggtggct caacaaggag aagggcatct tcaaaattga
1261 ggactcagcc caggtggccc ggctgtgggg catccgcaag aaccgtcccg ccatgaacta
1321 cgacaagctg agccgctcca tccgccagta ttacaagaag ggcatcatcc ggaagccaga
```

Figure 9 (Cont.)

1381 catctcccag cgcctcgtct accagttcgt gcaccccatc tgagtgcctg
gcccagggcc
    1441 tgaaacccgc cctcaggggc ctctctccrg cctgcctgc ctcagccagg
cctgagatg
    1501 ggggaaaacg ggcagtctgc tctgctgctc tgaccttcca gagcccaagg
tcagggaggg
    1561 gcaaccaact gcccagggg gatatggtc ctctgggcc ttcgggacca
tgggcaggg
    1621 gtgcttcctc ctcaggccca gctgctcccc tggaggacag agggagacag
ggctgctcc
    1681 caacacctgc ctctgacccc agcatttcca gagcagagcc tacagaaggg
cagtgactcg
    1741 acaaaggcca caggcagtcc aggcctctct ctgctccatc ccctgcctc
ccattctgca
    1801 ccacacctgg catggtcag ggagacatct gcaccctga gttgggcagc
caggagtgcc
    1861 cccgggaatg gataataaag atactagaga actg

NM_005230 (NET (ELK3; SAP3) SEQ ID NO:5)

1 gggcggaaaa gctgtttac acagactgca cacgcctgg ggaataagc agtaaggaa
    61 gtgagcggc tcggcctgac tgctccaact ttctgctcta acacacca
gaggggaaaa
    121 aaaaagagga gcgagagaaa gaaaaaagg gggaaaatc aggatctcat
tacaagagcc
    181 acagaccgtc tgcagacgcc tgtcagcatg gaaagtcggg ggctttcgcc
cgggtcctcc
    241 tagaaattcc cccgaagaa gactcccca catctgggta tggagagtgc
aatcacgctg
    301 tggcagttcc tgttgcagtt gctgctggat cagaaacatg agcatttgat
ctgctggacc
    361 tcgaacgatg gtgaattcaa gctcctcaaa gcagaagaag tggccaagct
gtgggactc
    421 cgaaaaaaca aaacaaatat gaactatgat aagctgagca gagccctgcg
atactattat
    481 gacaagaaca tcatcaagaa ggtgatcggg cagaagtttg tgtacaagtt
tgtctcttc
    541 ccggagatcc tgaagatgga tcctcacgcg gtggagatca gccgggagag
ccttctgctg
    601 caggacagcg actgcaaggc gtctccggag ggcgcgagg cccacaaaca
cggcctggcc
    661 gccctcagaa gcacgagccg caacgaatac atcactcag gcctgtactc
gtccttcacc
    721 attaattccc tgcagaaccc accagacgcc ttcaaggcca tcagacggga
gaagctggag
    781 gagccgcccg aagacagccc cccgtggaa gaagtcagga ctgtgatcag
gtttgtgacc
    841 aataaaaccg acaagcacgt caccaggccg gtggtgtccc tgccttccac
gtcagaggct
    901 gcggcgggt ccgccttcct ggcctcgtcc gtctcggcca agatctcctc
tttaatgttg
    961 ccaaacgctg ccagtattac atccgcctca ccttctcat ctcggtcccc
gtccctgtcc

Figure 9 (Cont.)

```
   1021 cccaactcac ccctccttc tgaacacaga agcctcttcc tggaggccgc
ctgccatgac
   1081 tccgattccc tggagcccTT gaacctgtca tcgggctcca agaccaagtc
tccatctctt
   1141 cccccaaagg ccaaaaaacc caaggcttg gaaatctaag cgccccgct
ggtgctctcc
   1201 ggcaccgaca tcggctccat cgccctcaac agccagccc tccctcggg
atccctcacc
   1261 ccagccttct tcaccgcaca gacaccaaat ggattgcttc tgactccgag
tccactgctc
   1321 tccagcatac atttctggag cagccttagt ccagttgctc cgctgagtcc
tgccaggccg
   1381 caaggccaa gcacgctgtt ccagttcccc acactgctta atggccacat
gccagtgcca
   1441 atcccagtc tggacagagc tgcttctcca gtactgcttt cttcaaactc
acagaaatcc
   1501 tgatgacgtc tggccacaat taaggactca ttaactgatg aaacaaattt
gtcccacgg
   1561 gctagttac ccgtgtcgtg agaaggacat tgcgaaactc ttgtaattt
ggtttgcact
   1621 tttcataaca tggaaagtct agatttatgt tagcatttta aaaacgttt
ttgatatatt
   1681 caagtatata tgaaaatctg tttggcatta agtgaatttt aatgttttg
tctttatatc
   1741 cttttagctc ttaagtgttg aacactgttg acagtgaaga acttttctta
atggttttca
   1801 gtataactaa taaggatgtg aagctttttt ctctttagtt ctgagtatgc
taaactgtgt
   1861 gcttatatag actaaaacca gttgtgcctt cctttgcatt taatgtaaat
gaatgattta
   1921 tatattttt agtattaaga ggaaatgttt gaaagatgaa aattagtatc
aaacagtctt
   1981 ctagtagaat ttcatatttt ttcaccagtg ggcaatatga aagcatatat
cacgttttgt
   2041 ttcacttca attgaataag aattgcttta gaacctcttt tgaactgaaa
ttcagtaaat
   2101 gtccaagtaa tgttttttata ataaactaag ccatatttag acaataaaca
tcgaaaaaaa
   2161 aaaaaaaaa aaaaaaaaa
```

RM_006874 (NRBF; KLF0) transcript variant 2 SEQ ID NO:50

```
  1 gttgccagct gcgggcgccg ccacagccac agccgccgcc gccgccgcg
ccgcccctgc
   61 cctgccgcc cctgccctgc ccgttaggtg gtggggttcc tcagccggc
ggcgggaggc
  121 gggccggct cggcttcctg tccaggacg cgcaaggatc cgggcgtcgg
agtgtgtcg
  181 agtgcgtgag tgtgtgtcgg tgcacggcg tgtgtctcg gccgcgggtt
ccgcctcctc
  241 ccctgccgcc gctgctcacg gtgtaagtca atgtgaagca gcagctccag
cccgggata
  301 aacatggcga cgtctctgca tgaggaccc acgaaccagc tggatctgct
catccgggcc
```

Figure 9 (Cont.)

```
 361 gtggaagcat cagttcacag cagtaatgca cactgtacag ataagacaat
tgaagctgct
 421 gaagccctgc ttcatsatgga atctcctacc tgcttgaggg attcaagaag
tcctgtggaa
 481 gtgtttgttc ctccttgtgt atcaactcca gaattcatcc atgctgctat
gaggccagat
 541 gtcattacag aaactgtagt ggagtgtca actgaagagt ctgaaccat
ggatccttct
 601 cctattccaa catcaccaga tagccatgaa ccaatgaaaa agaaaaaagt
tggccgtaaa
 661 ccaagaccc agcaatcacc aatttccaat gggtctcctg agttaggtat
aaagaagaaa
 721 ccaagagaag gaaaaggaaa cacaacctat ttgtgggagt ttctttaga
tctacttcaa
 781 gataaaaata cttgtccag gtatattaaa tggactcaga gagaaaaagg
catattcaag
 841 ctgtggatt caaaggctgt ctctaagctt tggggaaagc ataagaacaa
accagacatg
 901 aactatgaaa ccatggacg agctttgaga tactactacc aaagggaat
tcttgcaaag
 961 gttgaaggac agaggcttgt atatcagttc aaggatatgc cgaaaaacat
agtggtcata
1021 gatgatgaca aaagtgaaac ctgtaatgaa gatttagcag gaactactga
tgaaaaatca
1081 ttagaacgag tgtcactgtc tgcagaaagt ctcctgaaag cagcatcctc
tgttcgcagt
1141 ggaaaaaatt catcccctat aaactgctcc agagcagaga agggtgtagc
cagagttgtg
1201 aatatcactt cccctggca cgatgcttca tccaggtctc ctactaccac
tgcatctgtg
1261 tcagcaacag cagtccaag gacagttcgt gtggcaatgc aggtacctgt
tgtaatgaca
1321 tcattgggtc agaaaattc aactgtggca gtcagtcag ttaatgcagg
tgcaccatta
1381 ataaccagca ctagtccaac aacagcgacc tctccaaagg tagtcattca
gcaatccct
1441 actgtgatgc cagcttctac tgaaaatgga gacaaaatca ccatgcagcc
tgccaaaatt
1501 attaccatcc cagtacaca gttgcacag tgtcaactgc agacaaagtc
aaatctgact
1561 ggatcaggaa gcattaacat tgttggaacc ccattggtg tgagcact
taccctgtt
1621 tcaatagccc atggtacacc tgtaatgaga ctatcaatgc ctactcagca
ggcatctggc
1681 cagactcctc ctcgagttat cagtcagtc ataaagggc cagagttaa
atggaagca
1741 gtggcaaaaa agcaagaaca tgatgtgaaa actttgcagc tagtagaaga
aaaaccagca
1801 gatggaaata agacagtgac ccagtagtg gttgtcagtg cgcttcagc
tattgcctt
1861 cctgtaacta tgaaaacaga aggactagtg acatgtgaga aataaaatag
cagctccacc
1921 atggacttca ggctgttagt ggcagtactg acatasacat ttgcaaggga
agtcatcaag
```

Figure 9 (Cont.)

```
    1981 aaaagtcaaa gaagacttta aaacattttt aatgcatata caaaaacaat
cagacttact
    2041 ggaaataaat tacctatccc atgtttcagt gggaaatgaa ctacatattg
agatgctgac
    2101 agaaactgc ctcttacagt aggaaacaac tgaacccatc aataagaaaa
aggatcgaaa
    2161 ggaccaagc agctcactac gatatcaagt tacactaaga cttggaacac
taacattctg
    2221 taagaggtta tatagtttc agtgggaggg gttgggatgg gtaatctcat
tgttacatat
    2281 agcaattttt gatgcatttt atatgcatac cagcaattat tactgtgttc
gcacagttct
    2341 cacttaactg gtgctatgtg aagactctgc taatataggt attttagaat
gtgaattgaa
    2401 gaatggatcc caaaaacttc agaaagagga tagcaaaaa agatctagtg
cgattttata
    2461 tatatatata tatatatata catacatata tatatatcat atagcttaag
ctgatttaaa
    2521 acaaggcct tagactaatt ttcgattttc tttcttgaaa taagctaatg
gcttgtttgt
    2581 gtaagcttt tttattaaaa gaaaaatttt aaaaatcttg tacctagcac
agtattgtta
    2641 tagaatatac atgtaacatt ttatatggta gtttaagtct gtcagtttct
taattgtgga
    2701 caaattaaca gttggctctg gccttttgct gtaacatgcc cgtgtcactc
acttagcctt
    2761 ggcatttgtg cagacatacc attttcagtt ctgctgtcac ttggaagttc
aggctcagca
    2821 tgaatttttg gtaggtagct ctaatacctg gagttttctt tgttttttttt
tcttttttttt
    2881 agttgaagtt tatgagggaa ataccagtgt tcagtttga actataatag
ttgtatatt
    2941 caacatttga agtatattct attttgttgt actctgttt caaagtgtat
tcaagtaggt
    3001 tttctgaaat atagaaatga aatttatctt ctgttttggt ctctggtgat
attttaaaca
    3061 atatttaaaa gtcagtatag aagtgttta gttaggaagt gataaaacat
ctctcttctc
    3121 cttcccaact actgcatgaa gaaattctac ttccattata ttaatatttg g NM_201999 (NERF; ELF2) transcript variant 1 SEQ ID NO:53

1 aaaatagtga aggatgctta gactacttaa catacaaact gtttctggt taatcatctt
   61 tagaagactg gattctgga tatctactcc actccatctc tattgacttt
taaaacatga
  121 taatgcaaac ctataacact ggcaaccatc agtgaacctt taatttcatt
gattaatagc
  181 gttgaagct tcctcaggga ataacaatga catcagcagt ggttgacagt
ggaggtacta
  241 ttttggagct ttccagcaat ggagtagaaa atcaagagga aagtgaaaag
gtttctgaat
  301 atccagcagt gattgtggag ccagttccaa gtgccagatt agagcaggc
tatgcagccc
```

Figure 9 (Cont.)

```
 361 aggttctggt ttatgatgat gagacttata tgatgcaaga tgtggcagaa
gaacaagaag
 421 ttgagaccga gaatgtggaa acagtggaag catcagttca cagcagtaat
gcacactgta
 481 cagataagac aattgaagct gctgaagccc tgcttcatat ggaatctcct
acctgcttga
 541 gggattcaag aagtcctgaa ttcatccatg ctgctatgag gccagatgtc
attacagaaa
 601 ctgagtgga ggtgcaact gaagagtctg aacccaggga tacctctcct
attccaacat
 661 caccagatag ccatgaacca atgaaaaaga aaaagttgg ccgtaaacca
aagacccagc
 721 aatcaccaat ttccaatggg tctcctgagt taggtataaa gaagaaacca
agagaaggaa
 781 aaggaaacac aacctatttg tgggagtttc ttttagatct acttcaagat
aaaaatactt
 841 gtcccaggta tattaaatgg actcagagag aaaaaggcat attcaagctg
gtggattcaa
 901 aggctgtctc taagctttgg ggaaagcata agaacaaacc agacatgaac
tatgaaacca
 961 tgggacgagc tttgagatac tactaccaaa ggggaattct tgcaaaggtt
gaaggacaga
1021 ggcttgtata tcagttcaag gatatgccga aaaacatagt ggtcatagat
gatgacaaaa
1081 gtgaaacctg taatgaagat ttagcaggaa ctactgatga aaaatcatta
gaacgagtgt
1141 cactgtctgc agaaagtctc ctgaaagcag catcctctgt tcgcagtgga
aaaaattcat
1201 ccctataaa ctgctccaga gcagagaagg gtgtagctag agttgtgaat
atcacttccc
1261 ctgggcacga tgcttcatcc aggtctccta ctaccactgc atctgtgtca
gcaacagcag
1321 ctccaaggac agttcgtgtg gcaatgcagg tacctgttgt aatgacatca
ttgggtcaga
1381 aaatttcaac tgtggcagtt cagtcagtta atgcaggtgc accattaata
accagcacta
1441 gtccaacaac agcgacctct ccaaaggtag tcattcagac aatccctact
gtgatgccag
1501 cttctactga aaatggagac aaaatcacca tgcagcctgc caaaattatt
accatcccag
1561 ctacacagct tgcacagtgt caactgcaga caaagtcaaa tctgactgga
tcaggaagca
1621 ttaacattgt tggaacccca ttggctgtga gagcacttac ccctgtttca
atagcccatg
1681 gtacacctgt aatgagacta tcaatgccta tcagcaggc atctggccag
actcctcctc
1741 gagttatcag tgcagtcata aaggggccag aggttaaatc ggaagcagtg
gcaaaaaagc
1801 aagaacatga tgtgaaaact ttgcagctag tagaagaaaa accagcagat
ggaaataaga
1861 cagtgaccca cgtagtggtt gtcagtgcgc cttcagctat tgccttcct
gtaactatga
1921 aaacagaagg actagtgaca tgtgagaaat aaaatagcag ctccaccatg
gacttcaggc
```

Figure 9 (Cont.)

```
      1981 tgttagtggc agtactgaca taaacatttg caagggaagt catcaagaaa
agtcaaagaa
      2041 gactttaaaa cattttaat gcatatacaa aaacaatcag acttactgga
aataaattac
      2101 ctatccatg tttcagtggg aaatgaacta catattgaga tgctgacaga
aaactgcctc
      2161 ttacagtagg aaacaactga accatcaat aagaaaagg atcgaaaggg
accaagcagc
      2221 tcactacgat atcaagttac actaagactt ggaacactaa cattctgtaa
gaggttatat
      2281 agttttcagt gggagggtt gggatgggta atctcattgt tacatatagc
aattttttgat
      2341 gcattttata tgcataccag caattattac tgtgttcgca cagttctcac
ttaactggtg
      2401 ctatgtgaag actctgctaa tataggtatt ttagaatgtg aattgaagaa
tggatccaa
      2461 aaacttcaga aagaggatag caaaaaaga tctagtgcga ttttatatat
atatatatat
      2521 atatatacat acatatatat atatcatata gcttaagctg atttaaaaca
aaggcttag
      2581 actaattttc gattttcttt cttgaaataa gctaatggct tgtttgtgta
aagcttttt
      2641 attaaagaa aaattttaaa aatcttgtac ctagcacagt attgttatag
aatatacatg
      2701 taacatttta tatggtagtt taagtctgtc agtttcttaa ttgtggacaa
attaacagtt
      2761 ggctctggcc tttgctgta acatgcctgt gtcactcact tagccttggc
atttgtgcag
      2821 acataccatt ttcagttctg ctgtcacttg gaagttcagg ctcagcatga
atttttggca
      2881 ggtagctcta atcctggag ttttcttgt tttttttct tttttttagt
tgaagtttat
      2941 gagggaaata ccagtgttca gttttgaact ataatagttt gtatattcaa
catttgaagt
      3001 atattctatt ttgttgtact cttgtttcaa agtgtattca agtaggtttt
ctgaaatata
      3061 gaaatgaaat ttatcttctg ttttggtctc tggtgatatt ttaaacaata
tttaaaagtc
      3121 agtatagaag tgttttagtt aggaagtgat aaaacatctc tcttctcctt
cccaactact
      3181 gcatgaagaa attctactc cattatatta atattrgg
```

NM_017521 (FEV) SEQ ID NO:54

```
   1 gcggcgagtg gagcgggagc cgactggaag aagggctcta gggagggggc tgtggctgct
      61 ggggtccgag gtgggccgg gtacaccagc cccatcactg tttgcagaga
gtcagggagg
     121 cggaaaagac acgcgctcta ggctcccatc agggcacatg gccgggccc
atccccgcg
     181 cgtctcccg gctgcgggc gcgggggct gcgggtgcg cttggctgtg
gcgcggcgcg
     241 ttggagactt tattgcgatg ggacgataag agggcggg gcgggtcct
ggggccgag
```

Figure 9 (Cont.)

```
301 ggggcagcgc tttaattaaa acggaaattg cggcccggg ccgcgcggg
gccggagggt
361 tccagcggc ccttagctg gaagcgttc tccaggaccc cccgcaacc
accgcaacgc
421 ccgggctgcc ccctccagcc aggcctgcc ggacccggcg ccgtcttctc
ctccttgtca
481 cccgcggtcg cttcggtggg ggatcggtgc cacccgagcgc aaagcctgcc
tcgccccct
541 tccccgtccc ccccatctcc cacccgcccag tccccggcg cgatgagaca
gagcgggcc
601 tccagcccc tgctgatcaa catgtacctg ccagatcccg tcggagacgg
tctcttcaag
661 gacgggaaga accccgagctg gggccgctg agcccgcgg ttcagaaagg
cagcggacag
721 atccagctgt ggcagtttct gctggagctg ctggctgacc gcgcgaacgc
cggctgcatc
781 gcgtggaagg gcggtcacgg cgagttcaag ctcacggacc cggacgaggt
ggcgcggcgg
841 tggggcgagc gcaagagcaa gccaacatg aactacgaca agctgagccg
cgcctgcgc
901 tactactacg acaagaacat catgagcaag gtgcatggca agcgctacgc
ctacgcttc
961 gacttccagg gctggagca ggcctgccag ccgcgcccg cgcacgctca
tgccgccgcc
1021 gcagctgctg ccgccgcgc ggccgccag gacggcgcgc tctacaagct
gccgccggc
1081 ctcgcccgc tgccttccc cggcctctcc aaatcaacc tcatggccgc
ctcggccggg
1141 gtgcgccg ccggcttctc ctactggccg ggccgggcc ccgccgccac
cgctgccgcc
1201 gccaccgccg agctctaccc cagtccagc ttgcagccc cgccccggcc
ctcggggcc
1261 gtgccgcag cctgcactt gggggccat taccactaga cgggcggtc
ggtgcctgc
1311 ggcctcgcc gcagcctag agtctgacc gatccaacg gcatcccggg
gagggccccgg
1381 gagctccgt caaccgtcct ctaatccaga gtttactcca cctgccgcac
ttagcagggg
1441 gacgggaccg aagctccctc aatccttgtc tggtactaga tttgctcctg
tcccacccg
1501 cagtccctg aggaggggga tgtgcgcct cttcactt tttctttcta
ggtctccagg
1561 tcccggagg gatttgtgga cctctcttgt ctcccacca ctccagtgca
tttccgctg
1621 gctcctagaa gccccattca atatcactac tctttaacga gtgccaaatc
tttttccact
1681 ttgctcttc cccaaggaac tgctcccacc tcagcacgtg gaggcctctc
acggtcctcc
1741 ttcctgggac ctgagcaggt ttggtgaaag ccacgtcct ccgtgacaca
cggcccctt
1801 cctcctgtcc ccaacctccc aggagaaaact cccggtgtgt ttctgccct
ttcagcccca
1861 ttaaagctcc tgagctctca aaaaaaaaaa aaaaaaaaaa a
```

Figure 10

NM_005656 mRNA (SEQ ID NO: 307)

```
   1 cgcgagctaa gcaggaggcg gaggcggagg cggagggcga ggggcgggga gcgccgcctg
  61 gagcgcggca ggtcatattg aacattccag atacctatca ttactcgatg ctgttgataa
 121 cagcaagatg gctttgaact cagggtcacc accagctatt ggaccttact atgaaaacca
 181 tggataccaa ccggaaaacc cctatcccgc acagcccact gtggtcccca ctgtctacga
 241 ggtgcatccg gctcagtact acccgtcccc cgtgcccagt acgccccga gggtcctgac
 301 gcaggcttcc aaccccgtcg tctgcacgca gcccaaatcc ccatccggga cagtgtgcac
 361 ctcaaagact aagaaagcac tgtgcatcac cttgaccctg ggaccttcc tcgtgggagc
 421 tgcgctggcc gctggcctac tctggaagtt catgggcagc aagtgctcca actctgggat
 481 agagtgcgac tcctcaggta cctgcatcaa cccctctaac tggtgtgatg gcgtgtcaca
 541 ctgccccggc ggggaggacg agaatcggtg tgttcgcctc tacggaccaa acttcatcct
 601 tcagatgtac tcatctcaga ggaagtcctg gcaccctgtg tgccaagacg actggaacga
 661 gaactacggg cgggcggcct gcagggacat gggctataag aataattttt actctagcca
 721 aggaatagtg gatgacagcg gatccaccag ctttatgaaa ctgaacacaa gtgccggcaa
 781 tgtcgatatc tataaaaaac tgtaccacag tgatgcctgt tcttcaaaag cagtggtttc
 841 tttacgctgt atagcctgcg gggtcaactt gaactcaagc cgccagagca ggatcgtggg
 901 cggtgagagc gcgctcccgg gggcctggcc ctgcaggtc agcctgcacg tccagaacgt
 961 ccacgtgtgc ggaggctcca tcatcacccc cgagtggatc gtgacagccg cccactgcgt
1021 ggaaaaacct cttaacaatc catggcattg gacggcattt gcggggattt tgagacaatc
1081 tttcatgttc tatggagccg ataccaagt agaaaaagtg atttctcatc caaattatga
1141 ctccaagacc aagaacaatg acattgcgct gatgaagctg cagaagcctc tgactttcaa
1201 cgacctagtg aaaccagtgt gtctgcccaa cccaggcatg atgctgcagc cagaacagct
1261 ctgctggatt tccgggtggg gggccaccga ggagaaaggg aagacctcag aagtgctgaa
1321 cgctgccaag gtgcttctca ttgagacaca gagatgcaac agcagatatg tctatgacaa
1381 cctgatcaca ccagccatga tctgtgccgg cttcctgcag ggaacgtcg attcttgcca
1441 gggtgacagt ggagggcctc tggtcacttc gaagaacaat atctggtggc tgatagggga
1501 tacaagctgg ggttctggct gtgccaaagc ttacagacca ggagtgtacg ggaatgtgat
```

Figure 10 (cont.)

```
    1561 ggtattcacg gactggattt atcgacaaat gagggcagac ggctaatcca
catggtcttc
    1621 gtccttgacg tcgttttaca agaaaacaat ggggctggtt ttgcttcccc
gtgcatgatt
    1681 tactcttaga gatgattcag aggtcacttc attttatta aacagtgaac
ttgtctggct
    1741 ttggcactct ctgccattct gtgcaggctg cagtggctcc cctgcccagc
ctgctctccc
    1801 taacccttg tccgcaaggg gtgatggccg gctggttgtg ggcactggcg
gtcaagtgtg
    1861 gaggagaggg gtggaggctg ccccattgag atcttcctgc tgagtccttt
ccaggggcca
    1921 attttggatg agcatggagc tgtcacctct cagctgctgg atgacttgag
atgaaaaagg
    1981 agagacatgg aagggagac agccaggtgg cacctgcagc ggctgccctc
tggggccact
    2041 tggtagtgtc cccagcctac ctctccacaa ggggattttg ctgatgggtt
cttagagcct
    2101 tagcagccct ggatggtggc cagaaataaa gggaccagcc cttcatgggt
ggtgacgtgg
    2161 tagtcacttg taaggggaac agaaacattt ttgttcttat ggggtgagaa
tatagacagt
    2221 gcccttggtg cgagggaagc aattgaaaag gaacttgccc tgagcactcc
tggtgcaggt
    2281 ctccacctgc acattgggtg gggctcctgg gagggagact cagccttcct
cctcatcctc
    2341 cctgaccctg ctcctagcac cctggagagt gcacatgccc cttggtcctg
gcagggcgcc
    2401 aagtctggca ccatgttggc ctcttcaggc ctgctagtca ctggaaattg
aggtccatgg
    2461 gggaaatcaa ggatgctcag tttaaggtac actgtttcca tgttatgttt
ctacacattg
    2521 ctacctcagt gctcctggaa acttagcttt tgatgtctcc aagtagtcca
ccttcattta
    2581 actctttgaa actgtatcac ctttgccaag taagagtggt ggcctatttc
agctgctttg
    2641 acaaaatgac tggctcctga cttaacgttc tataaatgaa tgtgctgaag
caaagtgccc
    2701 atggtggcgg cgaagaagag aaagatgtgt tttgttttgg actctctgtg
gtcccttcca
    2761 atgctgtggg tttccaacca ggggaagggt ccctttttgca ttgccaagtg
ccataaccat
    2821 gagcactact ctaccatggt tctgcctcct ggccaagcag gctggtttgc
aagaatgaaa
    2881 tgaatgattc tacagctagg acttaacctt gaaatggaaa gtcttgcaat
cccatttgca
    2941 ggatccgtct gtgcacatgc ctctgtagag agcagcattc ccagggacct
tggaaacagt
    3001 tggcactgta aggtgcttgc tccccaagac acatcctaaa aggtgttgta
atggtgaaaa
    3061 cgtcttcctt ctttattgcc ccttcttatt tatgtgaaca actgtttgtc
ttttttttgta
    3121 tcttttttaa actgtaaagt tcaattgtga aatgaatat catgcaaata
aattatgcga
    3181 ttttttttc aaagcaaaaa aaaaaaaaaa aaaaaaaaaa aaaaaa
```

FLI1 overexpression without fusion transcript

Induction of ERG protein by Androgen in TMPRSS2-ERG+ Cells

Figure 20

Figure 21
Nuclear Interactors for ERG2 (Mass spec and Protein Arrays)

| Description | Symbol |
|---|---|
| PRPF8 pre-mRNA processing factor 8 homolog (yeast) | PRPF8 |
| T-box, brain, 1 | TBR1 |
| EBNA1 binding protein 2 | EBNA1BP2 |
| V-ets erythroblastosis virus E26 oncogene like (avian) | ERG |
| Fibrillarin | FBL |
| Exosome component 7 | EXOSC7 |
| Friend leukemia virus integration 1 | FLI1 |
| Nuclear mitotic apparatus protein 1 | NUMA1 |
| Poly(rC) binding protein 1 | PCBP1 |
| Small nuclear ribonucleoprotein 70kDa polypeptide (RNP antigen) | SNRP70 |
| Lectin, galactoside-binding, soluble, 3 (galectin 3) | LGALS3 |
| RNA binding motif protein 23 | RBM23 |
| TAF6 RNA polymerase II, TATA box binding protein (TBP)-associated factor, 80kDa | TAF6 |
| Zinc finger protein 306 | ZNF306 |
| Ras association (RalGDS/AF-6) domain family 5 | RASSF5 |
| Calcium/calmodulin-dependent protein kinase 1 | CAMK1 |

Figure 22

ERG11

```
MASTIKEAIS  VVSEDQSLFE  CAYGTPHLAK  TEMPASSSD     40
YGQTKMSPA   VPQQWLSQF   PARVIKMEC   KPSQVNGSRN    80
SPDECSVARG  GRMVGSPDTV  QMYGSTMEE   KHMPPPNMFT   120
NERRVYVPAD  PFLWSTDRYR  QWLEWAVKEY  GLPDVNILLP   160
QNTDGKELCK  MTEDPQRLI   PSYNADTLLS  RLAYLAETPL   200
PRLTSDSVDK  ALQMSPKLMS  ARNTGAAPI   PNMTSVYPRA   240
                       GAAPI       PNTSVVP
TQRITTRPDL  PYEPRRSAM   TGGHFTFQS   KAQFSTETY    280
PKTEDQRFQL  DPFQILGFFS  SRLANPGSGQ  IQLMQFLIEL   320
LSDSNSSCI   TWEGTMGEFK  MTDPDEVAKR  WGEREGKPMM   360
NYDKLSRALR  YYYDKNIMYK  VNGKRYAYKF  DPRGIAQALQ   400
PHPPESSLYK  YPSDLPYMGS  YHAHPQRMNF  VAHPPALPV    440
TSSSPTRAAPN PYWNSPPGGT  TPNTRLFTSH  MFSHLGTYY    478
```

Figure 23

ETV1 (NCBI)

```
    1 MDGFYDQQVP YMYTNSQRGR MCNEKPTVYR KRKFINRDLA HDSEELFQDL SQLQETWLAE
   61 AQVPDNDEQF VPDYQAESLA FHGLDLDKLK RKRSPCSEIS SPHSPCSEIS SACSQEQFFK FSYGEKCLYN
  121 YSAYDQKRQV GMRPSNFPTP SSTPVSPLHH ASPNSTHTPK PDRAFPAHLP PSQSIPDSSY
          TP SSTPVSPLHH A                RAFFAHLP PSQSIPDS
  181 PMDHRFRRQL SEPCNSFPPL PTMPREGRPM YQRQMSEPNI PFFKGFRQE YHDPVYEHNT
  241 MVGSAASQSF PPPLMIKQEP RDFAYDSEVP SCHSIYMRQE GFLAHPSRTE GCMEEGPRQ
  301 FYDTCVFH KFGDIKQEP GMYREGFTYQ RGSSLQLRQF LVALLDDPSH SHFIAWTGRG
  361 MEFKLIEDEE VARWGIQKN RPAMNYDKLS RSLRYYYEKG IMQKVAGERY VIKFVCDPEA
  421 LFSMAFPDNQ RPLLKTDMER HINEEDTVPL SHFDESMAYM PEGGCCNFHP INEGYVY
```

Figure 25

```
ETV-4 (NCBI)
  1 MERRMKAGYL DQQVPYTFSS KSPGNGSLRE ALIGPLGKIM DPGSLPPLDS EDLFQDLSHF
                GYL DQQVPYTPS           LRE ALIGPLGK
 61 QETWLAEAQV FDSDEQFVPD FHSENLAFHS PTTRIKKEPQ SPRTDPALSC SRKFFLFYHH
                                SENLAFH           TDPALSC
121 GEQCLYSSAY DPPRQIAIKS PAPGALGQSP LQFFPRAEQR NFLRSSGTSQ PHPGHGYLGE
121 GEQCLYSSAY DPPRQIAIKS PAPGALGQSP LQFF
181 HSSVPQQPLD ICHSF GREPLPAPPQ HQLSEPCPPY PQQSPQQYH DPLYEQAGQP
181 HSSVPQQPLD ICHSF EPLPAPPQ HQLSEPCPPY PQQ        YH DPLYEQ GQP
241 AVDQGVNGH RYPGAGVVIK QEQTDFAIDS DVTGCASMYL NEGrscpsY GDGAMGYGYE
    AVDQ       RYPGAGVVIK        YDS DVTGCASMY                    YE
301 KPLRPFPDDV CVVPEKFEGD IKQEGVGAPR EGPPYQRRGA LQLWQFLVAL LDDPTNAHFI
    KPLRPFPDDV CVVPE
361 AWFGRGMEFK LIEPEEVARL WGIQKNRPAM NYDKLSRSLR YYTEKGIMQK VAGERYVYKF
421 VCEPEALFSL AFPDMQRPAL KAEFDRPVSE EDTVPLSHLD ESPAYLPELA GPAQPFGPKG
481 GISY
```

Viral Overexpression Systems

Transgenic Mice

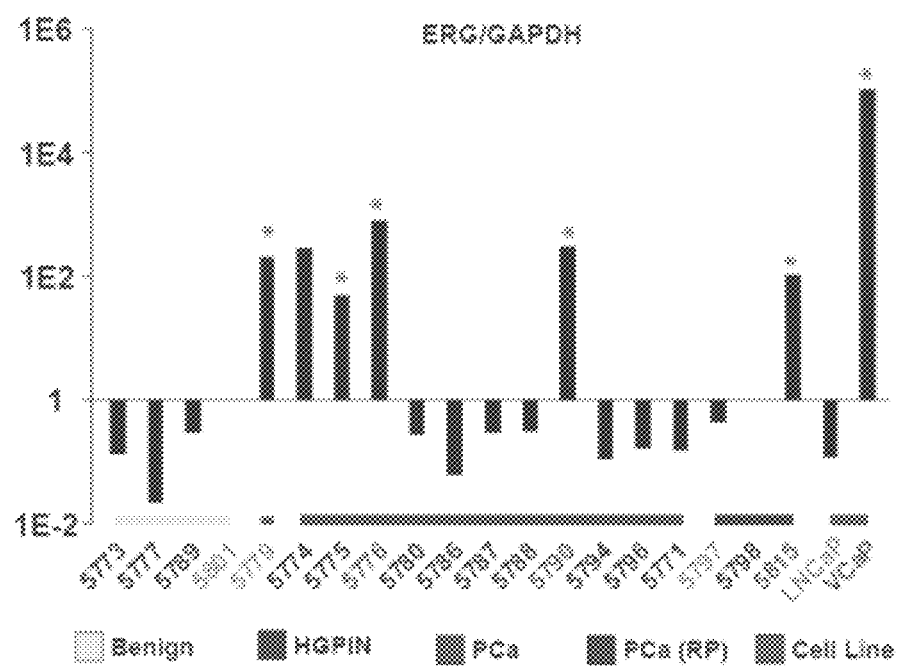

Figure 34
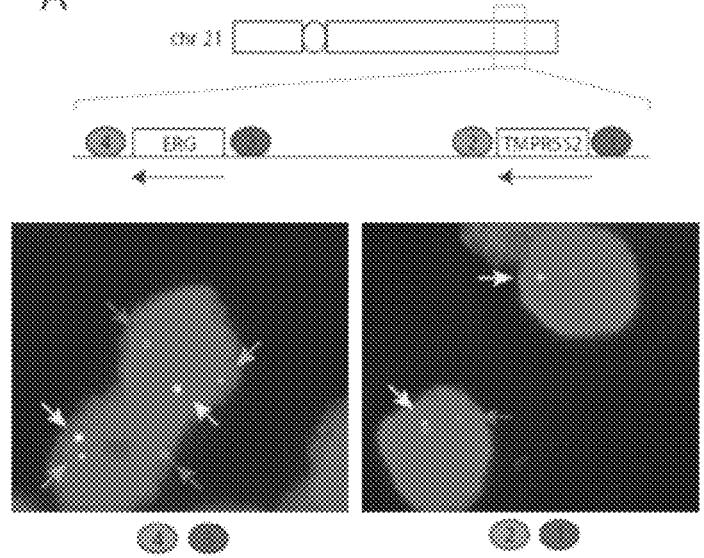
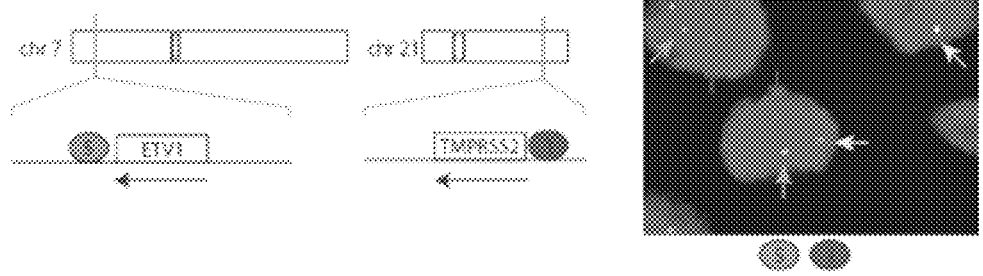
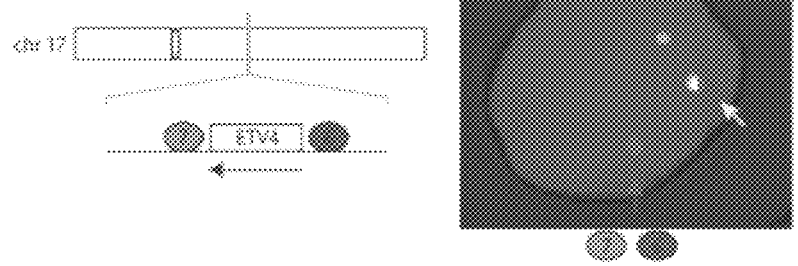

Figure 36

| Gene | Exon | Sequence |
|---|---|---|
| TMRPSS2 | 1 | cgcgagctaagcaggaggcggaggcggaggcggaggcgaggggcggggagcgccg cctggagcgcggcag |
| TMRPSS2 | 1,2 | cgcgagctaagcaggaggcggaggcggaggcggaggcgaggggcggggagcgccg cctggagcgcggcaggtcatatgaacattccagatacctatcattactcgatgctgttgataac agcaagatggcttgaactca |
| TMRPSS2 | 1,2,3 | cgcgagctaagcaggaggcggaggcggaggcggaggcgaggggcggggagcgccg cctggagcgcggcaggtcatatgaacattccagatacctatcattactcgatgctgttgataaca gcaagatggcttgaactcagggtcaccaccagctattggaccttactatgaaaaccatggatac caaccggaaaaccctatccgcacagcctactgtggtccccactgtctacgaggtgcatccg gctcagtactacccgtccccgtgccccagtacgccccgagggtcctgacgcaggcttccaac cccgtcgtctgacgcagcccaaatccccatccgggacagtgtgcacctcaa |
| TMRPSS2 | 1,2,3,4 | cgcgagctaagcaggaggcggaggcggaggcggaggcgaggggcggggagcgccg cctggagcgcggcaggtcatatgaacattccagatacctatcattactcgatgctgttgataac agcaagatggcttgaactcagggtcaccaccagctattggaccttactatgaaaaccatggat accaaccggaaaaccctatccgcacagcccactgtggtccccactgtctacgaggtgcat ccggctcagtactacccgtccccgtgccccagtacgccccgagggtcctgacgcaggctt ccaaccccgtcgtctgacgcagcccaaatccccatccgggacagtgtgcacctcaagac taagaagcactgtgcatcacctgccctgggggacttcctcgtgggagctgcgctggcg tggcctactctggaagtcatgggcagcaagtgctccaatctgggatagagtgcga |
| TMRPSS2 | 1,2,3,4,5 | cgcgagctaagcaggaggcggaggcggaggcggaggcgaggggcggggagcgcc gcctggagcgcggcaggtcatatgaacattccagatacctatcattactcgatgctgtgata acagcaagatggcttgaactcagggtcaccaccagctattggaccttactatgaaaaccatg gataccaaccggaaaaccctatccgcacagccactgtggtccccactgtctacgaggt gcatccggctcagtactacccgtccccgtgccccagtacgccccgagggtcctgacgcag gcttccaaccccgtcgtctgacgcagcccaaatccccatccgggacagtgtgcacctcaa agactaagaagcactgtgcatcacctgacctgggggacttcctcgtgggagctgcgctg gcgctggcctactctggaagtcatgggcagcaagtgctccaatctgggatagagtgcga tcctcaggtacctgcatcaaccctctactggtgtgatggcgtgcacactgccccggcgg agaggacgagaatcggtctg |
| TMRPSS2 | upstream long | CTTTGATAAATAAGTTTGTAAGAGGAGCCTCAGCATCGTAAAGAGC TTTTCTCCCCGCTTCTCGCAG |
| TMRPSS2 | upstream short | ATCGTAAAGAGCTTTTCTCCCCGCTTCTCGCAG |
| | | |
| ERG | 2 | gtattccaggatcttggagacccggaggaaagccgtgtgacaaaagcaagacaaatgactca cagagaaaataagatggctagaaccaaggcaactaaag |
| ERG | 3 | ccgtcaggtctgaacagatggtagatggctgctactgaaggacatgattcagactgtcccgga cccagcagctcatatcaag |
| ERG | 4 | gaagctatcagtgtgagtgaggaccaatgttgttgagtgtcctaggaacgccaactggctaagacaga gatgacaggtccttcccagcgacatggacagatccagatgagccacggtccctcagaggattggtg tctccaacccccagccagggtacatcaaatgaatgtaacccctagcaggtgaatggctaag |
| ERG | 5 | gaactctcctgatgaatgcagtgtggccaaaggcgggaagatgtggggcagcccagacacgttg ggatgaactacggcagctacatgaggagaagcacatgccaccccaaacatgacacgaacg |

Figure 36 (Cont.)

| Gene | # | Sequence |
|---|---|---|
| ERG | 6 | agcgcagagtatcgtgccagcag atcctacgctatggagtacagaccatgtgcggcagtggctgagtggcgggtgaaagaatatggcc ttccagagcgtcaacatctgttattccgaacatgatgggaaggaactgtgcaagatgaccaaggc tgacttccagaggctcacccccagctacaacgccgacatcctctctcacatcccactactcagag aga |
| ERG | 7 | ctcctcttccacattgacttcagatgatgttgataaagcctacaaaactctccacggttaatgcatgct agaaacacag |
| ERG | 7a | gaagtgcagcttatattcccaatactcagtatcctgagcagcaaagaattccaactaggccag |
| ERG | 8 | attaccatatgagccccccaggagatcagctggacggtcacggctaccccaacgcccagtc gaaag |
| ERG | 9 | ctgctcaaccatctcctccacagtgcccaaaactgaagaccaggtcctcagtag |
| ERG | 10 | atcctatcagatctggaccaacaagtagcgcgcctgcaaatccag |
| ERG | 11 | gcagtggccagatccagcttgcagtcctcctggactctgtcggacagctccaactccagctgc atcaccggaaggcaccacgacgagtcaagatgacggatcctctgtcggacagctccaactccagctgc ggagagcgggaagagcaaacgccaaatagaactacgataagctcagccgcgtcctcgttacta ttattgcaagaacatcatgaccaagtccatgggaagcgctacgccacagtcgacttccacgg gatgccaggccctccagcccaacccccggagtcatctctgtacaagtacccctcagaccatcc gtacatggggtcctatcacgtccatccacagaagatgaatttgtgggtgccccacctccagccctc ctccgtgaatatctccagttttttgtcgcccccaaaccccactactggaattccaccacactgggggtatatccc tccaactaggctcccaccccagccatatgcctctcatctggccactactactaa |
| | | |
| ETV1 | 4 | ctccaggtacctgacaatgatgagcagtttgtacccgactatcaggctgaaagtt |
| ETV1 | 5 | tggctttcatggcctgccactgaaaatcacgaagaactcccacagtccatgtcagaaatcag ctctgcctgcagtcaagacacagcccttaaattcagctatggagaaaagtgcctgtacaatgtcag g |
| ETV1 | 6 | tgcctatgatcagaagccacaagtgggaatgaggccctccaacccccccacaccatccagca cgccagtgtcccactgcatcatgcatctccaaactcaactcatacaccgaaacctgaccgggc cttcccagctctcctccctcatcgcagtccatccagatagcagctaccccatggacttacag |
| ETV1 | 7 | attcgccgccagctctctgaacctgtaactcctttcctcctttgccgacgatgccaagggaag gacgtcctatgtaccaacgccagatgtctgagctaaaactccccctccctacccacaaggcttaa gcaggagtaccacgacccagtgtatgaacacaacaccatggttggcagtgcggccagccaa agctttcccctctctgatgtaaacaggacccagagatttgtcatatgactcag |
| ETV1 | 8 | aagtgcctagctgccactccattatatgaggcaagaaggctcctggctcatcccagcaga acagaag |
| ETV1 | 9 | gcgtatgttgaaaaaggccccaggcagttatgatgacacctgtgttgtcccagaaaaatc gatg |
| ETV1 | 10 | gagacatcaaacagagccaggaatgtatcgggaaggcccacataccaacggcgaggat cactcagctctggcagttttggtagctctctgatgacccttcaaattctcatttattgcctgga ctgtcgaggcatggaattaaactgattgacctgaagag |
| ETV1 | 11 | gtggccccgacgttgggcattcagaaaacaggccagctatgaactatgataaacttagccgt tcactccgctattactatgagaaaggaattatgcaaaag |
| ETV1 | 12 | gtgggctggagagagatatgtctacaagttgtgtgtgatccagaagccctttctccatggccttt ccagataatcagcgtccactgctgaagacagacatggaccgtcacatcaccgaggaggaca cagtgcctcttctcacttgatgacggcatggcctacatgccggaaggggctgctgcaccc ctaccccctacaacgaaggctacgtgtattaa |

Figure 36 (Cont.)

| | | |
|---|---|---|
| ETV4 | 3 | aaatcgcccggaaatgggagcttgcgcgaagcgctgatcggcccgctggggaagctcatgg accccggctccctgccgccctcgactctgaag |
| ETV4 | 4 | atctcttccaggatchagtcacttccaggagacgtggctcgctgaag |
| ETV4 | 5 | ctcaggtacaagacagtgatgagagagttgttcctgattccattcagaaacc |
| ETV4 | 6 | tagcttccacagcccaccaccaggatcaagtaggagcccccagagtccccgcacagacccg gcctgtcctgcagcaggaagccgccactccctaccaccatggcgagcagtgccttactccag |
| ETV4 | 7 | tgcctatgaccccccagacaaatcgccatcaagtccctgccctggtgccctggacagtcg ccctacagcccttccccgggcagagcaacggaattcctgagatctctggaacctccagcccc accctggccatgggtacctcggggaacatag |
| ETV4 | 8 | ctccgtctccagcagcccccggacatttgccactcctccacatctcaggagggaggccggaa accctccagtcccctaccacacagctgtcggaggccctgccacctctcccagcagagcttaagtaagaatccatgatccctgtatgaacaggcgggccagccagccgtggccaggtggggtcaatgggcacaggtaccaggaggcgggggtggtgatcaaacaggaacagaacgacttcgcctacgactcag |
| ETV4 | 9 | gtgtcaccgggtgcgcatcaatgtacctccacacagagggctctctgggccctctccaggtg acgaggccatgg |
| ETV4 | 10 | gctatggctatgagaaactctgcgaccatcccagatgatgctgcgttgtcctgagaaattt gaag |
| ETV4 | 11 | gagacatcaagcaggaagggtcggtgcattcgagaggggccgccctaccagcgccggg gtgccctgcagctgtggcaatttctggttggcctgctctggatgcccaaccaatgccattcatt gcctgaccggccggggaatggagttcaagctcattgagcctgaggaag |
| ETV4 | 12 | gtcgccaggctctgggcatcctgaagaaccggccagccatgaattacgacaagctgagcc gctcgctccgatactattatgagaaaggcatcatgcaggag |
| ETV4 | 13 | gtggctggtgagcgttacgtgtacagtttgtgtgtgagccgaggccctctctcttggcctta ccggacaatcagcgtccagctctcaaggctgagttgaccggcctgtcagtgaggaggacaca gtccctttgtccacttggatgagagcccgcctacctcccagagctggctggccccgccagc cattggccccaagggtggctactcttactag |

| Name | Reference | TMPRSS2 | ETV1 |
|---|---|---|---|
| | TMPRSS2.ETV1a | 1 | 4-12 |
| | TMPRSS2.ETV1b | 1,2 | 4-12 |

| Name | Reference | TMPRSS2 Exon | ERG Exon |
|---|---|---|---|
| TMPRSS2:ERG(1,2) | TMPRSS2:ERGb | 1 | 2-11 |
| TMPRSS2:ERG(1,3) | 3 | 1 | 3-11 |
| TMPRSS2:ERG(1,4) | TMPRSS2:ERGa | 1 | 4-11 |
| TMPRSS2:ERG(1,5) | 2 | 1 | 5-11 |
| TMPRSS2:ERG(2,2) | 3 | 1,2 | 2-11 |
| TMPRSS2:ERG(2,3) | | 1,2 | 3-11 |
| TMPRSS2:ERG(2,4) | 1 | 1,2 | 4-11 |
| TMPRSS2:ERG(2,5) | 2 | 1,2 | 5-11 |
| TMPRSS2:ERG(3,4) | 3 | 1-3 | 4-11 |
| TMPRSS2:ERG(4,4) | 1 | 1-4 | 4-11 |
| TMPRSS2:ERG(4,5) | 1 | 1-4 | 5-11 |
| TMPRSS2:ERG(5,4) | 1 | 1-5 | 4-11 |

Figure 36 (Cont.)

| | | TMPRSS2 | ETV4 |
|---|---|---|---|
| | TMPRSS2:ETV4a | upstream long | intron 2, exons 3-13 |
| | TMPRSS2:ETV4b | upstream short | intron 2, exons 3-13 |
| | | | |
| Gene | Accession number | | |
| TMPRSS2 | NM_005656.2 | | |
| ERG | NM_004449.3 | | |
| ETV1 | NM_004956.3 | | |
| ETV4 | NM_001986.1 | | |
| | | | |
| TMPRSS2:ERGa | DQ204772 | | |
| TMPRSS2:ERGb | DQ204773.2 | | |
| TMPRSS2:ETV1a | DQ204770 | | |
| TMPRSS2:ETV1b | DQ204771 | | |
| TMPRSS2:ETV4a | DQ396625 | | |
| TMPRSS2:ETV4b | DQ396626 | | |
| | | | |
| References | 1 | PMID: 16875878 | Genes Chromosomes Cancer. 2006 Jul;45(7):717-9. |
| | 2 | PMID: 16829092 | Neoplasia. 2006 Jun;8(6):465-9. |
| | 3 | PMID: 16951141 | Cancer Res. 2006 Sep 1;66(17):8347-51. |

Figure 37

| Primer | | SEQ ID NO |
|---|---|---|
| FLI1_exon1-f | GCTGCAGACTTGGCCAAATGGAC | 202 |
| FLI1_exon2-r | TGACCACCGACAGAGCCTCCTTA | 203 |
| FLI1_exon2/3-f | ACCACATGAATGGATCCAGGGAGTCT | 204 |
| FLI1_exon3-r | ACCAGCTTGCTGCATTTGCTAACG | 205 |
| FLI1_exon4-f | CTCCGCGGCCACCACCCTCTA | 206 |
| FLI1_exon4/5-r | GGCCAGCAGTGAACTTTCCCTGAG | 207 |
| FLI1_exon3a-f | CTCCTCCCAACATGACCACCAAC | 208 |
| FLI1_exon3a-r | GTCTGCGGGGACGATGACTCTC | 209 |
| FLI1_exon4a-f | CATGTGAGGCAATGGCTGGAGTG | 210 |
| FLI1_exon4a-r | CCATCTTCTGGAAAAAGGATGTGTCG | 211 |
| FLI1_exon7-f | CCTTGGAGGGGCACAAACGAT | 212 |
| FLI1_exon8-r | GGTCGGGCCCAGGATCTGATAC | 213 |
| FLI1_exon9-f | CGCCAACGCCAGCTGTATCAC | 214 |
| FLI1_exon9-r | AGCGCCTGGCCACCTCATC | 215 |
| FLI1_exon10-f | ATGTTTTTATGACCAAAGCAGTTTCTTGTC | 216 |
| FLI1_exon10-r | ATGACGGGTTAAGTCCATGATTCTGTG | 217 |

ERG
forward-        CGAAAGCTGCTCAACCATCTC           218
reverse-        TAACTGAGGACGCTGGTCTTCA          219
FAM labeled MGB probe    CCACAGTGCCCAAAA        220

FLI1                                            221
forward-        CGGCAAAAGATATGCTTACAAATTT       222
reverse-        GACGACTCGGTCGGATGTG             223
FAM labeled MGB probe    CACGGCATTGCCCA         224

TMPRSS2:ERGa specific
forward-        CGCGGCAGGAAGCCTTA               225
reverse-        TCCGTAGGCACACTCAAACAAC          226
FAM labeled MGB probe    CAGTTGTGAGTGAGGACC     227

ETV4
forward-        GCTCGCTCCGATACTATTATGAGAA       228
reverse-        CACACACAAACTTGTACACGTAACG       229
FAM labeled MGB probe    ACCAGCCACCTTCTGC       230

ETV1
forward-        GGTCGAGGCATGGAATTTAAACTGA       231
reverse-        GCTGGCCTGTTTTTCTGAATGC          232
FAM labeled MGB probe    TCGGGCCACCTCTTC        233

RECURRENT GENE FUSIONS IN PROSTATE CANCER

CROSS REFERENCE TO RELATED APPLICATIONS

This application is a Divisional application of U.S. patent application Ser. No. 12/650,164, filed Dec. 30, 2009, which is a divisional application of U.S. patent application Ser. No. 11/519,397, filed Sep. 12, 2006, now U.S. Pat. No. 7,718,369 issued May 18, 2010, which claims priority to U.S. Provisional Patent Application Ser. Nos. 60/716,436, filed Sep. 12, 2005, 60/779,041, filed Mar. 3, 2006, 60/730,358, filed Oct. 27, 2005, and 60/795,590, filed Apr. 28, 2006, all of which are incorporated herein by reference in their entireties.

STATEMENT REGARDING FEDERALLY SPONSORED RESEARCH OR DEVELOPMENT

This invention was made with government support under CA069568, CA097063, CA111275, CA046592 and AG021404 awarded by the National Institutes of Health and W81XWH-05-1-0173 awarded by the Army Medical Research and Materiel Command. The government has certain rights in the invention.

FIELD OF THE INVENTION

The present invention relates to compositions and methods for cancer diagnosis, research and therapy, including but not limited to, cancer markers. In particular, the present invention relates to recurrent gene fusions as diagnostic markers and clinical targets for prostate cancer.

BACKGROUND OF THE INVENTION

A central aim in cancer research is to identify altered genes that are causally implicated in oncogenesis. Several types of somatic mutations have been identified including base substitutions, insertions, deletions, translocations, and chromosomal gains and losses, all of which result in altered activity of an oncogene or tumor suppressor gene. First hypothesized in the early 1900's, there is now compelling evidence for a causal role for chromosomal rearrangements in cancer (Rowley, Nat Rev Cancer 1: 245 (2001)). Recurrent chromosomal aberrations were thought to be primarily characteristic of leukemias, lymphomas, and sarcomas. Epithelial tumors (carcinomas), which are much more common and contribute to a relatively large fraction of the morbidity and mortality associated with human cancer, comprise less than 1% of the known, disease-specific chromosomal rearrangements (Mitelman, Mutat Res 462: 247 (2000)). While hematological malignancies are often characterized by balanced, disease-specific chromosomal rearrangements, most solid tumors have a plethora of non-specific chromosomal aberrations. It is thought that the karyotypic complexity of solid tumors is due to secondary alterations acquired through cancer evolution or progression.

Two primary mechanisms of chromosomal rearrangements have been described. In one mechanism, promoter/enhancer elements of one gene are rearranged adjacent to a proto-oncogene, thus causing altered expression of an oncogenic protein. This type of translocation is exemplified by the apposition of immunoglobulin (IG) and T-cell receptor (TCR) genes to MYC leading to activation of this oncogene in B- and T-cell malignancies, respectively (Rabbitts, Nature 372: 143 (1994)). In the second mechanism, rearrangement results in the fusion of two genes, which produces a fusion protein that may have a new function or altered activity. The prototypic example of this translocation is the BCR-ABL gene fusion in chronic myelogenous leukemia (CML) (Rowley, Nature 243: 290 (1973); de Klein et al., Nature 300: 765 (1982)). Importantly, this finding led to the rational development of imatinib mesylate (Gleevec), which successfully targets the BCR-ABL kinase (Deininger et al., Blood 105: 2640 (2005)). Thus, identifying recurrent gene rearrangements in common epithelial tumors may have profound implications for cancer drug discovery efforts as well as patient treatment.

SUMMARY OF THE INVENTION

The present invention provides, but is not limited to, methods for diagnosing prostate cancer in a patient comprising: providing a sample from the patient; and, detecting the presence or absence in the sample of a gene fusion having a 5' portion from a transcriptional regulatory region of an androgen regulated gene (ARG) and a 3' portion from an ETS family member gene, wherein the presence in the sample of the gene fusion is indicative of prostate cancer in the patient. The ARG may be TMPRSS2 or PSA. The ETS family member gene may be ERG, ETV1 (ER81), FLI1, ETS1, ETS2, ELK1, ETV6 (TEL1), ETV7 (TEL2), GABPα, ELF1, ETV4 (E1AF; PEA3), ETV5 (ERM), ERF, PEA3/E1AF, PU.1, ESE1/ESX, SAP1 (ELK4), ETV3 (METS), EWS/FLI1, ESE1, ESE2 (ELF5), ESE3, PDEF, NET (ELK3; SAP2), NERF (ELF2), or FEV. The transcriptional regulatory region of the ARG may comprise a promoter region of the ARG. The promoter region of the ARG may further comprise an androgen response element (ARE) of the ARG.

Detecting the presence or absence in the sample of a gene fusion may comprise detecting chromosomal rearrangements of genomic DNA having a 5' portion from a transcriptional regulatory region of an ARG and a 3' portion from an ETS family member gene. A variety of techniques may be used for detecting the chromosomal rearrangements of genomic DNA, including nucleic acid sequencing, nucleic acid hybridization, and, nucleic acid amplification. Nucleic acid hybridization techniques include in situ hybridization (ISH), microarray, and Southern blot. Nucleic acid amplification techniques include polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA).

Detecting the presence or absence in the sample of a gene fusion may alternatively comprise detecting chimeric mRNA transcripts having a 5' portion from a transcriptional regulatory region of an ARG and a 3' portion from an ETS family member gene. A variety of techniques may be used for detecting the chimeric mRNA, including nucleic acid sequencing, nucleic acid hybridization, and, nucleic acid amplification. Nucleic acid hybridization techniques include in situ hybridization (ISH) (e.g., Fluorescence in situ hybridization (FISH)), microarray, and Northern blot. Nucleic acid amplification techniques include, polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA).

Detecting the presence or absence in the sample of a gene fusion may also alternatively comprise detecting an amino-terminally truncated ETS family member protein resulting from a fusion of a transcriptional regulatory region of an ARG to an ETS family member gene, or detecting a chimeric protein having an amino-terminal portion from a transcriptional regulatory region of an ARG and a carboxy-terminal portion from an ETS family member gene. A variety of techniques may be used for detecting the truncated ETS family member protein or chimeric protein: protein sequencing; and, immunoassay. Immunoassay techniques include immunoprecipitation, Western blot, ELISA, immunohistochemistry, immunocytochemistry, flow cytometry, and immuno-PCR.

The present invention further provides, but is not limited to, compositions and kits for diagnosing prostate cancer in a patient. The compositions and kits may comprise: a single labeled probe comprising a sequence that hybridizes to the junction at which a 5' portion from a transcriptional regulatory region of an ARG fuses to a 3' portion from an ETS family member gene; a pair of labeled probes wherein the first labeled probe comprises a sequence that hybridizes to a transcriptional regulatory region of an ARG and the second labeled probe comprises a sequence that hybridizes to an ETS family member gene; a pair of amplification oligonucleotides wherein the first amplification oligonucleotide comprises a sequence that hybridizes to a transcriptional regulatory region of an ARG and the second amplification oligonucleotide comprises a sequence that hybridizes to an ETS family member gene; an antibody to an amino-terminally truncated ETS family member protein resulting from a fusion of a transcriptional regulatory region of an ARG to an ETS family member gene; or, an antibody to a chimeric protein having an amino-terminal portion from a transcriptional regulatory region of an ARG and a carboxy-terminal portion from an ETS family member gene.

The present invention also provides, but is not limited to, methods for treating prostate cancer in a patient comprising: administering to the patient an agent that inhibits at least one biological activity of a gene fusion having a 5' portion from a transcriptional regulatory region of an androgen regulated gene (ARG) and a 3' portion from an ETS family member gene. The ARG may be TMPRSS2 or PSA. The ETS family member gene may be ERG, ETV1 (ER81), FLI1, ETS1, ETS2, ELK1, ETV6 (TEL1), ETV7 (TEL2), GABPα, ELF1, ETV4 (E1AF; PEA3), ETV5 (ERM), ERF, PEA3/E1AF, PU.1, ESE1/ESX, SAP1 (ELK4), ETV3 (METS), EWS/FLI1, ESE1, ESE2 (ELF5), ESE3, PDEF, NET (ELK3; SAP2), NERF (ELF2), and FEV. The transcriptional regulatory region of the ARG may comprise a promoter region of the ARG. The promoter region of the ARG may further comprise an androgen response element (ARE) of the ARG. The agent may be a small molecule, an siRNA, an antisense nucleic acid, or an antibody.

Additional embodiments of the present invention are provided in the description and examples below.

DESCRIPTION OF THE FIGURES

FIG. 2 shows the identification and characterization of TMPRSS2:ETV1 and TMPRSS2:ERG gene fusions in prostate cancer (PCA). (A) Prostate cancer cell lines (DuCaP, LnCaP and VCaP) and hormone refractory metastatic (MET) prostate cancer tissues were analyzed for ERG (■) and ETV1 (□) mRNA expression by quantitative PCR (QPCR). (B) Loss of over-expression of ETV1 exons 2 and 3 in MET26 compared to LNCaP cells. (C) Schematic of 5' RNA ligase-mediated rapid amplification of cDNA ends (RLM-RACE) results for ETV1 in MET26-LN and ERG in MET28-LN revealing gene fusions with TMPRSS2. (D) Validation of TMPRSS2:ETV1 expression using translocation-specific QPCR in MET26-LN and MET26-RP. (E) Validation of TMPRSS2:ERG expression using translocation-specific QPCR in cell lines and PCA specimens.

FIG. 5 shows Cancer Outlier Profile Analysis (COPA). FIG. 5A shows a schematic of COPA analysis. FIG. 5B shows that RUNX1T1 (ETO) had the highest scoring outlier profile at the 90th percentile in the Valk et al. acute myeloid leukemia dataset (n=293).

FIG. 7 shows over-expression of ETS family members in prostate cancer. Expression of all monitored ETS family members in profiled benign prostate, prostatic intraepithelial neoplasia (PIN), clinically localized prostate cancer and metastatic prostate cancer from grossly dissected tissue (A) or tissue isolated by laser capture microdissection (B) was visualized using Oncomine.

FIG. 8 shows over expression of TMPRSS2 and ETV4 loci in a prostate cancer case that over-expresses ETV4. A. Expression of the indicated exons or region of ETV4 in pooled benign prostate tissue (CPP), prostate cancers that did not over-express ETV4 and were either TMPRSS2:ERG positive (PCA1-2) or negative (PCA3-4), and the prostate cancer case from our LCM cohort with ETV4 over-overexpression (PCA5). B. RLM-RACE reveals fusion of sequences upstream of TMPRSS2 with ETV4 in PCA5. C. Expression of TMPRSS2:ETV4a and TMPRSS2:ETV4b in PCA5 by QPCR. D. Interphase fluorescence in situ hybridization on formalin-fixed paraffin-embedded tissue confirms fusion of TMPRSS2 and ETV4 loci in PCA5.

FIG. 9 (SEQ ID NOS: 32-54) shows mRNA sequences of exemplary ETS family genes.

FIG. 10 (SEQ ID NO.: 307) shows the mRNA sequence of TMPRSS2.

FIG. 20 (SEQ ID NOS: 236-239) shows a schematic of the endogenous and fusion ERG polypeptides.

FIG. 21 shows Nuclear interactors for ERG2.

FIG. 22 (SEQ ID NOS: 240-241) shows sequences for peptide antibody and aqua probe generation against ERG1.

FIG. 23 (SEQ ID NOS: 242-245) shows sequences for peptide antibody and aqua probe generation against ETV1.

FIG. 25 (SEQ ID NOS: 253-268) shows sequences for peptide antibody and aqua probe generation against ETV4.

FIG. 26A shows expression signature of androgen-regulated genes in VCaP and LNCaP prostate cancer cell lines. FIG. 26B shows confirmation of PSA induction by androgen in both VCaP and LNCaP cells by quantitative PCR (QPCR). FIG. 26C shows ETV1 induction by androgen in LNCaP cells. FIG. 26D shows that ETV1 is markedly over-expressed in LNCaP cells.

FIG. 27A shows a schematic of BACs used as probes for fluorescence in situ hybridization (FISH). FIG. 27B shows that RP11-124L22 and RP11-1149J13 co-localize to chromosome 7 in normal peripheral lymphocytes (NPLs). FIG. 27C shows localization of BAC #1 and BAC #4 on metaphase spreads (top panel) and interphase cells (bottom panel) was determined in the near tetraploid LNCaP cell line. FIG. 27D shows signal from RP11-124L22 localizes to chromosome 14 in LNCaP cells.

FIG. 28A shows a schematic of BACs used in this experiment. FIG. 28B shows localization of RP11-124L22 (BAC #1) and RP11-313C20 (BAC #2) on metaphase spreads (top panel) and interphase cells (bottom panel) was determined by FISH in LNCaP cells.

FIG. 33 shows detection of ERG and ETV1 transcripts in urine. FIG. 33B shows detection of ERG and ETV1 in urine of patients suspected of having prostate cancer.

FIG. 34 shows assays used to detect TMPRSS2:ETS gene fusions in prostate cancer. FIG. 34A shows break apart assays for TMPRSS2 and ERG. An ERG rearrangement positive case (without deletion), as indicated by one pair of split 5' and 3' signals, is shown in the left panel. A TMPRSS2 rearrangement positive case (with deletion), as indicated by a loss of one 3' signal, is shown in the right panel. FIG. 34B shows a fusion assay for TMPRSS2:ETV1 gene fusions. FIG. 34C shows a break apart assay for ETV4.

FIG. 35A shows a Table of results for rearrangements in TMPRSS2, ERG, ETV1 and ETV4 as detected by the assays shown in FIG. 34. FIG. 34B shows a heat map representation of the TMPRSS2, ERG, ETV1 and ETV4 status from the 38 cases where all four assays were evaluable as described in A. FIG. 34C shows a heat map representation of cases with discordant TMPRSS2 and ETS rearrangement status.

FIG. 36 (SEQ ID NOS: 269-306) shows the sequences of gene fusions of the present invention.

FIG. 37 shows primers and probes for FLI-1 expression analysis.

DEFINITIONS

Figure 1:
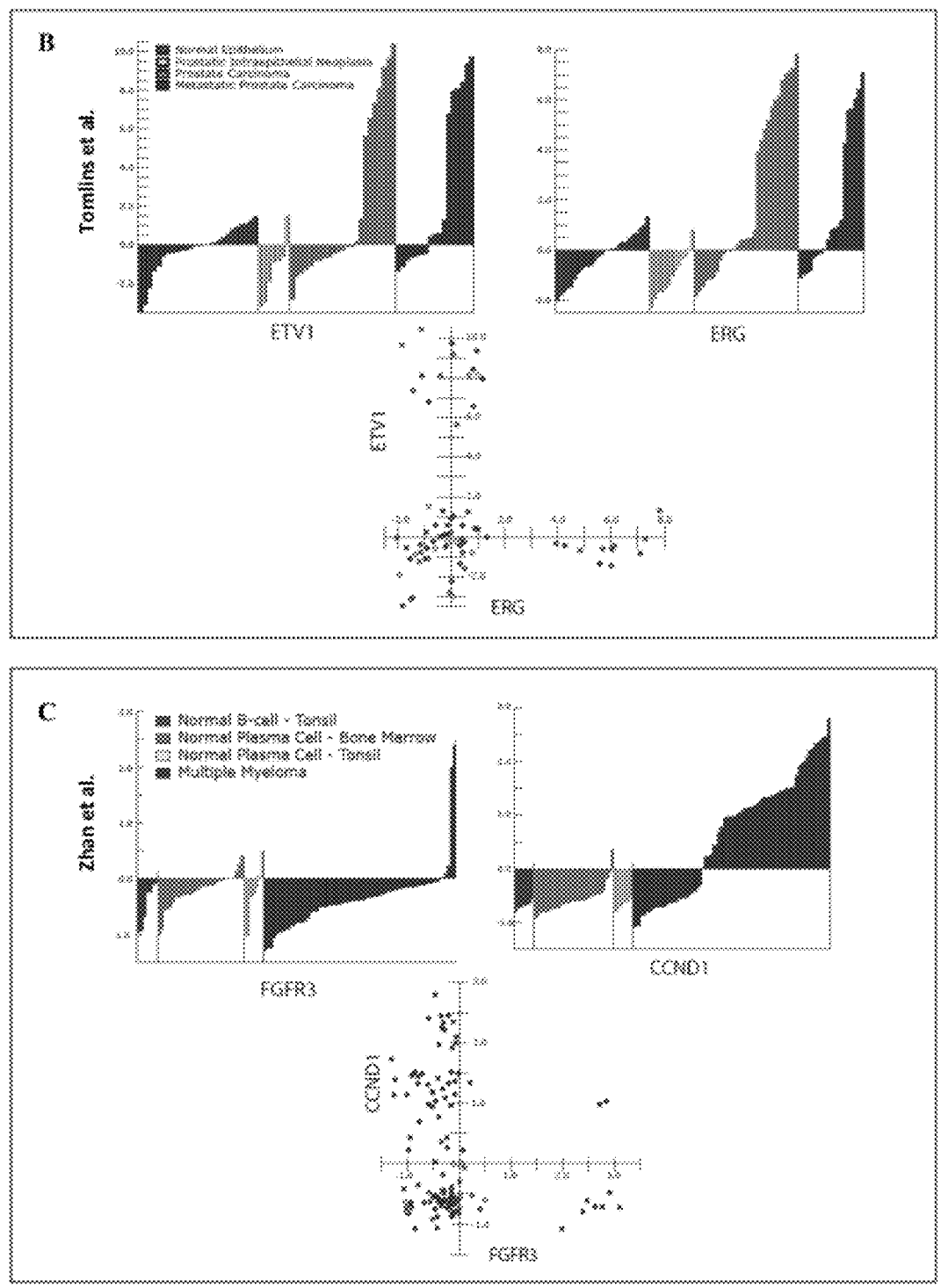
FIG. 1 shows the Cancer Outlier Profile Analysis (COPA) of microarray data. (A) ETV1 (left panels) and ERG (middle panels) expression (normalized expression units) are shown from all profiled samples in two large scale gene expression studies. (B) As in (A), except data from laser capture microdissected samples were used. (C) As in (A), except oncogenes (FGFR3 and CCND1) with known translocations to the immunoglobulin heavy chain promoter (IgH) in multiple myeloma were examined.

To facilitate an understanding of the present invention, a number of terms and phrases are defined below:

As used herein, the term "gene fusion" refers to a chimeric genomic DNA, a chimeric messenger RNA, a truncated protein or a chimeric protein resulting from the fusion of at least a portion of a first gene to at least a portion of a second gene. The gene fusion need not include entire genes or exons of genes.

As used herein, the term "transcriptional regulatory region" refers to the non-coding upstream regulatory sequence of a gene, also called the 5' untranslated region (5'UTR).

As used herein, the term "androgen regulated gene" refers to a gene or portion of a gene whose expression is initiated or enhanced by an androgen (e.g., testosterone). The promoter region of an androgen regulated gene may contain an "androgen response element" that interacts with androgens or androgen signaling molecules (e.g., downstream signaling molecules).

As used herein, the terms "detect", "detecting", or "detection" may describe either the general act of discovering or discerning or the specific observation of a detectably labeled composition.

As used herein, the term "inhibits at least one biological activity of a gene fusion" refers to any agent that decreases any activity of a gene fusion of the present invention (e.g., including, but not limited to, the activities described herein), via directly contacting gene fusion protein, contacting gene fusion mRNA or genomic DNA, causing conformational changes of gene fusion polypeptides, decreasing gene fusion protein levels, or interfering with gene fusion interactions with signaling partners, and affecting the expression of gene fusion target genes. Inhibitors also include molecules that indirectly regulate gene fusion biological activity by intercepting upstream signaling molecules.

As used herein, the term "siRNAs" refers to small interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to, or substantially complementary to, a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

As used herein, the term "stage of cancer" refers to a qualitative or quantitative assessment of the level of advancement of a cancer. Criteria used to determine the stage of a cancer include, but are not limited to, the size of the tumor and the extent of metastases (e.g., localized or distant).

As used herein, the term "gene transfer system" refers to any means of delivering a composition comprising a nucleic acid sequence to a cell or tissue. For example, gene transfer systems include, but are not limited to, vectors (e.g., retroviral, adenoviral, adeno-associated viral, and other nucleic acid-based delivery systems), microinjection of naked nucleic acid, polymer-based delivery systems (e.g., liposome-based and metallic particle-based systems), biolistic injection, and the like. As used herein, the term "viral gene transfer system" refers to gene transfer systems comprising viral elements (e.g., intact viruses, modified viruses and viral components such as nucleic acids or proteins) to facilitate delivery of the sample to a desired cell or tissue. As used herein, the term "adenovirus gene transfer system" refers to gene transfer systems comprising intact or altered viruses belonging to the family Adenoviridae.

As used herein, the term "site-specific recombination target sequences" refers to nucleic acid sequences that provide recognition sequences for recombination factors and the location where recombination takes place.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N-6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N-6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the terms "complementary" or "complementarity" are used in reference to polynucleotides (i.e., a sequence of nucleotides) related by the base-pairing rules. For example, the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein the term "stringency" is used in reference to the conditions of temperature, ionic strength, and the presence of other compounds such as organic solvents, under which nucleic acid hybridizations are conducted. Under "low stringency conditions" a nucleic acid sequence of interest will hybridize to its exact complement, sequences with single base mismatches, closely related sequences (e.g., sequences with 90% or greater homology), and sequences having only partial homology (e.g., sequences with 50-90% homology). Under "medium stringency conditions," a nucleic acid sequence of interest will hybridize only to its exact complement, sequences with single base mismatches, and closely relation sequences (e.g., 90% or greater homology). Under "high stringency conditions," a nucleic acid sequence of interest will hybridize only to its exact complement, and (depending on conditions such a temperature) sequences with single base mismatches. In other words, under conditions of high stringency the temperature can be raised so as to exclude hybridization to sequences with single base mismatches.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharamcia), 5 g BSA (Fraction V; Sigma)]

and 100 µg/ml denatured salmon sperm DNA followed by washing in a solution comprising 5×SSPE, 0.1% SDS at 42° C. when a probe of about 500 nucleotides in length is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.) (see definition above for "stringency").

As used herein, the term "amplification oligonucleotide" refers to an oligonucleotide that hybridizes to a target nucleic acid, or its complement, and participates in a nucleic acid amplification reaction. An example of an amplification oligonucleotide is a "primer" that hybridizes to a template nucleic acid and contains a 3' OH end that is extended by a polymerase in an amplification process. Another example of an amplification oligonucleotide is an oligonucleotide that is not extended by a polymerase (e.g., because it has a 3' blocked end) but participates in or facilitates amplification. Amplification oligonucleotides may optionally include modified nucleotides or analogs, or additional nucleotides that participate in an amplification reaction but are not complementary to or contained in the target nucleic acid. Amplification oligonucleotides may contain a sequence that is not complementary to the target or template sequence. For example, the 5' region of a primer may include a promoter sequence that is non-complementary to the target nucleic acid (referred to as a "promoter-primer"). Those skilled in the art will understand that an amplification oligonucleotide that functions as a primer may be modified to include a 5' promoter sequence, and thus function as a promoter-primer. Similarly, a promoter-primer may be modified by removal of, or synthesis without, a promoter sequence and still function as a primer. A 3' blocked amplification oligonucleotide may provide a promoter sequence and serve as a template for polymerization (referred to as a "promoter-provider").

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to at least a portion of another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

DETAILED DESCRIPTION OF THE INVENTION

The present invention is based on the discovery of recurrent gene fusions in prostate cancer. The present invention provides diagnostic, research, and therapeutic methods that either directly or indirectly detect or target the gene fusions. The present invention also provides compositions for diagnostic, research, and therapeutic purposes.

I. Gene Fusions

The present invention identifies recurrent gene fusions indicative of prostate cancer. The gene fusions are the result of a chromosomal rearrangement of an androgen regulated gene (ARG) and an ETS family member gene. Despite their recurrence, the junction where the ARG fuses to the ETS family member gene varies. The gene fusions typically comprise a 5' portion from a transcriptional regulatory region of an ARG and a 3' portion from an ETS family member gene. The recurrent gene fusions have use as diagnostic markers and clinical targets for prostate cancer.

A. Androgen Regulated Genes

Genes regulated by androgenic hormones are of critical importance for the normal physiological function of the human prostate gland. They also contribute to the development and progression of prostate carcinoma. Recognized ARGs include, but are not limited to: TMPRSS2; PSA; PSMA; KLK2; SNRK; Seladin-1; and, FKBP51 (Paoloni-Giacobino et al., Genomics 44: 309 (1997); Velasco et al., Endocrinology 145(8): 3913 (2004)). TMPRSS2 (NM_005656), in particular, has been demonstrated to be highly expressed in prostate epithelium relative to other normal human tissues (Lin et al., Cancer Research 59: 4180 (1999)). The TMPRSS2 gene is located on chromosome 21. This gene is located at 41,750,797-41,801,948 bp from the pter (51,151 total bp; minus strand orientation). The human TMPRSS2 protein sequence may be found at GenBank accession no. AAC51784 (Swiss Protein accession no. O15393)) and the corresponding cDNA at GenBank accession no. U75329 (see also, Paoloni-Giacobino, et al., Genomics 44: 309 (1997)).

The transcriptional regulatory region of an ARG may contain coding or non-coding regions of the ARG, including the promoter region. The promoter region of the ARG may further contain an androgen response element (ARE) of the ARG. The promoter region for TMPRSS2, in particular, is provided by GenBank accession number AJ276404.

B. ETS Family Member Genes

The ETS family of transcription factors regulate the intracellular signaling pathways controlling gene expression. As downstream effectors, they activate or repress specific target genes. As upstream effectors, they are responsible for the spacial and temporal expression of numerous growth factor receptors. Almost 30 members of this family have been identified and implicated in a wide range of physiological and pathological processes. These include, but are not limited to: ERG; ETV1 (ER81); FLI1; ETS1; ETS2; ELK1; ETV6 (TEL1); ETV7 (TEL2); GABPα; ELF1; ETV4 (E1AF; PEA3); ETV5 (ERM); ERF; PEA3/E1AF; PU.1; ESE1/ESX; SAP1 (ELK4); ETV3 (METS); EWS/FLI1; ESE1; ESE2 (ELF5); ESE3; PDEF; NET (ELK3; SAP2); NERF (ELF2); and FEV. Exemplary ETS family member gene sequences are given in FIG. 9.

ERG (NM_004449), in particular, has been demonstrated to be highly expressed in prostate epithelium relative to other normal human tissues. The ERG gene is located on chromosome 21. The gene is located at 38,675,671-38,955,488 base pairs from the pter. The ERG gene is 279,817 total bp; minus strand orientation. The corresponding ERG cDNA and protein sequences are given at GenBank accession no. M17254 and GenBank accession no. NP04440 (Swiss Protein acc. no. P11308), respectively.

The ETV1 gene is located on chromosome 7 (GenBank accession nos. NC_000007.11; NC_086703.11; and NT_007819.15). The gene is located at 13,708,330-13,803,555 base pairs from the pter. The ETV1 gene is 95,225 bp total, minus strand orientation. The corresponding ETV1 cDNA and protein sequences are given at GenBank accession no. NM_004956 and GenBank accession no. NP_004947 (Swiss protein acc. no. P50549), respectively.

The human ETV4 gene is located on chromosome 14 (GenBank accession nos. NC_000017.9; NT_010783.14; and NT_086880.1). The gene is at 38,960,740-38,979,228 base pairs from the pter. The ETV4 gene is 18,488 bp total, minus strand orientation. The corresponding ETV4 cDNA and protein sequences are given at GenBank accession no. NM_001986 and GenBank accession no. NP_01977 (Swiss protein acc. no. P43268), respectively.

C. ARG/ETS Gene Fusions

As described above, the present invention provides fusions of an ARG to an ETS family member gene. Exemplary gene fusion sequences are given in FIG. 36. For all involved genes (TMPRSS2, ERG, ETV1 and ETV4), the GenBank reference sequence ID's are provided and the exons are aligned using the May 2004 assembly of the UCSC Human Genome. For all identified fusions, FIG. 36 provides a complete sequence from the beginning of the TMPRSS2 gene through the fusion and the stop codon of the ETS family member gene. The deposited GenBank sequence for each of the published variants is also provided. Some TMPRSS2:ERG and TMPRSS2:ETV1 fusions are described by the breakpoint exons of TMPRSS2 and the ETS family member gene. For example, TMPRSS2:ERGa, which fuses exon 1 of TMPRSS2 to exons 4 through 11 of ERG, is identified as TMPRSS2:ERG(1,4).

The fusion of an ARG to an ETS family member gene is detectable as DNA, RNA or protein. Initially, the gene fusion is detectable as a chromosomal rearrangement of genomic DNA having a 5' portion from a transcriptional regulatory region of the ARG and a 3' portion from the ETS family member gene. Once transcribed, the gene fusion is detectable as a chimeric mRNA having a 5' portion from the transcriptional regulatory region of the ARG and a 3' portion from the ETS family member gene. Once translated, the gene fusion is detectable as an amino-terminally truncated ETS family member protein resulting from the fusion of the transcriptional regulatory region of the ARG to the ETS family member gene; a chimeric protein having an amino-terminal portion from the transcriptional regulatory region of the ARG and a carboxy-terminal portion from the ETS family member gene; or, an upregulated, but otherwise indistinguishable, native ETS family member protein. The truncated ETS family member protein and chimeric protein may differ from their respective native proteins in amino acid sequence, post-translational processing and/or secondary, tertiary or quaternary structure. Such differences, if present, can be used to identify the presence of the gene fusion. Specific methods of detection are described in more detail below.

Certain gene fusions are more common than others in prostate cancer. The present invention identifies 50-80% of prostate cancers as having recurrent gene fusions of TMPRSS2 with ERG, ETV1, ETV4, or FLI1. Of those, 50-70% are TMPRSS2-ERG, 50%-60% of which result from the deletion of genetic information between the TMPRSS2 and ERG locus on chromosome 21 (described in more detail below), 5-10% are TMPRSS2-ETV1, 1-2% are TMPRSS2-ETV4, and 1-2% are TMPRSS2-FLI1.

Experiments conducted during the course of development of the present invention indicated that certain fusion genes express fusion transcripts, while others do not express a functional transcript (Tomlins et al., Science, 310: 644-648 (2005); Tomlins et al., Cancer Research 66: 3396-3400 (2006)).

Further experiments conducted during the course of development of the present invention identified significant genomic deletions located between TMPRSS2 and ERG on chromosome 21q22.2-3. Deletions were seen in TMPRSS2:ERG fusion positive PCA samples. The deletions appear in a consensus area but show variability within this area. In previously published work by Paris et al. (Hum. Mol. Genet. 13:1303-13 (2004)), CGH analysis detected deletions in the CTD-2103O7 BAC that is 6 kb centromeric from TMPRSS2.

These deletions were observed in 12.5% (9/72) of clinically localized PCA samples and 33% (5/15) of the metastatic PCA samples. These results support the SNP array data from the current study and suggests that either PCA deletions become more common with progression or that deletions are identified more often in PCA that tend to progress more rapidly. Given the striking intra-tumoral homogeneity of the TMPRSS2:ERG rearrangements, it is more likely that these molecular sub-types are associated with different disease progression characteristics.

Figure 16:
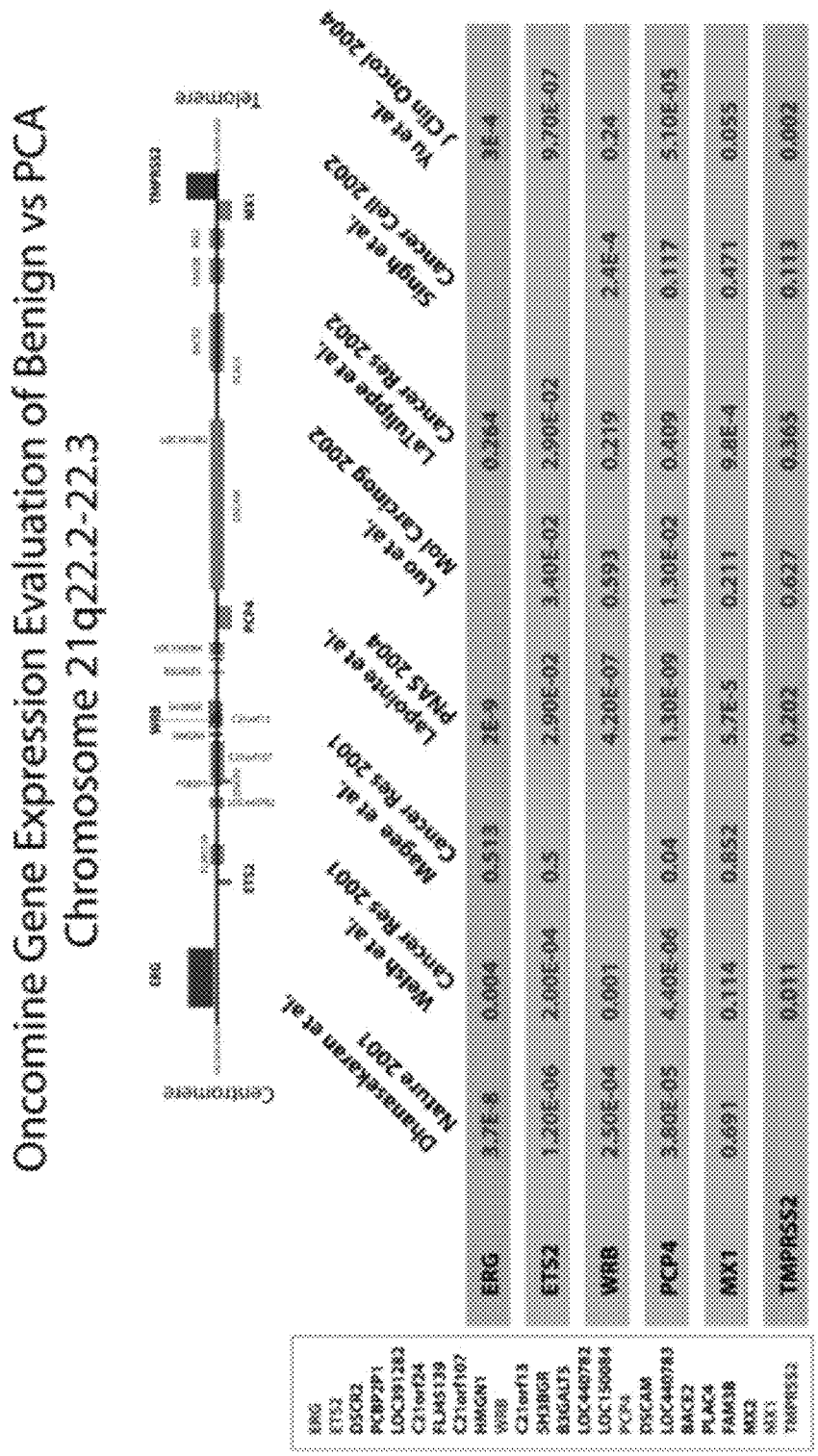
FIG. 16 shows meta-analysis of genes located between TMPRSS2 and ERG across 8 published expression array datasets.

One hundred eighteen clinically localized PCA cases with 49.2% harboring rearrangement of ERG were evaluated. Intronic deletions were observed in 60.3% of these TMPRSS2:ERG fusion positive cases. Almost all PCA samples with marked over expression of ERG have a rearrangement, and the over expression occurs in about the same number of cases as the rearrangement. Using Oncomine, a publicly available compendium of gene expression data, 4 significantly down regulated genes located in the area of the common deletion site were identified (FIG. 16).

The present invention is not limited to a particular mechanism. Indeed, an understanding of the mechanism is not necessary to practice the present invention. Nonetheless, the results suggest that nearly half of all PCAs can be defined by the TMPRSS2:ERG rearrangement. The majority of these tumors demonstrate an intronic deletion, which according to the oligonucleotide SNP array genomic analysis is variable in size. However, approximately 30-40% did not demonstrate a deletion and thus might harbor a balanced translocation of TMRPSS2 and ERG. This variability in the extent of the deletion may be associated with disease progression as has been observed with CML. The current study identified significant clinical associations with tumor stage and lymph node status. TMPRSS2:ERG rearranged tumors with deletion also showed a trend towards higher rates of PSA biochemical failure.

Additional experiments conducted during the course of development of the present invention explored the risk of developing metastases or prostate cancer specific death based on the presence of the TMPRSS2:ERG gene fusion in a watchful waiting cohort of early prostate cancers with long term follow-up. The frequency of the TMPRSS2:ERG gene fusion was assessed using 92 cases. The frequency of TMPRSS2:ERG gene fusion in this population-based cohort was 15.2% (14/92), lower than the 50% frequency observed in two hospital-based cohorts. The present invention is not limited to a particular mechanism. Indeed, an understanding of the mechanism is not necessary to practice the present invention. Nonetheless, this difference in TMPRSS2:ERG gene fusion prostate cancers may be due to ethnic and racial genetic differences. These differences may also be explained by the lower percentage of high grade cases in this watchful waiting cohort as compared to the other non-population based studies.

A significant association between TMPRSS2:ERG gene fusion and development of distant metastases and prostate cancer specific death was observed with a cumulative incidence ratio of 3.6 (P=0.004, 95% confidence interval=1.5 to 8.9). These data suggest that TMPRSS2:ERG gene fusion prostate cancers have a more aggressive phenotype. Further experiments indicated that genomic deletions in the TMPRSS2:ERG gene fusion were correlated with advanced and/or metastatic prostate cancer (See e.g., Example 5).

The present invention has also demonstrated that androgen can induce the overexpression of ERG, presumably through AREs, in a TMPRSS2-ERG-positive cell line. The present invention is not limited to a particular mechanism. Indeed, an understanding of the mechanism is not necessary to practice the present invention. Nonetheless, collectively, the results suggest that dysregulation of ETS family activity through AREs upstream of TMPRSS2 may drive prostate cancer development.

It is contemplated that the presence, molecular sub-type or amount of gene fusion expression is correlated with the stage, aggressiveness or progression of the disease, or the presence or risk of metastasis. It is further contemplated that similar recurrent gene fusions involving ETS family member genes occur in other epithelial cancers.

II. Antibodies

The gene fusion proteins of the present invention, including fragments, derivatives and analogs thereof, may be used as immunogens to produce antibodies having use in the diagnostic, research, and therapeutic methods described below. The antibodies may be polyclonal or monoclonal, chimeric, humanized, single chain or Fab fragments. Various procedures known to those of ordinary skill in the art may be used for the production and labeling of such antibodies and fragments. See, e.g., Burns, ed., *Immunochemical Protocols, 3$^{rd}$ ed.*, Humana Press (2005); Harlow and Lane, *Antibodies: A Laboratory Manual*, Cold Spring Harbor Laboratory (1988); Kozbor et al., *Immunology Today* 4: 72 (1983); Köhler and Milstein, *Nature* 256: 495 (1975). Antibodies or fragments exploiting the differences between the truncated ETS family member protein or chimeric protein and their respective native proteins are particularly preferred.

III. Diagnostic Applications

The present invention provides DNA, RNA and protein based diagnostic methods that either directly or indirectly detect the gene fusions. The present invention also provides compositions and kits for diagnostic purposes.

The diagnostic methods of the present invention may be qualitative or quantitative. Quantitative diagnostic methods may be used, for example, to discriminate between indolent and aggressive cancers via a cutoff or threshold level. Where applicable, qualitative or quantitative diagnostic methods may also include amplification of target, signal or intermediary (e.g., a universal primer).

An initial assay may confirm the presence of a gene fusion but not identify the specific fusion. A secondary assay is then performed to determine the identity of the particular fusion, if desired. The second assay may use a different detection technology than the initial assay.

The gene fusions of the present invention may be detected along with other markers in a multiplex or panel format. Markers are selected for their predictive value alone or in combination with the gene fusions. Exemplary prostate cancer markers include, but are not limited to: AMACR/P504S (U.S. Pat. No. 6,262,245); PCA3 (U.S. Pat. No. 7,008,765); PCGEM1 (U.S. Pat. No. 6,828,429); prostein/P501S, P503S, P504S, P509S, P510S, prostase/P703P, P710P (U.S. Publication No. 20030185830); and, those disclosed in U.S. Pat. Nos. 5,854,206 and 6,034,218, and U.S. Publication No. 20030175736, each of which is herein incorporated by reference in its entirety. Markers for other cancers, diseases, infections, and metabolic conditions are also contemplated for inclusion in a multiplex of panel format.

The diagnostic methods of the present invention may also be modified with reference to data correlating particular gene fusions with the stage, aggressiveness or progression of the disease or the presence or risk of metastasis. Ultimately, the information provided by the methods of the present invention will assist a physician in choosing the best course of treatment for a particular patient.

A. Sample

Any patient sample suspected of containing the gene fusions may be tested according to the methods of the present invention. By way of non-limiting examples, the sample may be tissue (e.g., a prostate biopsy sample or a tissue sample obtained by prostatectomy), blood, urine, semen, prostatic secretions or a fraction thereof (e.g., plasma, serum, urine supernatant, urine cell pellet or prostate cells). A urine sample is preferably collected immediately following an attentive digital rectal examination (DRE), which causes prostate cells from the prostate gland to shed into the urinary tract.

The patient sample typically requires preliminary processing designed to isolate or enrich the sample for the gene fusions or cells that contain the gene fusions. A variety of techniques known to those of ordinary skill in the art may be used for this purpose, including but not limited: centrifugation; immunocapture; cell lysis; and, nucleic acid target capture (See, e.g., EP Pat. No. 1 409 727, herein incorporated by reference in its entirety).

B. DNA and RNA Detection

The gene fusions of the present invention may be detected as chromosomal rearrangements of genomic DNA or chimeric mRNA using a variety of nucleic acid techniques known to those of ordinary skill in the art, including but not limited to: nucleic acid sequencing; nucleic acid hybridization; and, nucleic acid amplification.

1. Sequencing

Illustrative non-limiting examples of nucleic acid sequencing techniques include, but are not limited to, chain terminator (Sanger) sequencing and dye terminator sequencing. Those of ordinary skill in the art will recognize that because RNA is less stable in the cell and more prone to nuclease attack experimentally RNA is usually reverse transcribed to DNA before sequencing.

Chain terminator sequencing uses sequence-specific termination of a DNA synthesis reaction using modified nucleotide substrates. Extension is initiated at a specific site on the template DNA by using a short radioactive, or other labeled, oligonucleotide primer complementary to the template at that region. The oligonucleotide primer is extended using a DNA polymerase, standard four deoxynucleotide bases, and a low concentration of one chain terminating nucleotide, most commonly a di-deoxynucleotide. This reaction is repeated in four separate tubes with each of the bases taking turns as the di-deoxynucleotide. Limited incorporation of the chain terminating nucleotide by the DNA polymerase results in a series of related DNA fragments that are terminated only at positions where that particular di-deoxynucleotide is used. For each reaction tube, the fragments are size-separated by electrophoresis in a slab polyacrylamide gel or a capillary tube filled with a viscous polymer. The sequence is determined by reading which lane produces a visualized mark from the labeled primer as you scan from the top of the gel to the bottom.

Dye terminator sequencing alternatively labels the terminators. Complete sequencing can be performed in a single reaction by labeling each of the di-deoxynucleotide chain-terminators with a separate fluorescent dye, which fluoresces at a different wavelength.

2. Hybridization

Illustrative non-limiting examples of nucleic acid hybridization techniques include, but are not limited to, in situ hybridization (ISH), microarray, and Southern or Northern blot.

In situ hybridization (ISH) is a type of hybridization that uses a labeled complementary DNA or RNA strand as a probe to localize a specific DNA or RNA sequence in a portion or section of tissue (in situ), or, if the tissue is small enough, the entire tissue (whole mount ISH). DNA ISH can be used to determine the structure of chromosomes. RNA ISH is used to measure and localize mRNAs and other transcripts within tissue sections or whole mounts. Sample cells and tissues are usually treated to fix the target transcripts in place and to increase access of the probe. The probe hybridizes to the target sequence at elevated temperature, and then the excess probe is washed away. The probe that was labeled with either radio-, fluorescent- or antigen-labeled bases is localized and quantitated in the tissue using either autoradiography, fluorescence microscopy or immunohistochemistry, respectively. ISH can also use two or more probes, labeled with radioactivity or the other non-radioactive labels, to simultaneously detect two or more transcripts.

2.1 Fish

In some embodiments, fusion sequences are detected using fluorescence in situ hybridization (FISH). The preferred FISH assays for the present invention utilize bacterial artificial chromosomes (BACs). These have been used extensively in the human genome sequencing project (see *Nature* 409: 953-958 (2001)) and clones containing specific BACs are available through distributors that can be located through many sources, e.g., NCBI. Each BAC clone from the human genome has been given a reference name that unambiguously identifies it. These names can be used to find a corresponding GenBank sequence and to order copies of the clone from a distributor.

In some embodiments, the detection assay is a FISH assay utilizing a probe for ETV1 (e.g., bac RP11-692L4), a set of probes for c-ERG:t-ERG break apart (e.g., bac RP11-24A11 and as a probe for t-ERG RP11-372O17 or RP11-137J13). In other embodiments, the FISH assay is performed by testing for ETV1 deletion or amplification with a set of probes, wherein one probe spans the ETV1 locus (e.g., bac RP11-692L4) and the other probe hybridizes to chromosome 7 (e.g., a probe on the centromere of the chromosome). In still further embodiments, the method is performed by testing for ERG deletion or amplification with a set of probes, one spanning the ERG locus (e.g., bac RP11-476D17) and one reference probe on chromosome 21 (e.g., PR11-32L6; RP11-752M23; RP11-1107H21; RP11-639A7 or RP11-1077M21). In yet other embodiments, the method is performed by testing for TMPRSS2 deletion/amplification with a set of probes, one spanning the TMPRSS2 (e.g., RP11-121A5; RP11-120C17; PR11-814F13; or RR11-535H11) locus and one reference probe on chromosome 21 (e.g., PR11-32L6; RP11-752M23; RP11-1107H21; RP11-639A7 or RP11-1077M21). In some embodiments, the method further comprises a hybridization using a probe selected from the group including, but not limited to RP11-121A5; RP11-120C17; PR11-814F13; and RR11-535H11.

The present invention further provides a method of performing a FISH assay on human prostate cells, human prostate tissue or on the fluid surrounding said human prostate cells or human prostate tissue. In some embodiments, the assay comprises a hybridization step utilizing a probe selected from the group including, but not limited to, RP11-372O17; RP11-137J13; RP11-692L4; RP11-476D17; PR11-32L6; RP11-752M23; RP11-1107H21; RP11-639A7; RP11-1077M21; RP11-121A5; RP11-120C17; PR11-814F13; and RR11-535H11.

Specific BAC clones that can be used in FISH protocols to detect rearrangements relevant to the present invention are as follows:

For testing for an ETV1-TMPRSS2 fusion, one probe spanning the ETV1 and one spanning the TMPRSS2 locus may be used:
BAC for ETV1: RP11-692L4
BAC for TMPRSS2: RP11-121A5, (RP11-120C17, PR11-814F13, RR11-535H11)
Testing ERG translocation with set of probes for c-ERG: t-ERG break apart:
BAC for c-ERG: RP11-24A11
BACs for t-ERG: RP11-372O17, RP11-137J13
Testing ETV1 deletion/amplification with set of probes, one spanning the ETV1 locus and one reference probe on chromosome 7:
BAC for ETV1: RP11-692L4
Testing ERG deletion/amplification with set of probes, one spanning the ERG locus and one reference probe on chromosome 21:
BAC for ERG: RP11-476D17
BACs for reference probe on chromosome 21: *
Testing TMPRSS2 deletion/amplification with set of probes, one spanning the TMPRSS2 locus and one reference probe on chromosome 21:
BACs for TMPRSS2: RP11-121A5, (RP11-120C17, PR11-814F13, RR11-535H11)
BACs for reference probe on chromosome 21: PR1'-32L6, RP11-752M23, RP11-1107H21, RP11-639A7, (RP11-1077M21).

The most preferred probes for detecting a deletion mutation resulting in a fusion between TMPRSS2 and ERG are RP11-24A11 and RP11-137J13. These probes, or those described above, are labeled with appropriate fluorescent or other markers and then used in hybridizations. The Examples section provided herein sets forth one particular protocol that is effective for measuring deletions but one of skill in the art will recognize that many variations of this assay can be used equally well. Specific protocols are well known in the art and can be readily adapted for the present invention. Guidance regarding methodology may be obtained from many references including: *In situ Hybridization: Medical Applications* (eds. G. R. Coulton and J. de Belleroche), Kluwer Academic Publishers, Boston (1992); *In situ Hybridization: In Neurobiology; Advances in Methodology* (eds. J. H. Eberwine, K. L. Valentino, and J. D. Barchas), Oxford University Press Inc., England (1994); *In situ Hybridization: A Practical Approach* (ed. D. G. Wilkinson), Oxford University Press Inc., England (1992)); Kuo, et al., *Am. J. Hum. Genet.* 49:112-119 (1991); Klinger, et al., *Am. J. Hum. Genet.* 51:55-65 (1992); and Ward, et al., *Am. J. Hum. Genet.* 52:854-865 (1993)). There are also kits that are commercially available and that provide protocols for performing FISH assays (available from e.g., Oncor, Inc., Gaithersburg, Md.). Patents providing guidance on methodology include U.S. Pat. Nos. 5,225,326; 5,545,524; 6,121,489 and 6,573,043. All of these references are hereby incorporated by reference in their entirety and may be used along with similar references in the art and with the information provided in the Examples section herein to establish procedural steps convenient for a particular laboratory.

Table 13 below shows additional BAC clones that find use as FISH probes.

TABLE 13

| Gene | Chromosome | RefSeq | 5' BAC | 3' BAC | Paired |
|---|---|---|---|---|---|
| EHF | 11p13 | NM_012153 | RP5-1135K18 | RP5-1002E13 | 2 |
| ELF1 | 13q14 | NM_172373 | RP11-88n4 | RP11-53f19 | |
| ELF2 | 4q28 | NM_201999.1 | RP11-22o8 | RP11-375P1 | |
| ELF3 | 1q32 | NM_004433 | RP11-25B7 | RP11-246J15 | |
| ELF4 | Xq25 | NM_001421 | RP5-875H3 | RP4-753P9 | |
| ELF5 | 11p13 | NM_001422.2 | RP5-1002E13 | RP5-1135K18 | 2 |
| ELK1 | Xp11 | NM_005229 | RP1-54B20 | RP1-306D1 | |
| ELK3 | 12q22 | NM_005230 | RP11-69E3 | RP11-510I5 | |
| ELK4 | 1q32 | NM_001973.2 | RP11-131E5 | RP11-249h15 | |
| ERF | 19q13 | NM_006494.1 | RP11-208I3 | RP11-317E13 | |
| ERG | 21q22 | NM_004449.3 | RP11-137J13 | RP11-24A11 | 1 |
| ETS1 | 11q24 | NM_005238.2 | RP11-254C5 | RP11-112m22 | |
| ETS2 | 21q22 | NM_005239.4 | RP11-24A11 | RP11-137J13 | 1 |
| ETV1 | 7p21 | NM_004956.3 | RP11-1149J13 | RP11-34C22 | |
| ETV2 | 19q13 | NM_014209.1 | RP11-32h17 | RP11-92j4 | |
| ETV3 | 1q23 | NM_005240.1 | RP11-91G5 | RP11-1038N13 | 3 |
| ETV4 | 17q21 | NM_001986.1 | RP11-436J4 | RP11-100E5 | |
| ETV5 | 3q27 | NM_004454.1 | RP11-379C23 | RP11-1144N13 | |
| ETV6 | 12p13 | NM_001987.3 | RP11-90N7 | RP11-59h1 | |
| ETV7 | 6p21 | NM_016135.2 | RP3-431A14 | RP1-179N16 | |
| FEV | 2q35 | NM_017521.2 | RP11-316O14 | RP11-129D2 | |
| FLI1 | 11q24 | NM_002017.2 | RP11-112M22 | RP11-75P14 | |
| FLJ16478 | 1q23 | NM_001004341 | RP11-91G5 | RP11-1038N13 | 3 |
| SPDEF | 6p21 | NM_012391.1 | RP11-79j23 | RP11-119c22 | |
| SPI1 | 11p11 | NM_016135.2 | RP11-56e13 | RP11-29o22 | |
| SPIB | 19q13 | NM_003121.2 | RP11-510I16 | RP11-26P14 | |
| SPIC | 12q23 | NM_152323.1 | RP11-426H24 | RP11-938C1 | |
| TMPRSS2 | 21q22 | NM_005656.2 | RP11-35C4 | RP11-120C17 | |

2.2 Microarrays

Different kinds of biological assays are called microarrays including, but not limited to: DNA microarrays (e.g., cDNA microarrays and oligonucleotide microarrays); protein microarrays; tissue microarrays; transfection or cell microarrays; chemical compound microarrays; and, antibody microarrays. A DNA microarray, commonly known as gene chip, DNA chip, or biochip, is a collection of microscopic DNA spots attached to a solid surface (e.g., glass, plastic or silicon chip) forming an array for the purpose of expression profiling or monitoring expression levels for thousands of genes simultaneously. The affixed DNA segments are known as probes, thousands of which can be used in a single DNA microarray. Microarrays can be used to identify disease genes by comparing gene expression in disease and normal cells. Microarrays can be fabricated using a variety of technologies, including but not limiting: printing with fine-pointed pins onto glass slides; photolithography using pre-made masks; photolithography using dynamic micromirror devices; ink jet printing; or, electrochemistry on microelectrode arrays.

Southern and Northern blotting is used to detect specific DNA or RNA sequences, respectively. DNA or RNA extracted from a sample is fragmented, electrophoretically separated on a matrix gel, and transferred to a membrane filter. The filter bound DNA or RNA is subject to hybridization with a labeled probe complementary to the sequence of interest. Hybridized probe bound to the filter is detected. A variant of the procedure is the reverse Northern blot, in which the substrate nucleic acid that is affixed to the membrane is a collection of isolated DNA fragments and the probe is RNA extracted from a tissue and labeled.

3. Amplification

Chromosomal rearrangements of genomic DNA and chimeric mRNA may be amplified prior to or simultaneous with detection. Illustrative non-limiting examples of nucleic acid amplification techniques include, but are not limited to, polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA). Those of ordinary skill in the art will recognize that certain amplification techniques (e.g., PCR) require that RNA be reversed transcribed to DNA prior to amplification (e.g., RT-PCR), whereas other amplification techniques directly amplify RNA (e.g., TMA and NASBA).

The polymerase chain reaction (U.S. Pat. Nos. 4,683,195, 4,683,202, 4,800,159 and 4,965,188, each of which is herein incorporated by reference in its entirety), commonly referred to as PCR, uses multiple cycles of denaturation, annealing of primer pairs to opposite strands, and primer extension to exponentially increase copy numbers of a target nucleic acid sequence. In a variation called RT-PCR, reverse transcriptase (RT) is used to make a complementary DNA (cDNA) from mRNA, and the cDNA is then amplified by PCR to produce multiple copies of DNA. For other various permutations of PCR see, e.g., U.S. Pat. Nos. 4,683,195, 4,683,202 and 4,800, 159; Mullis et al., *Meth. Enzymol.* 155: 335 (1987); and, Murakawa et al., *DNA* 7: 287 (1988), each of which is herein incorporated by reference in its entirety.

Transcription mediated amplification (U.S. Pat. Nos. 5,480,784 and 5,399,491, each of which is herein incorporated by reference in its entirety), commonly referred to as TMA, synthesizes multiple copies of a target nucleic acid sequence autocatalytically under conditions of substantially constant temperature, ionic strength, and pH in which multiple RNA copies of the target sequence autocatalytically generate additional copies. See, e.g., U.S. Pat. Nos. 5,399,491 and 5,824,518, each of which is herein incorporated by reference in its entirety. In a variation described in U.S. Publ. No. 20060046265 (herein incorporated by reference in its entirety), TMA optionally incorporates the use of blocking moieties, terminating moieties, and other modifying moieties to improve TMA process sensitivity and accuracy.

The ligase chain reaction (Weiss, R., *Science* 254: 1292 (1991), herein incorporated by reference in its entirety), commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Strand displacement amplification (Walker, G. et al., *Proc. Natl. Acad. Sci. USA* 89: 392-396 (1992); U.S. Pat. Nos. 5,270,184 and 5,455,166, each of which is herein incorporated by reference in its entirety), commonly referred to as SDA, uses cycles of annealing pairs of primer sequences to opposite strands of a target sequence, primer extension in the presence of a dNTPαS to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (EP Pat. No. 0 684 315).

Other amplification methods include, for example: nucleic acid sequence based amplification (U.S. Pat. No. 5,130,238, herein incorporated by reference in its entirety), commonly referred to as NASBA; one that uses an RNA replicase to amplify the probe molecule itself (Lizardi et al., *BioTechnol.* 6: 1197 (1988), herein incorporated by reference in its entirety), commonly referred to as Qβ replicase; a transcription based amplification method (Kwoh et al., *Proc. Natl. Acad. Sci. USA* 86:1173 (1989)); and, self-sustained sequence replication (Guatelli et al., *Proc. Natl. Acad. Sci. USA* 87: 1874 (1990), each of which is herein incorporated by reference in its entirety). For further discussion of known amplification methods see Persing, David H., "In Vitro Nucleic Acid Amplification Techniques" in *Diagnostic Medical Microbiology: Principles and Applications* (Persing et al., Eds.), pp. 51-87 (American Society for Microbiology, Washington, D.C. (1993)).

4. Detection Methods

Non-amplified or amplified gene fusion nucleic acids can be detected by any conventional means. For example, the gene fusions can be detected by hybridization with a detectably labeled probe and measurement of the resulting hybrids. Illustrative non-limiting examples of detection methods are described below.

One illustrative detection method, the Hybridization Protection Assay (HPA) involves hybridizing a chemiluminescent oligonucleotide probe (e.g., an acridinium ester-labeled (AE) probe) to the target sequence, selectively hydrolyzing the chemiluminescent label present on unhybridized probe, and measuring the chemiluminescence produced from the remaining probe in a luminometer. See, e.g., U.S. Pat. No. 5,283,174 and Norman C. Nelson et al., Nonisotopic Probing, Blotting, and Sequencing, ch. 17 (Larry J. Kricka ed., 2d ed. 1995, each of which is herein incorporated by reference in its entirety).

Another illustrative detection method provides for quantitative evaluation of the amplification process in real-time. Evaluation of an amplification process in "real-time" involves determining the amount of amplicon in the reaction mixture either continuously or periodically during the amplification reaction, and using the determined values to calculate the amount of target sequence initially present in the sample. A variety of methods for determining the amount of initial target sequence present in a sample based on real-time amplification are well known in the art. These include methods disclosed in U.S. Pat. Nos. 6,303,305 and 6,541,205, each of which is herein incorporated by reference in its entirety. Another method for determining the quantity of target sequence initially present in a sample, but which is not based on a real-time amplification, is disclosed in U.S. Pat. No. 5,710,029, herein incorporated by reference in its entirety.

Amplification products may be detected in real-time through the use of various self-hybridizing probes, most of which have a stem-loop structure. Such self-hybridizing probes are labeled so that they emit differently detectable signals, depending on whether the probes are in a self-hybridized state or an altered state through hybridization to a target sequence. By way of non-limiting example, "molecular torches" are a type of self-hybridizing probe that includes distinct regions of self-complementarity (referred to as "the target binding domain" and "the target closing domain") which are connected by a joining region (e.g., non-nucleotide linker) and which hybridize to each other under predetermined hybridization assay conditions. In a preferred embodiment, molecular torches contain single-stranded base regions in the target binding domain that are from 1 to about 20 bases in length and are accessible for hybridization to a target sequence present in an amplification reaction under strand displacement conditions. Under strand displacement conditions, hybridization of the two complementary regions, which may be fully or partially complementary, of the molecular torch is favored, except in the presence of the target sequence, which will bind to the single-stranded region present in the target binding domain and displace all or a portion of the target closing domain. The target binding domain and the target closing domain of a molecular torch include a detectable label or a pair of interacting labels (e.g., luminescent/quencher) positioned so that a different signal is produced when the molecular torch is self-hybridized than when the molecular torch is hybridized to the target sequence, thereby permitting detection of probe:target duplexes in a test sample in the presence of unhybridized molecular torches. Molecular torches and a variety of types of interacting label pairs are disclosed in U.S. Pat. No. 6,534,274, herein incorporated by reference in its entirety.

Another example of a detection probe having self-complementarity is a "molecular beacon." Molecular beacons include nucleic acid molecules having a target complementary sequence, an affinity pair (or nucleic acid arms) holding the probe in a closed conformation in the absence of a target sequence present in an amplification reaction, and a label pair that interacts when the probe is in a closed conformation. Hybridization of the target sequence and the target complementary sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular beacons are disclosed in U.S. Pat. Nos. 5,925,517 and 6,150,097, herein incorporated by reference in its entirety.

Other self-hybridizing probes are well known to those of ordinary skill in the art. By way of non-limiting example, probe binding pairs having interacting labels, such as those disclosed in U.S. Pat. No. 5,928,862 (herein incorporated by reference in its entirety) might be adapted for use in the present invention. Probe systems used to detect single nucleotide polymorphisms (SNPs) might also be utilized in the present invention. Additional detection systems include "molecular switches," as disclosed in U.S. Publ. No. 20050042638, herein incorporated by reference in its entirety. Other probes, such as those comprising intercalating dyes and/or fluorochromes, are also useful for detection of amplification products in the present invention. See, e.g., U.S. Pat. No. 5,814,447 (herein incorporated by reference in its entirety).

C. Protein Detection

The gene fusions of the present invention may be detected as truncated ETS family member proteins or chimeric proteins using a variety of protein techniques known to those of ordinary skill in the art, including but not limited to: protein sequencing; and, immunoassays.

1. Sequencing

Illustrative non-limiting examples of protein sequencing techniques include, but are not limited to, mass spectrometry and Edman degradation.

Mass spectrometry can, in principle, sequence any size protein but becomes computationally more difficult as size increases. A protein is digested by an endoprotease, and the resulting solution is passed through a high pressure liquid chromatography column. At the end of this column, the solution is sprayed out of a narrow nozzle charged to a high positive potential into the mass spectrometer. The charge on the droplets causes them to fragment until only single ions remain. The peptides are then fragmented and the mass-charge ratios of the fragments measured. The mass spectrum is analyzed by computer and often compared against a database of previously sequenced proteins in order to determine the sequences of the fragments. The process is then repeated with a different digestion enzyme, and the overlaps in sequences are used to construct a sequence for the protein.

In the Edman degradation reaction, the peptide to be sequenced is adsorbed onto a solid surface (e.g., a glass fiber coated with polybrene). The Edman reagent, phenylisothiocyanate (PTC), is added to the adsorbed peptide, together with a mildly basic buffer solution of 12% trimethylamine, and reacts with the amine group of the N-terminal amino acid. The terminal amino acid derivative can then be selectively detached by the addition of anhydrous acid. The derivative isomerizes to give a substituted phenylthiohydantoin, which can be washed off and identified by chromatography, and the cycle can be repeated. The efficiency of each step is about 98%, which allows about 50 amino acids to be reliably determined.

2. Immunoassays

Illustrative non-limiting examples of immunoassays include, but are not limited to: immunoprecipitation; Western blot; ELISA; immunohistochemistry; immunocytochemistry; flow cytometry; and, immuno-PCR. Polyclonal or monoclonal antibodies detectably labeled using various techniques known to those of ordinary skill in the art (e.g., colorimetric, fluorescent, chemiluminescent or radioactive) are suitable for use in the immunoassays.

Immunoprecipitation is the technique of precipitating an antigen out of solution using an antibody specific to that antigen. The process can be used to identify protein complexes present in cell extracts by targeting a protein believed to be in the complex. The complexes are brought out of solution by insoluble antibody-binding proteins isolated initially from bacteria, such as Protein A and Protein G. The antibodies can also be coupled to sepharose beads that can easily be isolated out of solution. After washing, the precipitate can be analyzed using mass spectrometry, Western blotting, or any number of other methods for identifying constituents in the complex.

A Western blot, or immunoblot, is a method to detect protein in a given sample of tissue homogenate or extract. It uses gel electrophoresis to separate denatured proteins by mass. The proteins are then transferred out of the gel and onto a membrane, typically polyvinyldiflroride or nitrocellulose, where they are probed using antibodies specific to the protein of interest. As a result, researchers can examine the amount of protein in a given sample and compare levels between several groups.

An ELISA, short for Enzyme-Linked ImmunoSorbent Assay, is a biochemical technique to detect the presence of an antibody or an antigen in a sample. It utilizes a minimum of two antibodies, one of which is specific to the antigen and the other of which is coupled to an enzyme. The second antibody will cause a chromogenic or fluorogenic substrate to produce a signal. Variations of ELISA include sandwich ELISA, competitive ELISA, and ELISPOT. Because the ELISA can be performed to evaluate either the presence of antigen or the presence of antibody in a sample, it is a useful tool both for determining serum antibody concentrations and also for detecting the presence of antigen.

Immunohistochemistry and immunocytochemistry refer to the process of localizing proteins in a tissue section or cell, respectively, via the principle of antigens in tissue or cells binding to their respective antibodies. Visualization is enabled by tagging the antibody with color producing or fluorescent tags. Typical examples of color tags include, but are not limited to, horseradish peroxidase and alkaline phosphatase. Typical examples of fluorophore tags include, but are not limited to, fluorescein isothiocyanate (FITC) or phycoerythrin (PE).

Flow cytometry is a technique for counting, examining and sorting microscopic particles suspended in a stream of fluid. It allows simultaneous multiparametric analysis of the physical and/or chemical characteristics of single cells flowing through an optical/electronic detection apparatus. A beam of light (e.g., a laser) of a single frequency or color is directed onto a hydrodynamically focused stream of fluid. A number of detectors are aimed at the point where the stream passes through the light beam; one in line with the light beam (Forward Scatter or FSC) and several perpendicular to it (Side Scatter (SSC) and one or more fluorescent detectors). Each suspended particle passing through the beam scatters the light in some way, and fluorescent chemicals in the particle may be excited into emitting light at a lower frequency than the light source. The combination of scattered and fluorescent light is picked up by the detectors, and by analyzing fluctuations in brightness at each detector, one for each fluorescent emission peak, it is possible to deduce various facts about the physical and chemical structure of each individual particle. FSC correlates with the cell volume and SSC correlates with the density or inner complexity of the particle (e.g., shape of the nucleus, the amount and type of cytoplasmic granules or the membrane roughness).

Immuno-polymerase chain reaction (IPCR) utilizes nucleic acid amplification techniques to increase signal generation in antibody-based immunoassays. Because no protein equivalence of PCR exists, that is, proteins cannot be replicated in the same manner that nucleic acid is replicated during PCR, the only way to increase detection sensitivity is by signal amplification. The target proteins are bound to antibodies which are directly or indirectly conjugated to oligonucleotides. Unbound antibodies are washed away and the remaining bound antibodies have their oligonucleotides amplified. Protein detection occurs via detection of amplified oligonucleotides using standard nucleic acid detection methods, including real-time methods.

D. Data Analysis

In some embodiments, a computer-based analysis program is used to translate the raw data generated by the detection assay (e.g., the presence, absence, or amount of a given marker or markers) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression data), specific for the diagnostic or prognostic information desired for the subject.

The profile data is then prepared in a format suitable for interpretation by a treating clinician. For example, rather than providing raw expression data, the prepared format may represent a diagnosis or risk assessment (e.g., likelihood of cancer being present) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease.

E. In Vivo Imaging

The gene fusions of the present invention may also be detected using in vivo imaging techniques, including but not limited to: radionuclide imaging; positron emission tomography (PET); computerized axial tomography, X-ray or magnetic resonance imaging method, fluorescence detection, and chemiluminescent detection. In some embodiments, in vivo imaging techniques are used to visualize the presence of or expression of cancer markers in an animal (e.g., a human or non-human mammal). For example, in some embodiments, cancer marker mRNA or protein is labeled using a labeled antibody specific for the cancer marker. A specifically bound and labeled antibody can be detected in an individual using an in vivo imaging method, including, but not limited to, radionuclide imaging, positron emission tomography, computerized axial tomography, X-ray or magnetic resonance imaging method, fluorescence detection, and chemiluminescent detection. Methods for generating antibodies to the cancer markers of the present invention are described below.

The in vivo imaging methods of the present invention are useful in the diagnosis of cancers that express the cancer markers of the present invention (e.g., prostate cancer). In vivo imaging is used to visualize the presence of a marker indicative of the cancer. Such techniques allow for diagnosis without the use of an unpleasant biopsy. The in vivo imaging methods of the present invention are also useful for providing prognoses to cancer patients. For example, the presence of a marker indicative of cancers likely to metastasize can be detected. The in vivo imaging methods of the present invention can further be used to detect metastatic cancers in other parts of the body.

In some embodiments, reagents (e.g., antibodies) specific for the cancer markers of the present invention are fluorescently labeled. The labeled antibodies are introduced into a subject (e.g., orally or parenterally). Fluorescently labeled antibodies are detected using any suitable method (e.g., using the apparatus described in U.S. Pat. No. 6,198,107, herein incorporated by reference).

In other embodiments, antibodies are radioactively labeled. The use of antibodies for in vivo diagnosis is well known in the art. Sumerdon et al., (Nucl. Med. Biol 17:247-254 [1990] have described an optimized antibody-chelator for the radioimmunoscintographic imaging of tumors using Indium-111 as the label. Griffin et al., (J Clin One 9:631-640 [1991]) have described the use of this agent in detecting tumors in patients suspected of having recurrent colorectal cancer. The use of similar agents with paramagnetic ions as labels for magnetic resonance imaging is known in the art (Lauffer, Magnetic Resonance in Medicine 22:339-342 [1991]). The label used will depend on the imaging modality chosen. Radioactive labels such as Indium-111, Technetium-99m, or Iodine-131 can be used for planar scans or single photon emission computed tomography (SPECT). Positron emitting labels such as Fluorine-19 can also be used for positron emission tomography (PET). For MRI, paramagnetic ions such as Gadolinium (III) or Manganese (II) can be used.

Radioactive metals with half-lives ranging from 1 hour to 3.5 days are available for conjugation to antibodies, such as scandium-47 (3.5 days) gallium-67 (2.8 days), gallium-68 (68 minutes), technetiium-99m (6 hours), and indium-111 (3.2 days), of which gallium-67, technetium-99m, and indium-111 are preferable for gamma camera imaging, gallium-68 is preferable for positron emission tomography.

A useful method of labeling antibodies with such radiometals is by means of a bifunctional chelating agent, such as diethylenetriaminepentaacetic acid (DTPA), as described, for example, by Khaw et al. (Science 209:295 [1980]) for In-111 and Tc-99m, and by Scheinberg et al. (Science 215:1511 [1982]). Other chelating agents may also be used, but the 1-(p-carboxymethoxybenzyl)EDTA and the carboxycarbonic anhydride of DTPA are advantageous because their use permits conjugation without affecting the antibody's immunoreactivity substantially.

Another method for coupling DPTA to proteins is by use of the cyclic anhydride of DTPA, as described by Hnatowich et al. (Int. J. Appl. Radiat. Isot. 33:327 [1982]) for labeling of albumin with In-111, but which can be adapted for labeling of antibodies. A suitable method of labeling antibodies with Tc-99m which does not use chelation with DPTA is the pre-tinning method of Crockford et al., (U.S. Pat. No. 4,323,546, herein incorporated by reference).

A preferred method of labeling immunoglobulins with Tc-99m is that described by Wong et al. (Int. J. Appl. Radiat. Isot., 29:251 [1978]) for plasma protein, and recently applied successfully by Wong et al. (J. Nucl. Med., 23:229 [1981]) for labeling antibodies.

In the case of the radiometals conjugated to the specific antibody, it is likewise desirable to introduce as high a proportion of the radiolabel as possible into the antibody molecule without destroying its immunospecificity. A further improvement may be achieved by effecting radiolabeling in the presence of the specific cancer marker of the present invention, to insure that the antigen binding site on the antibody will be protected. The antigen is separated after labeling.

In still further embodiments, in vivo biophotonic imaging (Xenogen, Almeda, Calif.) is utilized for in vivo imaging. This real-time in vivo imaging utilizes luciferase. The luciferase gene is incorporated into cells, microorganisms, and animals (e.g., as a fusion protein with a cancer marker of the present invention). When active, it leads to a reaction that emits light. A CCD camera and software is used to capture the image and analyze it.

F. Compositions & Kits

Compositions for use in the diagnostic methods of the present invention include, but are not limited to, probes, amplification oligonucleotides, and antibodies. Particularly preferred compositions detect a product only when an ARG fuses to ETS family member gene. These compositions include: a single labeled probe comprising a sequence that hybridizes to the junction at which a 5' portion from a transcriptional regulatory region of an ARG fuses to a 3' portion from an ETS family member gene (i.e., spans the gene fusion junction); a pair of amplification oligonucleotides wherein the first amplification oligonucleotide comprises a sequence that hybridizes to a transcriptional regulatory region of an ARG and the second amplification oligonucleotide comprises a sequence that hybridizes to an ETS family member gene; an antibody to an amino-terminally truncated ETS family member protein resulting from a fusion of a transcriptional regulatory region of an ARG to an ETS family member gene; or, an antibody to a chimeric protein having an amino-terminal portion from a transcriptional regulatory region of an ARG and a carboxy-terminal portion from an ETS family member gene. Other useful compositions, however, include: a pair of labeled probes wherein the first labeled probe comprises a sequence that hybridizes to a transcriptional regulatory region of an ARG and the second labeled probe comprises a sequence that hybridizes to an ETS family member gene.

Any of these compositions, alone or in combination with other compositions of the present invention, may be provided in the form of a kit. For example, the single labeled probe and pair of amplification oligonucleotides may be provided in a kit for the amplification and detection of gene fusions of the present invention. Kits may further comprise appropriate controls and/or detection reagents.

The probe and antibody compositions of the present invention may also be provided in the form of an array.

IV. Prognostic Applications

Experiments conducted during the course of development of the present invention demonstrated a close correlation between gene fusions of the present invention and the prognosis of patients with prostate cancer (See e.g., Example 5 below). Especially in cases where a fusion results from a deletion of the genomic DNA lying between TMPRSS2 and ERG, it has been found that cancer cells assume a more aggressive phenotype. Thus, in some embodiments, assays that are capable of detecting gene fusions between TMPRSS2 and ERG in which there has been a deletion of intervening DNA are used to provide prognoses and help physicians decide on an appropriate therapeutic strategy. For example, in some embodiments, patients with tumors having this particular rearrangement are treated more intensively since their prognosis is significantly worse than patients that lack the rearrangement.

Any assay may be used to determine whether cells are present having a rearrangement of the type discussed above (e.g., those described above).

Although the present invention will most preferably be used in connection with obtaining a prognosis for prostate cancer patients, other epithelial cell tumors may also be examined and the assays and probes described herein may be used in determining whether cancerous cells from these tumors have rearrangements that are likely to make them particularly aggressive, i.e., likely to be invasive and metastatic. Examples of tumors that may be characterized using this procedure include tumors of the breast, lung, colon, ovary, uterus, esophagus, stomach, liver, kidney, brain, skin and muscle. The assays will also be of value to researchers studying these cancers in cell lines and animal models.

Further experiments conducted during the course of development of the present invention demonstrated that chromosomal deletions can be detected by assaying samples to determine whether there is a loss of expression of one or more genes located in the deleted region. For example, approximately 2.8 megabases of genomic DNA is typically deleted in forming a fusion between TMPRSS2 and ERG and at least four genes lying in this area are lost when this occurs. These are the ETS2 gene, the WRB gene, the PCP4 gene and the MX1 gene. A decrease in one or more of these in cancerous prostate cells suggests a poor prognosis.

Accordingly, in some embodiments, the present invention provides a method of assaying epithelial cells for the deletion of chromosomal DNA indicative of a cancer-associated rearrangement, comprising performing a FISH assay using at least a first and a second probe, wherein the first probe is at least 15 nucleotides in length (e.g., at least 15, 20, 35, etc.); is bound to a first fluorescent label; and hybridizes under stringent conditions to a first sequence in the human genome wherein the first sequence includes at least a portion of either an androgen responsive gene (e.g., the TMPRSS2 gene) or a ETS family gene (e.g., the ERG gene, the ETV1 gene, or the ETV4 gene); and the second probe: is at least 15 nucleotides in length; is bound to a second fluorescent label that is different from the first fluorescent label; and hybridizes under stringent conditions to a second sequence in the human genome that is different from the first sequence and which includes at least a portion of an androgen responsive gene (e.g., the TMPRSS2 gene) or a ETS family gene (e.g., the ERG gene, the ETV1 gene, or the ETV4 gene).

In further embodiments, the present invention provides a method for assaying epithelial cells (e.g., prostate cells) for a deletion of genomic DNA indicative of a cancer-associated rearrangement, comprising: obtaining a test sample of epithelial cells; assaying the sample of epithelial cells to determine the level of expression of one or more genes selected from the group including, but not limited to, ETS2; WRB; PCP4; and MX1; comparing the expression level determined in step b) with the level in a control sample; and concluding that a deletion has occurred if the level of expression determined for the gene in the test sample is lower than that for a control sample.

V. Drug Screening Applications

In some embodiments, the present invention provides drug screening assays (e.g., to screen for anticancer drugs). The screening methods of the present invention utilize cancer markers identified using the methods of the present invention (e.g., including but not limited to, ERG, ETV1, ETV4, and FLI1 gene fusions with TMPRSS2). For example, in some embodiments, the present invention provides methods of screening for compounds that alter (e.g., decrease) the expression of cancer marker genes. The compounds or agents may interfere with transcription, by interacting, for example, with the promoter region. The compounds or agents may interfere with mRNA produced from the fusion (e.g., by RNA interference, antisense technologies, etc.). The compounds or agents may interfere with pathways that are upstream or downstream of the biological activity of the fusion. In some embodiments, candidate compounds are antisense or interfering RNA agents (e.g., oligonucleotides) directed against cancer markers. In other embodiments, candidate compounds are antibodies or small molecules that specifically bind to a cancer marker regulator or expression products of the present invention and inhibit its biological function.

In one screening method, candidate compounds are evaluated for their ability to alter cancer marker expression by contacting a compound with a cell expressing a cancer marker and then assaying for the effect of the candidate compounds on expression. In some embodiments, the effect of candidate compounds on expression of a cancer marker gene is assayed for by detecting the level of cancer marker mRNA expressed by the cell. mRNA expression can be detected by any suitable method. In other embodiments, the effect of candidate compounds on expression of cancer marker genes is assayed by measuring the level of polypeptide encoded by the cancer markers. The level of polypeptide expressed can be measured using any suitable method, including but not limited to, those disclosed herein.

Specifically, the present invention provides screening methods for identifying modulators, i.e., candidate or test compounds or agents (e.g., proteins, peptides, peptidomimetics, peptoids, small molecules or other drugs) which bind to cancer markers of the present invention, have an inhibitory (or stimulatory) effect on, for example, cancer marker expression or cancer marker activity, or have a stimulatory or inhibitory effect on, for example, the expression or activity of a cancer marker substrate. Compounds thus identified can be used to modulate the activity of target gene products (e.g., cancer marker genes) either directly or indirectly in a therapeutic protocol, to elaborate the biological function of the target gene product, or to identify compounds that disrupt normal target gene interactions. Compounds that inhibit the activity or expression of cancer markers are useful in the treatment of proliferative disorders, e.g., cancer, particularly prostate cancer.

In one embodiment, the invention provides assays for screening candidate or test compounds that are substrates of a cancer marker protein or polypeptide or a biologically active portion thereof. In another embodiment, the invention provides assays for screening candidate or test compounds that bind to or modulate the activity of a cancer marker protein or polypeptide or a biologically active portion thereof.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 [1994]); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al., Proc. Natl. Acad. Sci. U.S.A. 90:6909 [1993]; Erb et al., Proc. Nad. Acad. Sci. USA 91:11422 [1994]; Zuckermann et al., J. Med. Chem. 37:2678 [1994]; Cho et al., Science 261:1303 [1993]; Carrell et al., Angew. Chem. Int. Ed. Engl. 33.2059 [1994]; Carell et al., Angew. Chem. Int. Ed. Engl. 33:2061 [1994]; and Gallop et al., J. Med. Chem. 37:1233 [1994].

Libraries of compounds may be presented in solution (e.g., Houghten, Biotechniques 13:412-421 [1992]), or on beads (Lam, Nature 354:82-84 [1991]), chips (Fodor, Nature 364: 555-556 [1993]), bacteria or spores (U.S. Pat. No. 5,223,409; herein incorporated by reference), plasmids (Cull et al., Proc. Nad. Acad. Sci. USA 89:18651869 [1992]) or on phage (Scott and Smith, Science 249:386-390 [1990]; Devlin Science 249: 404-406 [1990]; Cwirla et al., Proc. Natl. Acad. Sci. 87:6378-6382 [1990]; Felici, J. Mol. Biol. 222:301 [1991]).

In one embodiment, an assay is a cell-based assay in which a cell that expresses a cancer marker mRNA or protein or biologically active portion thereof is contacted with a test compound, and the ability of the test compound to the modulate cancer marker's activity is determined. Determining the ability of the test compound to modulate cancer marker activity can be accomplished by monitoring, for example, changes in enzymatic activity, destruction or mRNA, or the like.

The ability of the test compound to modulate cancer marker binding to a compound, e.g., a cancer marker substrate or modulator, can also be evaluated. This can be accomplished, for example, by coupling the compound, e.g., the substrate, with a radioisotope or enzymatic label such that binding of the compound, e.g., the substrate, to a cancer marker can be determined by detecting the labeled compound, e.g., substrate, in a complex.

Alternatively, the cancer marker is coupled with a radio-isotope or enzymatic label to monitor the ability of a test compound to modulate cancer marker binding to a cancer marker substrate in a complex. For example, compounds (e.g., substrates) can be labeled with $^{125}I$, $^{35}S$ $^{14}C$ or $^{3}H$, either directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a cancer marker substrate) to interact with a cancer marker with or without the labeling of any of the interactants can be evaluated. For example, a microphysiometer can be used to detect the interaction of a compound with a cancer marker without the labeling of either the compound or the cancer marker (McConnell et al. Science 257:1906-1912 [1992]). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and cancer markers.

In yet another embodiment, a cell-free assay is provided in which a cancer marker protein or biologically active portion thereof is contacted with a test compound and the ability of the test compound to bind to the cancer marker protein, mRNA, or biologically active portion thereof is evaluated. Preferred biologically active portions of the cancer marker proteins or mRNA to be used in assays of the present invention include fragments that participate in interactions with substrates or other proteins, e.g., fragments with high surface probability scores.

Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FRET) (see, for example, Lakowicz et al., U.S. Pat. No. 5,631,169; Stavrianopoulos et al., U.S. Pat. No. 4,968,103; each of which is herein incorporated by reference). A fluorophore label is selected such that a first donor molecule's emitted fluorescent energy will be absorbed by a fluorescent label on a second, 'acceptor' molecule, which in turn is able to fluoresce due to the absorbed energy.

Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label should be maximal. A FRET binding event can be conveniently measured through standard fluorometric detection means well known in the art (e.g., using a fluorimeter).

In another embodiment, determining the ability of the cancer marker protein or mRNA to bind to a target molecule can be accomplished using real-time Biomolecular Interaction Analysis (BIA) (see, e.g., Sjolander and Urbaniczky, Anal. Chem. 63:2338-2345 [1991] and Szabo et al. Curr. Opin. Struct. Biol. 5:699-705 [1995]). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal that can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize cancer markers, an anti-cancer marker antibody or its target molecule to facilitate separation of complexed from non-complexed forms of one or both of the proteins, as well as to accommodate automation of the assay. Binding of a test compound to a cancer marker protein, or interaction of a cancer marker protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase-cancer marker fusion proteins or glutathione-S-transferase/target fusion proteins can be adsorbed onto glutathione Sepharose beads (Sigma Chemical, St. Louis, Mo.) or glutathione-derivatized microtiter plates, which are then combined with the test compound or the test compound and either the non-adsorbed target protein or cancer marker protein, and the mixture incubated under conditions conducive for complex formation (e.g., at physiological conditions for salt and pH). Following incubation, the beads or microtiter plate wells are washed to remove any unbound components, the matrix immobilized in the case of beads, complex determined either directly or indirectly, for example, as described above.

Alternatively, the complexes can be dissociated from the matrix, and the level of cancer markers binding or activity determined using standard techniques. Other techniques for immobilizing either cancer markers protein or a target molecule on matrices include using conjugation of biotin and streptavidin. Biotinylated cancer marker protein or target molecules can be prepared from biotin-NHS (N-hydroxy-succinimide) using techniques known in the art (e.g., biotinylation kit, Pierce Chemicals, Rockford, EL), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-IgG antibody).

This assay is performed utilizing antibodies reactive with cancer marker protein or target molecules but which do not interfere with binding of the cancer markers protein to its target molecule. Such antibodies can be derivatized to the wells of the plate, and unbound target or cancer markers protein trapped in the wells by antibody conjugation. Methods for detecting such complexes, in addition to those described above for the GST-immobilized complexes, include immunodetection of complexes using antibodies reactive with the cancer marker protein or target molecule, as well as enzyme-linked assays which rely on detecting an enzymatic activity associated with the cancer marker protein or target molecule.

Alternatively, cell free assays can be conducted in a liquid phase. In such an assay, the reaction products are separated from unreacted components, by any of a number of standard techniques, including, but not limited to: differential centrifugation (see, for example, Rivas and Minton, Trends Biochem Sci 18:284-7 [1993]); chromatography (gel filtration chromatography, ion-exchange chromatography); electrophoresis (see, e.g., Ausubel et al., eds. Current Protocols in Molecular Biology 1999, J. Wiley: New York.); and immunoprecipitation (see, for example, Ausubel et al., eds. Current Protocols in Molecular Biology 1999, J. Wiley: New York). Such resins and chromatographic techniques are known to one skilled in the art (See e.g., Heegaard J. Mol. Recognit. 11:141-8 [1998]; Hageand Tweed J. Chromatogr. Biomed. Sci. Appl 699:499-525 [1997]). Further, fluorescence energy transfer may also be conveniently utilized, as described herein, to detect binding without further purification of the complex from solution.

The assay can include contacting the cancer markers protein, mRNA, or biologically active portion thereof with a known compound that binds the cancer marker to form an assay mixture, contacting the assay mixture with a test compound, and determining the ability of the test compound to interact with a cancer marker protein or mRNA, wherein determining the ability of the test compound to interact with a cancer marker protein or mRNA includes determining the ability of the test compound to preferentially bind to cancer markers or biologically active portion thereof, or to modulate the activity of a target molecule, as compared to the known compound.

To the extent that cancer markers can, in vivo, interact with one or more cellular or extracellular macromolecules, such as proteins, inhibitors of such an interaction are useful. A homogeneous assay can be used can be used to identify inhibitors.

For example, a preformed complex of the target gene product and the interactive cellular or extracellular binding partner product is prepared such that either the target gene products or their binding partners are labeled, but the signal generated by the label is quenched due to complex formation (see, e.g., U.S. Pat. No. 4,109,496, herein incorporated by reference, that utilizes this approach for immunoassays). The addition of a test substance that competes with and displaces one of the species from the preformed complex will result in the generation of a signal above background. In this way, test substances that disrupt target gene product-binding partner interaction can be identified. Alternatively, cancer markers protein can be used as a "bait protein" in a two-hybrid assay or three-hybrid assay (see, e.g., U.S. Pat. No. 5,283,317; Zervos et al., Cell 72:223-232 [1993]; Madura et al., J. Biol. Chem. 268.12046-12054 [1993]; Bartel et al., Biotechniques 14:920-924 [1993]; Iwabuchi et al., Oncogene 8:1693-1696 [1993]; and Brent WO 94/10300; each of which is herein incorporated by reference), to identify other proteins, that bind to or interact with cancer markers ("cancer marker-binding proteins" or "cancer marker-bp") and are involved in cancer marker activity. Such cancer marker-bps can be activators or inhibitors of signals by the cancer marker proteins or targets as, for example, downstream elements of a cancer markers-mediated signaling pathway.

Modulators of cancer markers expression can also be identified. For example, a cell or cell free mixture is contacted with a candidate compound and the expression of cancer marker mRNA or protein evaluated relative to the level of expression of cancer marker mRNA or protein in the absence of the candidate compound. When expression of cancer marker mRNA or protein is greater in the presence of the candidate compound than in its absence, the candidate compound is identified as a stimulator of cancer marker mRNA or protein expression. Alternatively, when expression of cancer marker mRNA or protein is less (i.e., statistically significantly less) in the presence of the candidate compound than in its absence, the candidate compound is identified as an inhibitor of cancer marker mRNA or protein expression. The level of cancer markers mRNA or protein expression can be determined by methods described herein for detecting cancer markers mRNA or protein.

A modulating agent can be identified using a cell-based or a cell free assay, and the ability of the agent to modulate the activity of a cancer markers protein can be confirmed in vivo, e.g., in an animal such as an animal model for a disease (e.g., an animal with prostate cancer or metastatic prostate cancer; or an animal harboring a xenograft of a prostate cancer from an animal (e.g., human) or cells from a cancer resulting from metastasis of a prostate cancer (e.g., to a lymph node, bone, or liver), or cells from a prostate cancer cell line.

This invention further pertains to novel agents identified by the above-described screening assays (See e.g., below description of cancer therapies). Accordingly, it is within the scope of this invention to further use an agent identified as described herein (e.g., a cancer marker modulating agent, an antisense cancer marker nucleic acid molecule, a siRNA molecule, a cancer marker specific antibody, or a cancer marker-binding partner) in an appropriate animal model (such as those described herein) to determine the efficacy, toxicity, side effects, or mechanism of action, of treatment with such an agent. Furthermore, novel agents identified by the above-described screening assays can be, e.g., used for treatments as described herein.

VI. Therapeutic Applications

In some embodiments, the present invention provides therapies for cancer (e.g., prostate cancer). In some embodiments, therapies directly or indirectly target cancer markers (e.g., including but not limited to, ERG, ETV1, and ETV4 gene fusions with TMPRSS2).

A. RNA Interference and Antisense Therapies

In some embodiments, the present invention targets the expression of cancer markers. For example, in some embodiments, the present invention employs compositions comprising oligomeric antisense or RNAi compounds, particularly oligonucleotides (e.g., those identified in the drug screening methods described above), for use in modulating the function of nucleic acid molecules encoding cancer markers of the present invention, ultimately modulating the amount of cancer marker expressed.

1. RNA Interference (RNAi)

In some embodiments, RNAi is utilized to inhibit fusion protein function. RNAi represents an evolutionary conserved cellular defense for controlling the expression of foreign genes in most eukaryotes, including humans. RNAi is typically triggered by double-stranded RNA (dsRNA) and causes sequence-specific mRNA degradation of single-stranded target RNAs homologous in response to dsRNA. The mediators of mRNA degradation are small interfering RNA duplexes (siRNAs), which are normally produced from long dsRNA by enzymatic cleavage in the cell. siRNAs are generally approximately twenty-one nucleotides in length (e.g. 21-23 nucleotides in length), and have a base-paired structure characterized by two nucleotide 3'-overhangs. Following the introduction of a small RNA, or RNAi, into the cell, it is believed the sequence is delivered to an enzyme complex called RISC(RNA-induced silencing complex). RISC recognizes the target and cleaves it with an endonuclease. It is noted that if larger RNA sequences are delivered to a cell, RNase III enzyme (Dicer) converts longer dsRNA into 21-23 nt ds siRNA fragments. In some embodiments, RNAi oligonucleotides are designed to target the junction region of fusion proteins.

Chemically synthesized siRNAs have become powerful reagents for genome-wide analysis of mammalian gene function in cultured somatic cells. Beyond their value for validation of gene function, siRNAs also hold great potential as gene-specific therapeutic agents (Tuschl and Borkhardt, Molecular Intervent. 2002; 2(3):158-67, herein incorporated by reference).

The transfection of siRNAs into animal cells results in the potent, long-lasting post-transcriptional silencing of specific genes (Caplen et al, Proc Natl Acad Sci U.S.A. 2001; 98: 9742-7; Elbashir et al., Nature. 2001; 411:494-8; Elbashir et al., Genes Dev. 2001; 15: 188-200; and Elbashir et al., EMBO J. 2001; 20: 6877-88, all of which are herein incorporated by reference). Methods and compositions for performing RNAi with siRNAs are described, for example, in U.S. Pat. No. 6,506,559, herein incorporated by reference.

siRNAs are extraordinarily effective at lowering the amounts of targeted RNA, and by extension proteins, frequently to undetectable levels. The silencing effect can last several months, and is extraordinarily specific, because one nucleotide mismatch between the target RNA and the central region of the siRNA is frequently sufficient to prevent silencing (Brummelkamp et al, Science 2002; 296:550-3; and Holen et al, Nucleic Acids Res. 2002; 30:1757-66, both of which are herein incorporated by reference). An important factor in the design of siRNAs is the presence of accessible sites for siRNA binding. Bahoia et al., (J. Biol. Chem., 2003; 278: 15991-15997; herein incorporated by reference) describe the use of a type of DNA array called a scanning array to find accessible sites in mRNAs for designing effective siRNAs. These arrays comprise oligonucleotides ranging in size from monomers to a certain maximum, usually Corners, synthesized using a physical barrier (mask) by stepwise addition of each base in the sequence. Thus the arrays represent a full oligonucleotide complement of a region of the target gene. Hybridization of the target mRNA to these arrays provides an exhaustive accessibility profile of this region of the target mRNA. Such data are useful in the design of antisense oligonucleotides (ranging from 7mers to 25mers), where it is important to achieve a compromise between oligonucleotide length and binding affinity, to retain efficacy and target specificity (Sohail et al, Nucleic Acids Res., 2001; 29(10): 2041-2045). Additional methods and concerns for selecting siRNAs are described for example, in WO 05054270, WO05038054A1, WO03070966A2, J Mol. Biol. 2005 May 13; 348(4):883-93, J Mol. Biol. 2005 May 13; 348(4):871-81, and Nucleic Acids Res. 2003 Aug. 1; 31(15): 4417-24, each of which is herein incorporated by reference in its entirety. In addition, software (e.g., the MWG online siMAX siRNA design tool) is commercially or publicly available for use in the selection of siRNAs.

2. Antisense

In other embodiments, fusion protein expression is modulated using antisense compounds that specifically hybridize with one or more nucleic acids encoding cancer markers of the present invention. The specific hybridization of an oligomeric compound with its target nucleic acid interferes with the normal function of the nucleic acid. This modulation of function of a target nucleic acid by compounds that specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity that may be engaged in or facilitated by the RNA. The overall effect of such interference with target nucleic acid function is modulation of the expression of cancer markers of the present invention. In the context of the present invention, "modulation" means either an increase (stimulation) or a decrease (inhibition) in the expression of a gene. For example, expression may be inhibited to potentially prevent tumor proliferation.

It is preferred to target specific nucleic acids for antisense. "Targeting" an antisense compound to a particular nucleic acid, in the context of the present invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding a cancer marker of the present invention. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). Eukaryotic and prokaryotic genes may have two or more alternative start codons, any one of which may be preferentially utilized for translation initiation in a particular cell type or tissue, or under a particular set of conditions. In the context of the present invention, "start codon" and "translation initiation codon" refer to the codon or codons that are used in vivo to initiate translation of an mRNA molecule transcribed from a gene encoding a tumor antigen of the present invention, regardless of the sequence(s) of such codons.

Translation termination codon (or "stop codon") of a gene may have one of three sequences (i.e., 5'-UAA, 5'-UAG and 5'-UGA; the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which refers to the region between the translation initiation codon and the translation termination codon, is also a region that may be targeted effectively. Other target regions include the 5' untranslated region (5' UTR), referring to the portion of an mRNA in the 5' direction from the translation initiation codon, and thus including nucleotides between the 5' cap site and the translation initiation codon of an mRNA or corresponding nucleotides on the gene, and the 3' untranslated region (3' UTR), referring to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The cap region may also be a preferred target region.

Although some eukaryotic mRNA transcripts are directly translated, many contain one or more regions, known as "introns," that are excised from a transcript before it is translated. The remaining (and therefore translated) regions are known as "exons" and are spliced together to form a continuous mRNA sequence. mRNA splice sites (i.e., intron-exon junctions) may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

In some embodiments, target sites for antisense inhibition are identified using commercially available software programs (e.g., Biognostik, Gottingen, Germany; SysArris Software, Bangalore, India; Antisense Research Group, University of Liverpool, Liverpool, England; GeneTrove, Carlsbad, Calif.). In other embodiments, target sites for antisense inhibition are identified using the accessible site method described in PCT Publ. No. WO0198537A2, herein incorporated by reference.

Once one or more target sites have been identified, oligonucleotides are chosen that are sufficiently complementary to the target (i.e., hybridize sufficiently well and with sufficient specificity) to give the desired effect. For example, in preferred embodiments of the present invention, antisense oligonucleotides are targeted to or near the start codon.

In the context of this invention, "hybridization," with respect to antisense compositions and methods, means hydrogen bonding, which may be Watson-Crick, Hoogsteen or reversed Hoogsteen hydrogen bonding, between complementary nucleoside or nucleotide bases. For example, adenine and thymine are complementary nucleobases that pair through the formation of hydrogen bonds. It is understood that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired (i.e., under physiological conditions in the case of in vivo assays or therapeutic treatment, and in the case of in vitro assays, under conditions in which the assays are performed).

Antisense compounds are commonly used as research reagents and diagnostics. For example, antisense oligonucleotides, which are able to inhibit gene expression with specificity, can be used to elucidate the function of particular genes. Antisense compounds are also used, for example, to distinguish between functions of various members of a biological pathway.

The specificity and sensitivity of antisense is also applied for therapeutic uses. For example, antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides are useful therapeutic modalities that can be configured to be useful in treatment regimes for treatment of cells, tissues, and animals, especially humans.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 30 nucleobases (i.e., from about 8 to about 30 linked bases), although both longer and shorter sequences may find use with the present invention. Particularly preferred antisense compounds are antisense oligonucleotides, even more preferably those comprising from about 12 to about 25 nucleobases.

Specific examples of preferred antisense compounds useful with the present invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In other preferred oligonucleotide mimetics, both the sugar and the internucleoside linkage (i.e., the backbone) of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., Science 254:1497 (1991).

Most preferred embodiments of the invention are oligonucleotides with phosphorothioate backbones and oligonucleosides with heteroatom backbones, and in particular —$CH_2$—, —NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$—, and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[$(CH_2)_n$O]$_m$$CH_3$, O($CH_2$)$_n$O$CH_3$, O($CH_2$)$_n$N$H_2$, O($CH_2$)$_n$$CH_3$, O($CH_2$)$_n$ON$H_2$, and O($CH_2$)$_n$ON[($CH_2$)$_n$$CH_3$)]$_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, S$CH_3$, OCN, Cl, Br, CN, $CF_3$, O$CF_3$, SO$CH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., Helv. Chim. Acta 78:486 [1995]) i.e., an alkoxyalkoxy group. A further preferred modification includes 2'-dimethylaminooxyethoxy (i.e., a O($CH_2$)$_2$ON($CH_3$)$_2$ group), also known as 2'-DMAOE, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_3$)$_2$.

Other preferred modifications include 2'-methoxy(2'-O—$CH_3$), 2'-aminopropoxy(2'-O$CH_2CH_2CH_2NH_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2. ° C. and are presently preferred base substitutions, even more particularly when combined with 2'-O-methoxyethyl sugar modifications.

Another modification of the oligonucleotides of the present invention involves chemically linking to the oligonucleotide one or more moieties or conjugates that enhance the activity, cellular distribution or cellular uptake of the oligonucleotide. Such moieties include but are not limited to lipid moieties such as a cholesterol moiety, cholic acid, a thioether, (e.g., hexyl-5-tritylthiol), a thiocholesterol, an aliphatic chain, (e.g., dodecandiol or undecyl residues), a phospholipid, (e.g., di-hexadecyl-rac-glycerol or triethylammonium 1,2-di-O-hexadecyl-rac-glycero-3-H-phosphonate), a polyamine or a polyethylene glycol chain or adamantane acetic acid, a palmityl moiety, or an octadecylamine or hexylamino-carbonyl-oxycholesterol moiety.

One skilled in the relevant art knows well how to generate oligonucleotides containing the above-described modifications. The present invention is not limited to the antisense oligonucleotides described above. Any suitable modification or substitution may be utilized.

It is not necessary for all positions in a given compound to be uniformly modified, and in fact more than one of the aforementioned modifications may be incorporated in a single compound or even at a single nucleoside within an oligonucleotide. The present invention also includes antisense compounds that are chimeric compounds. "Chimeric" antisense compounds or "chimeras," in the context of the present invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNaseH is a cellular endonuclease that cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the present invention may be formed as composite structures of two or more oligonucleotides, modified oligonucleotides, oligonucleosides and/or oligonucleotide mimetics as described above.

The present invention also includes pharmaceutical compositions and formulations that include the antisense compounds of the present invention as described below.

B. Gene Therapy

The present invention contemplates the use of any genetic manipulation for use in modulating the expression of cancer markers of the present invention. Examples of genetic manipulation include, but are not limited to, gene knockout (e.g., removing the fusion gene from the chromosome using, for example, recombination), expression of antisense constructs with or without inducible promoters, and the like. Delivery of nucleic acid construct to cells in vitro or in vivo may be conducted using any suitable method. A suitable method is one that introduces the nucleic acid construct into the cell such that the desired event occurs (e.g., expression of an antisense construct). Genetic therapy may also be used to deliver siRNA or other interfering molecules that are expressed in vivo (e.g., upon stimulation by an inducible promoter (e.g., an androgen-responsive promoter)).

Introduction of molecules carrying genetic information into cells is achieved by any of various methods including, but not limited to, directed injection of naked DNA constructs, bombardment with gold particles loaded with said constructs, and macromolecule mediated gene transfer using, for example, liposomes, biopolymers, and the like. Preferred methods use gene delivery vehicles derived from viruses, including, but not limited to, adenoviruses, retroviruses, vaccinia viruses, and adeno-associated viruses. Because of the higher efficiency as compared to retroviruses, vectors derived from adenoviruses are the preferred gene delivery vehicles for transferring nucleic acid molecules into host cells in vivo. Adenoviral vectors have been shown to provide very efficient in vivo gene transfer into a variety of solid tumors in animal models and into human solid tumor xenografts in immune-deficient mice. Examples of adenoviral vectors and methods for gene transfer are described in PCT publications WO 00/12738 and WO 00/09675 and U.S. Pat. Nos. 6,033,908, 6,019,978, 6,001,557, 5,994,132, 5,994,128, 5,994,106, 5,981,225, 5,885,808, 5,872,154, 5,830,730, and 5,824,544, each of which is herein incorporated by reference in its entirety.

Vectors may be administered to subject in a variety of ways. For example, in some embodiments of the present invention, vectors are administered into tumors or tissue associated with tumors using direct injection. In other embodiments, administration is via the blood or lymphatic circulation (See e.g., PCT publication 99/02685 herein incorporated by reference in its entirety). Exemplary dose levels of adenoviral vector are preferably $10^8$ to $10^{11}$ vector particles added to the perfusate.

C. Antibody Therapy

In some embodiments, the present invention provides antibodies that target prostate tumors that express a cancer marker of the present invention (e.g., ERG, ETV1, or ETV4 fusions with TMPRSS2). Any suitable antibody (e.g., monoclonal, polyclonal, or synthetic) may be utilized in the therapeutic methods disclosed herein. In preferred embodiments, the antibodies used for cancer therapy are humanized antibodies. Methods for humanizing antibodies are well known in the art (See e.g., U.S. Pat. Nos. 6,180,370, 5,585,089, 6,054,297, and 5,565,332; each of which is herein incorporated by reference).

In some embodiments, the therapeutic antibodies comprise an antibody generated against a cancer marker of the present invention (e.g., ERG, ETV1, or ETV4 fusions with TMPRSS2), wherein the antibody is conjugated to a cytotoxic agent. In such embodiments, a tumor specific therapeutic agent is generated that does not target normal cells, thus reducing many of the detrimental side effects of traditional chemotherapy. For certain applications, it is envisioned that the therapeutic agents will be pharmacologic agents that will serve as useful agents for attachment to antibodies, particularly cytotoxic or otherwise anticellular agents having the ability to kill or suppress the growth or cell division of endothelial cells. The present invention contemplates the use of any pharmacologic agent that can be conjugated to an antibody, and delivered in active form. Exemplary anticellular agents include chemotherapeutic agents, radioisotopes, and cytotoxins. The therapeutic antibodies of the present invention may include a variety of cytotoxic moieties, including but not limited to, radioactive isotopes (e.g., iodine-131, iodine-123, technicium-99m, indium-111, rhenium-188, rhenium-186, gallium-67, copper-67, yttrium-90, iodine-125 or astatine-211), hormones such as a steroid, antimetabolites such as cytosines (e.g., arabinoside, fluorouracil, methotrexate or aminopterin; an anthracycline; mitomycin C), vinca alkaloids (e.g., demecolcine; etoposide; mithramycin), and antitumor alkylating agent such as chlorambucil or melphalan. Other embodiments may include agents such as a coagulant, a cytokine, growth factor, bacterial endotoxin or the lipid A moiety of bacterial endotoxin. For example, in some embodiments, therapeutic agents will include plant-, fungus- or bacteria-derived toxin, such as an A chain toxins, a ribosome inactivating protein, α-sarcin, aspergillin, restrictocin, a ribonuclease, diphtheria toxin or pseudomonas exotoxin, to mention just a few examples. In some preferred embodiments, deglycosylated ricin A chain is utilized.

In any event, it is proposed that agents such as these may, if desired, be successfully conjugated to an antibody, in a manner that will allow their targeting, internalization, release or presentation to blood components at the site of the targeted tumor cells as required using known conjugation technology (See, e.g., Ghose et al., Methods Enzymol., 93:280 [1983]).

For example, in some embodiments the present invention provides immunotoxins targeted a cancer marker of the present invention (e.g., ERG or ETV1 fusions). Immunotoxins are conjugates of a specific targeting agent typically a tumor-directed antibody or fragment, with a cytotoxic agent, such as a toxin moiety. The targeting agent directs the toxin to, and thereby selectively kills, cells carrying the targeted antigen. In some embodiments, therapeutic antibodies employ crosslinkers that provide high in vivo stability (Thorpe et al., Cancer Res., 48:6396 [1988]).

In other embodiments, particularly those involving treatment of solid tumors, antibodies are designed to have a cytotoxic or otherwise anticellular effect against the tumor vasculature, by suppressing the growth or cell division of the vascular endothelial cells. This attack is intended to lead to a tumor-localized vascular collapse, depriving the tumor cells, particularly those tumor cells distal of the vasculature, of oxygen and nutrients, ultimately leading to cell death and tumor necrosis.

In preferred embodiments, antibody based therapeutics are formulated as pharmaceutical compositions as described below. In preferred embodiments, administration of an antibody composition of the present invention results in a measurable decrease in cancer (e.g., decrease or elimination of tumor).

D. Pharmaceutical Compositions

The present invention further provides pharmaceutical compositions (e.g., comprising pharmaceutical agents that modulate the expression or activity of gene fusions of the present invention). The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product.

Agents that enhance uptake of oligonucleotides at the cellular level may also be added to the pharmaceutical and other compositions of the present invention. For example, cationic lipids, such as lipofectin (U.S. Pat. No. 5,705,188), cationic glycerol derivatives, and polycationic molecules, such as polylysine (WO 97/30731), also enhance the cellular uptake of oligonucleotides.

The compositions of the present invention may additionally contain other adjunct components conventionally found in pharmaceutical compositions. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Certain embodiments of the invention provide pharmaceutical compositions containing (a) one or more antisense compounds and (b) one or more other chemotherapeutic agents that function by a non-antisense mechanism. Examples of such chemotherapeutic agents include, but are not limited to, anticancer drugs such as daunorubicin, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU), floxuridine (5-FUdR), methotrexate (MTX), colchicine, vincristine, vinblastine, etoposide, teniposide, cisplatin and diethylstilbestrol (DES). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Other non-antisense chemotherapeutic agents are also within the scope of this invention. Two or more combined compounds may be used together or sequentially.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models or based on the examples described herein. In general, dosage is from 0.01 μg to 100 g per kg of body weight, and may be given once or more daily, weekly, monthly or yearly. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the oligonucleotide is administered in maintenance doses, ranging from 0.01 μg to 100 g per kg of body weight, once or more daily, to once every 20 years.

VII. Transgenic Animals

The present invention contemplates the generation of transgenic animals comprising an exogenous cancer marker gene (e.g., gene fusion) of the present invention or mutants and variants thereof (e.g., truncations or single nucleotide polymorphisms). In preferred embodiments, the transgenic animal displays an altered phenotype (e.g., increased or decreased presence of markers) as compared to wild-type animals. Methods for analyzing the presence or absence of such phenotypes include but are not limited to, those disclosed herein. In some preferred embodiments, the transgenic animals further display an increased or decreased growth of tumors or evidence of cancer.

The transgenic animals of the present invention find use in drug (e.g., cancer therapy) screens. In some embodiments, test compounds (e.g., a drug that is suspected of being useful to treat cancer) and control compounds (e.g., a placebo) are administered to the transgenic animals and the control animals and the effects evaluated.

The transgenic animals can be generated via a variety of methods. In some embodiments, embryonal cells at various developmental stages are used to introduce transgenes for the production of transgenic animals. Different methods are used depending on the stage of development of the embryonal cell. The zygote is the best target for micro-injection. In the mouse, the male pronucleus reaches the size of approximately 20 micrometers in diameter that allows reproducible injection of 1-2 picoliters (pl) of DNA solution. The use of zygotes as a target for gene transfer has a major advantage in that in most cases the injected DNA will be incorporated into the host genome before the first cleavage (Brinster et al., Proc. Natl. Acad. Sci. USA 82:4438-4442 [1985]). As a consequence, all cells of the transgenic non-human animal will carry the incorporated transgene. This will in general also be reflected in the efficient transmission of the transgene to offspring of the founder since 50% of the germ cells will harbor the transgene. U.S. Pat. No. 4,873,191 describes a method for the microinjection of zygotes; the disclosure of this patent is incorporated herein in its entirety.

In other embodiments, retroviral infection is used to introduce transgenes into a non-human animal. In some embodiments, the retroviral vector is utilized to transfect oocytes by injecting the retroviral vector into the perivitelline space of the oocyte (U.S. Pat. No. 6,080,912, incorporated herein by reference). In other embodiments, the developing non-human embryo can be cultured in vitro to the blastocyst stage. During this time, the blastomeres can be targets for retroviral infection (Janenich, Proc. Natl. Acad. Sci. USA 73:1260 [1976]). Efficient infection of the blastomeres is obtained by enzymatic treatment to remove the zona pellucida (Hogan et al., in *Manipulating the Mouse Embryo*, Cold Spring Harbor Laboratory Press, Cold Spring Harbor, N.Y. [1986]). The viral vector system used to introduce the transgene is typically a replication-defective retrovirus carrying the transgene (Jahner et al., Proc. Natl. Acad. Sci. USA 82:6927 [1985]). Transfection is easily and efficiently obtained by culturing the blastomeres on a monolayer of virus-producing cells (Stewart, et al., EMBO J., 6:383 [1987]). Alternatively, infection can be performed at a later stage. Virus or virus-producing cells can be injected into the blastocoele (Jahner et al., Nature 298:623 [1982]). Most of the founders will be mosaic for the transgene since incorporation occurs only in a subset of cells that form the transgenic animal. Further, the founder may contain various retroviral insertions of the transgene at different positions in the genome that generally will segregate in the offspring. In addition, it is also possible to introduce transgenes into the germline, albeit with low efficiency, by intrauterine retroviral infection of the midgestation embryo (Jahner et al., supra [1982]). Additional means of using retroviruses or retroviral vectors to create transgenic animals known to the art involve the micro-injection of retroviral particles or mitomycin C-treated cells producing retrovirus into the perivitelline space of fertilized eggs or early embryos (PCT International Application WO 90/08832 [1990], and Haskell and Bowen, Mol. Reprod. Dev., 40:386 [1995]).

In other embodiments, the transgene is introduced into embryonic stem cells and the transfected stem cells are utilized to form an embryo. ES cells are obtained by culturing pre-implantation embryos in vitro under appropriate conditions (Evans et al., Nature 292:154 [1981]; Bradley et al., Nature 309:255 [1984]; Gossler et al., Proc. Acad. Sci. USA 83:9065 [1986]; and Robertson et al., Nature 322:445 [1986]). Transgenes can be efficiently introduced into the ES cells by DNA transfection by a variety of methods known to the art including calcium phosphate co-precipitation, protoplast or spheroplast fusion, lipofection and DEAE-dextran-mediated transfection. Transgenes may also be introduced into ES cells by retrovirus-mediated transduction or by micro-injection. Such transfected ES cells can thereafter colonize an embryo following their introduction into the blastocoel of a blastocyst-stage embryo and contribute to the germ line of the resulting chimeric animal (for review, See, Jaenisch, Science 240:1468 [1988]). Prior to the introduction of transfected ES cells into the blastocoel, the transfected ES cells may be subjected to various selection protocols to enrich for ES cells which have integrated the transgene assuming that the transgene provides a means for such selection. Alternatively, the polymerase chain reaction may be used to screen for ES cells that have integrated the transgene. This technique obviates the need for growth of the transfected ES cells under appropriate selective conditions prior to transfer into the blastocoel.

In still other embodiments, homologous recombination is utilized to knock-out gene function or create deletion mutants (e.g., truncation mutants). Methods for homologous recombination are described in U.S. Pat. No. 5,614,396, incorporated herein by reference.

EXPERIMENTAL

The following examples are provided in order to demonstrate and further illustrate certain preferred embodiments and aspects of the present invention and are not to be construed as limiting the scope thereof.

Example 1

ERG and ETV1 Gene Fusions

A. Materials and Methods
Cancer Outlier Profile Analysis (COPA)

COPA analysis was performed on 132 gene expression data sets in Oncomine 3.0 comprising 10,486 microarray experiments. In addition, data from 99 amplified laser-capture microdissected prostate tissue samples were included in the COPA analysis. COPA has three steps. First, gene expression values are median centered, setting each gene's median expression value to zero. Second, the median absolute deviation (MAD) is calculated and scaled to 1 by dividing each gene expression value by its MAD. Median and MAD were used for transformation as opposed to mean and standard deviation so that outlier expression values do not unduly influence the distribution estimates, and are thus preserved post-normalization. Third, the 75th, 90th, and 95th percentiles of the transformed expression values are tabulated for each gene and then genes are rank-ordered by their percentile scores, providing a prioritized list of outlier profiles.

Samples

Tissues utilized were from the radical prostatectomy series at the University of Michigan and from the Rapid Autopsy Program (Shah et al., Cancer Res 64, 9209 (Dec. 15, 2004)), which are both part of University of Michigan Prostate Cancer Specialized Program of Research Excellence (S.P.O.R.E.) Tissue Core.

Tissues were also obtained from a radical prostatectomy series at the University Hospital Ulm (Ulm, Germany). All samples were collected from consented patients with prior institutional review board approval at each respective institution. Total RNA from all samples was isolated with Trizol (Invitrogen) according to the manufacturer's instructions. Total RNA was also isolated from RWPE, PC3, PC3+AR (Dai et al., Steroids 61, 531 (1996)), LNCaP, VCaP and DuCaP cell lines. RNA integrity was verified by denaturing formaldehyde gel electrophoresis or the Agilent Bioanalyzer 2100. A commercially available pool of benign prostate tissue total RNA (CPP, Clontech) was also used.

Quantitative PCR (QPCR)

Quantitative PCR (QPCR) was performed using SYBR Green dye on an Applied Biosystems 7300 Real Time PCR system essentially as described (Chinnaiyan et al., Cancer Res 65, 3328 (2005); Rubin et al., Cancer Res 64, 3814 (2004)). Briefly, 1-5 µg of total RNA was reverse transcribed into cDNA using SuperScript III (Invitrogen) in the presence of random primers or random primers and oligo dT primers. All reactions were performed with SYBR Green Master Mix (Applied Biosystems) and 25 ng of both the forward and reverse primer using the manufacturer's recommended thermocycling conditions. All reactions were subjected to melt curve analysis and products from selected experiments were resolved by electrophoreses on 1.5% agarose gels. For each experiment, threshold levels were set during the exponential phase of the QPCR reaction using Sequence Detection Software version 1.2.2 (Applied Biosystems). The amount of each target gene relative to the housekeeping gene glyceraldehyde-3-phosphate dehydrogenase (GAPDH) for each sample was determined using the comparative threshold cycle (Ct) method (Applied Biosystems User Bulletin #2), with the cDNA sample serving as the calibrator for each experiment described in the figure legend. All oligonucleotide primers were synthesized by Integrated DNA Technologies. GAPDH primers were as described (Vandesompele et al., Genome Biol 3, RESEARCH0034 (2002)) and all other primers are listed (Table 4). Approximately equal efficiencies of the primers were confirmed using serial dilutions of prostate cancer cDNA or plasmid templates in order to use the comparative Ct method.

RNA Ligase Mediated Rapid Amplification of cDNA Ends (RLM-Race)

RNA ligase mediated rapid amplification of cDNA ends was performed using the GeneRacer RLM-RACE kit (Invitrogen), according to the manufacturer's instructions. Initially, samples were selected based on expression of ERG or ETV1 by QPCR. Five micrograms of total RNA was treated with calf intestinal phosphatase to remove 5' phosphates from truncated mRNA and non-mRNA and decapped with tobacco acid phyrophosphatase. The GeneRace RNA Oligo was ligated to full length transcripts and reverse transcribed using SuperScript III. To obtain 5' ends, first-strand cDNA was amplified with Platinum Taq High Fidelity (Invitrogen) using the GeneRacer 5' Primer and ETV1 exon 4-5_r for ETV1 or the GeneRacer 5' Primer and ERG exon 4a r or ERG exon 4b_r for ERG. Primer sequences are given (Table S2). Products were resolved by electrophoresis on 1.5% agarose gels and bands were excised, purified and TOPO TA cloned into pCR 4-TOPO. Purified plasmid DNA from at least 4 colonies was sequenced bi-directionally using M13 Reverse and M13 Forward (−20) primers or T3 and T7 primers on an ABI Model 3730 automated sequencer by the University of Michigan DNA Sequencing Core. RLM-RACEd cDNA was not used for the other assays.

Reverse-Transcription PCR for TMPRSS2:ERG Fusion

After identifying TMPRSS2:ERG positive cases using QPCR as described above, the same cDNA samples were PCR amplified with Platinum Taq High Fidelity and TPRSS2: ERG primers. Products were resolved by electrophoresis, cloned into pCR 4-TOPO and sequenced as described above.

In Vitro Androgen Responsiveness

RWPE, LNCaP, VCap DuCaP, PC3 and PC3 cells stably transfected with the human androgen receptor (PC3+AR) (3) were treated for 24 h with 1% ethanol control or 1 nM of the synthetic androgen R1881. Total RNA was isolated and subjected to reverse transcription and QPCR as described above with ERG exon 5-6_f and _r primers. The relative amount of ERG/GAPDH for each sample was calibrated to the RWPE control sample.

Fluorescence In Situ Hybridization (FISH)

Formalin-fixed paraffin-embedded (FFPE) tissue sections from normal peripheral lymphocytes and the metastatic prostate cancer samples MET-26 and MET-28 were used for interphase fluorescence in situ hybridization (FISH) analysis. In addition, interphase FISH was performed on a tissue microarray containing cores from FFPE sections of 13 clinically localized prostate cancer and 16 metastatic prostate cancer samples. A two-color, two-signal approach was employed to evaluate the fusion of TMPRSS2 and ETV1, with probes spanning most of the respective gene loci. The biotin-14-dCTP BAC clone RP11-124L22 was used for the ETV1 locus and the digoxin-dUTP labeled BAC clone RPP11-35CD was used for the TMPRSS2 locus. For analyzing gene rearrangements involving ERG, a split-signal probe strategy was used, with two probes spanning the ERG locus (biotin-14-dCTP labeled BAC clone RP11-476D17 and digoxin-dUTP labeled BAC clone RP11-95121). All BAC clones were obtained from the Children's Hospital of Oakland Research Institute (CHORI). Prior to tissue analysis, the integrity and purity of all probes were verified by hybridization to metaphase spreads of normal peripheral lymphocytes. Tissue hybridization, washing and color detection were performed as described (Rubin et al., Cancer Res 64, 3814 (2004); Garraway et al., Nature 436, 117 (2005)).

B. Results

Cancer Outlier Profile Analysis

In recent years, gene expression profiling with DNA microarrays has become a common method to study the cancer transcriptome. Microarray studies have provided great insight into the molecular heterogeneity of cancer, often identifying novel molecular subtypes of disease that correspond to tumor histology, patient outcome, and treatment response (Valk et al., N Engl J Med 350, 1617 (2004)). However, in general, transcriptome analysis has not led to the discovery of novel causal cancer genes. It was hypothesized that rearrangements and highlevel copy number changes that result in marked over-expression of an oncogene should be evident in transcriptome data, but not necessarily by traditional analytical approaches.

In the majority of cancer types, heterogeneous patterns of oncogene activation have been observed, thus traditional analytical methods that search for common activation of genes across a class of cancer samples (e.g., t-test or signal-to-noise ratio) will fail to find such oncogene expression profiles. Instead, a method that searches for marked over-expression in a subset of cases is needed. Experiments conducted during the course of development of the present invention resulted in the development of Cancer Outlier Profile Analysis (COPA). COPA seeks to accentuate and identify outlier profiles by applying a simple numerical transformation based on the median and median absolute deviation of a gene expression profile (Ross et al., Blood 102, 2951 (2003)). This approach is illustrated in FIG. 5A. COPA was applied to the Oncomine database (Bittner et al., Nature 406, 536 (2000)), which comprised a compendium of 132 gene expression datasets representing 10,486 microarray experiments. COPA correctly identified several outlier profiles for genes in specific cancer types in which a recurrent rearrangement or high-level amplification is known to occur. The analysis was focused on outlier profiles of known causal cancer genes, as defined by the Cancer Gene Census (Vasselli et al., Proc Natl Acad Sci USA 100, 6958 (2003)), that ranked in the top 10 outlier profiles in an Oncomine dataset (Table 1 and Table 3). For example, in the Valk et al. acute myeloid leukemia (AML) dataset, RUNX1T1 (ETO) had the strongest outlier profile at the 95th percentile, consistent with this gene's known translocation and oncogenic activity in a subset of AML (Davis et al., Proc Natl Acad Sci USA 100, 6051 (2003)) (Table 1). The outlier profile precisely associated with cases that had a documented t(8;21) translocation which fuses RUNX1 (AML1) and RUNX1T1 (ETO) (FIG. 5B). Similarly, in the Ross et al. acute lymphoblastic leukemia (ALL) dataset, PBX1 showed the strongest outlier profile at the 90th percentile, consistent with the E2A-PBX1 translocation known to occur in a subset of ALL (Segal et al., J Clin Oncol 21, 1775 (2003)) (Table 1). Again, the outlier expression profile perfectly correlated with the characterized t(1;19) E2A-PBX1 translocation in this panel of ALLs (FIG. S1C).

Identification of Outlier Profiles for ETS Family Members ERG and ETV1 in Prostate Cancer Novel COPA predictions were next examined. In several independent datasets, COPA identified strong outlier profiles in prostate cancer for ERG and ETV1, two ETS family transcription factors that are known to be involved in oncogenic translocations in Ewing's sarcoma and myeloid leukemias (Lapointe et al., Proc Natl Acad Sci USA 101, 811 (2004); Tian et al., N Engl J Med 349, 2483 (2003)). In the Dhanasekaran et al. (Keats et al., Blood 105, 4060 (2005)), Welsh et al. (Dhanasekaran et al., Faseb J 19, 243 (2005)) and Lapointe et al. (Wang et al., Lancet 365, 671 (2005)) prostate cancer gene expression datasets, ERG had the highest scoring outlier profile at the 75th percentile (Table 1), while in the Lapointe et al. and Tomlins et al. (Welsh et al., Cancer Res 61, 5974 (2001)) datasets, ETV1 had the highest scoring outlier profile at the 90th percentile (Table 1). In total, COPA ranked ERG or ETV1 within the top ten outlier genes nine times in seven independent prostate cancer profiling studies. Both ERG and ETV1 are involved in oncogenic translocations in Ewing's sarcoma. Fusion of the 5' activation domain of the EWS gene to the highly conserved 3' DNA binding domain of an ETS family member, such as ERG (t(21;22)(q22;q12)) or ETV1 (t(7;22)(p21;q12)), is characteristic of Ewing's sarcoma (Lapoint et al., supra; Zhan et al., Blood 99, 1745 (2002); Fonseca et al., Cancer Res 64, 1546 (2004)). Because translocations involving ETS family members are functionally redundant in oncogenic transformation, only one type of translocation is typically observed in each case of Ewing's sarcoma.

It was contemplated that if ERG and ETV1 are similarly involved in the development of prostate cancer, their outlier profiles should be mutually exclusive, that is, each case should over-express only one of the two genes. Mutations in functionally redundant genes, or genes in the same oncogenic pathway, are unlikely to be co-selected for in neoplastic progression. The joint expression profiles of ERG and ETV1 was examined across several prostate cancer datasets and it was found that they showed mutually exclusive outlier profiles. ERG and ETV1 expression profiles from two large-scale transcriptome studies (Wang et al., supra; Cheok et al., Nat Genet. 34, 85 (2003)), which profiled grossly dissected prostate tissues using different microarray platforms, were identified (FIG. 1A, left and middle panels). The study by Lapointe et al. profiled benign prostate tissue, clinically localized prostate cancer, and metastatic prostate cancer, with ERG and ETV1 outlier expression restricted to prostate cancer and metastatic prostate cancer, while the study by Glinsky et al. profiled clinically localized prostate cancer samples only. In both studies, prostate cancers exclusively expressed ERG or ETV1 (FIG. 1A, right panel). Similar results were found in a profiling study of 99 prostate tissue samples obtained by laser capture microdissection (LCM) (Welsh et al., supra). In addition to exclusive outlier expression of either ERG or ETV1 (FIG. 1B, right panel), results from the LCM study demonstrated that ETV1 and ERG are only over-expressed in epithelial cells from prostate cancer or metastatic prostate cancer, but not in the putative precursor lesion prostatic intraepithelial neoplasia (PIN) or adjacent benign epithelia. To directly determine whether the observed exclusive outlier pattern is consistent with other translocations where an activating gene can fuse with multiple partners, the Zhan et al. multiple myeloma dataset (Dhanasekaran et al., Nature 412, 822 (2001)) was examined. Recurrent fusions of the immunoglobulin heavy chain promoter to CCND1 or FGFR3, t(11,14) or t(4,14) respectively, characterize specific subsets of multiple myeloma (Wigle et al., Cancer Res 62, 3005 (2002)). These translocations were reflected in the outlier profile analysis (FIG. 1C), as CCND1 was the highest scoring outlier at the 75th percentile and FGFR3 was the third highest scoring outlier at the 95th percentile (Table 1). Except for two cases, myeloma samples showed exclusive over-expression of CCND1 or FGFR3 (FIG. 1C, right panel). Taken together, the outlier profiles of ERG and ETV1 across multiple prostate cancer data sets are consistent with other causal mutations in various human malignancies. The exclusive over-expression of ERG or ETV1 in individual prostate cancer samples is consistent with other neoplasms in which an activating gene can fuse with biologically redundant partner genes, such as in multiple myeloma.

Discovery of a Recurrent Gene Fusion of TMPRSS2 to ERG or ETV1 in Prostate Cancer.

The mechanism of ERG and ETV1 over-expression in individual prostate cancer samples was next determined. Prostate cancer cell lines and clinical specimens that over-expressed ERG or ETV1 were identified by performing quantitative PCR (QPCR) (FIG. 2A). The LNCaP prostate cancer cell line and two specimens obtained from a patient who died of hormone refractory metastatic prostate cancer (MET-26RP, residual primary carcinoma in the prostate and MET-26LN, a lymph node metastasis) markedly over-expressed ETV1 by QPCR (FIG. 2A). Five independent metastatic foci from different anatomical locations as well as the residual carcinoma in the prostate from this patient also over-expressed ETV1 by DNA microarray analysis (Welsh et al., supra), suggesting that ETV1 activation occurred in the primary tumor before widespread metastasis. A lymph node metastasis was also identified from a second patient who died of hormone refractory metastatic prostate cancer (MET-28LN) and two prostate cancer cell lines, VCaP and DuCaP, that over-expressed ERG (FIG. 2A). These cell lines were independently isolated from a vertebral metastasis (VCaP) and a dural metastasis (DuCaP) from a third patient with hormone-refractory prostate cancer (Golub et al., Science 286, 531 (1999); Rosenwald et al., Cancer Cell 3, 185 (2003)). The common over-expression of ERG in these two cell lines again suggests that ERG activation occurred before widespread metastasis. Taken together, these results suggest that specific genetic events may activate ERG or ETV1 in individual samples during prostate tumorigenesis.

In an effort to characterize these genetic events, samples with high ERG or ETV1 expression were tested for chromosomal amplifications at their respective loci (7p21.2 and 21q22.3). By QPCR on genomic DNA, amplification of ERG or ETV1 in samples with respective transcript over-expression (Sotiriou et al., Proc Natl Acad Sci USA 100, 10393 (2003)) was not found. Next, the occurrence of DNA rearrangements was assayed. Because the primers used for the QPCR described above were located 5' to the known breakpoints for ERG and ETV1 in Ewing's sarcoma, it was unlikely that the same translocations occur in prostate cancer. Accordingly, the expression level of ETV1 exons was measured by exonwalking QPCR in the samples identified above that displayed ETV1 over-expression. Five primer pairs spanning ETV1 exons 2 through 7 were used and LNCaP cells showed essentially uniform over-expression of all measured ETV1 exons, and both MET26 specimens showed >90% reduction in the expression of ETV1 exons 2 and 3 compared to exons 4-7 (FIG. 2B). Potential explanations for this result include alternative splicing, a novel cancer-specific isoform or an unreported rearrangement.

Figure 6:
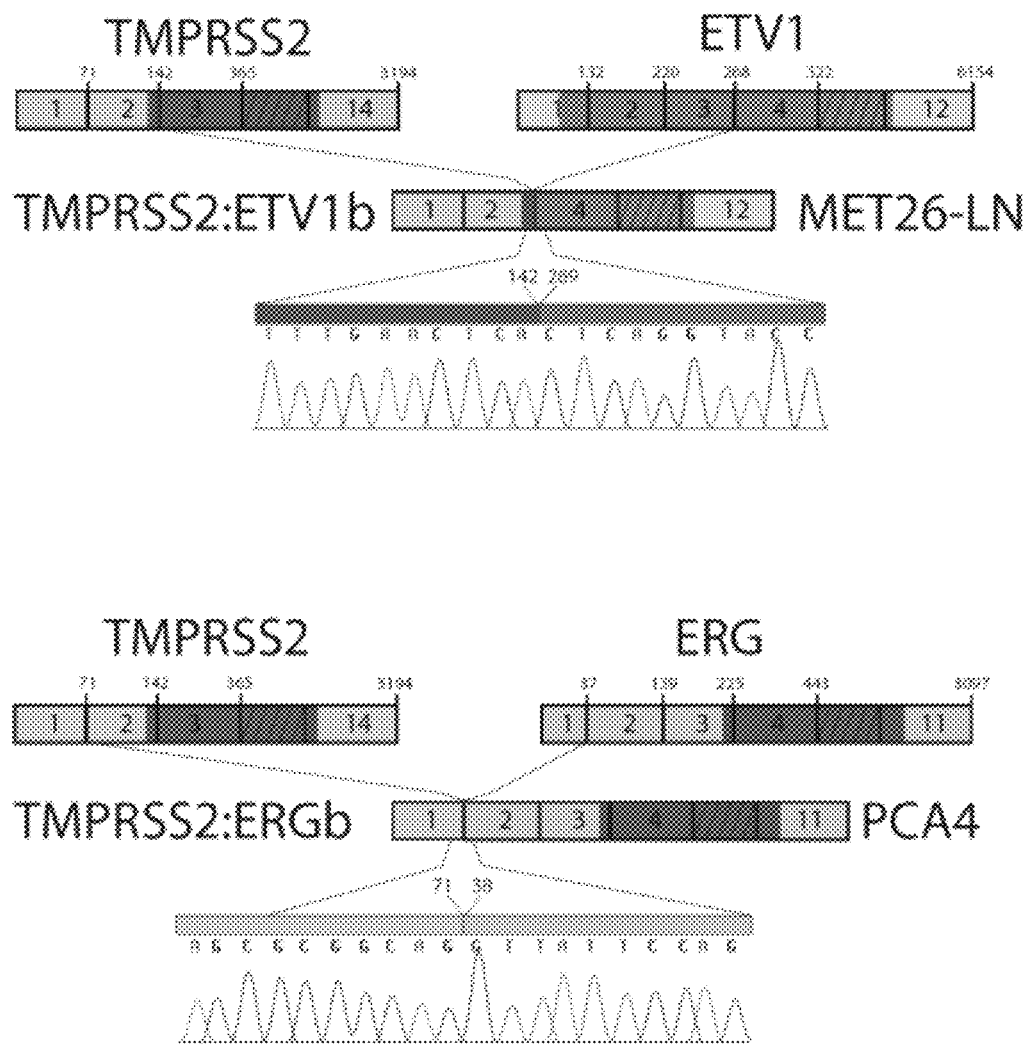
FIG. 6 shows a schematic of RNA ligase-mediated rapid amplification of cDNA ends (RLM-RACE) results for ETV1 in MET26-LN and ERG in PCA4 revealing gene fusions with TMPRSS2 (TMPRSS2:ERGb fusion).

In order to characterize the full length ETV1 transcript, 5' RNA ligase-mediated rapid amplification of cDNA ends (RLM-RACE) was performed on LNCaP cells and MET26-LN. In addition, RLM-RACE was performed to obtain the full length transcript of ERG in MET28-LN. For PCR amplification of ETV1 from the RLM-RACE cDNA, a forward primer complementary to the RNA-oligonucleotide ligated to the 5' end of complete transcripts and a reverse primer in exon 4, the 5'-most exon that was over-expressed in both LNCaP cells and MET26-LN was used. Utilizing a similar strategy as described above, it was determined that exon 4 of ERG was over-expressed in MET28-LN. A reverse primer in this exon was utilized for PCR amplification of RLM-RACE cDNA. Sequencing of the cloned products revealed fusions of the prostate specific gene TMPRSS2 (28) (21q22.2) with ETV1 in MET26-LN and with ERG in MET28-LN (FIG. 2C). In MET26-LN, two RLM-RACE PCR products were identified. The first product, TMPRSS2:ETV1a, resulted in a fusion of the complete exon 1 of TMPRSS2 with the beginning of exon 4 of ETV1 (FIG. 2C). The second product, TMPRSS2: ETV1b, resulted in a fusion of exons 1 and 2 of TMPRSS2 with the beginning of exon 4 of ETV1 (FIG. 6). Both products are consistent with the exon-walking QPCR described above, where MET26-LN showed loss of over-expression in exons 2 and 3. In MET28-LN, a single RLM-RACE PCR product was identified and sequencing revealed a fusion of the complete exon 1 of TMPRSS2 with the beginning of exon 4 of ERG (TMPRSS2:ERGa) (FIG. 2C).

Validation of TMPRSS2:ERG and TMPRSS2:ETV1 Gene Fusions in Prostate Cancer

Based on these results, QPCR primer pairs were designed with forward primers in TMPRSS2 and reverse primers in exon 4 of ERG and ETV1. SYBR Green QPCR was performed using both primer pairs across a panel of samples from 42 cases of clinically localized prostate cancer and metastatic prostate cancer, with representative results depicted (FIGS. 2, D and E). These results demonstrate that only samples with high levels of ETV1 or ERG express the respective fusion product with TMPRSS2. Although QPCR resulted in measurable product after 35 cycles in some negative samples, melt curve analysis revealed distinct products in positive and negative samples, and gel electrophoresis of products after the 40 cycle QPCR analysis revealed only primer dimmers in negative fusion samples (FIGS. 2, D and E). The formation of primer dimers may in part be explained by the difficulty in designing primers entirely in exon 1 of TMPRSS2 due to the high GC content (80.3%). However, the specific expression of TMPRSS2:ERGa, TMPRSS2:ETV1a and TMPRSS2:ETV1b fusions was confirmed using Taqman QPCR, with the forward primer spanning the respective fusion, and in each case, products were only detected in the same cases as the SYBR Green QPCR (Sotiriou et al., supra). To further confirm the specificity of the primers used for SYBR Green QPCR and the amplicons, standard reverse-transcription PCR was performed with the same primers as the SYBR Green QPCR on a panel of samples that expressed TMPRSS2:ERGa. Similar sized products were obtained and sequencing of cloned products confirmed the presence of TMPRSS2:ERGa. Two cases, PCA16 and PCA17, which expressed high levels of ETV1 or ERG respectively, but showed no evidence of the translocation by QPCR (FIGS. 2, D and E) were identified. RLM-RACE supported these results, as sequencing of the product produced with ETV1 primers in PCA16 revealed no evidence of a fusion transcript and no product could be obtained with ERG primers in PCA17. Similar results were obtained for LNCaP cells, with no evidence of a fusion by RLMRACE or QPCR, consistent with the exon walking QPCR described above.

Summary of Evidence for TMPRSS2 Fusion Transcripts with ETS Family Members in Prostate Cancer Samples Results from three different assays for the TMPRSS2:ERG and TMPRSS2:ETV1 fusion transcripts including sequencing of RLM-RACE products, QPCR and sequencing of RT-PCR products are summarized in Table 2. In addition to QPCR for TMPRSS2 fusions being performed in all samples, the existence of these fusions was confirmed using several techniques on selected samples. For example, in PCA1 (prostate cancer sample 1), TMPRSS2:ERGa was identified using sequencing of RLMRACE products, QPCR and sequencing of RT-PCR products. By QPCR melt curve analysis and gel electrophoresis of QPCR products, PCA4 produced a larger amplicon than expected. Subsequent RLM-RACE analysis confirmed a fusion of the complete exon 1 of TMPRSS2 with the beginning of exon 2 of ERG (TMPRSS2:ERGb) (FIG. 6). Taqman QPCR with the forward primer spanning the TMPRSS2:ERGb junction confirmed the presence of TMPRSS2:ERGb only in PCA4 and Taqman QPCR with the forward primer spanning the TMPRSS2:ERGa junction did not produce a product in this specimen (27). Evidence for the TMPRSS2:ERG and TMPRSS2:ETV1 fusions were only found in cases that over-expressed ERG or ETV1 respectively, by QPCR or DNA microarray. These results are in agreement with the exclusive expression observed in the outlier analysis.

Figure 3:
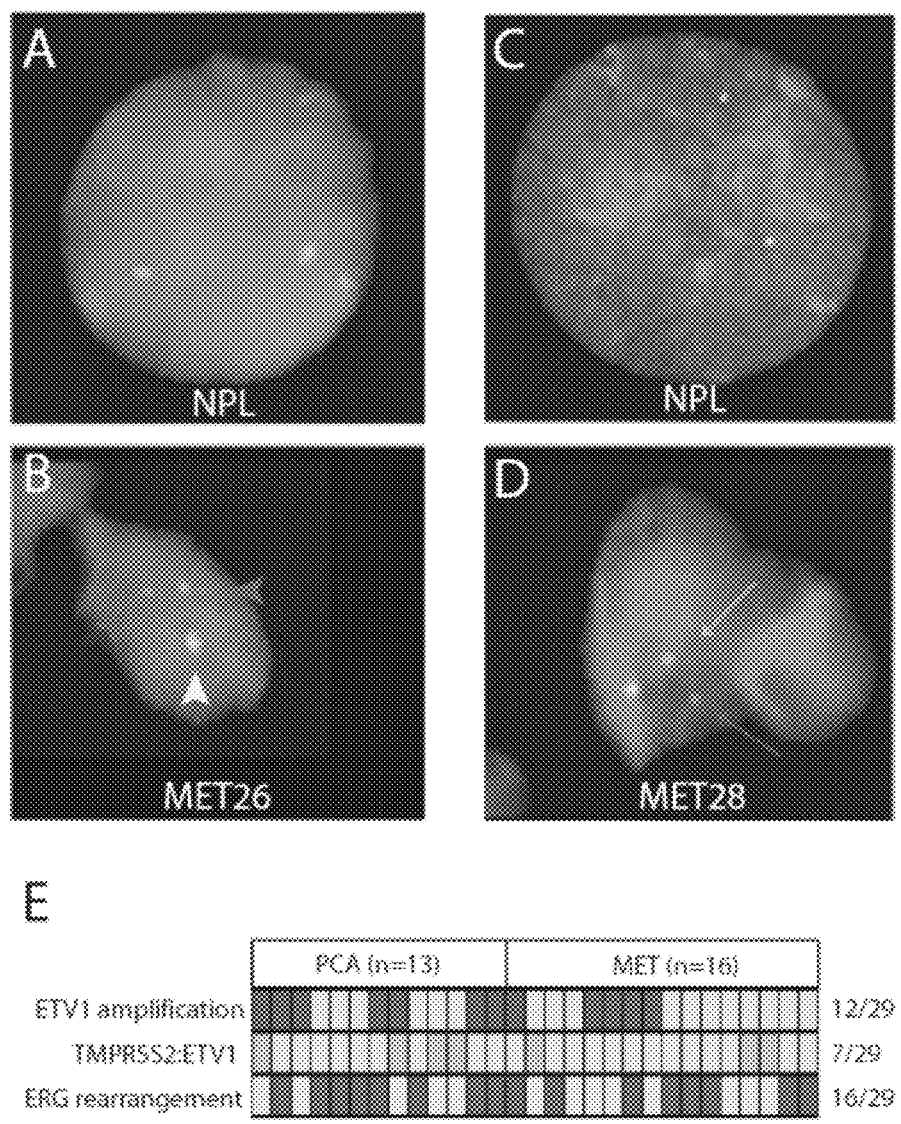
FIG. 3 shows interphase fluorescence in situ hybridization (FISH) on formalin-fixed paraffin embedded tissue sections that confirms TMPRSS2:ETV1 gene fusion and ERG gene rearrangement. (A and B) show two-color, fusion-signal approach to detect the fusion of TMPRSS2 (green signal) and ETV1 (red signal). (C and D) Detection of ERG gene rearrangements using a two-color split-signal approach with two probes spanning the 5' (green signal) and 3' (red signal) regions of ERG. (E) Matrix representation of FISH results using the same probes as (A-D) on an independent tissue microarray containing cores from 13 cases of clinically localized prostate cancer (PCA) and 16 cases of metastatic prostate cancer (MET).

Fluorescence In Situ Hybridization (FISH) Confirms TMPRSS2:ETV1 Translocation and ERG Rearrangement After confirming the existence of the TMPRSS2:ETV1 and TMPRSS2:ERG fusion transcripts, evidence of these rearrangements at the chromosomal level was obtained using interphase fluorescence in situ hybridization (FISH) on formalin fixed paraffin embedded (FFPE) specimens. Two different probe strategies were employed: a twocolor, fusion-signal approach to detect TMPRSS2:ETV1 translocations and a two-color, split-signal approach to detect rearrangements of the ERG locus. These probe strategies were validated on the two cases initially used for RLM-RACE, MET26 and MET28 (FIG. 3). Using probes for TMPRSS2 and ETV1, normal peripheral lymphocytes (NPLs) demonstrated a pair of red and a pair of green signals (FIG. 3A). MET26 showed fusion of one pair of signals, indicative of probe overlap (FIG. 3B, yellow arrowhead), consistent with the expression of the TMPRSS2:ETV1 transcript in this sample. In addition, consistent low-level amplification of the ETV1 locus was identified, as indicated by the two remaining signals for ETV1 (FIG. 3B, red arrowheads). Similarly, using probes spanning the 5' and 3' region of the ERG locus, a pair of yellow signals in NPLs was observed (FIG. 3C). In MET28, one pair of probes split into separate green and red signals, indicative of a rearrangement at the ERG locus (FIG. 3D, green and red arrows). This result is consistent with the expression of the TMPRSS2:ERG transcript in this case. Based on these results, the individual FISH analyses described above were performed on serial tissue microarrays containing cores from 13 cases of localized prostate cancer and 16 cases of metastatic prostate cancer (FIG. 3E). As indicated by the matrix, 23 of 29 cases (79.3%) showed evidence of TMPRSS2:ETV1 fusion (7 cases) or ERG rearrangement (16 cases). In addition, 12 of 29 cases (41.4%) showed evidence of low level amplification at the ETV1 locus. Previous reports have identified the genomic location of ETV1, 7p, as one of the most commonly amplified regions in localized and metastatic prostate cancer (Slamon et al., Science 235, 177 (1987)). However it does not appear that 7p amplification drives ETV1 expression, as ETV1 amplification occurred in 6 cases with ERG rearrangements and our transcript data demonstrates that 0 of 19 samples with high ERG expression and the TMPRSS2:ERG fusion also have high ETV1 expression. Furthermore, when both ETV1 amplification and the TMPRSS2:ETV1 fusion were present by FISH, only the individual ETV1 signal was amplified and not the fused signal. Nevertheless, results from this FISH analysis demonstrate the presence of TMPRSS2:ETV1 and ERG rearrangements at the genomic level consistent with the transcript data described above.

Figure 4:
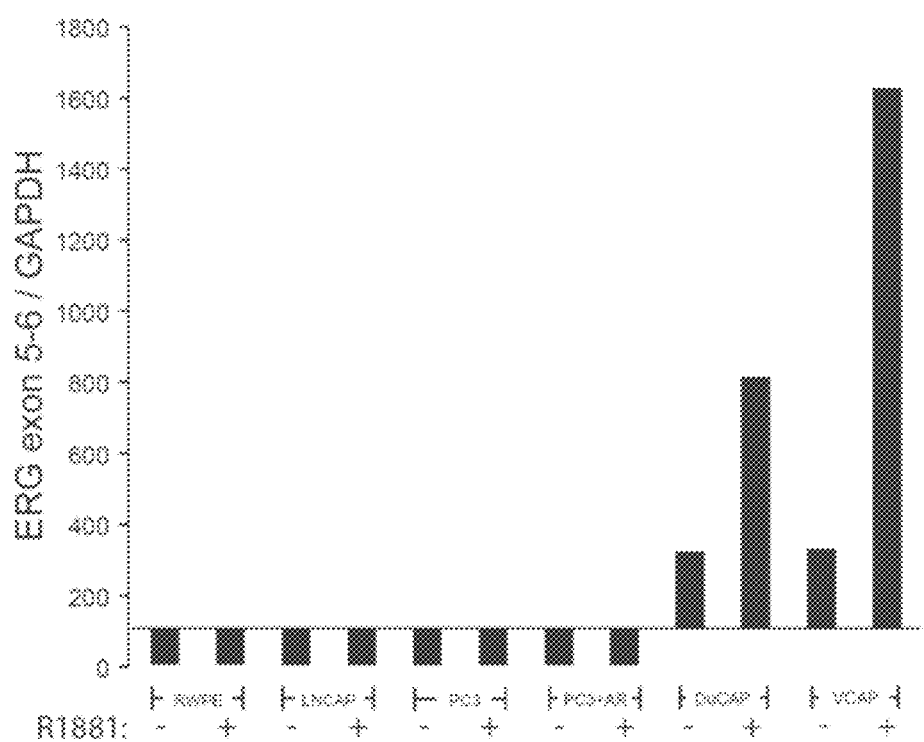
FIG. 4 shows androgen regulation of ERG in prostate cancer cells carrying the TMPRSS2:ERG translocation.

TMPRSS2 is an androgen-regulated gene and fusion with ERG results in androgen regulation of ERG. TMPRSS2 was initially identified as a prostate-specific gene whose expression was increased by androgen in LNCaP cells and also contains androgen responsive elements (AREs) in its promoter (Huang et al., Lancet 361, 1590 (2003); Schwartz et al., Cancer Res 62, 4722 (2002)). Subsequent studies have confirmed high expression in normal and neoplastic prostate tissue and demonstrated that TMPRSS2 is androgen-regulated in androgen-sensitive prostate cell lines (Schwartz et al., Cancer Res 62, 4722 (2002); Ferrando et al., Cancer Cell 1, 75 (2002); Chen et al., Mol Biol Cell 14, 3208 (2003); LaTulippe et al., Cancer Res 62, 4499 (2002)). In addition, while androgen does not increase the expression of TMPRSS2 in the androgen insensitive prostate cancer cell line PC3, stable expression of the androgen receptor in PC3 cells resulted in TMPRSS2 becoming androgen responsive (Schwartz et al., supra; Ferrando et al., supra; Chen et al., supra; LaTulippe et al., supra). In contrast, microarray studies of LNCaP prostate cell lines treated with androgen have not identified ERG or ETV1 as being androgen-responsive (Jain et al., Cancer Res 64, 3907 (2004)) and examination of their promoter sequences did not reveal consensus AREs (Sotiriou et al., supra). It was contemplated that the TMPRSS2:ERGa fusion in DuCaP and VCaP cell lines, which was confirmed by three independent assays in each cell line (Table 2), would result in the androgen regulation of ERG. Using QPCR to assay for ERG expression, it was confirmed that even though ERG was highly expressed in both VCaP and DuCaP cells, treatment with the synthetic androgen R1881 increased the expression of ERG 2.57 fold in DuCaP cells and 5.02 fold in VCaP cells compared to untreated controls (FIG. 4). Expression of ERG was minimal and essentially unchanged after R1881 treatment in RWPE (1.37 fold), LnCaP (0.86 fold), PC3 (1.28 fold) and PC3 cells expressing the androgen receptor (0.73 fold) compared to untreated controls.

Microarray analysis of the same samples confirmed that ERG was only up-regulated in response to androgen in DuCaP and VCaP cells (Sotiriou et al., supra). The present invention is not limited to a particular mechanism. Indeed, an understanding of the mechanism is not necessary to practice the present invention. Nonetheless, it is contemplated that these results suggest a possible mechanism for the aberrant expression of ERG or ETV1 in prostate cancer when respective fusions with TMPRSS2 are present.

TABLE 1

Cancer Outlier Profile Analysis (COPA).

| Rank | % | Score | Study | Cancer | Gene | Evidence |
|---|---|---|---|---|---|---|
| 1 | 95 | 20.056 | Valk et al., N Engl J Med 350, 1617 (2004) | Leukemia | RUNX1T1 | XX |
| 1 | 95 | 15.4462 | Vasselli et al., PNAS USA 100, 6958 (2003) | Renal | PRO1073 | X |
| 1 | 90 | 12.9581 | Ross et al., Blood 102, 2951 (2003). | Leukemia | PBX1 | XX |
| 1 | 95 | 10.03795 | Lapointe et al., PNAS USA 101, 811 (Jan. 20, 2004) | Prostate | ETV1 | ** |
| 1 | 90 | 9.1163 | | Prostate | ETV1 | ** |
| 1 | 90 | 7.4557 | Tian et al., N Engl J Med 349, 2483 (2003) | Myeloma | WHSC1 | X |
| 1 | 75 | 5.4071 | Dhanasekaran et al., Nature 412, 822 (2001) | Prostate | ERG | ** |
| 1 | 75 | 4.3628 | Welsh et al., Cancer Res 61, 5974 (2001) | Prostate | ERG | ** |
| 1 | 75 | 4.3425 | Zhan et al., Blood 99, 1745 (2002) | Myeloma | CCND1 | X |
| 1 | 75 | 3.4414 | Lapointe et al., supra | Prostate | ERG | ** |
| 1 | 75 | 3.3875 | Dhanasekaran et al., Faseb J 19, 243 (2005) | Prostate | ERG | ** |
| 2 | 90 | 6.7029 | | Prostate | ERG | ** |
| 3 | 95 | 13.3478 | Zhan et al., supra | Myeloma | FGFR3 | X |
| 4 | 75 | 2.5728 | Huang et al., Lancet 361, 1590 (2003) | Breast | ERBB2 | Y |
| 6 | 90 | 6.6079 | Sotiriou et al., PNAS USA 100, 10393 (2003) | Breast | ERBB2 | Y |
| 9 | 95 | 17.1698 | Glinsky et al., J Clin Invest 113, 913 (2004) | Prostate | ETV1 | ** |
| 9 | 90 | 6.60865 | Nielsen et al., Lancet 359, 1301 (2002) | Sarcoma | SSX1 | X |
| 9 | 75 | 2.2218 | Yu et al., J Clin Oncol 22, 2790 (2004) | Prostate | ERG | ** |

Genes known to undergo causal mutations in cancer that had strong outlier profiles.
"X", signifies literature evidence for acquired pathogenomic translocation.
"XX" signifies literature evidence for the specific translocation as well as the samples in the specific study that were characterized for that translocation.
"Y" signifies consistent with known amplification.
"**" signifies ERG and ETV1 outlier profiles in prostate cancer.

Table 2 shows a summary of TMPRSS2 fusion to ETS family member status in prostate cancer samples and cell lines. For all assays, positive results are indicated by "+" and negative results are indicated by "−". Blank cells indicate that the specific assay was not performed for that sample. Over-expression of ERG or ETV1 by quantitative PCR (QPCR) is indicated and samples marked with an asterisk indicate the sample was also assessed by cDNA microarray and over-expression was confirmed. In order to detect TMPRSS2:ERG or TMPRSS2:ETV1 gene fusions, selected samples were subjected to RLM-RACE for the over-expressed ETS family member and samples with the TMPRSS2 fusion after sequencing are indicated. All samples were assayed for TMPRSS2:ETV1 and TMPRSS2:ERG expression by QPCR. Selected cases were also amplified by standard reverse-transcription PCR (RT-PCR) using the same TMPRSS2 fusion primers as for QPCR and amplicons were sequenced. Samples with evidence for TMPRSS2:ETV1 or TMPRSS2:ERG fusion are indicated in the final column.

TABLE 2

| Case | Sample | QPCR Expression | TMPRSS2:ETS family member gene fusion assays | | | | TMPRSS2:ETS family member fusion |
|---|---|---|---|---|---|---|---|
| | | | RLM-RACE sequencing | QPCR TMPRSS2:ETV1 | QPCR TMPRSS2:ERG | RT-PCR sequencing | |
| 1 | MET26-LN | ETV1* | + | + | − | | + |
| 1 | MET26-RP | ETV1* | | + | − | | + |
| 2 | MET28-B | ERG | | − | + | | + |
| 2 | MET28-PTLN | ERG | | − | + | | + |
| 2 | MET28-41 | ERG | | − | + | | + |
| 2 | MET28-LN | ERG | + | − | + | | + |
| 3 | MET16-44 | ERG | | − | + | | + |
| 3 | MET16-47 | ERG | | − | + | | + |
| 4 | MET3 | ERG* | | − | + | | + |
| 5 | MET18-23 | ERG* | | − | + | + | + |
| 6 | PCA1 | ERG* | + | − | + | + | + |
| 7 | PCA2 | ERG* | | − | + | + | + |
| 8 | PCA3 | ERG* | | − | + | + | + |
| 9 | PCA4 | ERG* | + | − | + | | + |
| 10 | PCA5 | ERG* | + | − | + | | + |
| 11 | PCA6 | ERG* | | − | + | | + |
| 12 | PCA7 | ERG* | + | − | + | | + |
| 13 | PCA8 | ERG* | | − | + | | + |
| 14 | PCA9 | ERG* | | − | + | | + |
| 15 | PCA10 | ERG* | | − | + | | + |
| 16 | PCA11 | ERG* | | − | + | | + |
| 17 | PCA12 | ERG* | | − | + | | + |
| 18 | PCA13 | ERG* | | − | + | | + |
| 19 | PCA14 | ERG* | | − | + | | + |
| 20 | PCA15 | ERG* | | − | + | | + |
| 21 | PCA16 | ETV1* | − | − | − | | − |
| 22 | PCA17 | ERG* | − | − | − | | − |
| 23 | MET30-LN | − | | − | − | | − |
| 24 | MET17-12 | − | | − | − | | − |
| 25 | MET20-76 | − | | − | − | | − |
| 26 | MET22-61 | − | | − | − | | − |
| 27 | MET5-7 | − | | − | − | | − |
| 28 | PCA18 | − | | − | − | | − |
| 29 | PCA19 | − | | − | − | | − |
| 30 | PCA20 | − | | − | − | | − |
| 31 | PCA21 | − | | − | − | | − |
| 32 | PCA22 | − | | − | − | | − |
| 33 | PCA23 | − | | − | − | | − |
| 34 | PCA24 | − | | − | − | | − |
| 35 | PCA25 | − | | − | − | | − |
| 36 | PCA26 | − | | − | − | | − |
| 37 | PCA27 | − | | − | − | | − |
| 38 | PCA28 | − | | − | − | | − |
| 39 | PCA29 | − | | − | − | | − |
| 40 | PCA30 | − | | − | − | | − |
| 41 | PCA31 | − | | − | − | | − |
| 42 | PCA32 | − | | − | − | | − |
| Cell line | VCap | ERG | + | − | + | | + |
| Cell line | DUCaP | ERG | | − | + | + | + |
| Cell line | LnCaP | ETV1 | − | − | − | | − |
| Cell line | DU145 | − | | − | − | | − |

TABLE 2-continued

|  |  |  | TMPRSS2:ETS family member gene fusion assays | | | | TMPRSS2: ETS |
|---|---|---|---|---|---|---|---|
| Case | Sample | QPCR Expression | RLM-RACE sequencing | QPCR TMPRSS2: ETV1 | QPCR TMPRSS2: ERG | RT-PCR sequencing | family member fusion |
| Cell line | PC3 | − |  | − | − |  | − |
| Cell line | RWPE | − |  | − | − |  | − |

TABLE 3

Cancer Outlier Profile Analysis (COPA).

| Rank | % | Score | Study | Cancer | Reference | Gene | Evidence |
|---|---|---|---|---|---|---|---|
| 1 | 90 | 21.9346 | Bittner et al. | Melanoma | Nature 406, 536 (2000) | CDH1 |  |
| 1 | 95 | 20.056 | Valk et al. | Leukemia | Nature 406, 536 (2000) | RUNX1T1 | XX |
| 1 | 95 | 15.4462 | Vasselli et al. | Renal | PNAS USA 100, 6958 (2003) | PRO1073 | X (12) |
| 1 | 95 | 14.2008 | Segal et al. | Sarcoma | J Clin Oncol 21, 1775 (2003) | MYH11 |  |
| 1 | 90 | 12.9581 | Ross et al. | Leukemia | Blood 102, 2951 (2003) | PBX1 | XX |
| 1 | 95 | 10.03795 | Lapointe et al. | Prostate | PNAS USA 101, 811 (2004) | ETV1 | ** |
| 1 | 90 | 9.1163 |  | Prostate |  | ETV1 | ** |
| 1 | 90 | 7.4557 | Tian et al. | Myeloma | N Engl J Med 349, 2483 (2003) | WHSC1 | X (16) |
| 1 | 75 | 5.4071 | Dhanasekaran et al. | Prostate | Faseb J 19, 243 (2005) | ERG | ** |
| 1 | 75 | 5.2067 | Wang et al. | Breast | Lancet 365, 671 (2005) | FOXO3A |  |
| 1 | 75 | 4.3628 | Welsh et al. | Prostate | Cancer Res 61, 5974 (2001) | ERG | ** |
| 1 | 75 | 4.3425 | Zhan et al. | Myeloma | Blood 99, 1745 (2002) | CCND1 | X (21) |
| 1 | 75 | 3.724 | Cheok et al. | Leukemia | Nat Genet 34, 85 (May, 2003) | PCSK7 |  |
| 1 | 75 | 3.4414 | Lapointe et al. | Prostate | PNAS USA 101, 811 (2004) | ERG | ** |
| 1 | 75 | 3.3875 | Dhanasekaran et al. | Prostate | Nature 412, 822 (2001) | ERG | ** |
| 1 | 75 | 2.5913 | Wigle et al. | Lung | Cancer Res 62, 3005 (2002) | IGH@ |  |
| 2 | 90 | 12.7953 | Ross et al. | Leukemia | Blood 102, 2951 (2003) | HOXA9 |  |

TABLE 3-continued

Cancer Outlier Profile Analysis (COPA).

| Rank | % | Score | Study | Cancer | Reference | Gene | Evidence |
|---|---|---|---|---|---|---|---|
| 2 | 95 | 9.2916 | Golub et al. | Leukemia | Science 286, 531 (1999) | TRA@ | |
| 2 | 95 | 9.2916 | Golub et al. | Leukemia | Science 286, 531 (1999) | TRD@ | |
| 2 | 90 | 8.2292 | Cheok et al. | Leukemia | Nat Genet 34, 85 (May, 2003) | SSX2 | |
| 2 | 90 | 6.7029 | | Prostate | | ERG | ** |
| 3 | 95 | 13.3478 | Zhan et al. | Myeloma | Blood 99, 1745 (2002) | FGFR3 | X (21) |
| 3 | 95 | 10.2267 | Cheok et al. | Leukemia | Nat Genet 34, 85 (May, 2003) | ARHGAP26 | |
| 3 | 90 | 5.9174 | | Prostate | | REL | |
| 3 | 75 | 2.6162 | Rosenwald et al. | Lymphoma | Cancer Cell 3, 185 (2003) | TCL1A | |
| 3 | 75 | 2.036 | Sotiriou et al. | Breast | PNAS USA 100, 10393 (2003) | RAD51L1 | |
| 4 | 75 | 8.4985 | Bittner et al. | Melanoma | Nature 406, 536 (2000) | TP53 | |
| 4 | 90 | 5.4881 | Golub et al. | Leukemia | Science 286, 531 (1999) | LCK | |
| 4 | 75 | 2.5728 | Huang et al. | Breast | Lancet 361, 1590 (2003) | ERBB2 | Y(29) |
| 4 | 75 | 2.0229 | Schwartz et al. | Ovarian | Cancer Res 62, 4722 (2002) | IGL@ | |
| 6 | 90 | 17.3733 | Ferrando et al. | Leukemia | Cancer Cell 1, 75 (2002) | ZBTB16 | |
| 6 | 95 | 9.1267 | Chen et al. | Gastric | Mol Biol Cell 14, 3208 (2003) | FGFR2 | |
| 6 | 90 | 6.6079 | Sotiriou et al. | Breast | PNAS USA 100, 10393 (2003) | ERBB2 | Y(29) |
| 6 | 75 | 5.7213 | LaTulippe et al. | Prostate | Cancer Res 62, 4499 (2002) | NF1 | |
| 6 | 75 | 5.2752 | Jain et al. | Endocrine | Cancer Res 64, 3907 (2004) | PHOX2B | |
| 6 | 90 | 4.8383 | Lapointe et al. | Prostate | PNAS USA 101, 811 (2004) | LAF4 | |
| 6 | 90 | 4.1779 | Alizadeh et al. | Lymphoma | Nature 403, 503 (2000) | IRTA1 | |

TABLE 3-continued

Cancer Outlier Profile Analysis (COPA).

| Rank | % | Score | Study | Cancer | Reference | Gene | Evidence |
|---|---|---|---|---|---|---|---|
| 6 | 90 | 3.6325 | Rosenwald et al. | Lymphoma | N Engl J Med 346, 1937 (2002) | IRTA1 | |
| 6 | 75 | 1.85865 | Chen et al. | Liver | Mol Biol Cell 13, 1929 (2002) | HMGA1 | |
| 7 | 95 | 4.7561 | Alon et al. | Colon | Proc Natl Acad Sci USA 96, 6745 (1999) | NONO | |
| 7 | 75 | 1.8133 | Chen et al. | Liver | Mol Biol Cell 13, 1929 (2002) | GPC3 | |
| 8 | 90 | 4.7068 | Lacayo et al. | Leukemia | Blood 104, 2646 (2004) | EVI1 | |
| 8 | 90 | 4.7068 | Lacayo et al. | Leukemia | Blood 104, 2646 (2004) | MDS1 | |
| 9 | 95 | 17.1698 | Glinsky et al. | Prostate | J Clin Invest 113, 913 (2004) | ETV1 | ** |
| 9 | 90 | 15.3889 | Ferrando et al. | Leukemia | Ferrando et al., Cancer Cell 1, 75 (2002) | MN1 | |
| 9 | 90 | 6.60865 | Nielsen et al. | Sarcoma | Lancet 359, 1301 (2002) | SSX1 | X (42) |
| 9 | 90 | 4.4875 | Lapointe et al. | Prostate | PNAS USA 101, 811 (2004) | CHEK2 | |
| 9 | 75 | 2.2218 | Yu et al. | Prostate | J Clin Oncol 22, 2790 (2004) | ERG | ** |
| 10 | 95 | 10.6036 | Segal et al. | Sarcoma | Segal et al., J Clin Oncol 21, 1775 (2003) | KIT | |

Genes that are known to undergo causal mutations in cancer that had an outlier profile in the top 10 of a study in Oncomine are shown.

"X", signifies literature evidence for acquired pathognomonic translocation.

"XX" signifies literature evidence for the specific translocation as well as that the samples in the specific study were characterized for that translocation.

"Y" signifies consistent with known amplification.

"**" signifies ERG and ETV1 outlier profiles in prostate cancer.

TABLE 4

Oligonucleotide primers used in this study. For all primers, the gene, bases and exons (according to alignment of the reference sequences described in the text with the May 2004 assembly of the human genome using the UCSC Genome Browser) are listed. Forward primers are indicated with "f" and reverse primers with "r".

| Gene | Bases | Exon(s) | Primer | Sequence 5' to 3' | SEQ ID NO |
|---|---|---|---|---|---|
| ETV1 | 193-216 | 2 | Exon 2-3_f | AACAGAGATCTGGCTCATGATTCA | 1 |
| ETV1 | 268-245 | 3 | Exon 2-3_r | CTTCTGCAAGCCATGTTTCCTGTA | 2 |
| ETV1 | 248-271 | 3-4 | Exon 3-4_f | AGGAAACATGGCTTGCAGAAGCTC | 3 |
| ETV1 | 305-280 | 4 | Exon 3-4_r | TCTGGTACAAACTGCTCATCATTGTC | 4 |
| ETV1 | 269-294 | 4 | Exon 4-5_f | CTCAGGTACCTGACAATGATGAGCAG | 5 |
| ETV1 | 374-351 | 5 | Exon 4-5_r | CATGGACTGTGGGGTTCTTTCTTG | 6 |
| ETV1 | 404-429 | 5 | Exon 5-6_f | AACAGCCCTTTAAATTCAGCTATGGA | 7 |
| ETV1 | 492-472 | 6 | Exon 5-6_r | GGAGGGCCTCATTCCCACTTG | 8 |
| ETV1 | 624-645 | 6-7 | Exon 6-7_f | CTACCCCATGGACCACAGATTT | 9 |
| ETV1 | 771-750 | 7 | Exon 6-7_r | CTTAAAGCCTTGTGGTGGGAAG | 10 |
| ERG | 574-597 | 5-6 | Exon 5-6_f | CGCAGAGTTATCGTGCCAGCAGAT | 11 |
| ERG | 659-636 | 6 | Exon 5-6_r | CCATATTCTTTCACCGCCCACTCC | 12 |
| NA | NA | NA | Generace r_5_f | CGACTGGAGCACGAGGACACTGA | 13 |
| ETV1 | 374-351 | 5 | Exon 4-5_r | CATGGACTGTGGGGTTCTTTCTTG1 | 14 |
| ERG | 284-263 | 4 | Exon 4a_r | GGCGTTCCGTAGGCACACTCAA | 15 |
| ERG | 396-377 | 4 | Exon 4b-r | CCTGGCTGGGGTTGAGACA | 16 |
| TMPRSS2 | -4-17 | 1 | TMPRSS2:ERG_f | TAGGCGCGAGCTAAGCAGGAG | 17 |
| ERG | 276-252 | 4 | TMPRSS2:ERG_r | GTAGGCACACTCAAACAACGACTGG | 18 |
| TMPRSS2 | 1-19 | 1 | TMPRSS2:ETV1_f | CGCGAGCTAAGCAGGAGGC | 19 |
| ETV1 | 339-318 | 4-5 | TMPRSS2:ETV1_r | CAGGCCATGAAAAGCCAAACTT | 20 |

Example 2

ETV4 Gene Fusions

A. Materials and Methods
ETS Family Expression in Profiling Studies

To investigate the expression of ETS family members in prostate cancer, two prostate cancer profiling studies were utilized (Lapointe et al., Proc Natl Acad Sci USA 2004; 101:811-6 and Tomlins et al., Science 2005; 310:644-8) present in the Oncomine database (Rhodes et al., Neoplasia 2004; 6:1-6). Genes with an ETS domain were identified by the Interpro filter 'Ets' (Interpro ID: IPR000418). Heatmap representations were generated in Oncomine using the 'median-center per gene' option, and the color contrast was set to accentuate ERG and ETV1 differential expression.

Samples

Prostate cancer tissues (PCA1-5) were from the radical prostatectomy series at the University of Michigan, which is part of the University of Michigan Prostate Cancer Specialized Program of Research Excellence (S.P.O.R.E.) Tissue Core. All samples were collected with informed consent of the patients and prior institutional review board approval. Total RNA was isolated with Trizol (Invitrogen, Carlsbad, Calif.) according to the manufacturer's instructions. A commercially available pool of benign prostate tissue total RNA (CPP, Clontech, Mountain View, Calif.) was also used.

Quantitative PCR (QPCR)

QPCR was performed using SYBR Green dye on an Applied Biosystems 7300 Real Time PCR system (Applied Biosystems, Foster City, Calif.) as described (Tomlins et al., supra). The amount of each target gene relative to the housekeeping gene glyceraldehyde-3-phosphate dehydrogenase (GAPDH) for each sample was reported. The relative amount of the target gene was calibrated to the relative amount from the pool of benign prostate tissue (CPP). All oligonucleotide primers were synthesized by Integrated DNA Technologies (Coralville, Iowa). GAPDH primers were as described (Vandesompele et al., Genome Biol 2002; 3:RE-SEARCH0034). Primers for exons of ETV4 were as follows (listed 5' to 3'): ETV4_exon2-f: CCGGATGGAGCGGAG-GATGA (SEQ ID NO:21), ETV4_exon2-r: CGGGC-GATTTGCTGCTGAAG (SEQ ID NO:22), ETV4_exon3-f: GCCGCCCCTCGACTCTGAA (SEQ ID NO:23), ETV4_exon4-r: GAGCCACGTCTCCTGGAAGTGACT (SEQ ID NO:24), ETV4_exon11-f: CTGGCCGGTTCT-TCTGGATGC (SEQ ID NO:25), ETV4_exon12-r: CGGGC-CGGGGAATGGAGT (SEQ ID NO:26), ETV4_3'UTR-f: CCTGGAGGGTACCGGTTTGTCA (SEQ ID NO:27), ETV4_3'UTR-r: CCGCCTGCCTCTGGGAACAC (SEQ ID NO:28). Exons were numbered by alignment of the Ref-Seq for ETV4 (NM_001986.1) with the May 2004 freeze of the human genome using the UCSC Genome Browser. For QPCR confirmation of TMPRSS2:ETV4 fusion transcripts, TMPRSS2:ETV4a-f (AAATAAGTTTGTAAGAGGAGC-CTCAGCATC (SEQ ID NO:29)) and TMPRSS2:ETV4b-f (ATCGTAAAGAGCTTTTCTCCCCGC (SEQ ID NO:30)), which detects both TMPRSS2:ETV4a and TMPRSS2; ETV4b transcripts, were used with ETV4_exon4-r.

RNA Ligase Mediated Rapid Amplification of cDNA Ends (RLM-Race)

RLM-RACE was performed using the GeneRacer RLM-RACE kit (Invitrogen), according to the manufacturer's instructions as described (Tomlins et al., supra). To obtain the 5' end of ETV4, first-strand cDNA from PCA5 was amplified using the GeneRacer 5' Primer and ETV4_exon4-r or ETV4_exon7-r (GAAAGGGCTGTAGGGGCGACTGT (SEQ ID NO:31)). Products were cloned and sequenced as described (Tomlins et al., supra). Equivalent 5' ends of the TMPRSS2:ETV4 transcripts were obtained from both primer pairs.

Fluorescence In Situ Hybridization (FISH)

Formalin-fixed paraffin-embedded (FFPE) tissue sections were used for interphase FISH. Deparaffinized tissue was treated with 0.2 M HCl for 10 min, 2×SSC for 10 min at 80° C. and digested with Proteinase K (Invitrogen) for 10 min. The tissues and BAC probes were co-denatured for 5 min at 94° C. and hybridized overnight at 37° C. Post-hybridization washing was with 2×SSC with 0.1% Tween-20 for 5 min and fluorescent detection was performed using anti-digoxigenin conjugated to fluorescein (Roche Applied Science, Indianapolis, Ind.) and streptavidin conjugated to Alexa Fluor 594 (Invitrogen). Slides were counterstained and mounted in Pro-Long Gold Antifade Reagent with DAPI (Invitrogen). Slides were examined using a Leica DMRA fluorescence microscope (Leica, Deerfield, Ill.) and imaged with a CCD camera using the CytoVision software system (Applied Imaging, Santa Clara, Calif.).

All BACs were obtained from the BACPAC Resource Center (Oakland, Calif.) and probe locations were verified by hybridization to metaphase spreads of normal peripheral lymphocytes. For detection of TMPRSS2:ETV4 fusion, RP11-35C4 (5' to TMPRSS2) was used with multiple BACs located 3' to ETV4 (distal to ETV4 to proximal: RP11-266I24, RP11-242D8, and RP11-100E5). For detection of ETV4 rearrangements, RP11-436J4 (5' to ETV4) was used with the multiple BACs 3' to ETV4. For each hybridization, areas of cancerous cells were identified by a pathologist and 100 cells were counted per sample. The reported cell count for TMPRSS2:ETV4 fusions used RP11-242D8 and similar results were obtained with all 3' ETV4 BACs. To exclude additional rearrangements in PCA5, FISH was performed with two probes 3' to ETV4 (RP11-266I24 and RP11-242D8), ERG split signal probes (RP11-95I21 and RP11-476D17) and TMPRSS2:ETV1 fusion probes (RP11-35C4 and RP11-124L22). BAC DNA was isolated using a QIAFilter Maxi Prep kit (Qiagen, Valencia, Calif.) and probes were synthesized using digoxigenin- or biotin-nick translation mixes (Roche Applied Science).

B. Results

The initial COPA screen led to the characterization of TMPRSS2 fusions with ERG or ETV1 (Example 1). It was further contemplated that prostate cancers negative for these gene fusions harbor rearrangements involving other ETS family members. By interrogating the expression of all ETS family members monitored in prostate cancer profiling studies from the Oncomine database (Rhodes et al., supra), marked over-expression of the ETS family member ETV4 was identified in a single prostate cancer case from each of two studies—one profiling grossly dissected tissues (Lapointe et al., supra) (FIG. 7A) and the other profiling laser capture microdissected (LCM) tissues1 (FIG. 7B). As these cases did not over-express ERG or ETV1, and no benign prostate tissues showed over-expression, it was contemplated that fusion with TMPRSS2 was responsible for the over-expression of ETV4 in these cases. Although ELF3 was also over-expressed in a fraction of prostate cancer cases, in both studies normal prostate tissue samples also showed marked ELF3 over-expression, indicating that a gene fusion driving expression in both benign and cancerous tissue is unlikely. Thus, the ETV4 over-expressing case (designated here as PCA5) was further analyzed.

Total RNA was isolated from PCA5 and exon-walking quantitative PCR was used (QPCR) to confirm the over-expression of ETV4. QPCR demonstrated that exons 3' to exon 2 of ETV4 were markedly over-expressed in this case compared to pooled benign prostate tissue (CPP) (~900 fold) and prostate cancers that did not over-express ETV4 and were either TMPRSS2:ERG positive (PCA1-2) or negative (PCA3-4) (FIG. 8A). However, a dramatic decrease (>99%) in the expression of exon 2 of ETV4 relative to distal regions in PCA5 was observed, indicating a possible fusion with TMPRSS2, as observed previously in TMPRSS2:ERG and TMPRSS2:ETV1 positive cases (Tomlins et al., supra).

To identify the 5' end of the ETV4 transcript in PCA5, RNA-ligase mediated rapid amplification of cDNA ends (RLM-RACE) was performed using a reverse primer in exon 7. RLM-RACE revealed two transcripts, each containing 5' ends consisting of sequence located approximately 8 kb upstream of TMPRSS2 fused to sequence from ETV4 (FIG. 8B). Specifically, the 5' end of TMPRSS2:ETV4a has 47 base pairs from this region upstream of TMPRSS2, while the 5' end of TMPRSS2:ETV4b has the same terminal 13 base pairs. These 5' ends of both transcripts were fused to the same contiguous stretch consisting of the 9 base pairs of the intron immediately 5' to exon 3 of ETV4 and the reported reference sequence of exons 3 through the reverse primer in exon 7 of ETV4.

The existence of both transcripts in PCA5 and their absence in CPP and PCA1-4 was confirmed using QPCR. To further exclude the presence of fusion transcripts involving known exons from TMPRSS2, QPCR was performed using a forward primer in exon 1 of TMPRSS2 and the ETV4 exon 4 reverse primer, and as expected, no product was detected in CPP or PCA1-5.

Whether other prostate cancers with ETV4 dysregulation might contain TMPRSS2:ETV4 fusion transcripts structurally more similar to TMPRSS2:ERG and TMPRSS2:ETV1 transcripts (which involve known exons from TMPRSS2) is unknown. The TMPRSS2:ETV4 fusions reported here do not contain the well characterized AREs immediately upstream of TMPRSS2. However, evidence exists for androgen responsive enhancers located upstream of the TMPRSS2 sequences present in the TMPRSS2:ETV4 transcripts described here (Rabbitts, Nature 1994; 372:143-9). Nevertheless, the marked over-expression of only ETV4 exons involved in the fusion transcript strongly suggests that the gene fusion is responsible for the dysregulation of ETV4. Together, the structure of the TMPRSS2:ETV4 fusion transcripts supports the conclusion that the regulatory elements upstream of TMPRSS2, rather than transcribed TMPRSS2 sequences, drive the dysregulation of ETS family members.

To confirm the fusion of the genomic loci surrounding TMPRSS2 (21q22) and ETV4 (17q21) as demonstrated by RLM-RACE and QPCR, interphase fluorescence in situ hybridization (FISH) was used. Using probes 5' to TMPRSS2 and 3' to ETV4, fusion of TMPRSS2 and ETV4 loci was observed in 65% of cancerous cells from PCA5 (FIG. 8D). As further confirmation of the rearrangement of ETV4, using probes 5' and 3' to ETV4, 64% of cancerous cells from PCA5 showed split signals. FISH was also performed on PCA5 using two probes 3' to ETV4, ERG split signal probes and TMPRSS2:ETV1 fusion probes to exclude additional rearrangements, with negative results obtained for each hybridization.

Taken together, the results highlight the use of carefully examining outlier profiles in tumor gene expression data, as most analytical methods discount profiles that do not show consistent deregulation (Eisen et al., Proc Natl Acad Sci USA 1998; 95:14863-8; Golub et al., Science 1999; 286:531-7; Tusher et al., Proc Natl Acad Sci USA 2001; 98:5116-21) and would thus fail to identify ETV4 in prostate cancer, which appears rare (2 of 98 cases). Combined with the identification of TMPRSS2:ERG and TMPRSS2:ETV1 fusions, the results presented here show that dysregulation of ETS family members mediated by subversion of AREs or enhancers upstream of TMPRSS2 is a hallmark of prostate tumorigenesis.

Example 3

Detection of Gene Fusion RNA

This example describes target capture, amplification and qualitative detection of RNA (IVT) containing the sequences of the four gene fusions in four separate qualitative assays: TMPRSS2:ETV1a, TMPRSS2:ETV1b, TMPRSS2:ERGa and TMPRSS2:ERGb with APTIMA formulation reagents and HPA detection each spiked with the appropriate target specific oligonucleotides, primers and probes. Table 5 shows sequences of oligonucleotides used in the assay.

Enzyme reagent was a lyophilized form of a 1.45 mL solution containing 20 mM HEPES, 125 mM N-acetyl-L-cysteine, 0.1 mM EDTA disodium dihydrate, 0.2% (v/v) TRITON7 X-100 detergent, 0.2 M trehalose dihydrate, 0.90 RTU/mL Moloney murine leukemia virus (MMLV) reverse transcriptase, and 0.20 U/mL T7 RNA polymerase, at pH 7.0. One unit (RTU) of activity is defined as the synthesis and release of 5.75 fmol cDNA in 15 minutes at 37° C. for MMLV reverse transcriptase, and for T7 RNA polymerase, one unit (U) of activity is defined as the production of 5.0 fmol RNA transcript in 20 minutes at 37° C. Enzyme reagent was reconstituted in 3.6 mL of the enzyme reagent reconstitution solution (see below).

TABLE 5

| Gene Fusion | Sequence (5' to | SEQ ID NO |
|---|---|---|
| TMPRSS2 exon1/Target Capture | AAAAAAAAAAAAAAAAAAAAAAAAAAAAAATTTCUCGAUUCGUCCUCCG | 59 |
| TMPRSS2 exon1/Target Capture | AAAAAAAAAAAAAAAAAAAAAAAAAAAAAATTTAUCCGCGCUCGAUUCGUC | 60 |
| TMPRSS2 exon1/Non-T7 | GAGGGCGAGGGGCGGGGAGCGCC | 61 |
| TMPRSS2 exon2/Non-T7 | CCTATCATTACTCGATGCTGTTGATAACAGC | 62 |
| ETV1a/b exon4/T7 | AATTTAATACGACTCACTATAGGGAGAAACTTTCAGCCTGATA | 63 |
| ERGb exon2/T7 | AATTTAATACGACTCACTATAGGGAGACTCTGTGAGTCATTTGTCTTGCTT | 64 |
| ERGa exon4/T7 | AATTTAATACGACTCACTATAGGGAGAGCACACTCAAACAACGACTG | 65 |
| TMPRSS2exon1: ETV1a Junction/AE | GCGCGGCAG-CUCAGGUACCUGAC | 66 |
| TMPRSS2exon2: ETV1b Junction/AE | GCUUUGAACUCA-CUCAGGUACCUGAC | 67 |
| TMPRSS2exon1: ERGa Junction/AE | GAGCGCGGCAG-GAAGCCUUAUCAGUUG | 68 |
| TMPRSS2exon1: ERGb Junction/AE | GAGCGCGGCAG-GUUAUUCCAGGAUCUUU | 69 |

A. Materials and Methods
RNA Target Capture

Lysis buffer contained 15 mM sodium phosphate monobasic monohydrate, 15 mM sodium phosphate dibasic anhydrous, 1.0 mM EDTA disodium dihydrate, 1.0 mM EGTA free acid, and 110 mM lithium lauryl sulfate, pH 6.7.

Target capture reagent contained 250 mM HEPES, 310 mM lithium hydroxide, 1.88 M lithium chloride, 100 mM EDTA free acid, at pH 6.4, and 250 µg/ml 1 micron magnetic particles SERA-MAG MG-CM Carboxylate Modified (Seradyn, Inc., Indianapolis, Ind.) having dT$_{14}$ oligomers covalently bound thereto.

Wash solution contained 10 mM HEPES, 6.5 mM sodium hydroxide, 1 mM EDTA, 0.3% (v/v) ethanol, 0.02% (w/v) methyl paraben, 0.01% (w/v) propyl paraben, 150 mM sodium chloride, 0.1% (w/v) lauryl sulfate, sodium (SDS), at pH 7.5.

RNA Amplification & Detection

Amplification reagent was a lyophilized form of a 3.6 mL solution containing 26.7 mM rATP, 5.0 mM rCTP, 33.3 mM rGTP and 5.0 mM rUTP, 125 mM HEPES, 8% (w/v) trehalose dihydrate, 1.33 mM dATP, 1.33 mM dCTP, 1.33 mM dGTP and 1.33 mM dTTP, at pH 7.5. The Amplification reagent was reconstituted in 9.7 mL of the amplification reagent reconstitution solution (see below). Before use, 15 pmol each of primer oligomers was added.

Amplification reagent reconstitution solution contained 0.4% (v/v) ethanol, 0.10% (w/v) methyl paraben, 0.02% (w/v) propyl paraben, 33 mM KCl, 30.6 mM MgCl$_2$, 0.003% phenol red.

Enzyme reagent reconstitution solution contained 50 mM HEPES, 1 mM EDTA, 10% (v/v) TRITON7 X-100, 120 mM potassium chloride, 20% (v/v) glycerol anhydrous, at pH 7.0.

Hybridization reagent contained 100 mM succinic acid free acid, 2% (w/v) lithium lauryl sulfate, 100 mM lithium hydroxide, 15 mM aldrithiol-2, 1.2 M lithium chloride, 20 mM EDTA free acid, 3.0% (v/v) ethanol, at pH 4.7.

Selection reagent contained 600 mM boric acid, 182.5 mM sodium hydroxide, 1% (v/v) TRITON7 X-100, at pH 8.5.

The detection reagents comprised detect reagent I, which contained 1 mM nitric acid and 32 mM hydrogen peroxide, and detect reagent II, which contained 1.5 M sodium hydroxide.

B. Assay Protocol
Target Capture
1. Prepare samples by making dilutions of IVT stock solution into STM at indicated copy levels for 400 µL sample per reaction tube.
2. Using the repeat pipettor, add 100 µL of the TCR with the TCO to the appropriate reaction tube.
3. Using the micropipettor, add 400 µL of each sample to the properly labeled.
4. Cover the tubes with the sealing card(s) and shake the rack gently by hand. Do not vortex. Incubate the rack at 62°±1° C. in a water bath for 30±5 minutes.
5. Remove the rack from the water bath and blot bottoms of tubes dry on absorbent material.
6. Ensure the sealing cards are firmly seated. If necessary, replace with new sealing cards and seal tightly.

7. Without removing sealing cards, incubate the rack at room temperature for 30±5 minutes.
8. Place the rack on the TCS magnetic base for 5 to 10 minutes.
9. Prime the dispense station pump lines by pumping APTIMA Wash Solution through the dispense manifold. Pump enough liquid through the system so that there are no air bubbles in the line and all 10 nozzles are delivering a steady stream of liquid.
10. Turn on the vacuum pump and disconnect the aspiration manifold at the first connector between the aspiration manifold and the trap bottle. Ensure that the vacuum gauge reads greater than 25 in. Hg. It may take 15 seconds to achieve this reading. Reconnect the manifold, and ensure the vacuum gauge is between 7 and 12 in. Hg. Leave the vacuum pump on until all target capture steps are completed.
11. Firmly attach the aspiration manifold to the first set of tips. Aspirate all liquid by lowering the tips into the first TTU until the tips come into brief contact with the bottoms of the tubes. Do not hold the tips in contact with the bottoms of the tubes.
12. After the aspiration is complete, eject the tips into their original tip cassette. Repeat the aspiration steps for the remaining TTUs, using a dedicated tip for each specimen.
13. Place the dispense manifold over each TTU and, using the dispense station pump, deliver 1.0 mL of APTIMA Wash Solution into each tube of the TTU.
14. Cover tubes with a sealing card and remove the rack from the TCS. Vortex once on the multi-tube vortex mixer.
15. Place rack on the TCS magnetic base for 5 to 10 minutes.
16. Aspirate all liquid as in steps 13 and 14.
17. After the final aspiration, remove the rack from the TCS base and visually inspect the tubes to ensure that all liquid has been aspirated. If any liquid is visible, place the rack back onto the TCS base for 2 minutes, and repeat the aspiration for that TTU using the same tips used previously for each specimen.

Primer Annealing and Amplification
1. Using the repeat pipettor, add 75 μL of the reconstituted Amplification Reagent containing the analyte specific primers to each reaction tube. All reaction mixtures in the rack should now be red in color.
2. Using the repeat pipettor, add 200 μL of Oil Reagent.
3. Cover the tubes with a sealing card and vortex on the multi-tube vortex mixer.
4. Incubate the rack in a water bath at 62°±1° C. for 10±5 minutes.
5. Transfer the rack into a water bath at 42°±1° C. for 5±2 minutes.
6. With the rack in the water bath, carefully remove the sealing card and, using the repeat pipettor, add 25 μL of the reconstituted Enzyme Reagent to each of the reaction mixtures. All reactions should now be orange in color.
7. Immediately cover the tubes with a fresh sealing card, remove from the water bath, and mix the reactions by gently shaking the rack by hand.
8. Incubate the rack at 42°±1° C. for 60±15 minutes.

Hybridization
1. Remove the rack from the pre-amplification water bath and transfer to the post-amplification area. Add 100 μL of the reconstituted Probe Reagent with analyte specific probe, using the repeat pipettor. All reaction mixtures should now be yellow in color.
2. Cover tubes with a sealing card and vortex for 10 seconds on the multi-tube vortex mixer.
2. Incubate the rack in a 62°±1° C. water bath for 20±5 minutes.
3. Remove the rack from the water bath and incubate at room temperature for 5±1 minutes Selection
1. Using the repeat pipettor, add 250 μL of Selection Reagent to each tube. All reactions should now be red in color.
2. Cover tubes with a sealing card, vortex for 10 seconds or until the color is uniform, and incubate the rack in a water bath at 62°±1° C. for 10±1 minutes.
3. Remove the rack from the water bath. Incubate the rack at room temperature for 15±3 minutes.

Reading the TTUs
1. Ensure there are sufficient volumes of Auto Detection Regents I and II to complete the tests.
2. Prepare the LEADER Luminometer by placing one empty TTU in cassette position number 1 and perform the WASH protocol.
3. Load the TTUs into the luminometer and run the HC+ Rev B protocol.

C. Results

The results are shown in Tables 6-9 for 4 assays with each of the TMPRSS2:ERG and TMPRSS2:ETV1 gene fusion IVTs spiked into TCR.

TABLE 6

| TMPRSS2:ETV1a (copies IVT/reaction) | RLU |
|---|---|
| 0 | 4,945 |
| 0 | 4,599 |
| 10 | 2,185,959 |
| 10 | 2,268,090 |
| 10 | 2,284,908 |
| 100 | 2,270,369 |
| 100 | 2,302,023 |
| 100 | 2,272,735 |
| 1,000 | 2,279,627 |
| 1,000 | 2,285,742 |

TABLE 7

| TMPRSS2:ETV1b (copies IVT/reaction) | RLU |
|---|---|
| 0 | 7,743 |
| 0 | 6,622 |
| 0 | 7,370 |
| 0 | 6,181 |
| 0 | 7,409 |
| 10 | 7,712 |
| 10 | 7,178 |
| 10 | 7,302 |
| 10 | 8,430 |
| 10 | 8,331 |
| 100 | 774,792 |
| 100 | 285,712 |
| 100 | 3,361,878 |
| 100 | 1,349,368 |
| 100 | 2,757,334 |
| 1,000 | 3,647,502 |
| 1,000 | 3,790,087 |
| 1,000 | 3,813,812 |
| 1,000 | 3,753,743 |
| 1,000 | 3,667,242 |

TABLE 8

| TMPRSS2:ERGa (copies IVT/reaction) | RLU |
|---|---|
| 0 | 7,938 |
| 0 | 7,505 |
| 10 | 2,043,379 |
| 10 | 387,408 |
| 10 | 978,457 |
| 100 | 2,332,764 |
| 100 | 2,445,544 |
| 100 | 2,530,239 |

TABLE 9

| TMPRSS2:ERGb (copies IVT/reaction) | RLU |
|---|---|
| 0 | 5,978 |
| 0 | 6,284 |
| 10 | 2,700,069 |
| 10 | 2,768,541 |
| 100 | 2,883,091 |
| 100 | 2,779,233 |
| 1,000 | 2,857,247 |
| 1,000 | 2,957,914 |

Example 4

FISH Assay for Gene Fusions

This Example describes the use of fluorescence in situ hybridization (FISH), to demonstrate that 23 of 29 prostate cancer samples harbor rearrangements in ERG or ETV1. Cell line experiments suggest that the androgen-responsive promoter elements of TMPRSS2 mediate the overexpression of ETS family members in prostate cancer. These results have implications in the development of carcinomas and the molecular diagnosis and treatment of prostate cancer.

Below is a list of the specific BAC probes used in FISH assays.

Clinical FISH Assay for Testing Aberrations in ETS Family Members by FISH

Testing ETV1-TMPRSS2 fusion with one probe spanning the ETV1 and one spanning the TMPRSS2 locus BAC for ETV1: RP11-692L4

BAC for TMPRSS2: RP11-121A5, (RP11-120C17, PR11-814F13, RR11-535H11)

Testing ERG translocation with set of probes for c-ERG: t-ERG break apart:

BAC for c-ERG: RP11-24A11

BACs for t-ERG: RP11-372O17, RP11-137J13

Testing ETV1 deletion/amplification with set of probes, one spanning the ETV1 locus and one reference probe on chromosome 7:

BAC for ETV1: RP11-692L4

BAC for reference robe on chromosome 7: A commercial probe on centromere of chr.

Testing ERG deletion/amplification with set of probes, one spanning the ERG locus and one reference probe on chromosome 21:

BAC for ERG: RP11-476D17

BACs for reference probe on chromosome 21: *

Testing TMPRSS2 deletion/amplification with set of probes, one spanning the TMPRSS2 locus and one reference probe on chromosome 21:

BACs for TMPRSS2: RP11-121A5, (RP11-120C17, PR11-814F13, RR11-535H11)

BACs for reference probe on chromosome 21: *

*BACs for reference probe on chromosome 21: PR11-32L6, RP11-752M23, RP11-1107H21, RP11-639A7, (RP11-1077M21)

Example 5

TMPRSS2:ERG Fusion Associated Deletions

This example describes the presence of common deletions located between ERG and TMPRSS2 on chromosome 21q22.2-3 associated with the TMPRSS2:ERG fusion. Associations between disease progression and clinical outcome were examined using a wide range of human PCA samples, 6 cell lines, and 13 xenografts.

A. Materials and Methods

Clinical Samples

Prostate samples used for this study were collected under an IRB approved protocol. All clinically localized PCA samples were characterized by one pathologist and assigned a Gleason score to eliminate inter-observer differences in pathology reporting. Clinically localized PCA samples were collected as part of an on-going research protocol at the University of Ulm. The hormone refractory samples were taken from the Rapid Autopsy Program of the University of Michigan.

The FISH experiments were conducted on two PCA outcome arrays, which were composed of 897 tissue cores (histospots) from 214 patients. A summary of the patient demographics is presented in Table 10. All patients had undergone radical prostatectomy with pelvic lymphadenectomy at the University of Ulm (Ulm, Germany) between 1989 and 2001. Pre-operative PSA ranged between 1 and 314 ng/ml (mean 36 ng/ml). Mean and maximum follow-up was 3.4 and 8.4 yrs, respectively.

Cell Lines and Xenografts

Androgen independent (PC-3, DU-145, HPV10, and 22Rv1) and androgen sensitive (LNCaP) PCA cell lines were purchased from the American Type Culture Collection (Manassas, Va.) and maintained in their defined medium. HPV10 was derived from cells from a high-grade PCA (Gleason score 4+4=8), which were transformed by transfection with HPV18 DNA(18). 22Rv1 is a human PCA epithelial cell line derived from a xenograft that was serially propagated in mice after castration-induced regression and relapse of the parental, androgen-dependent CWR22 xenograft. The VCAP cell line was from a vertebral metastatic lesion as part of the Rapid Autopsy program at the University of Michigan.

LuCaP 23.1, 35, 73, 77, 81, 86.2, 92.1, and 105 were derived from patients with androgen independent hormone-refractory disease PCA. LuCaP 49 and 115 are from patients with androgen dependent PCA. LuCaP 58 is derived from an untreated patient with clinically advanced metastatic disease and LuCaP 96 was established from a prostate derived tumor growing in a patient with hormone refractory PCA. LuCaP 49 (established from an omental mass) and LuCaP 93 are hormone-insensitive (androgen receptor [AR]-negative) small cell PCAs. These two xenografts demonstrate a neuroendocrine phenotype. LuCaP 23.1 is maintained in SCID mice, and other xenografts are maintained by implanting tumors in male BALB/c nu/nu mice.

Determining TMPRSS2:ERG Fusion Status using Interphase FISH

Figure 11:
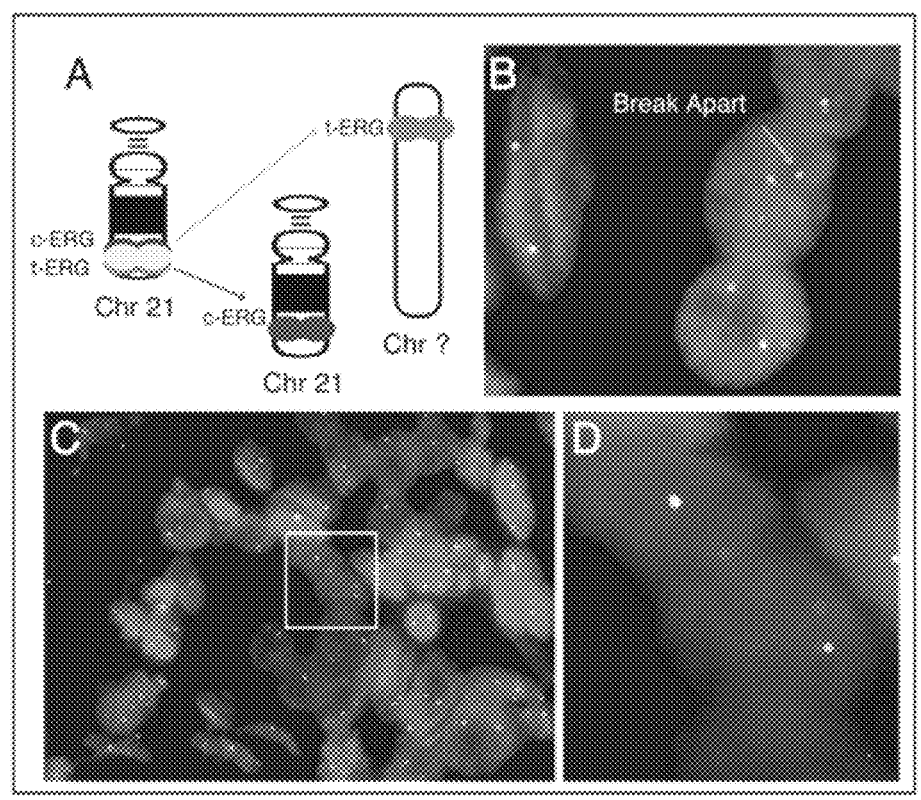
FIG. 11 shows TMPRSS2:ERG gene fusion analysis by FISH. Panel A: Ideogram, depicting a break apart assay for the indirect detection of TMPRSS2:ERG fusion. Panel B: Interphase nuclei of a stromal cell (left) and a prostate cancer gland (right). Panel C: Interphase nuclei of prostate cancer glands showing break apart and simultaneous deletion as indicated by loss of the telomeric probe (100× oil immersion objective magnification). Panel D. Magnified view of boxed area in C demonstrating two nuclei with break apart and loss of the telomeric probe. (60× oil immersion objective magnification).

The FISH analysis for the translocation of TMPRSS2:ERG is described above and previously (Tomlins, et al., Science 310:644-8 (2005)). This break apart assay is presented in FIGS. 11 and 14. For analyzing the ERG rearrangement on chromosome 21q22.2, a break apart probe system was applied, consisting of the Biotin-14-dCTP labeled BAC clone RP11-24A11 (eventually conjugated to produce a red signal) and the Digoxigenin-dUTP labeled BAC clone RP11-137J13 (eventually conjugated to produce a green signal), spanning the neighboring centromeric and telomeric region of the ERG locus, respectively. All BAC clones were obtained from the BACPAC Resource Center, Children's Hospital Oakland Research Institute (CHORI), Oakland, Calif.

Using this break apart probe system, a nucleus without ERG rearrangement exhibits two pairs of juxtaposed red and green signals. Juxtaposed red-green signals form a yellow fusion signal. A nucleus with an ERG rearrangement shows break apart of one juxtaposed red-green signal pair resulting in a single red and green signal for the translocated allele and a combined yellow signal for the non-translocated allele in each cell. Prior to tissue analysis, the integrity and purity of all probes were verified by hybridization to normal peripheral lymphocyte metaphase spreads. Tissue hybridization, washing, and fluorescence detection were performed as described previously (Garraway, et al., Nature 436:117-22 (2005); Rubin, et al., Cancer Res. 64:3814-22 (2004)). At least one TMA core could be evaluated in 59% PCA cases from two TMAs. The technical difficulties with this assay included the absence of diagnostic material to evaluate, weak probe signals, and overlapping cells preventing an accurate diagnosis. The remainder of the analysis focused on the 118 cases of clinically localized PCA that could be evaluated. 15 cases had corresponding hormone naïve metastatic lymph node samples that could also be evaluated.

The samples were analyzed under a 100× oil immersion objective using an Olympus BX-51 fluorescence microscope equipped with appropriate filters, a CCD (charge-coupled device) camera and the CytoVision FISH imaging and capturing software (Applied Imaging, San Jose, Calif.). Evaluation of the tests was independently performed by two pathologists both with experience in analyzing interphase FISH experiments. For each case, it was attempted to score at least 100 nuclei per case. If significant differences between the results of both pathologists were found, the case was refereed by a third pathologist.

Oligonucleotide SNP Array Analysis

Although SNP arrays were intended for genotyping alleles, the SNP array data can provide information on Loss-of-Heterozygosity (Lieberfarb, et al., Cancer Res 63:4781-5 (2003); Lin, et al., Bioinformatics 20:1233-40 (2004)) and detection of copy number alterations (Zhao, et al., Cancer Cell 3:483-95 (2003)). Using SNP array analysis, it was possible to identify and validate amplified genes in various cancers including melanoma (MITF) (Garraway, et al., Nature 436: 117-22 (2005)) and PCA (TPD52) (Rubin, et al., Cancer Res. 64:3814-22 (2004)).

SNP detection on the 100K array began with a reduction in genome representation. Two aliquots of 250 ng of genomic DNA were digested separately with XbaI HindIII. The digested fragments were independently ligated to an oligonucleotide linker. The resulting products were amplified using a single PCR primer under conditions in which 200-2000 bp PCR fragments were amplified. These fragments represent a sub-fraction of the genome. The SNPs tiled on the arrays have been pre-selected as they lie within these XbaI and HindIII fragments and have been validated as robustly detected on the arrays. The derived amplified pools of DNA were then labeled, fragmented further and hybridized to separate HindIII and XbaI oligonucleotide SNP arrays.

Arrays were scanned with a GeneChip Scanner 3000. Genotyping calls and signal quantification were obtained with GeneChip Operating System 1.1.1 and Affymetrix Genotyping Tools 2.0 software. Only arrays with genotyping call rates exceeding 90% were analyzed further. Raw data files were pre-processed and visualized in dChipSNP Lin, et al., Bioinformatics 20:1233-40 (2004)). In particular, preprocessing included array data normalization to a baseline array using a set of invariant probes and subsequent processing to obtain single intensity values for each SNP on each sample using a model based (PM/MM)method (Li, et al., Proc. Nat'l Acad. Sci. USA 98:31-6 (2001)).

Quantitative PCR for TMPRSS2:ERG and TMPRSS2:ETV1 Fusion Transcripts

QPCR was performed using SYBR Green dye (Qiagen) on a DNA engine Opticon 2 machine from MJ Research. Total RNA was reverse transcribed into cDNA using TAQMAN reverse transcription reagents (Applied Biosystems) in the presence of random Hexamers. All QPCR reactions were performed with SYBR Green Master Mix (Qiagen). All Oligonucleotide primers were designed at Integrated DNA Technologies. Primers that were described by Tomlin et al. (Science 310:644-8 (2005)) and are specific for the fusion were utilized:

```
TMPRSS2: ERG_f:
                                    (SEQ ID NO: 55)
TAGGCGCGAGCTAAGCAGGAG,

TMPRSS2: ERG_r:
                                    (SEQ ID NO: 56)
GTAGGCACACTCAAACAACGACTGG,

TMPRSS2: ETV1_f
                                    (SEQ ID NO: 57)
CGCGAGCTAAGCAGGAGGC,

TMPRSS2: ETV-1_r:
                                    (SEQ ID NO: 58)
CAGGCCATGAAAAGCCAAACTT.
```

GAPDH primers were previously described (Vandesompele, et al., Genome Biol 3: RESEARCH 0034 (2002)). 10 µMol of forward and reverse primer were used and procedures were performed according to the manufacturer's recommended thermocycling conditions. Threshold levels were set during the exponential phase of the QPCR reaction using Opticon Monitor analysis software version 2.02. The amount of each target gene relative to the housekeeping gene glyceraldehyde-3-phosphate dehydrogenase (GAPDH) for each sample was determined using the comparative threshold cycle (Ct) method (Applied Biosystems User Bulletin #2). All reactions were subjected to melt curve analysis and products from selected experiments were resolved by electrophoreses on 2% agarose gel.

Statistics

The clinical and pathology parameters were explored for associations with rearrangement status and with the presence of the deletion. Chi-squared test and Fisher exact test were used appropriately. Kaplan-Meier analysis was used to generate prostate-specific antigen recurrence free survival curves of the pathology and the genomic alteration parameters. Log-rank test was used to evaluate statistical significance of associations. Patients with prior neo-adjuvant hormone ablation therapy were excluded. All statistics were performed using SPSS 13.0 for Windows (SPSS Inc., Chicago, Ill.) with a significance level of 0.05.

B. Results

Figure 14:
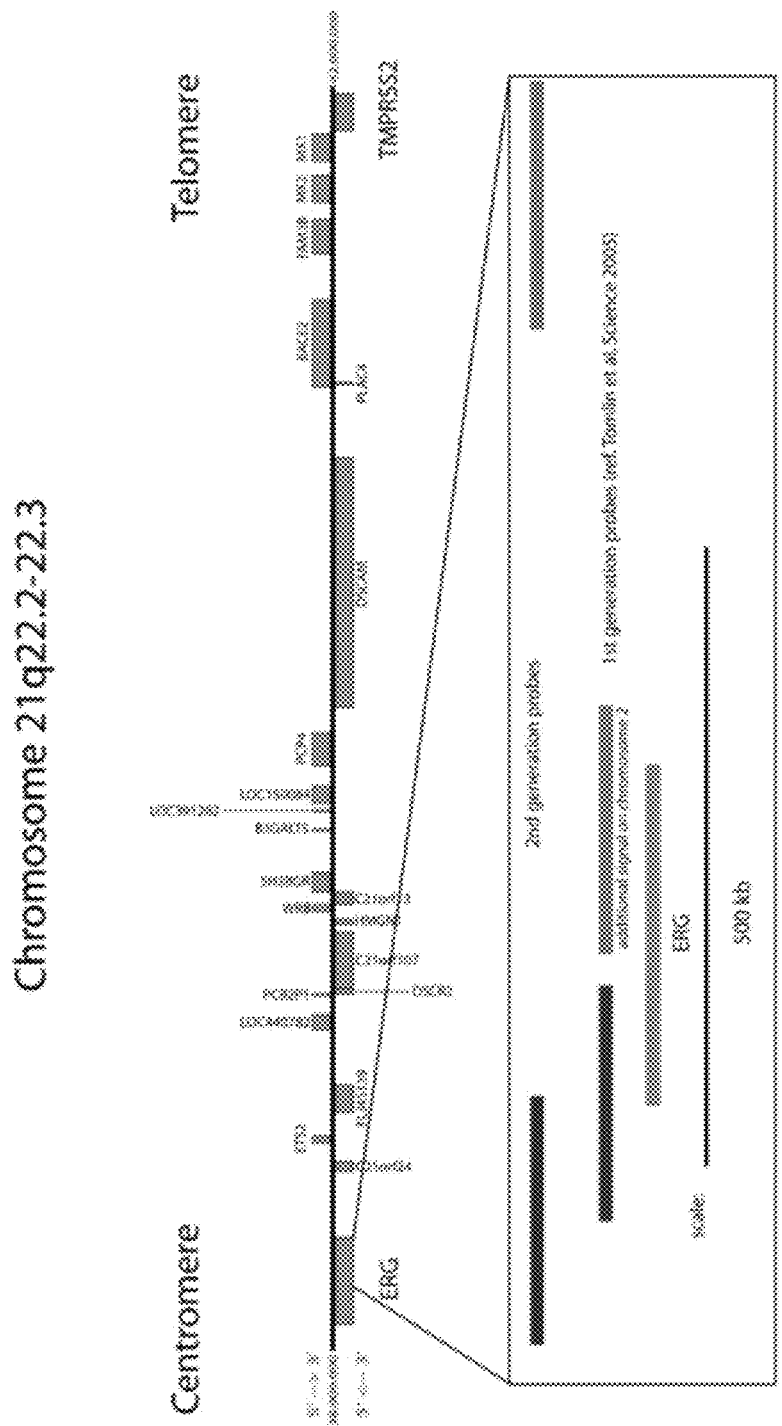
FIG. 14 shows known genes located on 21q22-23 between ERG (centromeric) and TMPRSS2 (telomeric). Genes above the black line are oriented 5'-centromeric to 3'-telomeric and genes below the black line are oriented 5'-telomeric to 3'-centromeric. In the lower half of the image, a magnification of the ERG locus is depicted with FISH probes.
Figure 15:
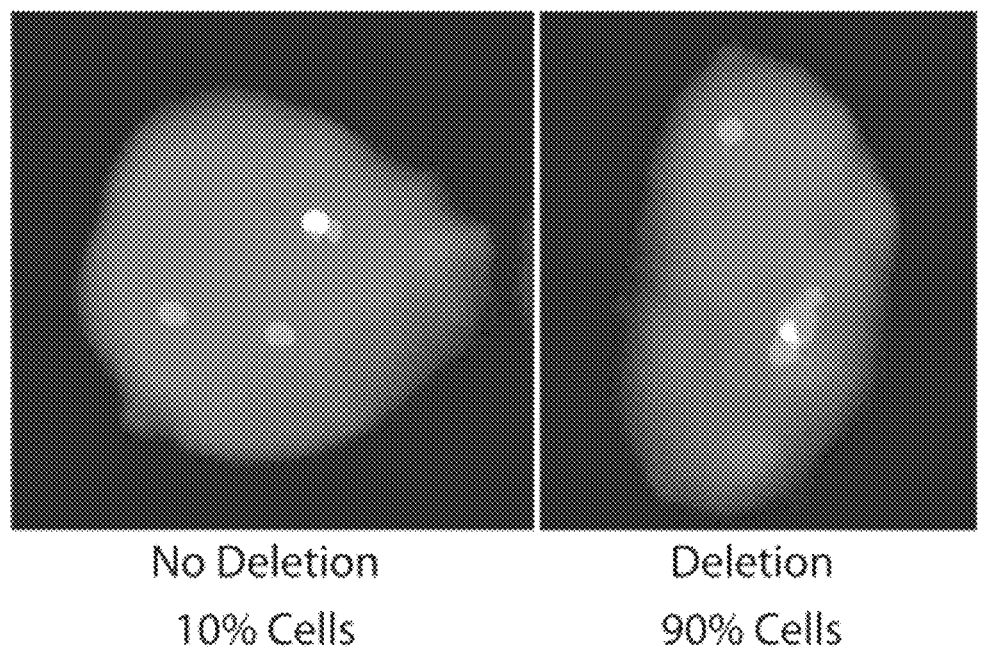
FIG. 15 shows 'heterogenous' prostate cancer case predominantly showing TMPRSS2:ERG rearrangement with the deletion (nucleus on the right) and only small areas showing the TMPRSS2:ERG rearrangement without the deletion (nucleus on the left).

Detection of Deletions on Chromosome 21 Associated with the TMPRSS2:ERG Gene Rearrangement In order to characterize the frequency of the TMPRSS2:ERG rearrangement in PCA, a modified FISH assay from the assay described by Tomlins, et al. (*Science* 310:644-8 (2005)) was utilized. The original FISH assay used two probes located on ERG at the centromeric 3' and telomeric 5' ends. The new assay moved the 5' probe in a telomeric direction (FIG. 14). Using a PCA screening tissue microarray (TMA), it was observed that approximately 70% of PCA demonstrating TMPRSS2:ERG rearrangement (FIGS. 11A and 11B) also showed a loss of the green signal corresponding to the telomeric 5' ERG probe (FIGS. 11C and 11D), suggesting that this chromosomal region was deleted. 100K oligonucleotide SNP arrays were used to characterize the extent of these deletions. By interrogating 30 PCA samples, including cell lines, xenografts and hormone naïve and hormone refractory metastatic PCA samples, genomic loss between ERG and TMPRSS2 on chromosome 21q23 was identified (FIG. 12A-C).

Figure 12:
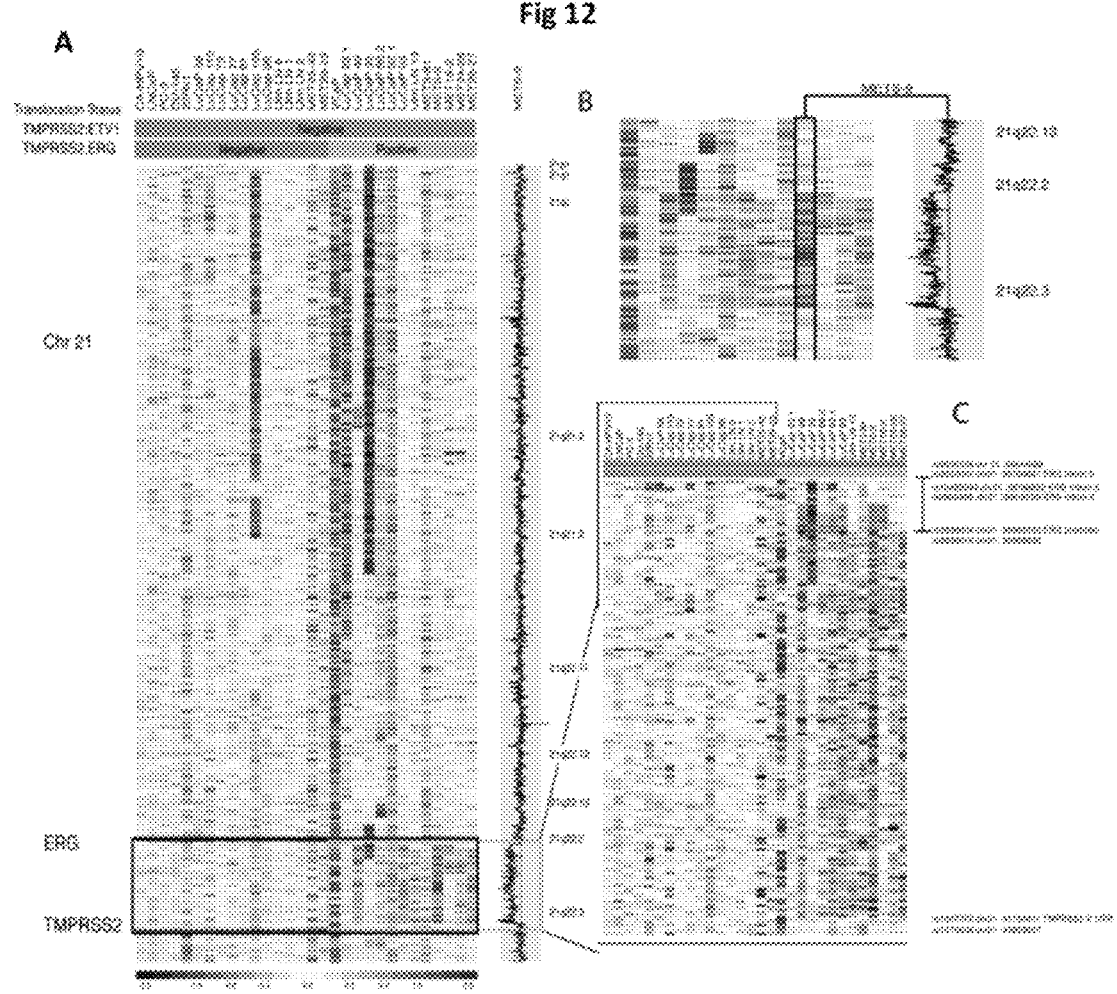
FIG. 12 shows Genomic deletions on chromosome 21 between ERG and TMPRSS2. Panel A: Samples, including 6 cell lines, 13 xenografts and 11 metastatic PCA samples, were characterized for TMPRSS2:ERG and TMPRSS2:ETV1 status (gray bars for negative and blue bar for positive status), by qPCR and/or by FISH. Panel B: Magnification of the green framed box in A. Panel C: Magnification of the black framed box in A.

The rearrangement status for TMPRSS2:ERG and TMPRSS2:ETV1 was determined for these 30 PCA by FISH and/or qPCR (FIG. 12A, gray and light blue bar). Discrete genomic loss was observed in TMPRSS2:ERG rearrangement positive samples involving an area between TMPRSS2 and the ERG loci for LuCaP 49, LuCaP 93, ULM LN 13, MET6-9, MET18-2, MET24-28, and MET28-27. The extent of these discrete deletions was heterogeneous. More extensive genomic loss on chromosome 21 including the area between TMPRSS2 and the ERG loci was observed in LuCaP 35, LuCaP 86.2, LuCaP 92.1, and MET3-81. The VCaP cell line and the xenograft LuCap 23.1 did not demonstrate loss in this region. For a subset of samples 45% (5 out of 11) the deletion occurs in proximity of ERG intron 3. For a majority of samples 64% (7 out of 11) the deletion ends in proximity of the SNP located on TMPRSS2 (the next SNP in the telomeric direction is about 100K bp distant). The VCaP cell line shows copy number gain along the entire chromosome 21.

For TMPRSS2:ERG rearrangement positive tumors, 71% (5 of 7) hormone refractory PCA demonstrate a deletion between TMPRSS2 and the ERG loci whereas deletion was only identified in 25% (1 of 4) hormone naïve metastatic PCA samples (ULM LN 13). There is significant homogeneity for the deletion borders with two distinct sub-classes, distinguished by the start point of the deletion—either at 38.765 Mb or 38.911 Mb. None of the standard PCA cell lines (PC-3, LNCaP, DU-145, or CWR22 (22Rv1)) demonstrated the TMPRSS2:ERG or TMPRSS2:ETV1 fusion. Several of the LuCap xenografts demonstrate TMPRSS2:ERG fusion with deletion including LuCaP 49 (established from an omental mass) and LuCaP 93, both hormone-insensitive (androgen receptor [AR]-negative) small-cell PCAs.

Copy number gain of ERG was observed in a small subset of cases both with and without the TMPRSS2:ERG rearrangement. The VCaP cell line derived from a hormone refractory PCA demonstrated significant copy number gain on chromosome 21 (FIG. 12A-C), which was confirmed by FISH.

TMPRSS2:ERG rearrangement in Primary Prostate Cancer Samples and Hormone Naïve Lymph Node Metastases To characterize the frequency and potential clinical significance of these observations, 118 clinically localized PCA cases were examined by FISH. The clinical and pathology demographics are presented in Table 10. This cohort of patients is at high risk of disease recurrence as demonstrated by high tumor grades (Gleason grade), pathology stage, and pre-treatment PSA levels. Using standard tissue sections from this cohort, where the large areas of the PCA could be studied microscopically, the TMPRSS2:ERG rearrangement was observed to be homogeneous for a given tumor. The TMA experiments confirmed these observations. In PCA cases where 3-6 cores were taken from different areas of the tumor, 100% concordance was observed for TMPRSS2:ERG rearrangement status (i.e. present or absent). It was also observed that in cases with the TMPRSS2:ERG rearrangement with deletion, the deletion was observed in all of the TMA cores from the same patient in 97.9% (94/96) of the cases.

TABLE 10

Clinical and Pathological Demographics of 118 Men with Clinically Localized Prostate Cancer Treated by Radial Protatectomy*

| | | Count | Column N % |
|---|---|---|---|
| Age | <=median | 55 | 50.0% |
| | >median | 55 | 50.0% |
| Preoperative PSA (ng/ml) | <=4 | 6 | 8.2% |
| | >4 and <10 | 13 | 17.8% |
| | >=10 | 54 | 74.0% |
| Gleason Score Sum | <7 | 7 | 6.0% |
| | =7 | 51 | 43.6% |
| | >7 | 59 | 50.4% |
| Nuclear Grade | 1 | — | — |
| | 2 | 38 | 35.5% |
| | 3 | 69 | 64.5% |
| Pathology Stage (pT) | PT2 | 26 | 22.2% |
| | PT3a | 34 | 29.1% |
| | PT3b | 57 | 48.7% |
| Surgical Margins status | Negative | 30 | 27.8% |
| | Positive | 78 | 72.2% |
| Lymph Node Status (pN) | $N_0$ | 52 | 44.1% |
| | $N_1$ | 56 | 47.5% |
| | $N_2$ | 10 | 8.5% |
| PSA Recurrence | no | 34 | 48.6% |
| | yes | 36 | 51.4% |

*Not all data points were available for all 118 cases

The TMPRSS2:ERG rearrangement was identified in 49.2% of the primary PCA samples and 41.2% in the hormone naïve metastatic LN samples (FIG. 13A). Deletion of the telomeric probe (green signal) (FIG. 1C-D) was observed in 60.3% (35/58) of the primary PCA samples and 42.9% (3/7) of the hormone naïve lymph node tumors with TMPRSS2:ERG rearrangement.

In the 15 cases where there was matched primary and hormone naïve lymph node tumors, there was 100% concordance for TMPRSS2:ERG rearrangement status with 47% (7 of 15) of the pairs demonstrating the rearrangement. Deletion of the telomeric (green signal) probe was concordantly seen in 42.9% (3 of 7) of the pairs.

TMPRSS2:ERG Rearrangement Status and Prostate Cancer Progression

Figure 13:
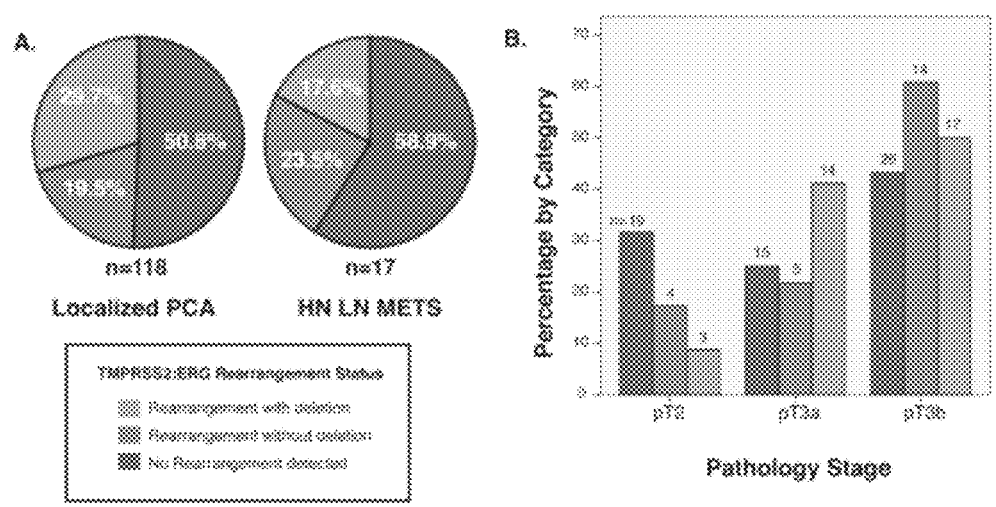
FIG. 13 shows TMPRSS2:ERG rearrangement in clinically localized prostate cancer and association with pathological parameters. Panel A. The TMPRSS2:ERG rearrangement was identified in 49.2% of the primary PCA samples and 41.2% in the hormone naïve metastatic LN samples. Panel B. TMPRSS2:ERG rearranged tumors with deletions tended to be observed in a higher percentage of PCA cases with advanced tumor stage (p=0.03).

The associations between rearrangement status and clinical and pathological parameters were observed (FIG. 13). TMPRSS2:ERG rearrangement with deletion was observed in a higher percentage of PCA cases with advanced tumor stage (pT)(p=0.03) (FIG. 13B), and the presence of metastatic disease to regional pelvic lymph nodes ($pN_0$ versus $pN_{1-2}$) (p=0.02). Associations between TMPRSS2:ERG rearrangement with and without deletion and clinical outcome as determined by prostate specific antigen (PSA) biochemical failure for 70 patients where follow up data was available were also assessed. Gleason grade, tumor stage, nuclear grade and lymph node status were good predictors of PSA biochemical failure (all p-values <0.0005). A trend was observed at the univariate level suggesting a PSA recurrence free survival advantage in TMPRSS2:ERG rearranged PCA cases without deletion as determined by the FISH assay.

Example 6

TMPRSS2:ERG Gene Fusion Associated with Lethal Prostate Cancer

Figure 17:
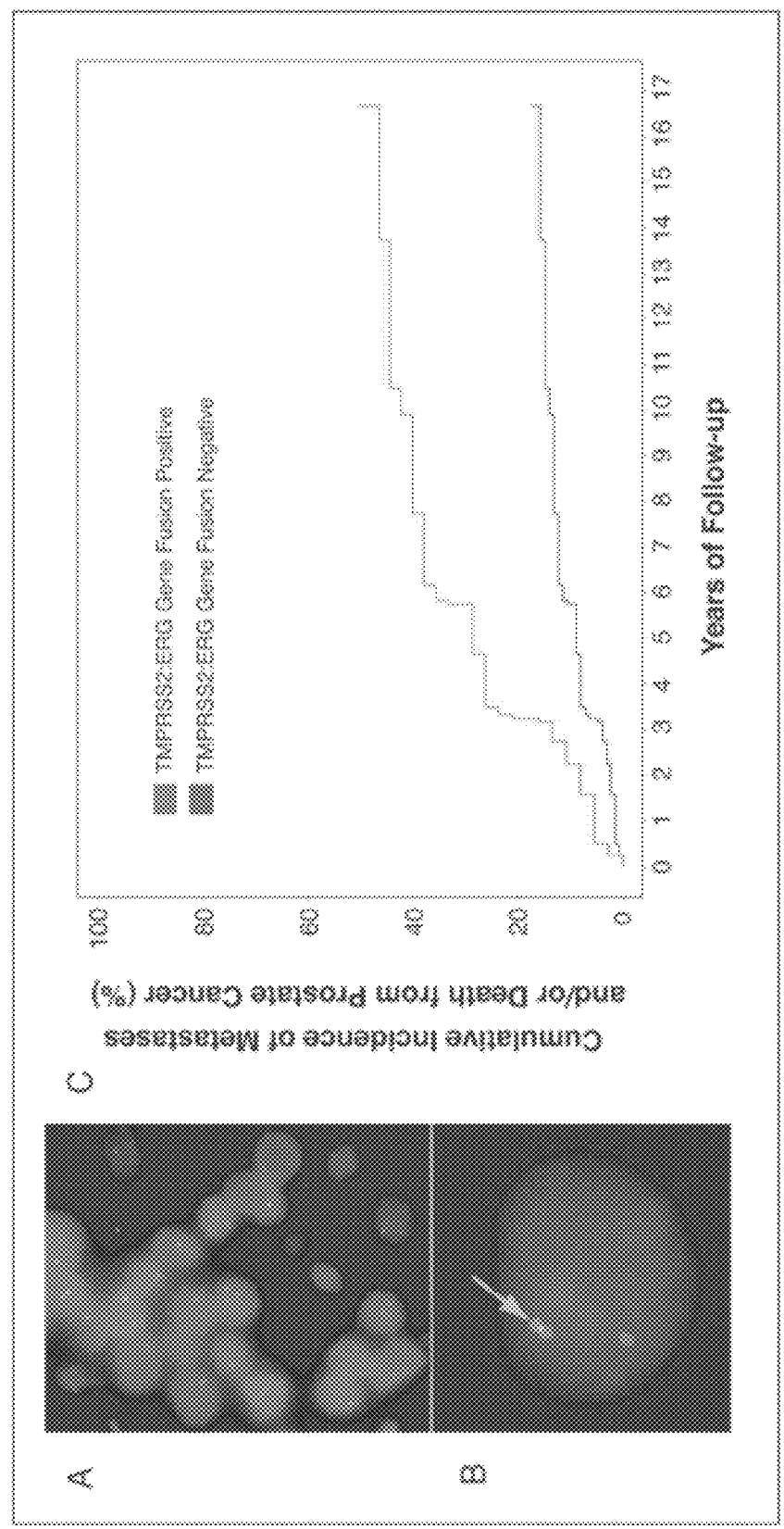
FIG. 17 shows that the FISH assay detects the characteristic deletion associated with TMPRSS2:ERG gene fusion, which is associated with disease progression. Panels A and B: For analyzing the ERG rearrangement on chromosome 21q22.2, a break apart probe system was applied, consisting of the Biotin-14-dCTP labeled BAC clone RP11-24A11 (eventually conjugated to produce a red signal) and the Digoxigenin-dUTP labeled BAC clone RP11-137J13 (eventually conjugated to produce a green signal), spanning the neighboring centromeric and telomeric region of the ERG locus, respectively. Using this break apart probe system, a nucleus without ERG rearrangement exhibits two pairs of juxtaposed red and green signals. Juxtaposed red-green signals form a yellow fusion signal (Panel B, arrow). Panel C: In a cumulative incidence regression model, TMPRSS2:ERG was evaluated as a determinant for the cumulative incidence or metastases or prostate cancer-specific death.

In previous studies, the gene fusions of the 5'-untranslated region of TMPRSS2 (21q22.3) with the ETS transcription factor family members, either ERG (21q22.2), ETV1 (7p21.2) (Tomlins, et al., *Science* 310:644-8 (2005)), or ETV4 (Tomlins, et al., *Cancer Res.* 66(7):3396-400 (2006)) provide a mechanism for the over expression of the ETS genes in the majority of prostate cancers. Furthermore, the fusion of an androgen regulated gene, TMPRSS2, and an oncogene suggests that disease progression may vary based on these molecular subtypes. The most common mechanism for gene fusion is loss of about 2.8 megabases of genomic DNA between TMPRSS2 and ERG (FIGS. 17A and B). This example describes the risk of metastases or prostate cancer specific death based on the presence of the common TMPRSS2:ERG gene fusion.

A. Methods

The study population comprises men with early prostate cancer (T1a-b, Nx, M0) diagnosed at the Örebro University Hospital, Sweden, between 1977 and 1991 by transurethral resection of the prostate (TURP) or transvesical adenoma enucleation for symptomatic benign prostatic hyperplasia as described by Andrén et al. (*J. Urol.* 175(4):1337-40 (2006)). Baseline evaluation at diagnosis included physical examination, chest radiography, bone scan and skeletal radiography (if needed). Nodal staging was not carried out. Because this evaluation provided no evidence for distant metastases, patients were followed expectantly and received clinical exams, laboratory tests and bone scans every 6 months during the first 2 years after diagnosis and subsequently at 12-month intervals. Patients, who developed metastases, as determined by bone scan, were treated with androgen deprivation therapy if they exhibited symptoms.

The cause of death in the cohort was determined by review of medical records by the study investigators. A validation study regarding cause of death compared to the Swedish Death Register showed greater than 90% concordance, with no systematic under- or over-reporting of any cause of death (Johansson, et al., *Lancet* 1(8642):799-803 (1989)). Follow-up of the cohort with respect to mortality was 100% and no patients were lost to follow-up through October 2005. The study endpoint was defined as development of distant metastases or prostate cancer specific death (median follow-up time 9.1 years, maximum 27 years).

All TURP samples were reviewed by one pathologist to confirm a diagnosis of prostate cancer, determine the Gleason score and nuclear grade, and estimate the tumor burden as previously described (*J. Urol.* 175(4):1337-40 (2006)). A tissue microarray was assembled using a manual arrayer (Rubin, et al., *Cancer Epidemiol. Biomarkers Prev.* 14(6):1424-32 (2005)). The frequency of the TMPRSS2:ERG rearrangement in prostate cancer was assessed using a modified florescence in situ hybridization (FISH) assay from the assay originally described by Tomlins et al (*Science* 310:644-8 (2005)). The new assay moved the 5' probe approximately 600 kb in a telomeric direction. At least one TMA core could be evaluated in 92 of the prostate cancer cases.

B. Results

In this population-based cohort of men diagnosed with localized cancer, the frequency of TMPRSS2:ERG fusion was 15.2% (14/92) (FIGS. 17A and B). TMPRSS2:ERG fusion positive tumors were more likely to have a higher Gleason score (two-sided P=0.014) (Table 11). To assess the relation of fusion status and lethal prostate cancer, cumulative incidence regression was used. A significant association between the presence of the TMPRSS2:ERG gene fusion and metastases or disease specific death (FIG. 17C) with a cumulative incidence ratio (CIR) of 3.6 (P=0.004, 95% confidence interval [CI]=1.5 to 8.9) was observed. When adjusting for Gleason Score, the CIR was 2.4 (P=0.07 and 95% CI=0.9 to 6.1). The present invention is not limited to a particular mechanism. Indeed, an understanding of the mechanism is not necessary to practice the present invention. Nonetheless, it is contemplated that, based on the homogeneity of the TMPRSS2:ERG gene fusion in cells in a given tumor and its presence only in invasive prostate cancers (compared to Prostatic Intraepithelial Neoplasia), it is contemplated that this is an early event, which might, in part, contribute to the biology behind the phenotype of the Gleason patterns.

TABLE 11

Prognostic Factors for a Cohort of Men Expectantly Managed for Localized Prostate Cancer Stratified by the TMPRSS2:ERG Gene Fusion Status

| Variable | TMPRSS2:ERG Fusion Status | | P value* |
|---|---|---|---|
| | Negative | Positive | |
| No. of patients | 78 | 14 | |
| Age at diagnosis, y | 73 (60 to 103) | 73 (58 to 90) | .683 |
| Gleason Score** | | | |
| Gleason Score < 7 | 48 (61.5%) | 3 (21.4%) | .014 |
| Gleason Score = 7 | 20 (25.6%) | 6 (42.9%) | |
| Gleason Score > 7 | 10 (12.8%) | 5 (35.7%) | |
| Pathologic Stage | | | |
| pT1a | 28 (35.9%) | 2 (14.3%) | .112 |
| pT1b | 50 (64.1%) | 12 (85.7%) | |
| Nuclear grade*** | | | |
| 1 | 53 (67.9%) | 7 (53.8%) | .585 |
| 2 | 18 (23.1%) | 4 (30.8%) | |
| 3 | 7 (9.0%) | 2 (15.4%) | |
| Status**** | | | |
| Survived 12 years without metastases or cancer death | 20 (25.6%) | 1 (7.1%) | .016 |
| Death due to other causes within 12 years | 45 (57.7%) | 6 (42.9%) | |
| Distant metastases or death due to prostate Cancer | 13 (16.7%) | 7 (50.0%) | |

*Clinical parameters of subjects having the TMPRSS2:ERG fusion and of subjects not having the TMPRSS2:ERG fusion were compared by use of t tests or chi-square tests for continuous variable and categorical variables, respectively.
**Gleason Score is obtained by summing the major and minor Gleason patterns.
***For one case nuclear grade was not assessed.
****Individuals who lived at least 12 years and have not developed metastases or died of prostate cancer as of October 2005 are classified as long-term survivors. Individuals who lived less than 12 years and did not develop metastases are classified as short-term survivors.

Example 7

Detection of TMPRSS2:ETS Fusions in the Urine of Patients with Prostate Cancer

A. Materials and Methods

Urine Collection, RNA Isolation and Amplification

Urine samples were obtained from patients following a digital rectal exam before either needle biopsy or radical prostatectomy. Urine was voided into urine collection cups containing DNA/RNA preservative (Sierra Diagnostics). For isolation of RNA, a minimum of 30 ml of urine were centrifuged at 400 rpm for 15 min at 4° C. RNAlater (Ambion) was added to the urine sediments and stored at −20° C. until RNA isolation. Total RNA was isolated using a Qiagen RNeasy Micro kit according to the manufacturer's instructions. Total RNA was amplified using an OmniPlex Whole Transcriptome Amplification (WTA) kit (Rubicon Genomics) according to the manufacturer's instructions (Tomlins et al., Neoplasia 8:153 [2006]). Twenty five nanograms of total RNA were used for WTA library synthesis and the cDNA library was subjected to one round of WTA PCR amplification. Amplified product was purified using a QIAquick PCR Purification kit (Qiagen). For cell line proof of concept experiments, the indicated number of VCaP or LNCaP cells was spiked into 1 ml of sterile urine and the samples were processed as for voided urine.

Quantitative PCR

Quantitative PCR (QPCR) was used to detect ERG, ETV1 and TMPRSS2:ERG transcripts from WTA amplified cDNA essentially as described (Tomlins et al., Neoplasia 8:153 [2006], Tomlins et al., Science 310:644 [2005], Example 1 above). For each QPCR reaction, 10 ng of WTA amplified cDNA was used as template. Reactions for ERG, ETV1, PSA and GAPDH used 2× Power SYBR Green Master Mix (Applied Biosystems) and 25 ng of both the forward and reverse primers. Reactions for TMPRSS2:ERGa used 2× Taqman Universal PCR Master Mix and a final concentration of 900 nM forward and reverse primers, and 250 nM probe. For the Taqman assay, samples with Ct values greater than 38 cycles were considered to show no amplification. For all samples, the amount of ERG and ETV1 were normalized to the amount of GAPDH. Samples with inadequate amplification of PSA, indicating poor recovery of prostate cells in the urine, were excluded from further analysis. ERG (exon5_6 forward) and ETV1 (exon6_7)[2], GAPDH[3], and PSA[4] primers were as described. The Taqman primers and probe (MGB labeled) specific for TMPRSS2:ERGa are as follows:

```
TM-ERGa2_MGB-f;
                                (SEQ ID NO: 70)
CGCGGCAGGAAGCCTTA

TM-ERGa2_MGB-r;
                                (SEQ ID NO: 71)
TCCGTAGGCACACTCAAACAAC,

TM-ERGa2_MGB-probe;
                                (SEQ ID NO: 72)
5'-MGB-CAGTTGTGAGTGAGGACC-NFQ-3'
```

Fluorescene In Situ Hybridization (FISH)

Four μm thick formalin-fixed paraffin-embedded (FFPE) sections from matched needle biopsies were used for interphase fluorescence in situ hybridization (FISH), processed and hybridized as described previously (Example 2 and Tomlins et al., Cancer Res 66:3396 [2006]). BAC probes to detect ERG rearrangements, RP11-95121 (5' to ERG) and RP11-476D17 (3' to ERG) were prepared as described previously (Tomlins et al., Cancer Res 66:3396 [2006]; Tomlins et al., Science 310:644 [2005]; Examples 1 and 2 above).

B. Results

Figure 33A:
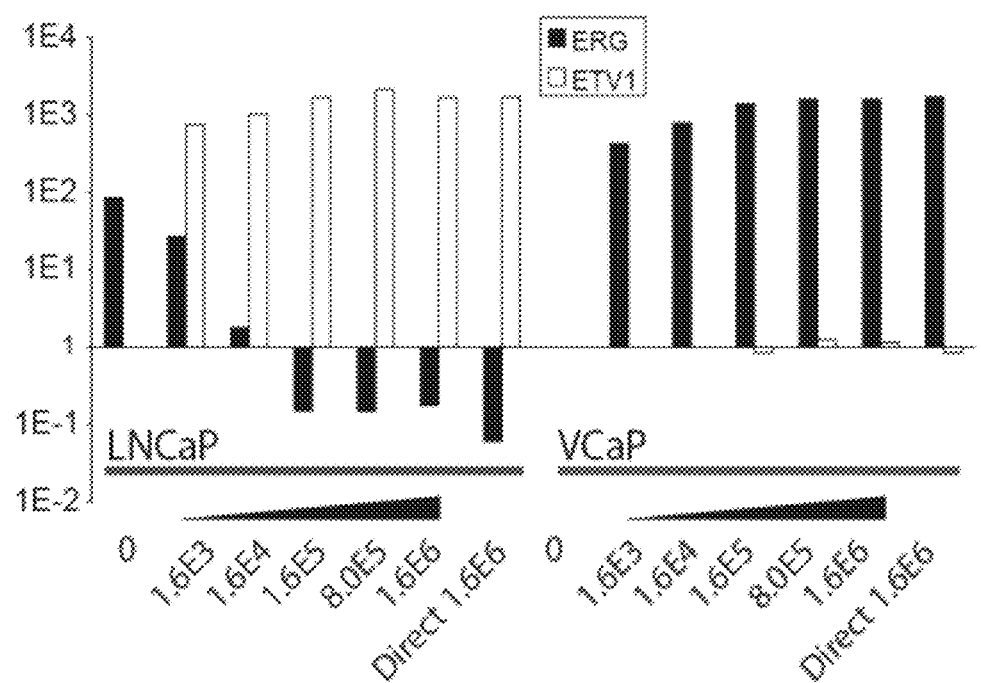
FIG. 33A shows detection of ERG and ETV1 in LNCaP (high ETV1 expression) or VCaP (high ERG and TMPRSS2:ERG expression) prostate cancer cells.

This example describes a non-invasive method to detect prostate cancer by the presence of TMPRSS2:ETS fusion transcripts in prostate cancer cells shed into the urine after a digital rectal exam. Results are shown in FIG. 33. As a proof of concept, sterile urine spiked with prostate cancer cell lines expressing high levels of ERG and TMPRSS2:ERG (VCaP) or high levels of ETV1 (LNCaP) was used. As shown in FIG. 33A, it was possible to detect ERG over-expression exclusively in VCaP at 1,600 cells and ETV1 over-expression exclusively in LNCaP at 16,000 cells by quantitative PCR (QPCR).

By correlating the number of spiked VCaP and LNCaP cells to GAPDH $C_t$ (threshold cycle) values, it was observed that, in some cases, urine obtained from patients after a digital rectal exam contained insufficient cell numbers to reliably detect ERG or ETV1 over-expression. Thus, total RNA collected from the urine of patients suspected of having prostate cancer was amplified using OmniPlex Whole Transcriptome Amplification before QPCR analysis. Using this strategy, a cohort of 16 patients where urine was obtained after a digital rectal exam before a needle biopsy to detect prostate cancer was assesed. Subsequent assessment of needle biopsies demonstrated that this cohort contained 4 patients with benign prostates, 1 with high grade prostatic intraepithelial neoplasia (HGPIN) and 11 with prostate cancer. In addition, a cohort of 3 patients with prostate cancer where urine was collected after a digital rectal exam before radical prostatectomy was assessed.

Cohort characteristics are presented in Table 12. Each urine specimen was from a unique patient and was assigned an ID. The source of the sample (pre biopsy or radical prostatectomy (RP) is indicated. The diagnosis following needle biopsy (including benign, high grade prostatic intraepithelial neoplasia (HGPIN), and prostate cancer (PCa)) is indicated. For patients diagnosed as having prostate cancer following needle biopsy, major Gleason, minor Gleason, and Gleason sum score are indicated. For all patients, pre biopsy PSA (ng/ml) and age are reported, if available.

TABLE 12

| Sample source | Diagnosis | Biopsy Gleason Major | Biopsy Gleason Minor | Biopsy Gleason Score | Pre-Biopsy PSA (ng/ml) |
|---|---|---|---|---|---|
| Pre-Biopsy | Benign | | | | 4.7 |
| Pre-Biopsy | Benign | | | | 8.3 |
| Pre-Biopsy | Benign | | | | 6.7 |
| Pre-Biopsy | Benign | | | | 4 |
| Pre-Biopsy | HGPIN | | | | 9.7 |
| Pre-Biopsy | Pca | 3 | 4 | 7 | 3.3 |
| Pre-Biopsy | Pca | 3 | 3 | 6 | 5.99 |
| Pre-Biopsy | Pca | 3 | 3 | 6 | 2.8 |
| Pre-Biopsy | Pca | 3 | 3 | 6 | 5.9 |
| Pre-Biopsy | Pca | 4 | 4 | 8 | 10.6 |
| Pre-Biopsy | Pca | | | | |
| Pre-Biopsy | Pca | 4 | 5 | 9 | 11.8 |
| Pre-Biopsy | Pca | 3 | 4 | 7 | 5.5 |
| Pre-Biopsy | Pca | 3 | 3 | 6 | 3.8 |
| Pre-Biopsy | Pca | 4 | 5 | 9 | 19.3 |
| Pre-Biopsy | Pca-treated | 3 | 3 | 6 | |
| Pre-RP | Pca | | | | |
| Pre-RP | Pca | | | | |
| Pre-RP | Pca | | | | |

From the needle biopsy cohort, 5 patients were identified with marked over-expression of ERG, 1 of which was diagnosed by needle biopsy as having HGPIN, while the other 4 were diagnosed as having prostate cancer. From the radical prostatectomy cohort, 1 of 3 patients with prostate cancer were identified as having high ERG expression (FIG. 33B). ETV1 over-expression was not detected in any patients from either cohort. To confirm the expression of TMPRSS2:ERG in the samples which over-expressed ERG, a TaqMan primer/probe assay designed to specifically amplify TMPRSS2:ERGa was utilized. This assay robustly amplified product from VCaP cells, which express TMPRSS2:ERGa (Tomlins et al., Science 310:644 [2005]). In addition, 5 of the 6 urine samples from patients with prostate cancer that over-expressed ERG also expressed TMPRSS2:ERGa (Ct values 29.8-38.9), while 0 of the 10 samples from patients without ERG over-expression expressed TMPRSS2:ERGa. As one sample over-expressed ERG without expression of TMPRSS2:ERGa, it is likely that this sample expresses other isoforms of the fusion transcript, such as TMPRSS2:ERGb or more recently identified fusion transcripts (Soller et al., Genes Chromosomes Cancer 45:717 [2006]; Yoshimoto et al., Neoplasia 8:465:2006). To confirm that the presence of TMPRSS2:ERG fusion transcripts indicates the presence of TMPRSS2:ERG positive cancerous tissue, fluorescence in situ hybridization (FISH) was performed using probes designed to detect ERG rearrangements on matched tissue sections from representative cases. Matched tissue was obtained from three patients with detectable TMPRSS2:ERG transcripts in the urine and a diagnosis of cancer, one patient with detectable TMPRSS2:ERG transcripts in the urine and a diagnosis of high grade PIN, and two patients without detectable TMPRSS2:ERG transcripts and a diagnosis of cancer. As shown in FIG. 33B, both patients diagnosed with cancer but without detectable TMPRSS2:ERG transcripts in their urine did not harbor ERG rearrangements in cancerous tissue by FISH. All three patients diagnosed with cancer and with detectable TMPRSS2:ERG transcripts in their urine also showed ERG rearrangements in cancerous tissue by FISH. Finally, the patient with a diagnosis of high grade PIN with detectable TMPRSS2:ERG in their urine did not show ERG rearrangements in high grade PIN tissue. This indicates that this patient may have undiagnosed cancer elsewhere in the prostate, resulting in the presence of detectable TMPRSS2:ERG transcripts in their urine.

Example 8

TMPRSS2 and ETS Family Genes Fusions in Prostate Cancer

This study describes a comprehensive analysis of the frequency for the TMPRSS2 and ETS family genes rearrangements in a screening-based cohort of 111 American men surgically treated for clinically localized prostate cancer.
A. Materials and Methods
Study Population, Clinical Data and Prostate Sample Collection:
As a source of clinically localized prostate cancers, a tissue microarray (TMA) containing—cores representing cancer and benign tissue was constructed from 111 men who underwent radical prostatectomy at the University of Michigan as the primary monotherapy (i.e., no adjuvant or neoadjuvant hormonal or radiation therapy). The radical prostatectomy series is part of the University of Michigan Prostate Cancer Specialized Program of Research Excellence (SPORE) Tissue Core. Three cores (0.6 mm in diameter) were taken from each representative tissue block to construct the TMA. The TMA construction protocol has been described (Kononen et al., Nat. Med. 4:844 [1998]; Rubin et al., Am J surg Pathol 26:312 [2002]). Detailed clinical, pathological, and TMA data re maintained on a secure relational database as previously described (Manley et al., Am J. Pathol. 159:837 [2001]).
Assessment of TMPRSS2-ETS Gene Fusion Using an Interphase Fluorescence In Situ Hybridization Assay
Four µm thick tissue micro array sections were used for interphase fluorescence in situ hybridization (FISH), processed and hybridized as described previously (Tomlins et al., Science 310:644 [2005]; Tomlins et al., Cancer Res 66:3396 [2006]). Slides were examined using an Axioplan ImagingZ1 microscope (Carl Zeiss) and imaged with a CCD camera using the ISIS software system in Metafer image analysis system (Meta Systems, Altlussheim, Germany). FISH signals were scored manually (100× oil immersion) by pathologists in morphologically intact and non-overlapping nuclei and a minimum of 30 cells or the maximum numbers of cancer cells available in three cores from a case were recorded. Cases without 30 evaluable cells were reported as insufficient hybridization. All BACs were obtained from the BACPAC Resource Center (Oakland, Calif.), and probe locations were verified by hybridization to metaphase spreads of normal peripheral lymphocytes. For detection of TMPRSS2, ERG and ETV4 rearrangements we used the following probes: RP11-35C4 (5' to TMPRSS2) and RP11-120C17 (3' to TMPRSS2), RP11-95121 (5' to ERG) and RP11-476D17 (3' to ERG), and RP11-100E5 (5' to ETV4) and RP11-436J4 (3' to ETV4). For detection of TMPSS2-ETV1 fusion, RP11-35C4 (5' to TMPRSS2) was used with RP11-124L22 (3' to ETV1). BAC DNA was isolated using a QIAFilter Maxi Prep kit (Qiagen, Valencia, Calif.), and probes were synthesized using digoxigenin- or biotin-nick translation mixes (Roche Applied Science, Indianapolis, Ind.). The digoxigenin and biotin labeled probes were detected using fluorescein conjugated anti-digoxigenin antibodies (Roche Applied Science) and Alexa 594 conjugated sptreptavidin (Invitrogen, Carlsbad, Calif.), respectively.

Figure 35:
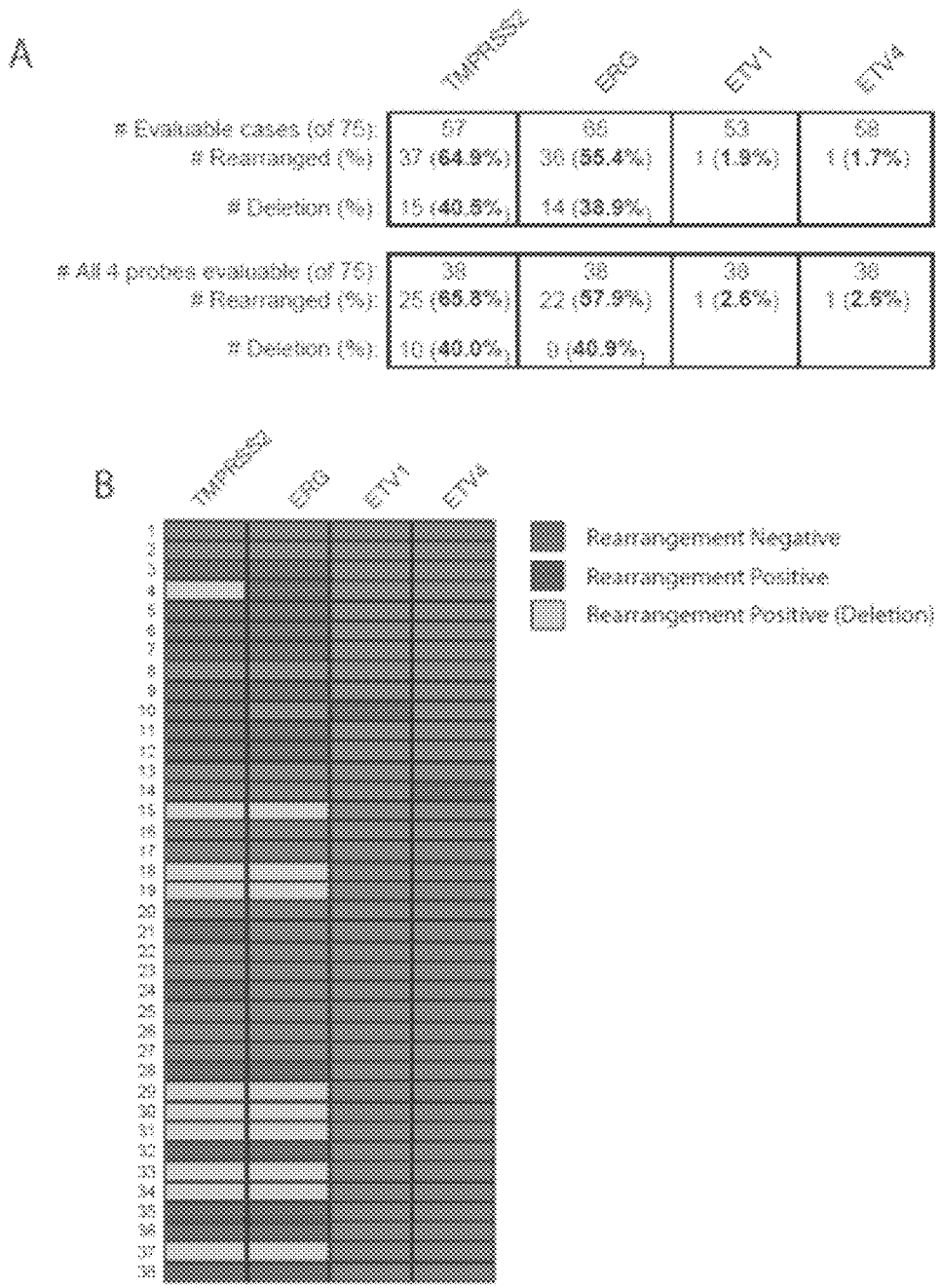
FIG. 35 shows TMPRSS2, ERG, ETV1 and ETV4 rearrangements as detected by FISH.

A break apart (TMPRSS2, ERG, ETV4) or fusion (TMPRSS2-ETV1) probe strategy was employed to detect rearrangements at the chromosomal level. Normal signal patterns for TMPRSS2, ERG and ETV4 in DAPI stained nuclei were indicated by two pairs of colocalized green and red signals. For these probes, a rearrangement was confirmed by break apart of one of the two colocalized signals. For TMPRSS2-ETV1 fusion, two pairs of separate red and green were recorded as normal, while one pair of separate and one pair of colocalized signals was recorded as a rearrangement.
B. Results and Discussion
This example describes a comprehensive analysis outlining the signature of TMPRSS2 and ETS transcription factor genes rearrangement in a large screening-based cohort of American men surgically treated for clinically localized prostate cancer. A TMPRSS2 split probe FISH assay approach was used to detect the overall frequency of gene rearrangement in prostate cancer with known ETS family partners ERG, ETV1, ETV4 and other unknown partners, as shown in FIG. 34. It was hypothesized that prostate cancers negative for three known ETS partners (ERG, ETV1 and ETV4) may harbor rearrangements involving other ETS family members. The results demonstrate complex molecular signature of TMPRSS and ETS family genes rearrangement in clinically localized prostate cancer (FIGS. 35A and B). Overall TMPRSS2 was rearranged in 65% of evaluable cases, while ERG, ETV1 and ETV4 were rearranged in 55%, 2% and 2% of evaluable cases (FIG. 35A). In 40.5% of cases with TMPRSS2 rearrangement, loss of the 3' probe was observed, consistent with a chromosomal deletion between TMPRSS2 and ERG as a mechanism of gene fusion. These results confirm the high frequency of TMPRSS2:ETS fusions in prostate cancer and confirm previous studies showing that TMPRSS2:ERG are by far the most common type (Tomlins et al., Science 310:644; Perner et al., Cancer Res 66:3396 [2006]; Yoshimoto et al., Neoplasia 8:4665 [2006]; Soller et al., Genes Chromosomes Cancer 45:717 [2006]; Wang et al., Cancer Res 66:8347 [2006] and above examples).

Similar results were observed when the cohort was limited to just those cases where all four probes were evaluable (FIGS. 35A and B). This analysis confirmed that TMPRSS2: ETS rearrangements are mutually exclusive, as no cases showed rearrangements of multiple ETS family members. This analysis also demonstrates that a single TMPRSS2 assay can effectively detect almost all ETS rearrangements, as 23 of the 24 cases with ERG, ETV1 or ETV4 rearrangement were detected by the TMPRSS2 assay. In all 9 cases where the 5' ERG probe was deleted, deletion of the 3' TMPRSS2 probe was identified.

Furthermore, two cases were identified with break apart of the TMPRSS2 probes, indicating a rearrangement, without rearrangement of ERG, ETV1 or ETV4 (cases 32 and 36) and cases with TMPRSS2 rearrangement without ERG rearrangement where ETV1 and/or ETV4 could not be evaluated. These cases suggest that TMPRSS2 may be partnering with novel ETS family members or unrelated oncogenes in prostate cancer. Together, these results suggest that a single TMPRSS2 assay can provide diagnostic and prognostic information in prostate cancer.

Example 9

PSA Gene Fusions

FISH experiments were used to identify cases that show a split signal by FISH for probes located 5' and 3' to PSA. The 5' and 3' BACs used to detect the PSA split are RP11-510I16 and RP11-26P14, respectively. A partner for the PSA gene fusion has not yet been identified. These same probes also pick up a split in the ETS family member SPIB, as it is located very close to PSA.

Example 10

FLI1 Overexpression

Figure 18:
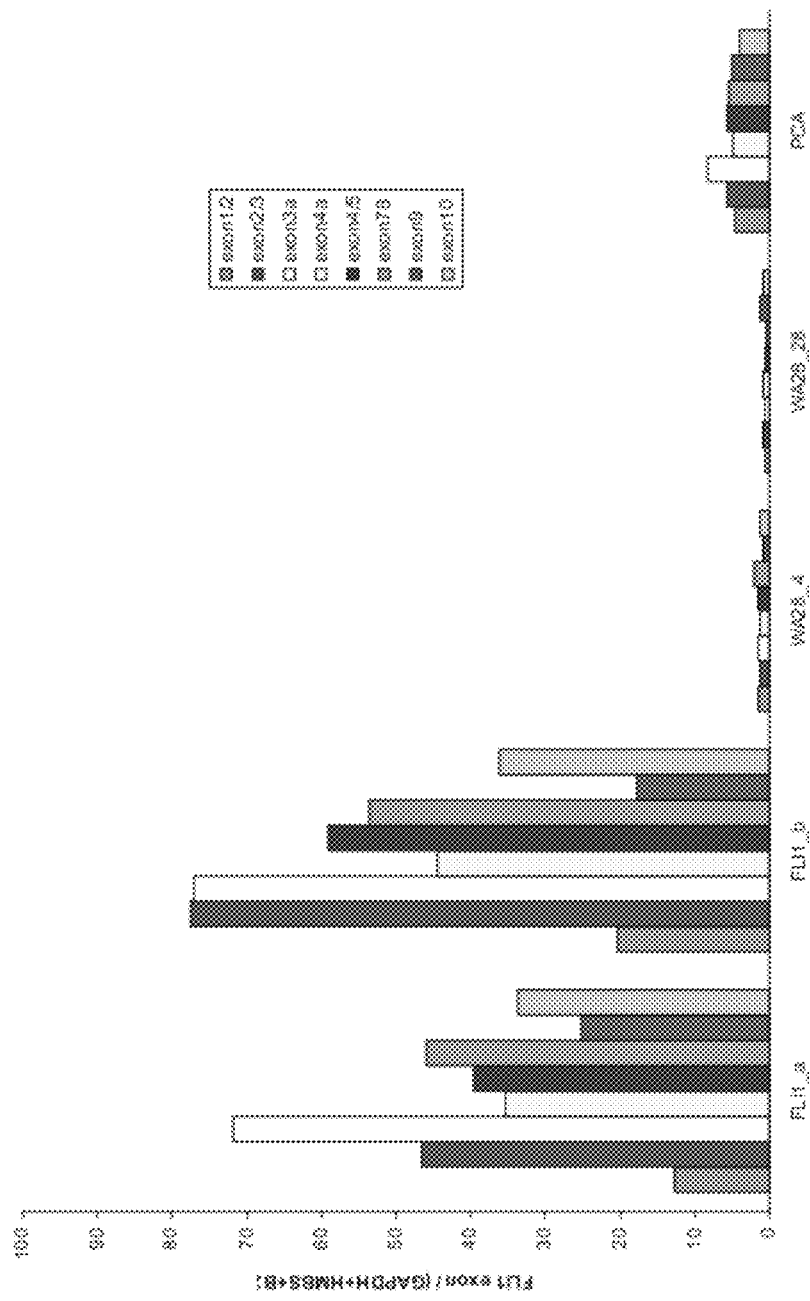
FIG. 18 shows FLI1 overexpression without fusion transcript.

FLI1 expression was assayed in different cell samples not harboring a FLI1 gene fusion. The expression of 5' and 3' exons of FLI1 was measured from a case with high FLI1 expression. Results are shown in FIG. 18. No difference in the 5' and 3' transcript abundance was detected. RACE also did not indicate a fusion transcript. FLI1 was overexpressed in prostate cancer relative to control samples. Primers for Fli1 amplification, as well as TaqMan probes, are shown in FIG. 37.

FISH was also used to identify samples that have split signals for FLI1, indicating a rearrangement, but these cases do not have TMPRSS2:FLI1 fusion by FISH. BAC probes are shown in Table 13. These cases also have high FLI1 expression.

Example 11

Tissue Microarrays

Tissue microarrays were used to assay for the presence of gene fusions. TMAs used included prostate cancer progression array, prostate cancer outcome array, warm autopsy array, prostate cancer screening array, Erg negative prostate cancer array, and individual prostate cancer cases. The following gene probes were used on tissue microarrays: TMPRSS2-ETV1 fusion probes, Erg split probes, TMPRSS2 split probes, ETV1 split probes, ETV4 split probes, and FL1 split probes.

In addition, Erg split probes were used on an outcome array. The results are as follows: negative cases: 30, positive case: 29, marginal cases: 1. There was a weak association of Erg positive cases with higher Gleason score ($\geq 7$).

Protein arrays and mass spec were used to identify nuclear interactors for ERG2. The results are shown in FIG. 21.

Example 12

Androgen Regulation of Erg Expression

Figure 19:
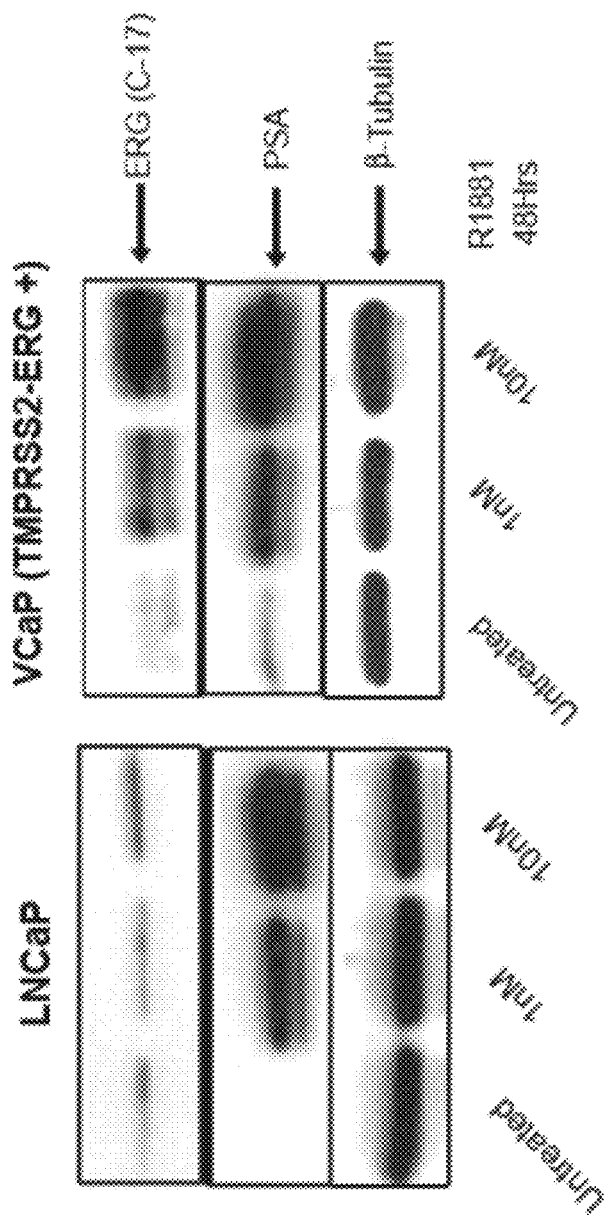
FIG. 19 shows induction of ERG protein expression by androgen in TMPRSS2-ERG+ cells.
Figure 24:
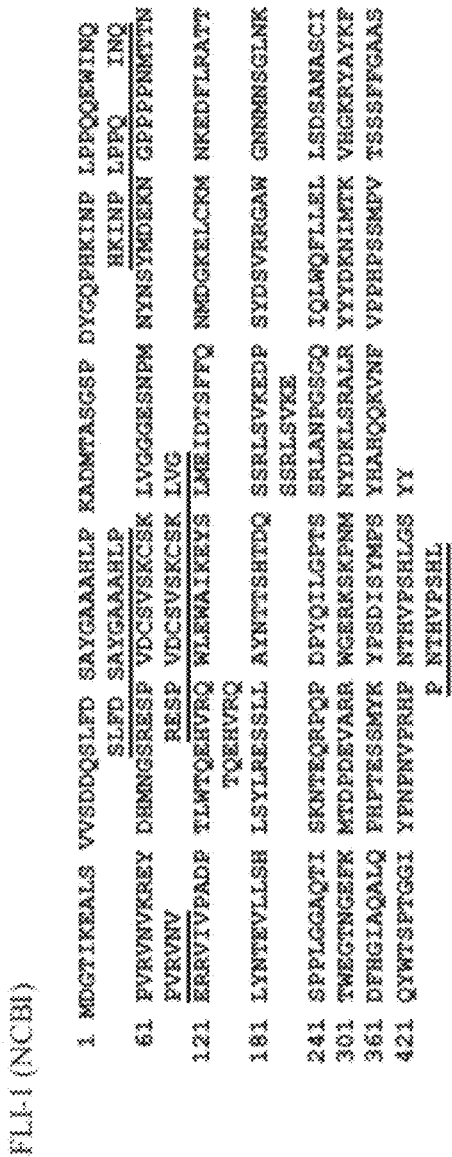
FIG. 24 (SEQ ID NOS: 246-252) shows sequences for peptide antibody and aqua probe generation against FLI1.

This Example describes the androgen regulation of Erg expression. LNCap (TMPRSS2-ERG−) and VCaP (TMPRSS2-ERG+) cell lines were used. The cells were contacted with varying amounts of R1881 for 48 hrs. Expression of Erg, PSA (+ control) and beta-tubulin (− control) were assayed. The results are shown in FIG. 19. ERG expression was found to be androgen dependent in the VCaP, but not the LNCap cells.

Example 13

Peptide Antibody and Aqua Probe Generation

FIGS. 22-25 shows sequences (underlined) of ERG1, ETV1, FLI-1, and ETV4 for use in peptide antibody generation and for making aqua probes. Primers are designed by Applied Biosystems for all ETS family members. Expression is monitored in prostate cancer cases, with high expression being an indicator of a possible gene fusion and an indicator for FISH.

Example 14

ETV1 in LnCaP Cells

This Example describes an analysis of the transcriptional response to androgen in VCaP and LNCaP. In addition to detecting a number of transcripts differentially expressed in both cell lines were identified, such as PSA, a number of transcripts uniquely dysregulated in VCaP or LNCaP cells were also identified. This analysis identified ETV1 as being exclusively responsive to androgen in LNCaP cells. Combined with the over-expression of ETV1 in LNCaP cells, FISH was used to interrogate the ETV1 loci in LNCaP cells.
A. Materials And Methods
Cell Lines The prostate cancer cell lines LNCaP (originally derived from a lymph node prostate cancer metastasis) and VCaP (Korenchuk, S. et al., In vivo 15, 163-8 (2001)) (originally derived from a vertebral prostate cancer metastasis) were used for this study. For microarray studies, VCaP and LNCaP cells were grown in charcoal-stripped serum containing media for 24 hours before treatment for 48 hours with 0.1% ethanol or 1 nM of the synthetic androgen methyltrienolone (R1881, NEN Life Science Products, Boston, Mass.) dissolved in ethanol. For quantitative PCR (QPCR) studies, cells were grown in charcoal-stripped serum containing media for 24 hours, preincubated with 0.1% ethanol, Casodex dissolved in acetone (10 uM, bicalutamide, AstraZeneca Pharmaceuticals, Wilmington, Del.) or flutamide dissolved in ethanol (10 uM, Sigma, St. Louis, Mo.). After 2 hours, 0.1% ethanol or 0.5 nM of R1881 was added and the cells were harvested after 48 hours. Total RNA was isolated from all samples with Trizol (Invitrogen, Carlsbad, Calif.) according to the manufacturer's instructions. RNA integrity was verified by denaturing formaldehyde gel electrophoresis or the Agilent Bioanalyzer 2100 (Agilent Technologies, Palo Alto, Calif.).

Microarray Analysis

The cDNA microarrays used for this study were constructed essentially as described, except the array contains 32,448 features. Protocols for printing and postprocessing of arrays are available on the Internet. cDNA microarray analysis was done essentially as described. Briefly, total RNA from control and R1881 treated VCaP and LNCaP cell lines were reverse transcribed and labeled with cy5 fluorescent dye. Pooled total RNA from control VCaP or LNCaP samples were reverse transcribed and labeled with cy3 fluorescent dye for all hybridizations from the respective cell lines. The labeled products were then mixed and hybridized to the cDNA arrays. Images were flagged and normalized using the Genepix software package (Axon Instruments Inc., Union City, Calif.). Data were median-centered by arrays and only genes that had expression values in at least 80% of the samples were used in the analysis.

Quantitative PCR (QPCR)

QPCR was performed using SYBR Green dye on an Applied Biosystems 7300 Real Time PCR system (Applied Biosystems, Foster City, Calif.) as described (Tomlins et al., Cancer Res 66, 3396-400 (2006); Tomlins et al., Science 310, 644-8 (2005)). The amount of each target gene relative to the housekeeping gene glyceraldehyde-3-phosphate dehydrogenase (GAPDH) for each sample was reported. The relative amount of the target gene in each cell line and/or experiment was calibrated to controls. All oligonucleotide primers were synthesized by Integrated DNA Technologies (Coralville, Iowa). GAPDH (Vandesompele et al., Genome Biol 3, RESEARCH0034 (2002)), PSA (Specht et al., Am J Pathol 158, 419-29 (2001)), ERG (Exon 5-6_f and Exon 5-6_r) and ETVJ (Exon 6-7_f and Exon 6-7_r) primers (Tomlins et al., Science 310, 644-8 (2005)) were as described.

Fluorescence In Situ Hybridization (FISH)

Metaphase spreads were prepared from normal peripheral lymphocytes (NPLs) and LNCaP cells using standard techniques. Slides were treated with 2×SSC for 2 min, 70% ethanol for 2 min and 100% ethanol for 2 min before addition of the probe. Slides were coverslipped and incubated at 75° for 2 min and hybridized overnight at 37° C. Post-hybridization washing was with 2×SSC at 42° C. for 5 min, followed by 3 washes in PBST. Fluorescent detection was performed using anti-digoxigenin conjugated to fluorescein (Roche Applied Science, Indianapolis, Ind.) and streptavidin conjugated to Alexa Fluor 594 (Invitrogen, Carlsbad, Calif.). Slides were counterstained and mounted in ProLong Gold Antifade Reagent with DAPI (Invitrogen). Slides were examined using a Zeiss Axio Imager Z1 fluorescence microscope (Zeiss, Thornwood, N.Y.) and imaged with a CCD camera using ISIS software (Metasystems, Altlussheim, Germany).

All BACs were obtained from the BACPAC Resource Center (Oakland, Calif.) and probe locations were verified by hybridization to metaphase spreads of normal peripheral lymphocytes. For hybridization to the ETV1 region on chromosome 7p, four BACs were used (telomeric to centromeric): RP11-124L22, RP11-313C20, RP11-703A4 and RP11-1149J13. For localization to chromosome 14q, the FISH mapped BAC RP11-483K13, which we also confirmed as hybridizing to 14q using NPLs. BAC DNA was isolated using a QIAFilter Maxi Prep kit (Qiagen, Valencia, Calif.) and probes were synthesized using digoxigenin- or biotin-nick translation mixes (Roche Applied Science).

B. Results

Figure 26:
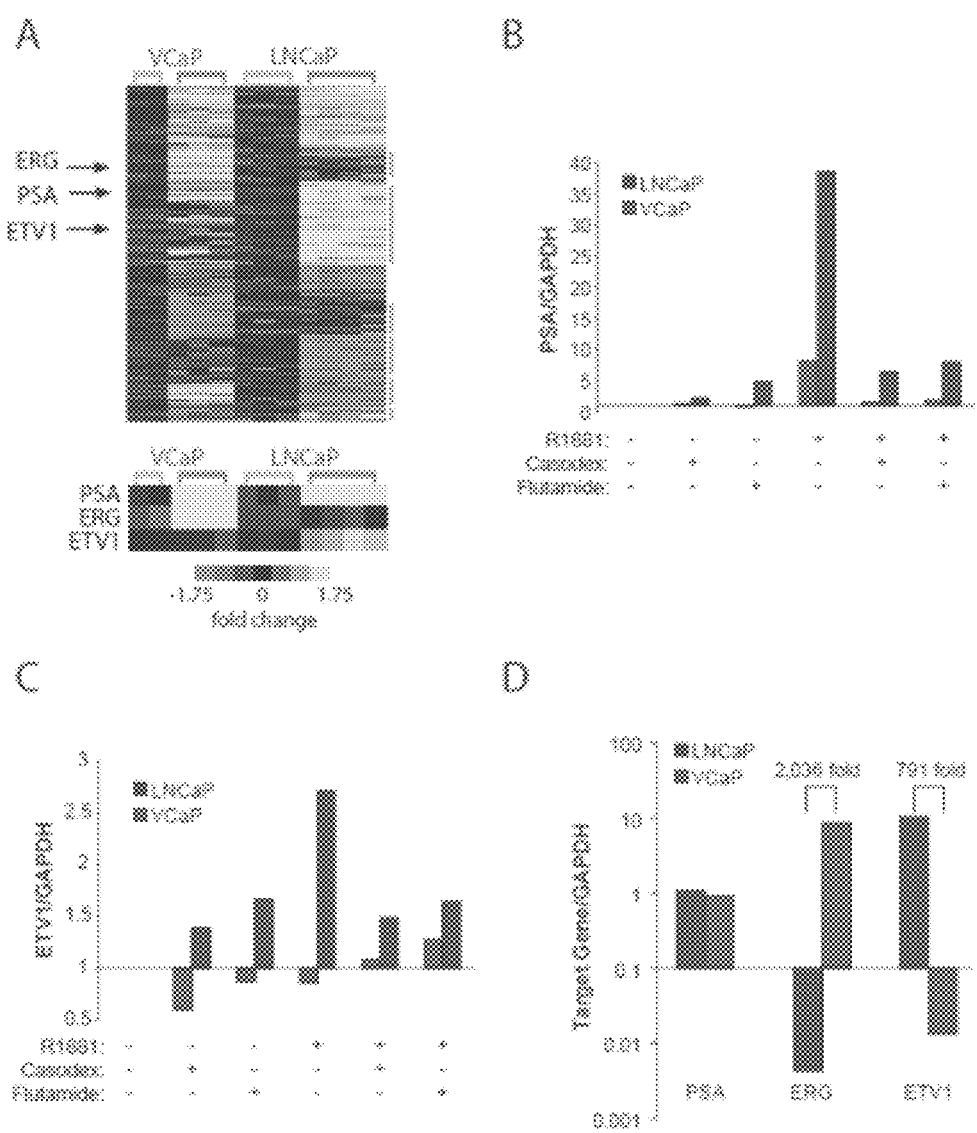
FIG. 26 shows the over-expression and androgen regulation of ETV1 in the LNCaP prostate cancer cell line.
Figure 27:
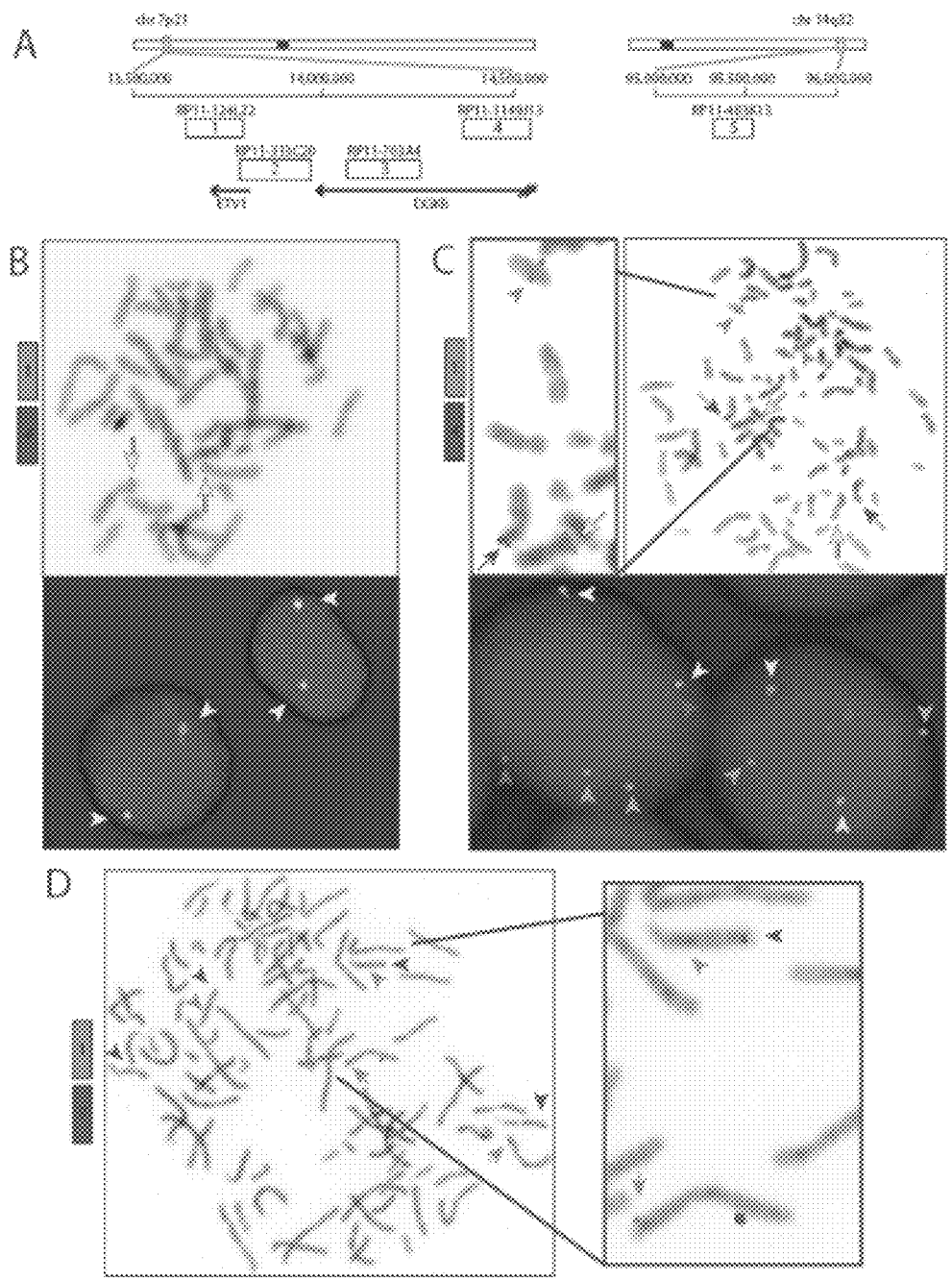
FIG. 27 shows rearrangement of ETV1 in LNCaP cells.
Figure 28:
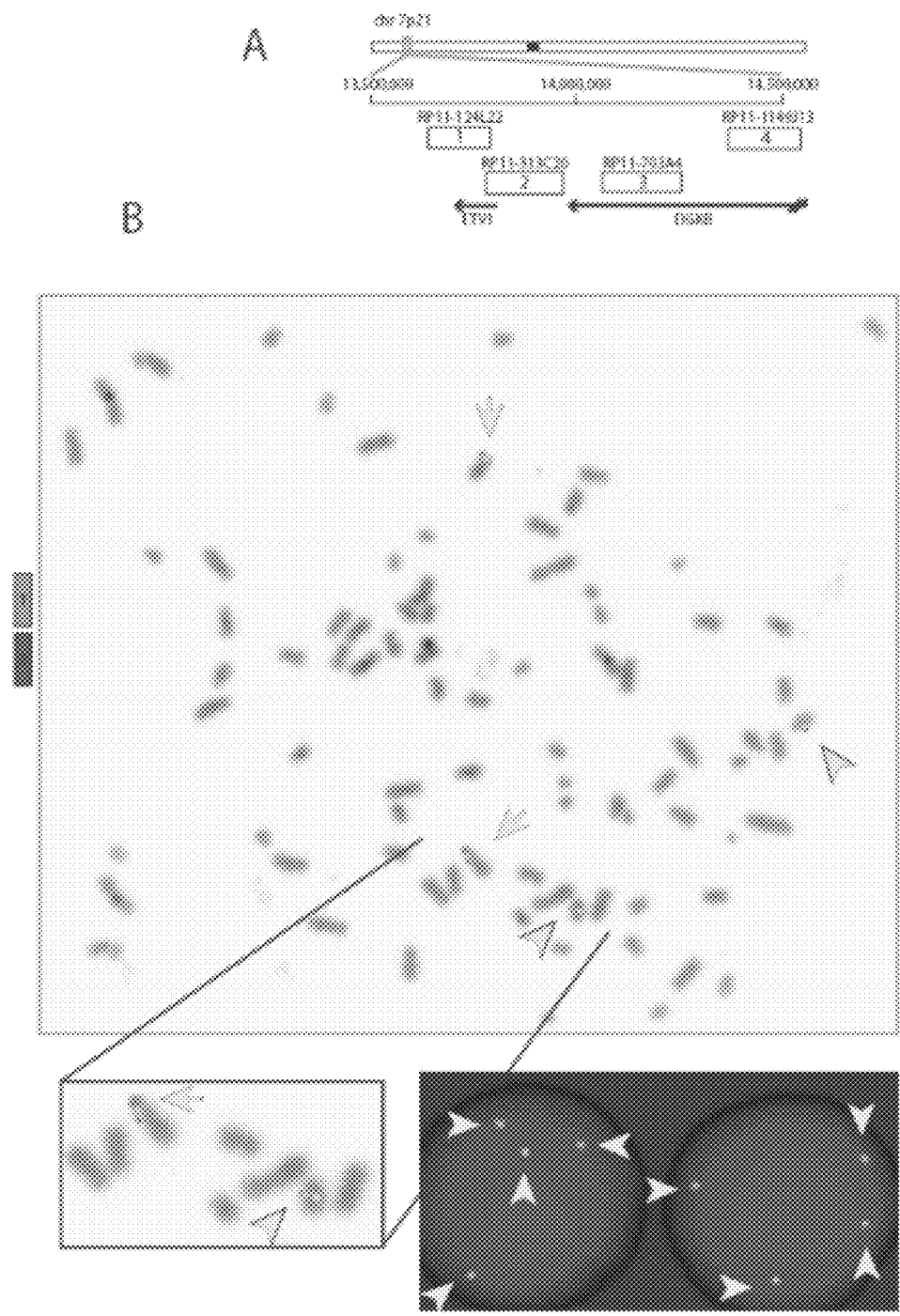
FIG. 28 shoes that the entire ETV1 locus is inserted into chromosome 14 in LNCaP cells.

Results are shown in FIGS. 26-28. FIG. 26 shows the over-expression and androgen regulation of ETV1 in the LNCaP prostate cancer cell line. FIG. 26A shows expression signature of androgen-regulated genes in VCaP and LNCaP prostate cancer cell lines. Heatmap of genes showing induction or repression in either cell line (3,499 features, p<0.05 and fold change ratio>=1.5) by 1 nM synthetic androgen R1881 (green) compared to vehicle treatment (gray). Each row represents a gene; each column represents a sample. Yellow and blue cells indicate over- or under-expression, respectively, according to the color scale. Gray cells indicate missing data. Values for each cell line are centered on the corresponding control samples. The locations of PSA, ERG and ETV1 in the heatmap are indicated and their expression is shown in the inset. FIG. 26B shows confirmation of PSA induction by androgen in both VCaP and LNCaP cells by quantitative PCR (QPCR). The relative expression of PSA (normalized to GAPDH) in LNCaP (red) and VCaP (blue) cell lines was determined by QPCR. Cells were treated with vehicle or 1 nM R1881 for 48 hours in the presence or absence of the anti-androgens Casodex or Flutamide as indicated. The relative amount of PSA in each sample was calibrated to the amount in the control sample for each cell line. FIG. 26C shows ETV1 induction by androgen in LNCaP cells. Using the same samples as B, the relative amount of ETV1 was determined by QPCR. FIG. 26D shows that ETV1 is markedly over-expressed in LNCaP cells. The relative expression of PSA, ETV1 and ERG were determined in the 48 hour control samples from each cell line by QPCR. The relative amount of target gene in each sample was calibrated to the average amount of PSA from both cell lines. The fold difference in ERG and ETV1 expression between LNCaP and VCaP is indicated.

FIG. 27 shows rearrangement of ETV1 in LNCaP cells. FIG. 27A shows a schematic of BACs used as probes for fluorescence in situ hybridization (FISH). The location and coordinates at 7p21 (including the ETV1 locus and surrounding BACs) and 14q32 was determined on the May 2004 freeze of the human genome using the UCSC Genome Browser. BACs used in this study are indicated as numbered rectangles. The location of ETV1 and DGKB are shown with the arrowhead indicating the direction of transcription. FIG. 27B shows that RP11-124L22 and RP11-1149J13 co-localize to chromosome 7 in normal peripheral lymphocytes (NPLs). Localization of RP11-124L22 (BAC #1) and RP11-1149J13 (BAC #4) on metaphase spreads (top panel) or interphase cells (bottom panel) was determined by FISH in NPLs. For all metaphase pictures, signals on chromosome 7 are indicated by arrows, while signals on chromosome 14 are indicated by arrowheads of the corresponding probe color. Higher magnification of informative regions of metaphase spreads are shown in boxes. FIG. 27C shows localization of BAC #1 and BAC #4 on metaphase spreads (top panel) and interphase cells (bottom panel) was determined in the near tetraploid LNCaP cell line. Two co-localized signals on chromosome 7, two red signals on chromosome 7 and two green signals on a different chromosome were observed. FIG. 27D shows signal from RP11-124L22 localizes to chromosome 14 in LNCaP cells. As in C, except RP11-124L22 (BAC #1) was co-hybridized with RP11-483K13 (BAC #5, FISH mapped to chromosome 14q) on LNCaP metaphase spreads. Four red signals from RP11-483K13 localize to chromosome 14q; two green signals localize to chromosome 7p and two green signals localize to chromosome 14q.

FIG. 28 shoes that the entire ETV1 locus is inserted into chromosome 14 in LNCaP cells. FIG. 28A shows a schematic of BACs used in this experiment. FIG. 28B shows localization of RP11-124L22 (BAC #1) and RP11-313C20 (BAC #2) on metaphase spreads (top panel) and interphase cells (bottom panel) was determined by FISH in LNCaP cells. In metaphase spreads, two pairs of co-localized signals were observed on chromosome 7 (yellow arrows) and chromosome 14 (yellow arrowheads).

These results demonstrate that the entire ETV1 locus is translocated from chromosome 7 to chromosome 14. Although the genomic sequence upstream of the insertion on chromosome 14 is unknown, it is likely that this region contains AREs, which drive the high level of ETV1 observed only in LNCaP cells and the androgen responsiveness. These results suggest that LNCaP cells find use as an in vitro model of ETS gene fusions seen in human prostate cancers.

Example 15

Knockdown of ETS Family Members in PCA

Figure 29:
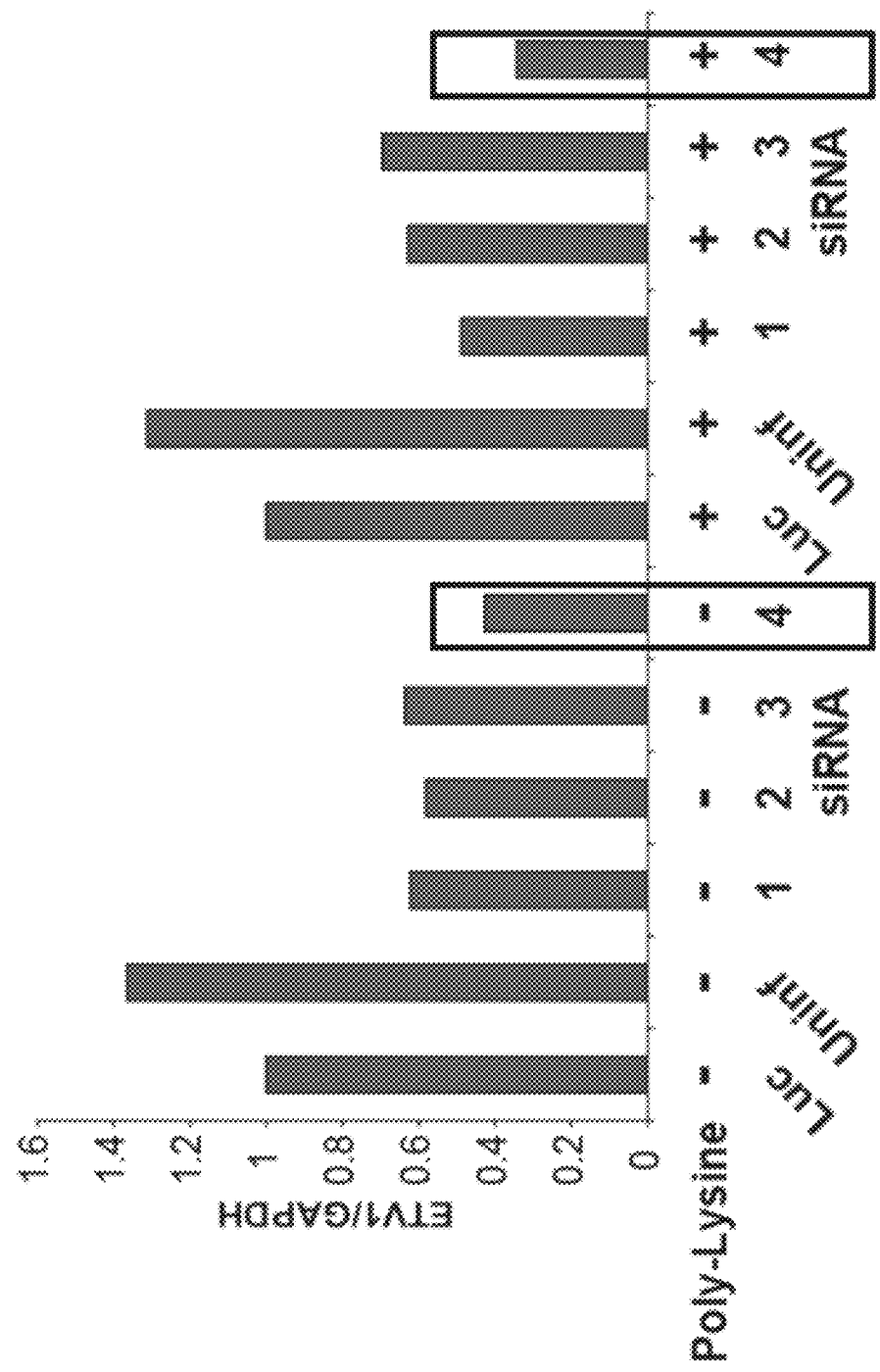
FIG. 29 shows siRNA knockdown of ETV1 in LnCaP.
Figure 30:
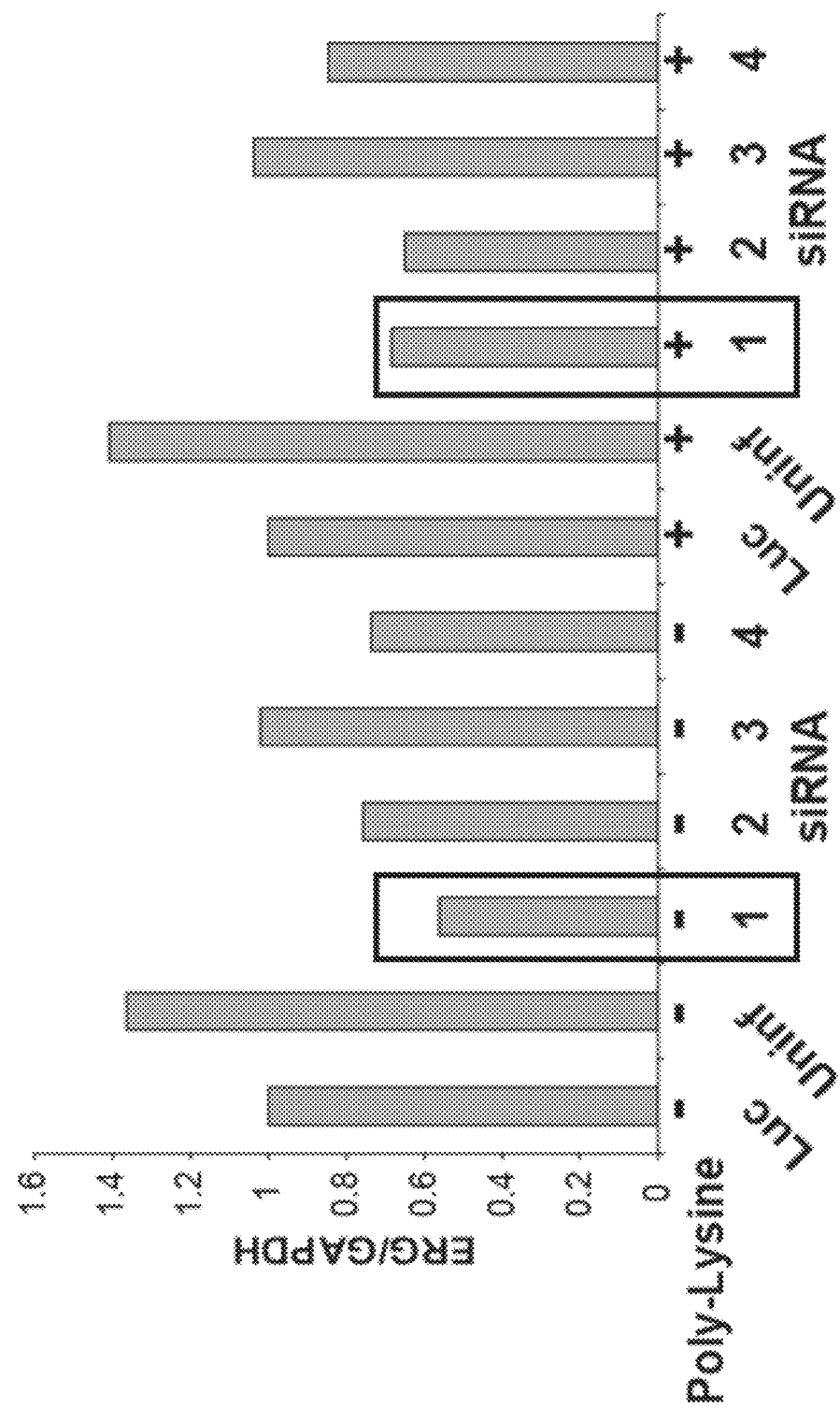
FIG. 30 shows siRNA knockdown of ERG in VCAP.

This Example describes the knockdown of ETS family members in prostate cancer. siRNAs were used to knockdown expression of ETV1 and ERG in LnCaP and VCAP. Quantitative PCR was used to confirm the knockdown. Results are shown in FIGS. 29 and 30. The knockdown did not affect proliferation. Lentivirus expressing shRNA are generated for stable knockdowns.

Microarrays were performed on Agilent 44K Whole Genome arrays to determine which genes were differentially expressed when ERG expression was knocked down in VCaP cells (which have the TMPRSS2:ERG fusion). For this experiment, three conditions were used: knockdown using Dharmacon siRNA for ERG (ERGsi), knockdown of luciferase (control), and untransfected (untrans) VCaP cells. Three hybridizations of ERG/untrans and two of control/untrans were performed. The genes were called as present in all five experiments, had standard deviations less than 0.5 (of the average for both conditions), and showed a fold difference between the ERG and control of <0.75 or >1.5. The ERGdif field indicates the fold difference between the ERG and control knockdown experiments, so value less than one means the gene is underexpressed in the ERG knockdown (ERG itself ranks 81st in this analysis).

Example 16

Transgenic Mice

Figure 31:
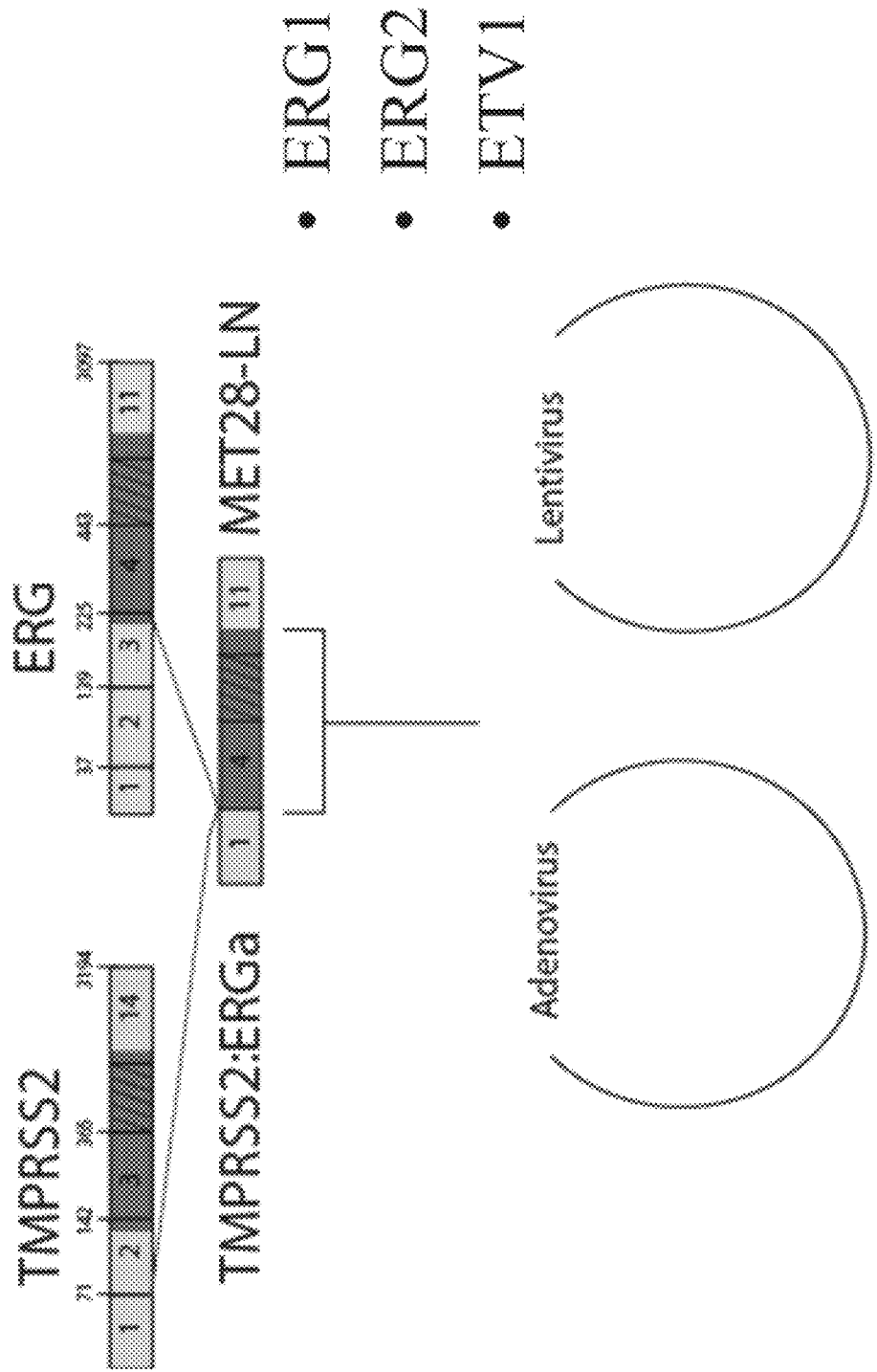
FIG. 31 shows viral overexpression systems.
Figure 32:
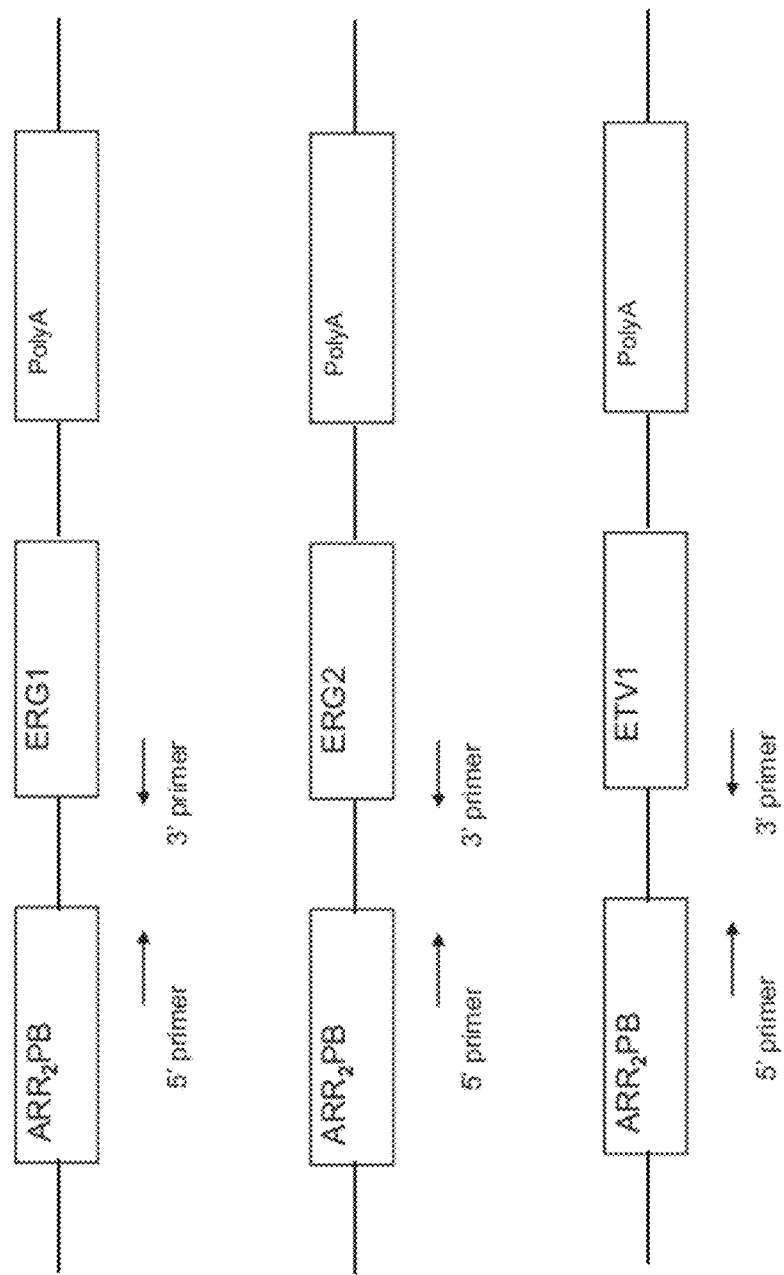
FIG. 32 shows a schematic of transgenic mice.

Transgenic mice that over express gene fusions of the present invention, as well as ETS and androgen responsive genes are generated. FIG. 31 shows viral overexpression systems for use in generating mice. FIG. 32 shows a schematic of genomic insertions in transgenic mice. Such mice find use in research (e.g., mechanistic studies) and drug screening applications.

Example 17

Identification of TMPRSS2:ERGa

As described above (Example 1), fusions of TMPRSS2 to ERG were observed. To determine the expressed protein from the TMPRSS2:ERGa gene fusion, PCR was used to amplify the portion of ERG (NM_004449) from the fusion breakpoint at the beginning of exon 4 to the presumed stop codon in exon 11, inserting a 3× Flag tag immediately upstream of the stop codon, from the VCaP prostate cancer cell line. The product was TA cloned into pCR8/GW/TOPO TA (Invitrogen) and bi directionally sequenced. Sequencing revealed the presence of two distinct isoforms, herein designated as ERG1 (includes exon 6 from ERG isoform 1 (NM_182918, GGGGTGCAGCTTTTATTTTC-CCAAATACTTCAGTATATCCTGAAGCTACGCAA AGAATTACAACTAGGCCAG; SEQ ID NO:73) and ERG2 (does not include this exon). The product was Gateway cloned into the pLenti6/V5-DEST destination vector. This plasmid was transfected directly into PHINX cells for ERG protein production.

A. Methods

Transfection Assay: Phinx cells were transfected with either ERG2 or the empty vector using Fugene transfection reagent (Roche) as per manufacturer's instructions. A total of ten 150 mm diameter plates were used for each construct. The cells were harvested 48 h post-transfection and used for immunoprecipitation assay as described below.

Protein Lysis and Immunoprecipitation: Cells were washed in ice cold PBS containing protease inhibitors and lysed by homogenization in TBS containing 1% NP40. The supernatant containing proteins were estimated for their protein content using Bradfords Protein Assay (Biorad Laboratories, Hercules, Calif.) as per manufacturer's instructions. Equal amounts of protein (approximately 30 mg in 15 ml buffer) from all samples were used for immunoprecipitation studies. About 200 microliters of a 50% slurry of EZVIEW Red ANTI-FLAG M2 Affinity Gel (Sigma, St Louis, Mo.) was added to each sample and incubated overnight at 4 C. The immunoprecipitate was washed thrice each with TBS containing 0.1% NP40 and TBS alone. Bound proteins were eluted using FLAG peptide (Sigma, St Louis, Mo.) as per manufacturer's instruction. The elution was performed three times. Proteins in the eluate were preicipitated using 50% TCA (Sigma, St Louis, Mo.). The precipitate was washed thrice with ice cold acetone, resuspended in Laemmeli buffer and electrophoresed on 4-20% BIS-TRIS gel (Invitrogen Corporation, Carlbad, Calif.). The gels were stained with mass spectrometry compatible silver stain (Silver Quest, Invitrogen Corporation, Carsbad, Calif.). Bands corresponding to ERG2 and the corresponding region in the vector lane were excised into 6 pieces of 1 cm each. Each of the gel pieces were labeled bands 1-6 starting from higher molecular weight region on the gel moving down. Thus Band 1 corresponds to the region containing high molecular weight proteins while band 6 corresponds to region of low molecular weight. Based on its native molecular mass of ERG2 (approximately 55 KDa) would migrate in Bands 4 and 5. ERG2 sequence identification was repeated three times and the data was consolidated from all the experiments.

Protein Identification

The gel bands were collected, destained using the destaining solution provided in the Silver Stain Kit as per manufacturers instruction (Invitrogen Corporation, Carsbad, Calif.). In gel digestion was performed using Porcine Trypsin (1:50, Promega Corporation, Madison, Wis.) in 1M Ammonium Bicarbonate, pH 9. The digestion was performed for 16 h at 37° C. At the end of 24 h the trypsin activity was stopped using 3% formic acid. The peptides were extracted using 50% Acetonitrile. The peptides were dried and resuspended in 2% Acetonitrile containing 0.1% formic acid and separated by reversed-phase chromatography using a 0.075 mm×150 mm C18 column attached to a Paradigm HPLC pump (Michrome Bio Resources Inc.). Peptides were eluted using a 45-min gradient from 5 to 95% B (0.1% formic acid/95% acetonitrile), where solvent A was 0.1% formic acid/2% acetonitrile. A Finnigan LTQ mass spectrometer (Thermo Electron Corp.) was used to acquire spectra, the instrument operating in data-dependent mode with dynamic exclusion enabled. The MS/MS spectra on three most abundant peptide ions in full MS scan were obtained. The spectra are searched using the MASCOT search tool against the composite, non-identical NCBI human reference sequence database. These database search results are validated for peptide assignment accuracy using the PeptideProphet program. This is a mixture model; an expectation maximization evaluation assigning a probability of correct peptide identification based on search result scores and various peptide features including the number of tryptic termini. A second program, ProteinProphet, is used to group peptides by protein and combine their probabilities to assign a probability of a correct protein assignment. Discriminatory power increases with the subsequent re-estimation of individual peptide probabilities by way of their NSP value, or number of sibling peptides, which amounts to peptide grouping information and the status of a possible multi-hit protein. Results:

TABLE 14

COVERAGE MAP (ERG2)

| MIQTVPDPAA HI . . . (SEQ ID NO: 234) | NCBI N-terminal, BAND05-20060217 | SEQ ID NO |
|---|---|---|
| MASTIKEALS VVSEDQSLFE CAYGTPHLAK TEMTASSSSD | 40 | 74 |
| SSSSD | BAND03-20060206 | 75 |
| YGQTSKMSPR VPQQDWLSQP PARVTIKMEC NPSQVNGSRN | 80 | 76 |
| VPQQDWLSQP PAR | BAND01-20060217 | 77 |
| VPQQDWLSQP PAR | BAND02-20060206 | 78 |
| VPQQDWLSQP PAR | BAND02-20060209 | 79 |
| VPQQDWLSQP PAR | BAND02-20060217 | 80 |
| YGQTSKMS VPQQDWLSQP PAR | BAND03-20060206 | 81 |
| VPQQDWLSQP PAR | BAND03-20060209 | 82 |
| VPQQDWLSQP PAR | BAND03-20060217 | 83 |
| VPQQDWLSQP PAR | BAND04-20060206 | 84 |
| VPQQDWLSQP PAR    MEC NPSQVNGSR | BAND04-20060209 | 85 |
| VPQQDWLSQP PAR | BAND04-20060217 | 86 |
| VPQQDWLSQP PAR | BAND05-20060217 | 87 |
| SPDECSVAKG GKMVGSPDTV GMNYGSYMEE KHMPPPNMTT | 120 | 88 |
| HMPPPNMTT | BAND01-20060206 | 89 |
| HMPPPNMTT | BAND02-20060206 | 90 |
| HMPPPNMTT | BAND02-20060209 | 91 |
| NYGSYMEE KHMP | BAND02-20060217 | 92 |
| MVGSPDTV GMNYGSYMEE KHMPPPNMTT | BAND03-20060206 | 93 |
| HMPPPNMTT | BAND03-20060209 | 94 |
| HMPPPNMTT | BAND04-20060206 | 95 |
| MVGSPDTV GMNYGSYMEE KHMPPPNMTT | BAND04-20060209 | 96 |
| MVGSPDTV GMNYGSYMEE KHMPPPNMTT | BAND04-20060217 | 97 |
| NERRVIVPAD PTLWSTDHVR QWLEWAVKEY GLPDVNILLF | 160 | 98 |
| NER VIVPAD PTLWSTDHVR QWLEWAVKEY GLPDVNILLF | BAND01-20060206 | 99 |
| NER                                    EY GLPDVNILLF | BAND02-20060206 | 100 |
| NER | BAND02-20060209 | 101 |
| NER VIVPAD PTLWSTDHVR QWLEWAVK | BAND03-20060206 | 102 |
| NERRVIVPAD PTLWSTDHVR            EY GLPDVNILLF | BAND03-20060209 | 103 |
| NER VIVPAD PTLWSTDHVR QWLEWAVKEY GLPDVNILLF | BAND04-20060206 | 104 |
| NERRVIVPAD PTLWSTDHVR QWLEWAVKEY GLPDVNILLF | BAND04-20060209 | 105 |

TABLE 14-continued

COVERAGE MAP (ERG2)

| MIQTVPDPAA HI . . . (SEQ ID NO: 234) | NCBI N-terminal, BAND05-20060217 | SEQ ID NO |
|---|---|---|
| NERRVIVPAD PTLWSTDHVR | BAND04-20060217 | 106 |
| EY GLPDVNILLF | BAND05-20060206 | 107 |
| QNIDGKELCK MTKDDFQRLT PSYNADILLS HLHYLRETPL | 200 | 108 |
| QNIDGK                LT PSYNADILLS HLHYLRETPL | BAND01-20060206 | 109 |
| ETPL | BAND01-20060217 | 110 |
| QNIDGK ETPL | BAND02-20060206 | 111 |
| ETPL | BAND02-20060217 | 112 |
| ETPL | BAND03-20060206 | 113 |
| QNIDGK                LT PSYNADILLS HLHYLRETPL | BAND03-20060209 | 114 |
| ETPL | BAND03-20060217 | 115 |
| QNIDGK                LT PSYNADILLS HLHYLRETPL | BAND04-20060206 | 116 |
| QNIDGK                LT PSYNADILLS HLHYLRETPL | BAND04-20060209 | 117 |
| LT PSYNADILLS HLHYLRETPL | BAND04-20060217 | 118 |
| QNIDGK | BAND05-20060206 | 119 |
| PSYNADILLS HLHYLRETPL | BAND05-20060217 | 120 |
| PHLTSDDVDK ALQNSPRLMH ARNTGGAAFI FPNTSVYPEA | 240 | 121 |
| PRLMH ARNT | BAND01-20060206 | 122 |
| PHLTSDDVDK | BAND01-20060206 | 123 |
| PHLTSDDVDK ALQNSPR | BAND01-20060217 | 124 |
| PHLTSDDVDK ALQNSPR | BAND02-20060206 | 125 |
| PHLTSDDVDK ALQNSPR | BAND02-20060217 | 126 |
| PHLTSDDVDK ALQNSPR | BAND03-20060206 | 127 |
| PHLTSDDVDK | BAND03-20060209 | 128 |
| PHLTSDDVDK ALQNSPR | BAND03-20060217 | 129 |
| PHLTSDDVDK ALQNSPR | BAND04-20060206 | 130 |
| PHLTSDDVDK ALQNSPR | BAND04-20060209 | 131 |
| RNT | BAND04-20060209 | 132 |
| PHLTSDDVDK ALQNSPR | BAND04-20060217 | 133 |
| PHLTSDDVDK ALQNSPRL | BAND05-20060217 | 134 |
| TQRITTRPDL PYEPPRRSAW TGHGHPTPQS KAAQPSPSTV | 280 | 135 |
| DLPYEPPR | BAND01-20060206 | 136 |
| SAW TGHGHPTPQS KAAQPSPSTV | BAND01-20060206 | 137 |
| PYEPPRR | BAND01-20060217 | 138 |
| SAW TGHGHPTPQS KAAQPSPSTV | BAND02-20060206 | 139 |
| SAW TGHGHPTPQS KAAQPSPSTV | BAND02-20060209 | 140 |
| PYEPPRRSAW TGHGHPTPQS KAAQPSPSTV | BAND02-20060217 | 141 |
| SAW TGHGHPTPQS KAAQPSPSTV | BAND03-20060206 | 142 |
| SAW TGHGHPTPQS KAAQPSPSTV | BAND03-20060209 | 143 |

TABLE 14-continued

COVERAGE MAP (ERG2)

| MIQTVPDPAA HI . . . (SEQ ID NO: 234) | NCBI N-terminal, BAND05-20060217 | SEQ ID NO |
|---|---|---|
| DL PYEPPRR | BAND03-20060217 | 144 |
| PYEPPRRSAW TGHGHPTPQS KAAQPSPSTV | BAND04-20060206 | 145 |
| DL PYEPPRRSAW TGHGHPTPQS KAAQPSPSTV | BAND04-20060209 | 146 |
| DL PYEPPRR | BAND04-20060209 | 147 |
| DL PYEPPRRSAW TGHGHPTPQS KAAQPSPSTV | BAND04-20060217 | 148 |
| AAQPSPSTV | BAND05-20060206 | 149 |
| SAW TGHGHPTPQS KAAQPSPSTV | BAND05-20060209 | 150 |
| DL PYEPPRRSAW TGHGHPTPQS KAAQPSPSTV | BAND05-20060217 | 151 |
| SAW TGHGHPTPQS KAAQPSPSTV | BAND06-20060209 | 235 |
| PKTEDQRPQL DPYQILGPTS SRLANPGSGQ IQLWQFLLEL | 320 | 152 |
| PK | BAND01-20060206 | 153 |
| TEDQRPQL DPYQILGPTS SR | BAND01-20060217 | 154 |
| PKTEDQRPQL DPYQILGPTS SR | BAND02-20060206 | 155 |
| PKTEDQRPQL DPYQILGPTS SR | BAND02-20060209 | 156 |
| PKTEDQRPQL DPYQILGPTS SR | BAND02-20060217 | 157 |
| PKTEDQRPQL DPYQILGPTS SR | BAND03-20060206 | 158 |
| PKTEDQRPQL DPYQILGPTS SR | BAND03-20060209 | 159 |
| TEDQRPQL DPYQILGPTS SR | BAND03-20060217 | 160 |
| PKTEDQRPQL DPYQILGPTS SR | BAND04-20060206 | 161 |
| PKTEDQRPQL DPYQILGPTS SR | BAND04-20060209 | 162 |
| PKTEDQRPQL DPYQILGPTS SR | BAND04-20060217 | 163 |
| PK | BAND05-20060206 | 164 |
| PKTEDQRPQL DPYQILGPTS SR | BAND05-20060209 | 165 |
| PKTEDQRPQL DPYQILGPTS SR | BAND05-20060217 | 166 |
| PK | BAND06-20060209 | 167 |
| LSDSSNSSCI TWEGTNGEFK MTDPDEVARR WGERKSKPNM | 360 | 168 |
| MTDPDEVAR | BAND01-20060206 | 169 |
| MTDPDEVAR | BAND02-20060206 | 170 |
| MTDPDEVAR | BAND03-20060206 | 171 |
| MTDPDEVAR | BAND03-20060209 | 172 |
| MTDPDEVAR | BAND04-20060206 | 173 |
| MTDPDEVARR | BAND04-20060209 | 174 |
| TDPDEVARR KSKPNM | BAND04-20060217 | 175 |
| MTDPDEVAR | BAND05-20060209 | 176 |
| KSKPNM | BAND05-20060217 | 177 |

TABLE 14-continued

COVERAGE MAP (ERG2)

| MIQTVPDPAA HI ... (SEQ ID NO: 234) | NCBI N-terminal, BAND05-20060217 | SEQ ID NO |
|---|---|---|
| <u>NYDKLSRALR YYYDKNIMTK VHGKRYAYKF DFHGIAQALQ</u> | 400 | 178 |
| F DFHGIAQALQ | BAND02-20060206 | 179 |
| F DFHGIAQALQ | BAND02-20060209 | 180 |
| F DFHGIAQALQ | BAND03-20060206 | 181 |
| F DFHGIAQALQ | BAND03-20060209 | 182 |
| YYYDKNIMTK YAYKF DFHGIAQALQ | BAND04-20060209 | 183 |
| NYDKLSR | BAND04-20060217 | 184 |
| NYDKLSR YYYDKNIMTK | BAND05-20060217 | 185 |
| <u>PHPPESSLYK YPSDLPYMGS YHAHPQKMNF VAPHPPALPV</u> | 440 | 186 |
| PHPPESSLYK | BAND02-20060206 | 187 |
| PHPPESSLYK YPSDLPYMGS YHAH | BAND02-20060209 | 188 |
| PHPPESSLYK YPSDLPYMGS YHAHPQK | BAND03-20060206 | 189 |
| PHPPESSLYK YPSDLPYMGS YHAHPQK | BAND03-20060209 | 190 |
| YPSDLPYMGS YHAHPQK | BAND04-20060206 | 191 |
| PHPPESSLYK YPSDLPYMGS YHAHPQK | BAND04-20060209 | 192 |
| <u>TSSSFFAAPN PYWNSPTGGI YPNTRLPTSH MPSHLGTYY</u> | 479 | 193 |
| NSPTG | BAND02-20060217 | 194 |
| SPTGGI YPNTR | BAND04-20060209 | 195 |

NOTE:
E*BAND*-* represent ERG2 peptides in ERG1 experiments

The table shows the coverage map for ERG2 obtained over 3 different experiments. The underlined aminoacid sequence corresponds to the in silico translated sequence of ERG1 that was cloned from VCAP cells. The aminoacid sequence GGAAFI FPNTSVYPEATQRITTRP (SEQ ID NO:196) corresponds to the exon that is specific to ERG1 and is missing in ERG2. The remaining amino acid sequence correspond to ERG2 sequence identified in each of the three experiments. ERG2 was identified in Bands 1-5 in all the experiments. The peptide sequences for ERG2 obtained in each of these bands is illustrated. A very high coverage of the ERG2 protein was observed over the three experiments. The coverage map showed that the coverage of peptides in the N-terminal region of the cloned protein, corresponding to the first 50 aminoacid residues were rarely observed in the mass spectrometry coverage map. However, the peptide VPQQDWLSQP (SEQ ID NO:197) that starts with aminoacid valine was found to be highly abundant and thus identified in all the experiments. Closer evaluation suggested that aminoacid in the 47$^{th}$ position was an in frame Methionine. The lack of any peptide upstream (Nterminus) of the 47 th methionine in multiple experiments confirms that it is the N-terminal aminoacid of ERG2. Further, the presence of a Arginine residue at the 50$^{th}$ position makes it a potential tryptic cleavage site. Digestion by trypsin at this site would result in a shorter N-terminal peptide MSPR, which is too small for identification by ion trap mass spectrometer and a longer C-terminal peptide VPQQDWLSQP (SEQ ID NO:198), which was identified in all the experiments. Also the peptide sequence MIQTVPDPAA HI (SEQ ID NO:199) was identified in a single experiment at a very low probablility score. This maps to the N-terminus of ERG as reported in NCBI. This sequence was not a part of the ectopically overexpressed construct that was cloned from the VCAP cells. This could have been obtained from the in vivo ERG that is expressed in PHINX cells and thus may represent part of the ERG associated with benign cells. Thus, in summary, the results indicate that the third Methionine is the translational Start site for the TMPRSS2-ERG fusion product. MASTIKEALS VVSEDQSLFE CAYGTPHLAK TEMTA YGQTSKMSPR VPQQDWLSQP (SEQ ID NO:200)

The First Methionine is the translational START Site for endogenous ERG.

MIQTVPDPAA HI (SEQ ID NO:201)

FIG. 20 shows a schematic of the endogenous and fusion polypeptides.

Example 18

FISH Analysis on Urine Samples

To isolate and prepare prostatic cells from urine, ~30 ml of urine is collected following an attentive digital rectal exam. Immediately, 15 ml of PreservCyt is added, and the sample is centrifuged at 4000 rpm in a 50 ml tube for 10 min at room temperature. The supernatant is discarded, the pellet is resuspended in 15 ml of 0.75 M KCl for 15 min at room temperature, and centrifuged at 4000 rpm in a 50 ml tube for 10 min at room temperature. The supernatant is discarded, and the pellet is resuspended in 10 ml of a 3:1 ratio of methanol: glacial acetic acid. This is then centrifuged at 4000 rpm for 8 min. The supernatant is discarded, except for 200 μl, and the pellet is resuspended. The resuspended pellet is then dropped onto glass slides and allowed to air dry. Hybridization and probe preparation are as in Example 2 above, with the ERG 5'/3' and TMPRSS 5/3' probe pairs.

All publications, patents, patent applications and accession numbers mentioned in the above specification are herein incorporated by reference in their entirety. Although the invention has been described in connection with specific embodiments, it should be understood that the invention as claimed should not be unduly limited to such specific embodiments. Indeed, various modifications and variations of the described compositions and methods of the invention will be apparent to those of ordinary skill in the art and are intended to be within the scope of the following claims.

We claim:

1. A composition comprising an antibody that is specific for a truncated ERG1 protein, wherein the truncated ERG1 protein has an amino acid sequence that begins at a methionine that is the 47th amino acid of SEQ ID NO: 240 and the antibody binds an epitope comprising the 47th amino acid of SEQ ID NO: 240.

2. The composition of claim 1, wherein the truncated ERG1 protein is encoded by a gene fusion resulting from rearrangement of TMPRSS2 and ERG1 genes.

3. The composition of claim 2, wherein the gene fusion comprises a 5' portion from the TMPRSS2 gene and a 3' portion from the ERG1 gene.

4. The composition of claim 3, wherein the gene fusion comprises a 5' portion from a transcriptional regulatory region of the TMPRSS2 gene.

5. The composition of claim 4, wherein the transcriptional regulatory region comprises a promoter region of the TMPRSS2 gene.

6. A composition comprising an antibody that binds an epitope comprising the 47th amino acid of SEQ ID NO: 240.

7. The composition of claim 6 wherein said epitope results from a gene fusion resulting from the fusion of, rearrangement of TMPRSS2 and ERG1 genes.

8. A composition comprising an antibody that binds an epitope comprising the 47th amino acid of SEQ ID NO: 240 that is a truncated ERG1 protein encoded by a gene fusion resulting from rearrangement of TMPRSS2 and ERG1 genes.

9. The composition of claim 8, wherein the gene fusion comprises a 5' portion from the TMPRSS2 gene and a 3' portion from the ERG1 gene.

10. The composition of claim 9, wherein the gene fusion comprises a 5' portion from a transcriptional regulatory region of the TMPRSS2 gene.

11. The composition of claim 10, wherein the transcriptional regulatory region comprises a promoter region of the TMPRSS2 gene.

* * * * *

```
SEQUENCE LISTING

<160> NUMBER OF SEQ ID NOS: 307

<210> SEQ ID NO 1
<211> LENGTH: 24
<212> TYPE: DNA
<213> ORGANISM: Homo sapiens

<400> SEQUENCE: 1
aacagagatc tggctcatga ttca                                              24

<210> SEQ ID NO 2
<211> LENGTH: 24
<212> TYPE: DNA
<213> ORGANISM: Homo sapiens

<400> SEQUENCE: 2
cttctgcaag ccatgtttcc tgta                                              24

<210> SEQ ID NO 3
<211> LENGTH: 24
<212> TYPE: DNA
<213> ORGANISM: Homo sapiens

<400> SEQUENCE: 3
aggaaacatg gcttgcagaa gctc                                              24

<210> SEQ ID NO 4
<211> LENGTH: 26
<212> TYPE: DNA
<213> ORGANISM: Homo sapiens

<400> SEQUENCE: 4
tctggtacaa actgctcatc attgtc                                            26

<210> SEQ ID NO 5
<211> LENGTH: 26
<212> TYPE: DNA
<213> ORGANISM: Homo sapiens

<400> SEQUENCE: 5
ctcaggtacc tgacaatgat gagcag                                            26

<210> SEQ ID NO 6
<211> LENGTH: 24
<212> TYPE: DNA
<213> ORGANISM: Homo sapiens

<400> SEQUENCE: 6
catggactgt ggggttcttt cttg                                              24

<210> SEQ ID NO 7
<211> LENGTH: 26
<212> TYPE: DNA
<213> ORGANISM: Homo sapiens
```

-continued

```
<400> SEQUENCE: 7
aacagccctt taaattcagc tatgga                                          26

<210> SEQ ID NO 8
<211> LENGTH: 21
<212> TYPE: DNA
<213> ORGANISM: Homo sapiens

<400> SEQUENCE: 8
ggagggcctc attcccactt g                                               21

<210> SEQ ID NO 9
<211> LENGTH: 22
<212> TYPE: DNA
<213> ORGANISM: Homo sapiens

<400> SEQUENCE: 9
ctaccccatg gaccacagat tt                                              22

<210> SEQ ID NO 10
<211> LENGTH: 22
<212> TYPE: DNA
<213> ORGANISM: Homo sapiens

<400> SEQUENCE: 10
cttaaagcct tgtggtggga ag                                              22

<210> SEQ ID NO 11
<211> LENGTH: 24
<212> TYPE: DNA
<213> ORGANISM: Homo sapiens

<400> SEQUENCE: 11
cgcagagtta tcgtgccagc agat                                            24

<210> SEQ ID NO 12
<211> LENGTH: 24
<212> TYPE: DNA
<213> ORGANISM: Homo sapiens

<400> SEQUENCE: 12
ccatattctt tcaccgccca ctcc                                            24

<210> SEQ ID NO 13
<211> LENGTH: 23
<212> TYPE: DNA
<213> ORGANISM: Homo sapiens

<400> SEQUENCE: 13
cgactggagc acgaggacac tga                                             23

<210> SEQ ID NO 14
<211> LENGTH: 24
<212> TYPE: DNA
<213> ORGANISM: Homo sapiens

<400> SEQUENCE: 14
catggactgt ggggttcttt cttg                                            24

<210> SEQ ID NO 15
<211> LENGTH: 22
<212> TYPE: DNA
```

```
<213> ORGANISM: Homo sapiens

<400> SEQUENCE: 15
ggcgttccgt aggcacactc aa                                            22

<210> SEQ ID NO 16
<211> LENGTH: 20
<212> TYPE: DNA
<213> ORGANISM: Homo sapiens

<400> SEQUENCE: 16
cctggctggg ggttgagaca                                               20

<210> SEQ ID NO 17
<211> LENGTH: 21
<212> TYPE: DNA
<213> ORGANISM: Homo sapiens

<400> SEQUENCE: 17
taggcgcgag ctaagcagga g                                             21

<210> SEQ ID NO 18
<211> LENGTH: 25
<212> TYPE: DNA
<213> ORGANISM: Homo sapiens

<400> SEQUENCE: 18
gtaggcacac tcaaacaacg actgg                                         25

<210> SEQ ID NO 19
<211> LENGTH: 19
<212> TYPE: DNA
<213> ORGANISM: Homo sapiens

<400> SEQUENCE: 19
cgcgagctaa gcaggaggc                                                19

<210> SEQ ID NO 20
<211> LENGTH: 22
<212> TYPE: DNA
<213> ORGANISM: Homo sapiens

<400> SEQUENCE: 20
caggccatga aaagccaaac tt                                            22

<210> SEQ ID NO 21
<211> LENGTH: 20
<212> TYPE: DNA
<213> ORGANISM: Homo sapiens

<400> SEQUENCE: 21
ccggatggag cggaggatga                                               20

<210> SEQ ID NO 22
<211> LENGTH: 20
<212> TYPE: DNA
<213> ORGANISM: Homo sapiens

<400> SEQUENCE: 22
cgggcgattt gctgctgaag                                               20

<210> SEQ ID NO 23
<211> LENGTH: 19
```

```
<212> TYPE: DNA
<213> ORGANISM: Homo sapiens

<400> SEQUENCE: 23
gccgcccctc gactctgaa                                              19

<210> SEQ ID NO 24
<211> LENGTH: 24
<212> TYPE: DNA
<213> ORGANISM: Homo sapiens

<400> SEQUENCE: 24
gagccacgtc tcctggaagt gact                                        24

<210> SEQ ID NO 25
<211> LENGTH: 21
<212> TYPE: DNA
<213> ORGANISM: Homo sapiens

<400> SEQUENCE: 25
ctggccggtt cttctggatg c                                           21

<210> SEQ ID NO 26
<211> LENGTH: 18
<212> TYPE: DNA
<213> ORGANISM: Homo sapiens

<400> SEQUENCE: 26
cgggccgggg aatggagt                                               18

<210> SEQ ID NO 27
<211> LENGTH: 22
<212> TYPE: DNA
<213> ORGANISM: Homo sapiens

<400> SEQUENCE: 27
cctggagggt accggtttgt ca                                          22

<210> SEQ ID NO 28
<211> LENGTH: 20
<212> TYPE: DNA
<213> ORGANISM: Homo sapiens

<400> SEQUENCE: 28
ccgcctgcct ctgggaacac                                             20

<210> SEQ ID NO 29
<211> LENGTH: 30
<212> TYPE: DNA
<213> ORGANISM: Homo sapiens

<400> SEQUENCE: 29
aaataagttt gtaagaggag cctcagcatc                                  30

<210> SEQ ID NO 30
<211> LENGTH: 24
<212> TYPE: DNA
<213> ORGANISM: Homo sapiens

<400> SEQUENCE: 30
atcgtaaaga gcttttctcc ccgc                                        24

<210> SEQ ID NO 31
```

```
<211> LENGTH: 23
<212> TYPE: DNA
<213> ORGANISM: Homo sapiens

<400> SEQUENCE: 31
gaaagggctg tagggcgac tgt                                              23

<210> SEQ ID NO 32
<211> LENGTH: 327
<212> TYPE: DNA
<213> ORGANISM: Homo sapiens

<400> SEQUENCE: 32
ccgtcggcgc cgagggagtt agtgcgaccc ggctcggcgc gcacggccaa ggcacgcgcg      60
ctggcacacg cgggcgcgga cacgcgcgga cacacacgtg cgggacacgc cctcccccga    120
cggcggcgct aacctctcgg ttattccagg atctttggag acccgaggaa agccgtgttg    180
accaaaagca agacaaatga ctcacagaga aaaagatgg cagaaccaag ggcaactaaa     240
gccgtcaggt tctgaacagc tggtagatgg gctggcttac tgaaggacat gattcagact    300
gtcccggacc cagcagctca tatcaag                                        327

<210> SEQ ID NO 33
<211> LENGTH: 6158
<212> TYPE: DNA
<213> ORGANISM: Homo sapiens

<400> SEQUENCE: 33
gttgatagaa gtccagatcc tgaggaaatc tccagctaaa tgctcaaaat ataaatact      60 gagctgagat ttgcgaagag cagcagcatg gatgatttt atgaccagca agtgccttac     120
atggtcacca atagtcagcg tgggagaaat tgtaacgaga accaacaaa tgtcaggaaa     180 agaaaattca ttaacagaga tctggctcat gattcagaag aactctttca agatctaagt    240
caattcaggg aaacatggct tgcagaagct caggtacctg acaatgatga gcagtttgta    300
ccagactatc aggctgaaag tttggctttt catggcctgc cactgaaaat caagaaagaa    360
ccccacagtc catgttcaga aatcagctct gcctgcagtc aagaacagcc ctttaaattc    420
agctatggag aaaagtgcct gtacaatgtc agtgcctatg atcagaagcc acaagtggga    480
atgaggccct ccaacccccc cacaccatcc agcacgccag tgtccccact gcatcatgca    540
tctccaaact caactcatac accgaaacct gaccgggcct tccagctca cctccctcca    600 tcgcagtcca taccagatag cagctacccc atggaccaca gatttcgccg ccagcttttct    660 gaaccctgta actcctttcc tcctttgccg acgatgccaa gggaaggacg tcctatgtac    720
caacgccaga tgtctgagcc aaacatcccc ttcccaccac aaggctttaa gcaggagtac    780
cacgacccag tgtatgaaca caacaccatg gttggcagtg cggccagcca aagctttccc    840
cctcctctga tgattaaaca ggaacccaga gattttgcat atgactcaga agtgcctagc    900
tgccactcca tttatatgag gcaagaaggc ttcctggctc atcccagcag aacagaaggc    960
tgtatgtttg aaaagggccc caggcagttt tatgatgaca cctgtgttgt cccagaaaaa   1020
ttcgatggag acatcaaaca agagccagga atgtatcggg aaggaccac ataccaacgg    1080 cgaggatcac ttcagctctg gcagttttg gtagctcttc tggatgaccc ttcaaattct   1140
cattttattg cctggactgg tcgaggcatg gaatttaaac tgattgagcc tgaagaggtg   1200
gcccgacgtt gggcattca gaaaacagg ccagctatga actatgataa acttagccgt     1260
tcactccgct attactatga gaaggaatt atgcaaaagg tggctggaga gagatatgtc   1320
```

```
tacaagtttg tgtgtgatcc agaagcccett ttctccatgg cctttccaga taatcagcgt    1380
ccactgctga agacagacat ggaacgtcac atcaacgagg aggacacagt gcctctttct    1440
cactttgatg agagcatggc ctacatgccg gaaggggct gctgcaaccc ccaccccctac    1500 aacgaaggct acgtgtatta acacaagtga cagtcaagca gggcgttttt gcgcttttcc    1560
ttttttctgc aagatacaga gaattgctga atctttgttt tatttctgtt gtttgtattt    1620
tatttttaaa taataataca caaaaagggg ctttttcctgt tgcattattc tatggtctgc    1680
catggactgt gcactttatt tgagggtggg tgggagtaat ctaaacattt attctgtgta    1740
acaggaagct aatgggtgaa tgggcagagg gatttgggga ttactttta cttaggcttg    1800 ggatggggtc ctacaagttt tgagtatgat gaaactatat catgtctgtt tgatttcata    1860
acaacataag ataatgttta ttttatcggg gtatctatgg tacagttaat ttcacgttgt    1920
gtaaatatcc acttggagac tatttgcctt gggcattttc ccctgtcatt tatgagtctc    1980
tgcaggtgta caaaaaaacc ccaatctact gtaaatggca gtttaattgt tagaaatgac    2040 tgttttttgca ccacttgtaa aaaggtattt agcgattgca tttgctgttt gttgttttat    2100
tttgctttat atatgacttg cagaggataa ccataaaatg ggtaattctc tctgaagttg    2160
aataatcacc atgactgtaa atgaggggca caattttgga ctctggcgcc aaactgagtc    2220
ataggccagt agcattacgt gtatctggtg ccaccttgct gtttagatac aaatcatacc    2280
gtcttttaaa tattttgaag cccatttcag ttaaataatg acatgtcatg gtcctttgga    2340
atcttcattt aaatgttaaa tctggaatca aaatgaagca aaaaatatct gtctcctttt    2400
cactttcttc agtacataaa tacattattt aatcaataag aattaactgt actaaatcat    2460
gtattatgct gttctagtta cagcaaacac tctttaagaa aaatatccaa tacactaaat    2520
aggtactata gtaatttta gacatggtac ccattgatat gcatttaaac cttttactgc    2580
tgtgttatgt tgataacata tataaatatt agataatgct aatgcttctg ctgctgtctt    2640
ttctgtaata ttctctttca tgctgaattt actatgacca tttataagca gtgcagttaa    2700
ctacagatag catttcagga caaaatagat gactcaaacc atttattgct taaaaaatag    2760
cttacgccat gctatgctat aagcagcttt tatgcacatt gacaaatgaa gagtaagctt    2820
cagcttgcta aaggaaactg tggaaccttt tgtaacttt ggtgatatgg aaaattattt    2880
acaaaccgtc aaagaatatg aggaagttgc tgtatgacat agtgctggca ctgatattat    2940
ccatcatctc ttttttggaca cttctgtaaa tgtgattgga ttgtttgaaa gaagatttaa    3000
agtttcaaag ttttttgttc tgttttttgct ttgcatttgg agaaaatatt gaaagcaggg    3060
tatgttgttt cattcacctt gaaaaaacca tgagtaaatg gggatataga atctctgaat    3120
agctcgctaa aagattcaag caagggacat gaattttgtt ccatctatca ataatatcca    3180
gaagaacaac tttttttaaag agtctatagc aaaaagcaaa aaaaaaaaaa aattctaaac    3240
acaaagtcaa aataaaccta ttgtaaaagc atttcgtgat gagcatgaaa aagattgttt    3300
aaagatgatc cccccagcta cccattttcc aaaactacac agatcacagc tcatttctct    3360
aagtggagca gttatcaaga aacccaaaca ccaaaattgc tactcttcac atttaatcct    3420
acaaaaagta ctccaatttc aaaatatgta tgtaacctgc gatttcaatg attgttgttc    3480
atatacatca tgtattattt tggcccattt tgggcctaaa aagaaaact atgccttaaa    3540 aatcagaacc ttttctcccc actatgctta tgtggccatc tacagcactt agaataaaaa    3600
cagatgttaa aatattcagt gaaagttta ttggaaaaag gaattgagat atataattga    3660
```

```
gatttggtga aattgaagga gaaaatttaa gtgagtcttt aaaatatatt ctgaatgaaa    3720
actgtattga ggattcattt ttgttccttt tttttctttt tctcttttct ccttttcttt    3780
cttttaata gtctagtttt agtcagtcag tgaggaagaa ttgggccatg ctaacgttat    3840
cacaagagaa caatggcaga aatggtatta gttatataat atttaaggac aaactatatg    3900
ttttgctgtt ttaacgtagt gactcactga actaaataca taattgacca acattaagtg    3960
tatttccaat acagaagggt tgaaaatatt acattataaa ctcttttgaa aaatgtatct    4020
aaaatttttt aagttctgtt ttgattccac tttttggttg agtttttatg ttttgtttt     4080
caggtagatt aataaatctg gcagctgatt tctgcaagat tcttgtgttt tgaatttctc    4140
attgaattgg ctactcaaac atagaaatca tttgttaatg atgtaatgtc ttctctcagc    4200
ttttatcttc actgctgttt gctgtctctt gatgatgaca tgttaatacc caatagatta    4260
attgcaacaa acacttatac tcaaataact aagtaaaaat aattttctt gttatgtcca     4320
tgaaaagtgc ttcagaataa aaatccacaa gactgacagt gcagaacatt tttctcaaat    4380
catgggcgga tcttggaggt ctagtttccc gtagatgctg taaccaatta ccacaacttc    4440
agtaatttac acaaatttat cttatagttc tggaggcaga agttcaaaag aagccttaag    4500
agactaaaac caagatgtcc ttaggtctgg ttccttctgg aggctccagg ggagattctt    4560
ccagctttca cttctagagt ctgctgacat tccttggctc ctggctacat cacttcaatc    4620
tctgcttcca tggtcacata ctcttctact atagtcaaat ttccttcctg cctcttataa    4680
ggatgcttgt gattacattt aggggatgct cagataatcc aggacaatct ctccatctca    4740
agatccttaa cttaatgacg tgtgccaagt cccttggct agataattat tcataggtcc      4800
cagggattag gacatggatg taaggggtga gggcagggct gttattcaga acaccgcacg    4860
gaggaggaag actgtgtagc aaagactcta attgatttac tcaggaacag tggagttctg    4920
ctgagggatc taggatttga aagtactaga gtttgctttt atttaccact gagatatttt    4980
cccttatc tgcataaata atttgaaaa ctttctatat taaatttcaa ctattccact        5040
aaatgtctg gtaatcacat caagccttta gattattcaa atccttcccc agccccagg       5100
aaacactaa gtcatgaaac agaaaaacag aaggtatgat aataatagta ataacagtta     5160
aatcagtggt ctaatccaga ttttatttt taatacattt cttttggtgt taatatgggt     5220
tactatgtga tcttatcatt tgctagtgat tattacttat taggtaagaa caatgtgtaa    5280
aatatgtcta ttactcaaaa gaacaattgc aaaatgagtc aacttatctt tatataacca    5340
ggaaagaaat atattgccag aagctacaga attttgccag atgatagga tttctaaaat      5400
gagccacttt gtctatcatg cagccttttc agagcttgta atgagaaaac attacagagg    5460
agaaggtcat ttggatgttt gttacttgga atcctagaaa acaaaaacta aaatttaaaa    5520
ataagaagtg agtaagctat tttccatttg cgatttggta tggagaagag aggaaataga    5580
attattaaaa aaatacaaat tgggtaaaag tgatggtgga aaaatataa agaaggcaaa      5640
tgtacatatt aagcaattct actaagaatt ggaaaaatca agtttcaaaa agatggtaat    5700
agttgggcat gatactagaa aatttcaccc agtttattca gagctcaact agtactttta    5760
ggacttcttt ttttatatac atgagactca ctttgacata cttaaaaaaa aaacagttta    5820
tggaaagtac agtttaagag gagaatttga ttagactaag tggatatctt tatagaaata    5880
ttaatgattt cagaatttc agttacaagt gtataccg tggctattgt ttatggattc       5940
atatgtaagg tagggtcttt tttgcatata gactccagta ttagttactt tcattctaaa    6000
attatattta tgcttctatg gggaagaaaa tttttaattc acttggttgt attaaaatta    6060
```

```
tacttacggt ttgagaaaac atgctatgaa aatcatgatt atagcaaatt aaatatgctc    6120
aaaatttaaa tctaaaataa aagcccagaa actgaaaa                            6158

<210> SEQ ID NO 34
<211> LENGTH: 5228
<212> TYPE: DNA
<213> ORGANISM: Homo sapiens

<400> SEQUENCE: 34
cgggcgaggg ccgggcagga ggagcgggcg cggcgcgggc gaggctggga cccgagcgcg      60
ctcacttcgc cgcaaagtgc caacttcccc tggagtgccg ggcgcgcacc gtccgggcgc     120
gggggaaaga aaggcagcgg gaatttgaga ttttgggaa gaaagtcgga ttccccccgt      180
cccctttccc ctgttactaa tcctcattaa aaagaaaaac aacagtaact gcaaacttgc     240
taccatcccg tacgtccccc actcctggca ccatgaaggc ggccgtcgat ctcaagccga     300
ctctcaccat catcaagacg gaaaaagtcg atctggagct tttcccctcc ccggatatgg     360
aatgtgcaga tgtcccacta ttaactccaa gcagcaaaga aatgatgtct caagcattaa     420
aagctacttt cagtggtttc actaaagaac agcaacgact ggggatccca aaagaccccc     480
ggcagtggac agaaacccat gttcgggact gggtgatgtg ggctgtgaat gaattcagcc     540
tgaaaggtgt agacttccag aagttctgta tgaatggagc agccctctgc ccctgggta      600 aagactgctt tctcgagctg gccccagact tgttgggga catcttatgg aacatctag      660 agatcctgca gaaagaggat gtgaaaccat atcaagttaa tggagtcaac ccagcctatc     720
cagaatcccg ctatacctcg gattacttca ttagctatgg tattgagcat gcccagtgtg     780
ttccaccatc ggagttctca gagcccagct tcatcacaga gtcctatcag acgctccatc     840
ccatcagctc ggaagagctc ctctccctca gtatgagaa tgactacccc tcggtcattc     900
tccgagaccc tctccagaca gacaccttgc agaatgacta ctttgctatc aaacaagaag     960 tcgtcaccc agacaacatg tgcatgggga ggaccagtcg tggtaaactc ggggccagg     1020 actcttttga aagcatagag agctacgata gttgtgatcg cctcacccag tcctggagca    1080
gccagtcatc tttcaacagc ctgcagcgtg ttccctccta tgacagcttc gactcagagg    1140
actatccggc tgccctgccc aaccacaagc caagggcac cttcaaggac tatgtgcggg    1200
accgtgctga cctcaataag gacaagcctg tcattcctgc tgctgcccta gctggctaca    1260
caggcagtgg accaatccag ctatggcagt ttcttctgga attactcact gataaatcct    1320
gtcagtcttt tatcagctgg acaggagatg gctgggaatt caaactttct gacccagatg    1380
aggtggccag gagatgggga aagaggaaaa acaaacctaa gatgaattat gagaaactga    1440
gccgtggcct acgctactat tacgacaaaa acatcatcca aagacagcg gggaaacgct    1500 acgtgtaccg ctttgtgtgt gacctgcaga gcctgctggg gtacacccct gaggagctgc    1560
acgccatgct ggacgtcaag ccagatgccg acgagtgatg cactgaagg ggctggggaa    1620 accctgctga gaccttccaa ggacagccgt gttggttgga ctctgaattt tgaattgtta    1680 ttctatttt tatttttccag aactcatttt ttaccttcag gggtgggagc taagtcagtt    1740
gcagctgtaa tcaattgtgc gcagtttgga aaggaaagcc aggacttgtg gggtgggtgg    1800
gaccagaaat tcttgagcaa atttttcagga gagggagaag ggccttctca gaagcttgaa    1860
ggctctggct taacagagaa agagactaat gtgtccaatc attttttaaaa atcatccatg    1920 aaaaagtgtc ttgagttgtg gacccattag caagtgacat tgtcacatca gaactcatga    1980
```

```
aactgatgta aggcaattaa tttgcttctg tttttaggtc tgggagggca aaaagaggt   2040 gggtgggatg aaacatgttt tggggggggga tgcactgaaa atctgagaac tatttaccta   2100
tcactctagt tttgaagcaa agatggactt cagtggggag gggccaaaac cgttgttgtg   2160
ttaaaattta ttttattaaa ttttgtgcca gtatttttt  tcttaaaaat cgtcttaagc   2220
tctaaggtgg tctcagtatt gcaatatcat gtaagtttgt ttttatttgc cggctgagga   2280
ttctgtcaca atgaaagaaa actgtttata tagaccccat tggaaaagca aaacgctctc   2340
actgagatca gggatcccaa attcatggga cttatataag aaggacaatt aatgctgatt   2400
tgggtacagg ggaattatgt gtgtgaatgt catctacaat taaaaaaaat tagcacatcc   2460
ctttacttac ttgttatcag tggattctcg gggtttggac ttaatgttga gctaagaagc   2520
attaagtctt tgaactgaat gtattttgca tccctggttt tggacgacag taaacgtagg   2580
agcactgttg aagtcctgga agggagatcg aaggaggaag attgacttgg ttctttctta   2640
gtcctatatc tgtagcatag atgacttgga ataaaagctg tatgcatggg cattacccct   2700
caggtcctaa gaaataagtc ctgaatgcat gtcgttccaa actaacactc tgtaattttt   2760
cttttatgtc ttattttcca agagtcctcc atttttgca  ccccctcacc gccaactctg   2820
ttattcagta gagagaagtg tacggctttc tgattggtga gtgaaaaagt aacttgagac   2880
acgacctaag ttgaagagtt tagacttgct gagttttaga agtgatggaa attaagagag   2940
catttcaata aaatgtgact tggctgtctt tggaagagaa gtgcaaggct ttcctttgaa   3000
gaatttaaat tagtccggta ggatgtcagg tgagactgtg tatgcaaaat gaatggcaca   3060
ggtgatgcca gggcctcttg cttgggtctg atgtcttggc acagggtaag tgaaggttaa   3120
ttccagaaga gaggaatgac ttgaaggcaa aggaaactaa ggaaggaggt tcagtgagga   3180
aaataaggtt gtccatgaga tttgaataga ttttttagttc ccccaaggtt taaatacaaa   3240
catagtcaag caaggtagtc atctttctgc tggttgtgag ggggaatctg aaaatggagt   3300
tttagaggaa aagtcaacat ctaactagtg aggaaaagtg cctaatacaa ttagaatctc   3360
cctcactcta tagttgccca gttgaaagga taaggaggag gggtggcttt tatggacttc   3420
catgagagaa ggaaagaaat atttcaggta agcttctcag ggctggccct ttttgggatt   3480
tggatgagaa attggaagta ctaactactt tctagcatat ctttaagaaa attgattgtt   3540
atttactccc agatcctctt gcagacccag aattatcagg aacatagctc tgtgattcat   3600
gagtgtcccc atactgatga attggagcat ccatatggaa agcaaaggca gaattatccc   3660
agctgtatta ttttgatctt ttggatgcag gtgccttaat gaagctctca aaatatttta   3720
ggagctgctc agggagtgtt gggtggaact gtttggacta cattgttttc tcttagatta   3780
tgtgattttt gttgggcact ggcaaaaggt gtgtgtgtga atgtgtgcat gtgtgtgaat   3840
gttgtgtgtg tgtgtgtgtg tgtgtgtgtg tgtgtgtgtg tttgcagaca tgcaaaactg   3900
cagctgaaat aataccttag atttctaggt aagtctttcc acatttcaat aatgggtaag   3960
agtagaacca gggccgggta tcaattattg cttgctgttt gcaaccaggc ataaaatcac   4020
tttctcaaat catccaccgt tcctattaaa tttatgccgg aaactctcct tctgtgagta   4080
taactcctgc agttcctata gcagataaga tataagaaag tgcctcctag tgctcctccg   4140
cccgcttgtt tgctaaaatt ccctttctct ctaagtccac catttttcaag atttgtagat   4200 agtgtattag ttaagacagc tttgtcgatc tggccagatg ttttttctcc tttgtccaaa   4260
ggccagagac catcccagga agagtggtgg gtggtttata cactgaaat gttgcgttta    4320 tgctttttaa aaacacacgt taacttcaga ggaaggatgg gcaaatctgg tctagctggg   4380
```

```
tgaaacccct attttcccag agatgcctta acctttgttg gttttggctt tagggttcag    4440
agtcactttt gttcccttct ccattctgga gagggacttc ccctacatag agccctgatt    4500
tttgtggctg tggggattgg aggtagcatt caaagatcag atgtgctttt cctcactttg    4560
gagatgaaca ctctgggttt tacagcatta acctgcctaa ccttcatggt gagaaataca    4620
ccatctctct tctagtcatg ctgtgcatgc cgcttactct gttggggtct atataaattt    4680
gttgaactct tacctacatt ccaaagaagt ttcaaggaac cataaatata tgtatacata    4740
tacatatata aaatatatat attaaaataa aattatcagg aatactgcct cagttattga    4800 acttttttt ttaagaatac tttttttta agctgagaag tatagggatg aaaaagatgt    4860
tatattgtgt ttgactattt tccaacttgt attttcatat aatttatatt ttttaaaagc    4920
tgaaaattta gaagcaagat gaaaaaaagg aaaagcaggt gcttttttaaa aatcagaact    4980 gaggtagctt agagatgtag cgatgtaagt gtcgatgttt ttttaaaaaa aaatgcaaaa    5040
aaattcttat ggcggagttt tttgtttgtt tattttagta gctgatgctg gcacatcatt    5100
ttgctggaga gtttttttata tactgtagcc tgatttcata ttgtattttta aactgtgtga    5160 aattaaaaac aaagaatttc attcataaaa aaaaaaaaaa aaaaaaaaaa aaaaaaaaaa    5220
aaaaaaaa                                                             5228

<210> SEQ ID NO 35
<211> LENGTH: 3672
<212> TYPE: DNA
<213> ORGANISM: Homo sapiens

<400> SEQUENCE: 35
gcccggttac ttcctccaga gactgacgag tgcggtgtcg ctccagctca gagctcccgg      60
agccgcccgg ccagcgtccg gcctccctga tcgtctctgg ccggcgccct cgccctcgcc     120
cggcgcgcac cgagcagccg cgggcgccga gcagccaccg tcccgaccaa cgcgcggccc     180
tgcccgcagc ggcaggatga atgatttcgg aatcaagaat atggaccagg tagccctgt     240 ggctaacagt tacagaggga cactcaagcc cagccagcc tttgacacct ttgatgggtc     300
cctgtttgct gttttttcctt ctctaaatga agagcaaaca ctgcaagaag tgccaacagg     360
cttggattcc atttctcatg actccgccaa ctgtgaattg cctttgttaa ccccgtgcag     420
caaggctgtg atgagtcaag ccttaaaagc taccttcagt ggcttcaaaa aggaacagcg     480
gcgcctgggc attccaaaga acccctggct gtggagtgag caacaggtat gccagtggct     540
tctctgggcc accaatgagt tcagtctggt gaacgtgaat ctgcagaggt tcggcatgaa     600
tggccagatg ctgtgtaacc ttggcaagga acgctttctg gagctggcac ctgactttgt     660
gggtgacatt ctctgggaac atctggagca aatgatcaaa gaaaaccaag aaaagacaga     720
agatcaatat gaagaaaatt cacacctcac ctccgttcct cattggatta acagcaatac     780
attaggtttt ggcacagagc aggcgcccta tggaatgcag acacagaatt accccaaagg     840
cggcctcctg gacagcatgt gtccggcctc cacacccagc gtactcagct ctgagcagga     900
gtttcagatg ttccccaagt ctcggctcag ctccgtcagc gtcacctact gctctgtcag     960
tcaggacttc ccaggcagca acttgaattt gctcaccaac aattctggga ctcccaaaga    1020
ccacgactcc cctgagaacg gtgcggacag cttcgagagc tcagactccc tcctccagtc    1080
ctggaacagc cagtcgtcct tgctggatgt gcaacgggtt ccttccttcg agagcttcga    1140
agatgactgc agccagtctc tctgcctcaa taagccaacc atgtctttca aggattacat    1200
```

```
ccaagagagg agtgacccag tggagcaagg caaaccagtt atacctgcag ctgtgctggc    1260
cggcttcaca ggaagtggac ctattcagct gtggcagttt ctcctggagc tgctatcaga    1320
caaatcctgc cagtcattca tcagctggac tggagacgga tgggagttta agctcgccga    1380
ccccgatgag gtggcccgcc ggtggggaaa gaggaaaaat aagcccaaga tgaactacga    1440
gaagctgagc cggggcttac gctactatta cgacaagaac atcatccaca agacgtcggg    1500
gaagcgctac gtgtaccgct cgtgtgcgca cctccagaac ttgctggggt tcacgcccga    1560
ggaactgcac gccatcctgg gcgtccagcc cgacacggag gactgaggtc gccgggacca    1620
ccctgagccg gccccaggct cgtggactga gtgggaagcc catcctgacc agctgctccg    1680
aggacccagg aaaggcagga ttgaaaatgt ccaggaaagt ggccaagaag cagtggcctt    1740
attgcatccc aaaccacgcc tcttgaccag gctgcctccc ttgtggcagc aacggcacag    1800
ctaattctac tcacagtgct tttaagtgaa aatggtcgag aaagaggcac caggaagccg    1860
tcctggcgcc tggcagtccg tgggacggga tggttctggc tgtttgagat tctcaaagga    1920
gcgagcatgt cgtggacaca cacagactat ttttagattt tcttttgcct tttgcaacca    1980
ggaacagcaa atgcaaaaac tctttgagag ggtaggaggg tgggaaggaa caaccatgt     2040 catttcagaa gttagtttgt atatattatt ataatcttat aattgttctc agaatccctt    2100
aacagttgta tttaacagaa attgtatatt gtaatttaaa ataattatat aactgtattt    2160
gaaataagaa ttcagacatc tgaggtttta tttcattttt caatagcaca tatggaattt    2220
tgcaaagatt taatctgcca agggccgact aagagaagtt gtaaagtatg tattatttac    2280
atttaataga cttacaggga taaggcctgt gggggtaat ccctgctttt tgtgttttt     2340 tgtttgtttg tttgtttgtt tttgggggt tttcttgcct tggttgtctg gcaaggactt     2400
tgtacatttg ggagttttta tgagaaactt aaatgttatt atctgggctt atatctggcc    2460
tctgctttct cctttaattg taaagtaaaa gctataaagc agtattttc ttgacaaatg     2520 gcatatgttt tccacttctt tgcatgcgtt taagtcagtt tatacacaaa atggatttta    2580
ttttttagtt taactgtgtt ctccgacag ctcacctctc tctgaccacc cagccatttc     2640
cttcctgtgc tccacgttct tctgtgtgat taaaataaga atattatttt tggaaatatg    2700
caactccttt tcagagatca ggagggattt atgtagcagc tatttttact gcaaaagtaa    2760
ttcactggaa aaaaaatgta atttgtaaga aagcttatt tttatctcag ctctatgtaa     2820
agttaaagtt actgtacaga gctgaaggac ggggggcggt aggggtcttg atgaaacctc    2880
ttgaacgaag cacagtttgt cccatctttg ttcactcgtg tgtctcaacc atcttaatag    2940
catgctgctc ctttttgctc agtgtccaca gcaagatgac gtgattctta ttttcttgga    3000
cacagactat tctgaggcac agagcgggga cttaagatgg gaaagagaaa gcatcggagc    3060
cattcattcg gagaaaacgt tttgatcaaa atggagactt ttgtagtcgt ttcaaaagag    3120
cacctgagtc atgtgtattc ccggcccttta taaatgaccc ggtcaagttg gtttcaaagt    3180
ccgacaggct tgtctgttta ctagctgcgt ggccttggac gggtggctga catctgtaaa    3240
gaatcctcct gtgatgaaac tgaggaatcg ggtggccggg caagctggga agagcaaagc    3300
cagagctgcg ctgcctcaat acccacaaaa gaccattccc agtatacata agcacaggat    3360 gttttttctca agagggatgt atttatcact tggacatctg tttataatat aaacagacat    3420
gtgactggga acatcttgct gccaaaagaa tcctaggcag tggctcattg tatgtgaggt    3480
tgaaccacgt gaaattgcca atattaggct ggcttttatc tacaaagaag gagtttcatg    3540
gggttcagcc taacagttat ggaaactaca gtccttataa accattggca tggtaataaa    3600
```

```
cagatcttaa gtataaaaat tttgtaattg ggcctttact ctctcaataa taaagtattt    3660
tgtttatata aa                                                         3672

<210> SEQ ID NO 36
<211> LENGTH: 2668
<212> TYPE: DNA
<213> ORGANISM: Homo sapiens

<400> SEQUENCE: 36
cgctacacac aggtacccct gggatggcgt gagcactccc ccagcgatgg acccatctgt      60
gacgctgtgg cagtttctgc tgcagctgct gagagagcaa ggcaatggcc acatcatctc     120
ctggacttca cgggatggtg gtgaattcaa gctggtggat gcagaggagg tggcccggct     180 gtggggggcta cgcaagaaca agaccaacat gaattacgac aagctcagcc gggccttgcg    240
gtactactat gacaagaaca tcatccgcaa ggtgagcggc cagaagttcg tctacaagtt     300
tgtgtcctac cctgaggtcg cagggtgctc cactgaggac tgcccgcccc agccagaggt     360
gtctgttacc tccaccatgc caaatgtggc ccctgctgct atacatgccg ccccagggga    420
cactgtctct ggaaagccag gcacacccaa gggtgcagga atggcaggcc caggcggttt     480
ggcacgcagc agccggaacg agtacatgcg ctcgggcctc tattccacct tcaccatcca    540
gtctctgcag ccgcagccac cccctcatcc tcggcctgct gtggtgctcc ccagtgcagc    600
tcctgcaggg gcagcagcgc cccctcgggg agcaggagc accagtccaa gcccttgga     660 ggcctgtctg gaggctgaag aggccggctt gcctctgcag gtcatcctga ccccgcccga    720
ggccccaaac ctgaaatcgg aagagcttaa tgtggagccg gtttgggcc gggcttttgcc    780 cccagaagtg aaagtagaag ggcccaagga agagttggaa gttgcggggg agagagggtt     840
tgtgccagaa accaccaagg ccgagccaga agtccctcca caggagggcg tgccagcccg    900
gctgcccgcg gttgttatgg acaccgcagg caggcgggc ggccatgcgg cttccagccc     960
tgagatctcc cagccgcaga agggccggaa gccccgggac ctagagcttc cactcagccc    1020
gagcctgcta ggtgggccgg acccgaacg gaccccagga tcgggaagtg gctccggcct    1080
ccaggctccg gggccggcgc tgaccccatc cctgcttcct acgcatacat tgaccccggt    1140
gctgctgaca cccagctcgc tgcctcctag cattcacttc tggagcaccc tgagtcccat    1200
tgcgccccgt agcccggcca agctctcctt ccagtttcca tccagtggca cgcccaggt    1260 gcacatccct tctatcagcg tggatggcct ctcgaccccc gtggtgctct cccagggcc    1320 ccagaagcca tgactactac caccaccacc accacccctt ctggggtcac tccatccatg   1380
ctctctccag ccagccatct caaggagaaa catagttcaa ctgaaagact catgctctga    1440
ttgtggtggg gtggggatcc ttgggaagaa ttactcccaa gagtaactct cattatctcc   1500
tccacagaaa acacacagct tccacaactt ctctgttttc tgtcagtccc ccagtggccg   1560
cccttacacg tctcctactt caatggtagg ggcggtttat ttatttattt tttgaaggcc    1620
actgggagga gcctgaccta accttttagg gtggttagga catctccccc acctccccac   1680
ttttttcccc aagacaagac aatcgaggtc tggcttgaga acgacctttc tttctttatt    1740
tctcagcctg cccttgggga gatgagggag ccctgtctgc gttttggat gtgagtagaa    1800 gagttagttt gttttgtttt attattcctg gccatactca ggggtccagg aagaatttgt   1860
accatttaat gggttgggag tcttggccaa ggaagaatca cacccttgga atagaaattt    1920
ccacctcccc aaccttctc tcagacagct tatcctttc aaccaacttt ttggccaggg     1980
```

```
aggaatgtcc cttttgttct tccccctgag aagccattcc tttgtctgcc aacctccctg    2040
gggtcctgcc tgtttcctcc caatggaggg ttttttttggg gggtggtccc cgtctggggg    2100 gccctccag ccagtactcc aggtctccct gtctctcccc cgctgccatt ttgatagtat     2160
aatctatttt taaatgggc ttttcaatag gggagaggga gtcatctctt cctatatttg     2220
gtggggtggg tgggaaggaa gggatttggg ggggaatctt cctgccgcct ccccactcc     2280 aagtgtttat ttttgatacc aaacatgaat tttcagttcc ctccctccca gcccccaat    2340 ttcctgcggg cgggtacaaa ggacccttc aatgtccctg gagttgggag ggaggaatgg    2400
gggacataaa gcctgtcctg tctctattct aggcaagaga gagtgggttc aaaagactcc    2460
tgggctcacc tgttagcgct ggcccagccc aggccttggg acctggggt tggtgatttg      2520 ggggacagtg ctacactcgt ctccactgtt tgttttactt ccccaaaatg gacctttttt    2580
ttttctaaag agtcccagag aatggggaat tgttcctgta aatatatatt tttcaaagtg    2640
aaaaaaaaaa aaaaaaaaaa aaaaaaaa                                         2668

<210> SEQ ID NO 37
<211> LENGTH: 5992
<212> TYPE: DNA
<213> ORGANISM: Homo sapiens

<400> SEQUENCE: 37
gcgtcccggg tccccgcgcc gcgccgcgac ctgcagaccc cgccgccgcg ctcgggcccg      60
tctcccacgc ccccgccgcc ccgcgcgccc aactccgccg gccgccccgc cccgccccgc     120
gcgctccaga ccccgggc ggctgccggg agagatgctg gaagaaactt cttaaatgac     180
cgcgtctggc tggccgtgga gccttctctgg gttggggaga ggaaaggaaa gtggaaaaaa    240
cctgagaact tcctgatctc tctcgctgtg agacatgtct gagactcctg ctcagtgtag    300
cattaagcag gaacgaattt catatacacc tccagagagc ccagtgccga gttacgcttc    360
ctcgacgcca cttcatgttc cagtgcctcg agcgctcagg atggaggaag actcgatccg    420
cctgcctgcg cacctgcgct tgcagccaat ttactggagc agggatgacg tagcccagtg     480
gctcaagtgg gctgaaaatg agttttcttt aaggccaatt gacagcaaca cgtttgaaat    540
gaatggcaaa gctctcctgc tgctgaccaa agaggacttt cgctatcgat ctcctcattc    600
aggtgatgtg ctctatgaac tccttcagca tattctgaag cagaggaaac ctcggattct    660 ttttttcacca ttcttccacc ctggaaactc tatacacaca cagccggagg tcatactgca   720
tcagaaccat gaagaagata actgtgtcca gaggaccccc aggccatccg tggataatgt     780
gcaccataac cctcccacca ttgaactgtt gcaccgctcc aggtcaccta tcacgacaaa    840
tcaccggcct tctcctgacc ccgagcagcg gcccctccgg tcccccctgg acaacatgat    900
ccgccgcctc tcccggctg agagagctca gggacccagg ccgcaccagg agaacaacca    960
ccaggagtcc taccctctgt cagtgtctcc catggagaat aatcactgcc cagcgtcctc    1020
cgagtcccac ccgaagccat ccagcccccg gcaggagagc acacgcgtga tccagctgat    1080
gcccagcccc atcatgcacc ctctgatcct gaaccccccgg cactccgtgg atttcaaaca    1140
gtccaggctc tccgaggacg ggctgcatag ggaaggggaag cccatcaacc tctctcatcg    1200
ggaagacctg gcttacatga accacatcat ggtctctgtc tccccgcctg aagagcacgc    1260
catgcccatt gggagaatag cagactgtag actgctttgg gattacgtct atcagttgct    1320
ttctgacagc cggtacgaaa acttcatccg atgggaggac aaagaatcca aaatattccg    1380
gatagtggat cccaacggac tggctcgact gtggggaaac cataagaaca gaacaaacat    1440
```

| | | | | |
|---|---|---|---|---|
| gacctatgag | aaaatgtcca | gagccctgcg | ccactactac | aaactaaaca ttatcaggaa | 1500 |
| ggagccagga | caaaggcttt | tgttcaggtt | tatgaaaacc | ccagatgaaa tcatgagtgg | 1560 |
| ccgaacagac | cgtctggagc | acctagagtc | ccaggagctg | gatgaacaaa tataccaaga | 1620 |
| agatgaatgc | tgaaggaacc | aacagtccac | ctcagcgggc | cagcagccca gggaacccct | 1680 |
| gcccaccagg | attgctggaa | gtgtgacgga | gcaggcgggc | tgaggagagt ggaaaaggaa | 1740 |
| gcgacccaga | aatggcaggg | acacttctct | tgcagaccaa | gagggaccct ggagcacctt | 1800 |
| agacaaacta | cccagcacag | gcggggctgg | aattctggcg | gagggcatga gcctgggact | 1860 |
| ccatgtcacg | tttccttctg | atttggaatc | tctccatctg | taattcctca ccctcaccct | 1920 |
| tccaccgttg | ttagtatcat | ggtgttttg | ttttttgtttt | tgttttaaga acctgcagtt | 1980 |
| tgactcttca | tcgttcatct | aggggaagac | atctgatgtt | gttttcctat ggaaatatat | 2040 |
| atctattata | tatatatttt | ttgcaaatct | cacaaagtgc | ggcaagccca gctggtcagg | 2100 |
| aaagagaata | cttgcagagg | ggttcaggtt | cctcttttc | ctgccacgtg gatcaggtct | 2160 |
| gttcctgtta | ctgttgggtc | ttggctgaaa | aaaaaaatg | cttttaaaaa agataaaatg | 2220 |
| aaaaggagag | ctctctttt | ctctctcttg | ctctgttctt | cccttggtcc cctctgtcct | 2280 |
| cccgccctgc | ctgcagttga | gattcagatg | ccttctgaca | gagttcagcc tcttggagag | 2340 |
| tcttggggat | tgttggcacc | taaacagaat | cagtgacccg | ggtgctttgt ggccagcagc | 2400 |
| acagaatcaa | acccgcatcc | cagcattggg | ccacccatct | gagggaggcc aaaatcatca | 2460 |
| cagatgctgc | tgtgctgcag | acagatacat | gctagtccag | agagccgccc ctgagatggc | 2520 |
| tgtgagaacc | atgtgtctaa | ggcgtaagat | aaggatggaa | ggctgtccaa gttatttgga | 2580 |
| aggcctcggc | agcttgggat | tagcttggga | gcgcagcgct | gcaaagtgga aaatatgaaa | 2640 |
| agaccacaca | ggcccagcag | tccagaaact | gggcaaaaat | attctgcagt ggggatttat | 2700 |
| ttttccaaag | caggtaacag | aggctagtga | gaaagaaaag | ctcctctctg ctccattcca | 2760 |
| aaggccatct | tgtggtcagt | ttcatgccct | cacctgattt | tttttttttt ttttttttt | 2820 |
| caattcctaa | cctttttaa | agtttcctgg | tctccactgg | acacagagct ttggagacgg | 2880 |
| aggatcccag | agggcagtct | cagttgcaat | cagtgtgtgc | ccagcctggg cagacaggaa | 2940 |
| attcctcgga | tacattattt | ttctttctt | tcatagctgt | gtctcagaaa ggacccattt | 3000 |
| gtggctctt | ttcacctcaa | aataagatcg | atggtatctt | gtaaatgag ggtagtgcca | 3060 |
| cttcttagta | ttttgaaag | ctgttttaga | ttttttttt | ttttccttttt ctagccatct | 3120 |
| aaaattgactc | ttccaatata | ggtctcagaa | atccaatatt | tggagtacaa tttcttttaa | 3180 |
| tccagattac | acctgcctta | caaagcaccc | cctccttgtt | ccctctgtt tcctctactc | 3240 |
| agttggggga | gaaactcaca | gctcctccgg | gatacatatg | tgccctcagc agcagctccc | 3300 |
| aggtgaagtt | accagacccc | tgggcttctc | cccagctttt | tctgagttga gtcagacatg | 3360 |
| tagagtttgg | gtcacacagg | caagaggaat | tttccctcgg | ccttactgac aaggacacca | 3420 |
| acctagggtg | caaacagatg | gactatggtt | caaggacact | ggaattgagg agctgatcaa | 3480 |
| ggctctcttc | agccttgctc | tgtccctgcc | tcttatcaga | gcacaggtag acacacgggc | 3540 |
| atagccagcc | cactcctact | gtcacaggcg | ccccaccatt | caaccttccg ggaggtcagg | 3600 |
| gaccttctat | atgaggcgag | tgggtctcag | tctgcttgaa | tggtgatgag attctgctgg | 3660 |
| atctcagcac | gctgcaggtg | tcttttgaga | gcattcagta | ggacatggtg atccctattt | 3720 |
| cagcctctaa | gatgactggt | attctatctg | aaatgcagag | attaagccaa ataccctgatg | 3780 |

```
tattgtgaaa gccactgatt ttaagaatgg agagaaaggg attttttact gcatccctct    3840
gtatgaatat gaaatcagag accagggcat gatgttgcta ggattagagc ctctcagtct    3900
ggcctcttca cccaagtgca agaactcagt ctcttactgt tcaaagaatc ttaacagttg    3960
aattatggag ggaaattccc ttttgcccca agcatttcta tatttaaagc aatatcccag    4020
gagaatatgt tagacttagg atgatacctt cagccacttg aagaagaaat agaaggcgct    4080
cattccaata tagtctttat ttcccattca gatacaggtt gagcatccct aatctgaaca    4140
gttaaaaccc ccaaatgccc caaaatccaa accttcctga acgctatgac accatgagtg    4200
gaaaattcca cacctaacaa acacatttgc tttcttatgg ttcaatgtac acaaactgtt    4260
ttatatagaa aatgatttca aatatcataa aattaccttc aggctatgtg tataaagtat    4320
atatgagcca taaatgaatt ttgtgtttag actttgtgtc catccccaag atctctcatt    4380
ttatatatat atatatatat atatatatat atatatatat atatatatac acacacacac    4440
acatacacaa atattccagg atacaaaaaa aaacatttaa aaatccgaga cccagaacac    4500
ttctggtccc aagcatttca gataagggat atcaatctgt actaccaata aggatttcgt    4560 aattcccta actgcaaatg tcctcttcat ttgttcttta tgagaaaacc cgggtagtgc    4620
cagcacctgg atacagtatt tacaccctgc agaccctaaa gatttcagat tcagttagca    4680
aaccttgatg aagcacctgc tggacactga gggacccaaa gctcaatcag ccataatccc    4740
tgctttcaga gtttatattg tacctgccta atccacccgg cgtgactcat ttcaacacta    4800
agtactaggg gtgttgtcag gagacaaatc tgaagtcagg agaggaaaat gcaaaggagc    4860
cctgccgtgt gatggatgtg cattctcact tgggtcttga agttctcatt cctacatctc    4920
aagctagcca ggcagtctcc tctctatcag aagaaagcac tggtaattgg ctagactggc    4980
tatgttgaag gtaacatgaa ctctaagatc ttgacccagg cgacttggt tttgcttaag     5040 gtggcatcac caatgttcca aatcctttag ggagatgagg gtatccccac agaaaaagag    5100
gaataataga ccaatggatt ttctccttc accagtatgt ttggaaccct ctgatccaat    5160
gtcctttgat actgatctct tgtccaaatg agaatgtcgc tttagctgaa attcaaatgg    5220
ctgtgacaat ttaccgaaat gatgaagtaa ccaccattcc cacctttcac tgcctaggct    5280
ccaagtctga atacattttt gaaataggaa ctcccttttg caaaaaagaa acctgggtgt    5340
cagggaggtg aagtgacttg ccctaggagc agacagcatg ccaagaatgg aattaggctc    5400
aggatccagc ctgggctcac cctgtgtggc tcattcccac ccaggaaact gaagataaaa    5460
gatttgggaa aacacaccaa gaaaaagggg cagttttctt tgcccaagca tttggtgcta    5520
gttagaggct gttcactctc tcctgctcct cttcggagta gaaataaagg ctgtgacaca    5580
aggaagccag tggggtggga gggaggcacc ataatccctc cctaaaaccc acagaagact    5640
aacctgatac tcttttgacc caactgcatc aacactaaac agctgcagac cccctgaatc    5700
tttcacacat gccaagtgaa cattcttgat gatttctctt tgtgaccgca accacctgca    5760
aaccagaacg actctagaat ttccttcccc gcccccttt ttgtttagtt tctaatctct    5820
tgtttatgag gtgtggggtt tataagggac tgaatcaaat gaatgtaaca aaaaagaaaa    5880
aaaaaacaaa aaaaaatgcc ttttctcagg gccagtgagt tgcaaataat ttttaaagaa    5940
aagcctataa ttacatcatc tcaataaatt ttttataaaa aaaaaaaaaa aa            5992
```

<210> SEQ ID NO 38
<211> LENGTH: 1670
<212> TYPE: DNA
<213> ORGANISM: Homo sapiens

<400> SEQUENCE: 38

```
gatttcctcc cacgcgacct tccagttctc ggagccaggt taggggtttg gcggaggagg      60
actgcggggc gcgggcctag ggccccagca gccacggcca ggggagcgct caagacagaa     120
agccggtggc ttcctcacct ccacctgtaa tgcaggaggg agaattggct atttctccta     180
taagccctgt ggcagccatg cctccctag gcacccacgt gcaagccaga tgtgaagctc      240
aaattaacct gctgggtgaa gggggatct gcaagctgcc aggaagactc cgcatccagc      300
ccgcactgtg gagcagggag gacgtgctgc actggctgcg ctgggcagag caggagtact     360
ctctgccatg caccgcggag cacgggttcg agatgaacgg acgcgccctc tgcatcctca     420
ccaaggacga cttccggcac cgtgcgccca gctcaggtga cgtcctgtat gagctgctcc     480
agtacatcaa gacccagcgg cgagccctgg tgtgtggacc cttttttgga gggatcttca     540
ggctgaagac gcccacccag cactctccag tcccccggga agaggtgact ggcccctctc     600
agatggacac ccgaaggggc cacctgctgc agccaccaga cccagggctt accagcaact     660
tcggccacct ggatgaccct ggcctggcaa ggtggacccc tggcaaggag gagtccctca     720
acttatgtca ctgtgcagag ctcggctgca ggacccaggg ggtctgttcc ttccccgcga     780
tgccgcaggc ccccattgac ggcaggatcg ctgactgccg cctgctgtgg gattacgtgt     840
atcagctgct ccttgatacc cgatatgagc cctacatcaa gtgggaagac aaggacgcca     900
agatcttccg agttgtggat ccaaatgggc tcgccagact ctggggaaat cacaagaacc     960
gggtgaacat gacctacgag aagatgtctc gtgccctgcg ccactattat aagcttaata    1020
tcattaagaa ggaaccgggg cagaaactcc tgttcagatt tctaaagact ccgggaaaga    1080
tggtccagga caagcacagc cacctggagc cgctggagag ccaggagcag gacagaatag    1140
agttcaagga caagaggcca gaaatctctc cgtgagggc aggtggactc caggcacccg     1200
gtaccgatgg ggcagggacc gagtctccca tgaaggcaga ctcctcctcc cagcagagca    1260
gcaggatccc cagccagact ctgtacccac aggattacag ccattgcttg ggaaggctgg    1320
gaggcctccc atccaggaca ctgggggcag gagtgtcatc tttttgggcag ggcaatcctg    1380
gggctaaatg aggtacaggg gaatggactc tcccctactg caccctggg agaggaagcc     1440
aggcaccgat agagcacca gccccacccc tgtaaatgga atttaccaga tgaagggaat     1500
gaagtccctc actgagcctc agatttcctc acctgtgaaa tgggctgagg caggaaatgg    1560
gaaaaagtgt tagtgcttcc aggcggcact gacagcctca gtaacaataa aaacaatggt    1620
agctgaaaaa aaaaaaaaaa aaaaaaaaaa aaaaaaaaaa aaaaaaaaaa                1670
```

<210> SEQ ID NO 39
<211> LENGTH: 4071
<212> TYPE: DNA
<213> ORGANISM: Homo sapiens

<400> SEQUENCE: 39

```
gagtccagcc gctggtgcgc ggagcggttc accgtcttcg gagcggttcg gcccagcctt      60
tcgcccaggc gcccaggccc gctgcgcgcg tgcgtgagcg cgcctgcgcc gccagggccg     120
ctgcaagggg aggagagcgg ccgcctcagg aggatcccct tccccccaga aattactcaa     180
tgctgaaacc tctcaaagtg gtattagaga cgctgaaagc accatggacg ggttttatga     240
tcagcaagtc cctttatgg tcccagggaa atctcgatct gaggaatgca gagggcggcc      300
tgtgattgac agaaagagga gttttttgga cacagatctg gctcacgatt ctgaagagct     360
```

```
atttcaggat ctcagtcaac ttcaagaggc ttggttagct gaagcacaag ttcctgatga    420
tgaacagttt gtcccagatt ttcagtctga taacctggtg cttcatgccc cacctccaac    480
caagatcaaa cgggagctgc acagcccctc ctctgagctg tcgtcttgta gccatgagca    540
ggctcttggt gctaactatg agaaaagtg cctctacaac tattgtgcct atgataggaa     600
gcctccctct gggttcaagc cattaacccc tcctacaacc ccctctcac ccacccatca     660 gaatccccta tttcccccac ctcaggcaac tctgcccacc tcagggcatg ccctgcagc    720 tggcccagtt caaggtgtgg gccccgcccc cgcccccat tcgcttccag agcctggacc    780
acagcagcaa acatttgcgg tcccccgacc accacatcag ccctgcaga tgccaaagat    840 gatgcctgaa aaccagtatc catcagaaca gagatttcag agacaactgt ctgaaccctg    900
ccaccccttc cctcctcagc caggagttcc tggagataat cgccccagtt accatcggca    960
aatgtcagaa cctattgtcc ctgcagctcc cccgccccct cagggattca acaagaata    1020 ccatgaccca ctctatgaac atggggtccc gggcatgcca gggcccccag cacacggtt    1080 ccagtcacca atgggaatca gcaggagcc tcggattac tgcgtcgatt cagaagtgcc    1140
taactgccag tcatcctaca tgagagggg ttatttctcc agcagccatg aaggttttc    1200 atatgaaaaa gatccccgat tatactttga cgacacttgt gttgtgcctg agagactgga    1260
aggcaaagtc aaacaggagc ctaccatgta tcgagagggg ccccttacc agaggcgagg    1320 ttcccttcag ctgtggcagt tcctggtcac ccttcttgat gacccagcca atgcccactt    1380
cattgcctgg acaggtcgag gcatggagtt caagctgata gaaccggaag aggttgctcg    1440
gcgctggggc atccagaaga accggccagc catgaactat gacaagctga ccgctctct    1500 ccgctattac tatgaaaagg gcatcatgca aaggtggct ggagagcgat acgtctacaa    1560
atttgtctgt gacccagatg ccctcttctc catggctttc ccggataacc agcgtccgtt    1620
cctgaaggca gagtccgagt gccacctcag cgaggaggac accctgccgc tgacccactt    1680
tgaagacagc cccgcttacc tcctggacat ggaccgctgc agcagcctcc cctatgccga    1740
aggctttgct tactaagttt ctgagtggcg gagtggccaa accctagagc tagcagttcc    1800
cattcaggca aacaagggca gtggttttgt ttgtgttttt ggttgttcct aaagcttgcc    1860
ctttgagtat tatctggaga acccaagctg tctctggatt ggcacccttta agacagata    1920 cattggctgg ggagtgggaa cagggagggg cagaaaacca ccaaaaggcc agtgcctcaa    1980
ctcttgattc tgatgaggtt tctgggaaga gatcaaaatg gagtctcctt accatggaca    2040
atacatgcaa agcaatatct tgttcaggtt agtacccgca aaacgggaca tgatgtgaca    2100
atctcgatcg atcatggact actaaatggc ctttacatag aagggctctg atttgcacaa    2160
tttgttgaaa aatcacaaac ccatagaaaa gtgagtaggc taagttgggg aggctcaaac    2220
cattaagggt taaaaataca tcttaaacat tggaaagctc ttctagctga atctgaaata    2280
ttaccccttg tctagaaaaa ggggggcagt cagaacagct gttccccact ccgtgttctc    2340
aaaatcataa accatggcta ctcttgggaa ccacccggcc atgtggtcgc caagtagagc    2400
aagccccctt tctcttccca atcacgtggc tgagtgtgga tgacttttat tttaggagaa    2460
gggcgattaa cactttttgac agtatttttgt tttgccctga tttgggggat tgttttgttt    2520
tggtggttgt tttggaaaaa cagtttataa actgattttt gtagttttgg tatttaaagc    2580
aaaaaaacga aaacaaaaa acaaaaacaa accttttggt aatgtgcact gtgtctttag    2640
ccagggccgt gcaacttatg aagacactgc agcttgagag gggctttgct gaggcttccc    2700
cttggccatg tgaaagcccg ccttgttgcc tgctttgtgc tttctgcacc agacaacctg    2760
```

```
atggaacatt tgcacctgag ttgtacattt ttgaagtgtg cagggcagcc tggacacaag    2820
cttagattct ctatgtatag ttccccgtgt tcactaacat gccctctctg gaaagcatat    2880
gtatataaca tgtgtcatgt cctttggaaa cctggtcacc tggtgaaaac ccttgggatt    2940
cttccctggg catgactgat gacaatttcc atttcatcag tttgttttgt tttccttttt    3000
ctttaaatct tggactttaa accctacctg tgtgattcag tagggtttga gacttagctg    3060
tgatactgac aggtaagcaa cagtgctagc attctagatt cctgcctttt tttaaaaaga    3120
aattattctc attgctgtat tatattggaa aagttttaaa caaccaagct aaagctatgt    3180
gaaagttgag ctcaaagtag aggaaaagtt actggtggta ccttgctgcc tgctctgctg    3240
gtagaattct gtgctccccg tgacacttag tacattaaga atgactacac tgttcctcgt    3300
atgtgaagga ggcagtgctg actccgtgag tgtgagacac gtgctttgaa ctgcttttct    3360
attcatggag cactccatag tctcaaactg tcccccttat gaccaacagc acatttgtga    3420
agaggttcgc agggataagg ggtgcacttt atagctatgg aaacatgaga ttctcctcta    3480
ttggaagcta attagcccac aaaggtggta aacctgtaga ttgggcctta attagcattg    3540
tactctaatc aaaggactct ttctaaacca tatttatagc tttcttaacc tacacatagt    3600
ctatacatag atgcatattt taccccagc tggctagaga tttatttgtt gtaaatgctg     3660
tatagatttg gttttccttt ctttacttac cctggtttgg atttttttt ttttttttt     3720 tgaatggatt tatgctgtct tagcaatatg acaataatcc tctgtagctt gagctacccc    3780 tccctgctg taacttacgt gacctgtgct gtcactgggc ataggacagc ggcatcacgg     3840
ttgcattccc attggactca tgcacctccc ggatggtttt tgttttttc ggggttctt     3900 tggggtttgt ttgtttgctt cttttccaga gtgtggaaag tctacagtgc agaaaggctt    3960
gaacctgcca gctgatttga aatactttca ccctgcgcag ggccgtatgc atcctgccaa    4020
gctgcgttat attctgtact gtgtacaata aagaagtttg cttttcgttt a             4071
```

<210> SEQ ID NO 40
<211> LENGTH: 3499
<212> TYPE: DNA
<213> ORGANISM: Homo sapiens

<400> SEQUENCE: 40

```
gccaagaagc ttgagagaag aaaaatttca gaaaaattgt ctcaatttga ctagaatatc      60
aatgaaccag gaaaactgaa gcaccttccc taaagaaaac ttgggtatac aattactcca     120
cagacagagc tgagggtttt ttacccaaat cagtcactgg attttgctgc ctgatacgtg     180
aatcttcttg gaattttct catgtggatc taaggggaat gctttattat ggctgctgtt      240
gtccaacaga acgacctagt atttgaattt gctagtaacg tcatggagga tgaacgacag     300
cttggtgatc cagctatttt tcctgccgta attgtggaac atgttcctgg tgctgatatt     360
ctcaatagtt atgccggtct agcctgtgtg gaagagccca atgacatgat tactgagagt     420
tcactggatg ttgctgaaga agaaatcata gacgatgatg atgatgacat caccccttaca    480 gttgaagctt cttgtcatga cggggatgaa acaattgaaa ctattgaggc tgctgaggca    540
ctcctcaata tggattcccc tggccctatg ctggatgaaa acgaataaa taataatata     600 tttagttcac ctgaagatga catggttgtt gccccagtca cccatgtgtc cgtcacatta    660
gatgggattc ctgaagtgat ggaaacacag caggtgcaag aaaatatgc agactcaccg    720 ggagcctcat caccagaaca gcctaagagg aaaaaaggaa gaaaaactaa accaccacga    780
```

```
ccagattccc cagccactac gccaaatata tctgtgaaga agaaaaacaa agatggaaag      840
ggaaacacaa tttatctttg ggagttttta ctggcactgc tccaggacaa ggctacttgt      900
cctaaataca tcaagtggac ccagcgagag aaaggcattt ttaaattggt ggattctaaa      960
gcagtgtcca ggttgtgggg gaagcacaaa aacaaacctg atatgaatta tgagaccatg     1020
ggaagagcac tcaggtacta ttaccaaagg ggtattctgg caaaagtgga aggtcagcgc     1080
ttggtgtatc agtttaaaga aatgccaaaa gatcttatat atataaatga tgaggatcca     1140
agttccagca tagagtcttc agatccatca ctatcttcat cagccacttc aaataggaat     1200
caaaccagcc ggtcgagagt atcttcaagt ccagggtaa aaggaggagc cactacagtt      1260
ctaaaaccag ggaattctaa agctgcaaaa cccaaagatc ctgtggaagt tgcacaacca     1320
tcagaagttt tgaggacagt gcagcccacg cagtctccat atcctaccca gctcttccgg     1380
actgttcatg tagtacagcc agtacaggct gtcccagagg gagaagcagc tagaaccagt     1440
accatgcagg atgaaacatt aaattcttcc gttcagagta ttaggactat acaggctcca     1500
acccaagttc cagtggttgt gtctcctagg aatcagcagt tgcatacagt aacactccaa     1560
acagtgccac tcacaacagt tatagccagc acagatccat cagcaggtac tggatctcag     1620
aagtttattt tacaagccat tccatcatca cagcccatga cagtactgaa agaaaatgtc     1680
atgctgcagt cacaaaaggc gggctctcct ccttcaattg tcttgggccc tgcccaggtt     1740
cagcaggtcc ttactagcaa tgttcagacc atttgcaatg gaaccgtcag tgtggcttcc     1800
tctccatcct tcagtgctac tgcacctgtg gtgacctttt ctcctcgcag ttcacagctg     1860
gttgctcacc cacctggcac tgtaatcact tcagttatca aaactcaaga aacaaaaact     1920
cttacacagg aagtagagaa aaaggaatct gaagatcatt tgaaagagaa cactgagaaa     1980
acggagcagc agccacagcc ttatgtgatg gtagtgtcca gttccaatgg atttacttct     2040
caggtagcta tgaaacaaaa cgaactgctg gaacccaact cttttttagtt aatataccaa     2100 agcttatgaa taattgtttg ttaattgaac attttcaatt atatgcagac tgactgattc     2160
taagataaat tctaaggagg tttctaattt tgtaattgtt aaaaatagag ttaattttga     2220
ctttgttaga tgagggagga aaactcaact gtttctcttt gttatctaaa tgtttcagaa     2280
ttcaatcgtg aaggaacagg cattttacac tatgaagaca ttcttttgag attttttattt     2340 cagttgctat atcataagca ttttttaaagt ttcttttcta attttacatt gtattagatt     2400
ttctgattct tttgtaaata cagaacttaa atagaaggca acaggaaatt tatataggaa     2460 ctatttttcat tccacttgtg taagttaagt cttgactctt tcaaatgcaa aaaacctatt     2520
ttatgctttg ttaaaattat ggtgtcactt agattgactt tagttgactg cactatataa     2580
tatagaacta tgaatatgta gaataacatg aaaaattgga ggtgctggtg gtatggctga     2640
ccctgtttca gaagcaggat agtataaaag catcagccta agaatggcac tcccactaac     2700
tagctatgta atcttgacct ctttgggctt tagttcctct cataaaagga agagatgtat     2760
tggattagac tagattatca ccactttctc ttctagttct aattttttta attctaatac     2820
ctatattttc aagttatgtc aattaaatca ttatcaggtt atttcctaat gtaagaatag     2880
ctaaaatgtt gcagagaaat aagtgaccca acaaaattta ttcatctgtt atgggtaaga     2940
tctgccataa attcttccta ataaatttgt ttactaactc tttaggccac tgtgctttgc     3000
ggtccattag taaacttgtg ttgctaagtg ctaaacagaa tactgctatt ttgagagagt     3060
caagactctt tcttaagggc caagaaagca acttgagcct tgggctaatc tggctgagta     3120
gtcagttata aaagcataat tgctttatat tttggatcat tttttactgg gggcggactt     3180
```

```
gggggggggtt gcatacaaag ataacatata tatccaactt tctgaaatga aatgttttta    3240
gattactttt tcaactgtaa ataatgtaca tttaatgtca caagaaaaaa atgtcttctg    3300 caaatttct  agtataacag aaattttgt  agatgaaaaa aatcattatg tttagaggtc    3360
taatgctatg ttttcatatt acagagtgaa tttgtattta aacaaaaatt taaatttgg     3420 aatcctctaa acattttgt  atctttaatt ggtttattat taaataaatc atataaaaat    3480
tctcaaaaaa aaaaaaaa                                                  3499

<210> SEQ ID NO 41
<211> LENGTH: 2212
<212> TYPE: DNA
<213> ORGANISM: Homo sapiens

<400> SEQUENCE: 41
gcccggctcc tgggagcagg tctcggcccc cgcttggggc cccggccgtg cggccggagg      60
gagcggccgg atggagcgga ggatgaaagc cggatacttg gaccagcaag tgccctacac     120
cttcagcagc aaatcgcccg gaaatgggag cttgcgcgaa gcgctgatcg gcccgctggg     180
gaagctcatg gacccgggct ccctgccgcc cctcgactct gaagatctct tccaggatct     240
aagtcacttc caggagacgt ggctcgctga agctcaggta ccagacagtg atgagcagtt     300
tgttcctgat ttccattcag aaaacctagc tttccacagc cccaccacca ggatcaagaa     360
ggagccccag agtccccgca cagacccggc cctgtcctgc agcaggaagc cgccactccc     420
ctaccaccat ggcgagcagt gcctttactc cagtgcctat gacccccca gacaaatcgc      480 catcaagtcc cctgcccctg gtgcccttgg acagtcgccc ctacagccct tccccggggc     540
agagcaacgg aatttcctga gatcctctgg cacctcccag ccccaccctg gccatgggta     600
cctcggggaa catagctccg tcttccagca gcccctggac atttgccact ccttcacatc     660
tcagggaggg ggccgggaac ccctcccagc ccctaccaa caccagctgt cggagccctg     720 cccacccta tccccagcaga gctttaagca agaataccat gatcccctgt atgaacaggc     780
gggccagcca gccgtggacc agggtggggt caatgggcac aggtacccag ggcgggggt     840 ggtgatcaaa caggaacaga cggacttcgc ctacgactca gatgtcaccg ggtgcgcatc     900
aatgtacctc cacacagagg gcttctctgg gccctctcca ggtgacgggg ccatgggcta     960
tggctatgag aaacctctgc gaccattccc agatgatgtc tgcgttgtcc ctgagaaatt    1020
tgaaggagac atcaagcagg aaggggtcgg tgcatttcga gaggggccgc cctaccagcg    1080
ccggggtgcc ctgcagctgt ggcaatttct ggtggccttg ctggatgacc aacaaatgc     1140 ccatttcatt gcctggacgg gccggggaat ggagttcaag ctcattgagc ctgaggaggt    1200
cgccaggctc tggggcatcc agaagaaccg gccagccatg aattacgaca gctgagccg     1260 ctcgctccga tactattatg agaaaggcat catgcagaag gtggctggtg agcgttacgt    1320
gtacaagttt gtgtgtgagc ccgaggccct cttctctttg gccttccgg acaatcagcg    1380 tccagctctc aaggctgagt ttgaccggcc tgtcagtgag aggacacag tccctttgtc    1440 ccacttggat gagagccccg cctacctccc agagctggct ggccccgccc agccatttgg    1500
ccccaagggt ggctactctt actagccccc agcggctgtt ccccctgccg caggtgggtg    1560
ctgccctgtg tacatataaa tgaatctggt gttggggaaa ccttcatctg aaacccacag    1620
atgtctctgg ggcagatccc cactgtccta ccagttgccc tagcccagac tctgagctgc    1680
tcaccggagt cattgggaag gaaaagtgga gaaatggcaa gtctagagtc tcagaaactc    1740
```

| | |
|---|---|
| ccctgggggt tteacctggg ccctggagga attcagctca gcttcttcct aggtccaagc | 1800 |
| cccccacacc ttttcccaa ccacagagaa caagagtttg ttctgttctg ggggacagag | 1860 |
| aaggcgcttc ccaacttcat actggcagga gggtgaggag gttcactgag ctccccagat | 1920 |
| ctcccactgc ggggagacag aagcctggac tctgccccac gctgtggccc tggagggtac | 1980 |
| cggtttgtca gttcttggtg ctctgtgttc ccagaggcag gcggaggttg aagaaaggaa | 2040 |
| cctgggatga ggggtgctgg gtataagcag agagggatgg gttcctgctc caagggaccc | 2100 |
| tttgcctttc ttctgcccctt tcctaggccc aggcctgggt tgtacttcc acctccacca | 2160 |
| catctgccag accttaataa aggcccccac ttctcccaaa aaaaaaaaaa aa | 2212 |

<210> SEQ ID NO 42
<211> LENGTH: 2667
<212> TYPE: DNA
<213> ORGANISM: Homo sapiens

<400> SEQUENCE: 42

| | |
|---|---|
| tctgagaggc gaggccgggt gaggcggcga gggcggcccg acgggcgcgg gacgggacgg | 60 |
| ggcagcgagg gcgccgggag ccgcggcccg gaatcggggc gcttcgcccc gggccccca | 120 |
| gcatgaagac cccggcggac acagggtttg ccttcccgga ttgggcctac aagccagagt | 180 |
| cgtcccctgg ctcaaggcag atccagctgt ggcactttat cctggagctg ctgcggaagg | 240 |
| aggagtacca gggcgtcatt gcctggcagg gggactacgg ggaattcgtc atcaaagacc | 300 |
| ctgatgaggt ggcccggctg tggggcgttc gcaagtgcaa gccccagatg aattacgaca | 360 |
| agctgagccg ggccctgcgc tattactata caagcgcat tctgcacaag accaagggga | 420 |
| aacggttcac ctacaagttc aatttcaaca aactggtgct ggtcaattac ccattcattg | 480 |
| atgtgggggtt ggctgggggt gcagtgcccc agagtgcccc gccagtgccg tcgggtggta | 540 |
| gccacttccg cttccctccc tcaacgccct ccgaggtgct gtcccccacc gaggaccccc | 600 |
| gctcaccacc agcctgctct tcatcttcat cttccctctt ctcggctgtg gtggcccgcc | 660 |
| gcctgggccg aggctcagtc agtgactgta gtgatggcac gtcagagctg aggaaccgc | 720 |
| tgggagagga tccccgcgcc cgaccacccg gccctccgga tctgggtgcc ttccgagggc | 780 |
| ccccgctggc ccgcctgccc catgaccctg tgtcttccg agtctatccc cggcctcggg | 840 |
| gtggccctga ccctcagc cccttcctg tgtcgcctct ggccggtcct ggatccctgc | 900 |
| tgccccctca gctctccccg gctctgccca tgacgccac ccacctggcc tacactccct | 960 |
| cgcccacgct gagcccgatg tacccccagtg gtggcggggg gccagcggc tcagggggag | 1020 |
| gctcccactt ctccttcagc cctgaggaca tgaaacggta cctgcaggcc cacacccaaa | 1080 |
| gcgtctacaa ctaccacctc agcccccgcg ccttcctgca ctaccctggg ctggtggtgc | 1140 |
| cccagcccca gcgccctgac aagtgcccgc tgccgcccat ggcacccgag accccaccgg | 1200 |
| tcccctcctc ggcctcgtca tcctcttctt cttcttcctc cccattcaag tttaagctcc | 1260 |
| agcggccccc actcggacgc cggcagcggg cagctgggga gaaggccgta gccgctgctg | 1320 |
| acaagagcgg tggcagtgca ggcgggctgg ctgagggggc aggggcgcta gccccaccgc | 1380 |
| ccccgccacc acagatcaag gtggagccca tctcggaagg cgagtcggag gaggtagagg | 1440 |
| tgactgacat cagtgatgag gatgaggaag acggggaggt gttcaagacg cccgtgccc | 1500 |
| cacctgcacc ccctaagcct gagcccggcg aggcacccgg ggcatcccag tgcatgcccc | 1560 |
| tcaagctacg ctttaagcgg cgctggagtg aagactgtcg cctcgaaggg ggtgggggcc | 1620 |
| ccgctggggg cttttgaggat gagggtgagg acaagaaggt gcgtggggag gggcctgggg | 1680 |

```
aggctggggg gcccctcacc ccaaggcggg tgagctctga cctccagcat gccacggccc    1740
agctctccct ggagcaccga gactcctgag ggctgtgggc aggggacctg tgtgccccgc    1800
accccccatg cttcttttgc tgccttaagc cccctatgcc ctggaggtga gggcagctct    1860
cttgtctctt ccctgcctcc tccttttcc ctccccacat tttgtataaa actttaattt     1920 cttttttta aaaatggtgg gggtgggtgg gtgcccaggg ctaggggcta ttccctgtct     1980
ctgtgggttt ctaagctctg gcaaattgg tggtagggg agggaggggg aagttaaggg      2040
ggtcacctcc attctgggga atttatattt gaattgaggc tttggcctta cacccagga    2100 acttttctat tacaatcgct taggaagtaa agccttgtct ccctcctgt tctctgcctc     2160 ttgtacccct ctgacccacc cgctctgccc cactcccagc cctcctcagc cccagccctg    2220
cctgccctgc ccctccaggg ggccatgagt gcctaggttt ctcatacccc acaaggtcac    2280
agcaggggag ggagggacaa ttttataatg aaccaaaaat tccatgtgtt gggggtggg    2340 gggcggagga gggtgagggg tgccgcccat gggccacaaa tctctacaag tgcctgctat    2400
ccctctccca ctccccaccc cagcaccggt ccaaccccctt catccccagc tgctcctagg    2460
actggcccat gggcaggcgg gtggggggat gggaaggggg tgccctgaaa ccaaactgga    2520
agccccctct gcctcccagc tggggcctct ggggtgggt gggggctgt ggtcaagcct     2580 tattctgtat tggggactga gggtggggg agtagagggg ccgctggaga atgtattcaa    2640
aacaataaac tttggacctt tggaaaa                                          2667

<210> SEQ ID NO 43
<211> LENGTH: 1364
<212> TYPE: DNA
<213> ORGANISM: Homo sapiens

<400> SEQUENCE: 43
aaaatcagga acttgtgctg gccctgcaat gtcaagggag ggggctcacc cagggctcct     60
gtagctcagg gggcaggcct gagccctgca cccgccccac gaccgtccag cccctgacgg    120 gcacccatc ctgagggggct ctgcattggc ccccaccgag gcagggatc tgaccgactc     180 ggagcccggc tggatgttac aggcgtgcaa aatggaaggg tttcccctcg tccccctcc    240 atcagaagac ctggtgccct atgacacgga tctataccaa cgccaaacgc acgagtatta    300
cccctatctc agcagtgatg gggagagcca tagcgaccat tactgggact ccaccccca    360 ccacgtgcac agcgagttcg agagcttcgc cgagaacaac ttcacggagc tccagagcgt    420 gcagccccccg cagctgcagc agctctaccg ccacatggag ctggagcaga tgcacgtcct    480
cgataccccc atggtgccac cccatcccag tcttggccac caggtctcct acctgccccg    540
gatgtgcctc cagtacccat ccctgtcccc agcccagccc agctcagatg aggaggaggg    600
cgagcggcag agcccccac tggaggtgtc tgacggcgag gcggatggcc tggagcccgg    660
gcctgggctc ctgcctgggg agacaggcag caagaagaag atccgcctgt accagttcct    720
gttggacctg ctccgcagcg gcgacatgaa ggacagcatc tggtgggtgg acaaggacaa    780
gggcaccttc cagttctcgt ccaagcacaa ggaggcgctg cgcaccgct ggggcatcca     840 gaagggcaac cgcaagaaga tgacctacca gaagatggcg cgcgcgctgc gcaactacgg    900
caagacgggc gaggtcaaga aggtgaagaa aagctcacc taccagttca gcggcgaagt    960
gctgggccgc ggggccctgg ccgagcgcg ccacccgccc cactgagccc gcagccccg    1020 ccggccccgc caggcctccc cgctggccat agcattaagc cctcgcccgg cccggacaca    1080
```

```
gggaggacgc tcccggggcc cagaggcagg actgtggcgg gccgggctcc gtcacccgcc      1140
cctcccccca ctccaggccc cctccacatc ccgcttcgcc tccctccagg actccacccc      1200
ggctcccgac gccagctggg cgtcagaccc accggcaacc ttgcagagga cgacccgggg      1260
tactgccttg ggagtctcaa gtccgtatgt aaatcagatc tccctctca ccctcccac       1320 ccattaacct cctcccaaaa aacaagtaaa gttattctca atcc                      1364

<210> SEQ ID NO 44
<211> LENGTH: 3034
<212> TYPE: DNA
<213> ORGANISM: Homo sapiens

<400> SEQUENCE: 44
tttcttgtta aacaaacacc taatttattt cttggaggtt ttgttcagct gtcctaattt       60
atgactttac attccttctg gtgctaaact gctcaagtag cctcttgtat caagtgtgac      120
ctgattcctt aagaatttta cttaatgaga acctctaagc tagaaactct tgctaggtgt      180
ttcatgcacc ttattttctt taatcattac aacaactcta agattgggtt ctctccacct      240
tataaatgat gactgtttta gagaggttaa ggttgcttaa aattggtgag ttagtgaggg      300
gtagagccac gaatggattt ctggtcgctg cctccatcgt cagggcaagc ttttcccacg      360
actccagcgc ttccatttgt cagtccccag gctagaaagc cacagtgcta atttagtatt      420
tatcaagcgt ttgtagtgtc ctgggatctg gcacttcgat gagaaagctg tgacggcccc      480
aacttctaac agcgagtggt aaggaggacg agggacacag gagggaggag actctcccca      540
aagcttagca ccaacagaag tggtcccccg caggttgctc tgcgagcgcc acctcttccc      600
tccaaccgag gagaaagtgg cgcgcctttg aggagtccga ggtcccggcc caggcggcag      660
cttgggtcct ggcgggttcc ggacgggcgc tcagggacc tggaagcaac cgcaccgaac       720
gcgacggaga gcggcgagac gactccagga ggcgcccgag ctacatcccc cggccacacc      780
aaacccgggt ttgctggcag acgcggctca cgacacccct tagggtcgca gcccctcccc      840
cggaagtgac gtgtagcgac tacggcgtct gggagggacc caggagcagt cgggggtttt     900
gagagtggcg gcggccgcgg agggcctggc aggccccgcc gctgcaagga acgccccgaa      960
cgcgcgcgcc cggcgtgtag cggccccaag acccgcgccg ccgctgccgc gtgcgggggc     1020
ggggagggcg gggcgccagg agccgcggcg cgggagatg cggcggctg cgggcacccg       1080 gcgggctcgg cttggccgcc gccgccttct acggctccgc cgcgggggtc gcagcggctg     1140
ccgcgccgtc ctcgagtttc cagcgtgagg aggaggctga gggcggagag gcgcatcgtg     1200
ttcgaggcgg agaccgaggg ggagccccgc gcgcggcgtc gctcattgct atggacagtg     1260
ctatcaccct gtggcagttc cttcttcagc tcctgcagaa gcctcagaac aagcacatga     1320
tctgttggac ctctaatgat gggcagttta agcttttgca ggcagaagag gtggctcgtc     1380
tctgggggat tcgcaagaac aagcctaaca tgaattatga caaactcagc cgagccctca     1440
gatactatta tgtaaagaat atcatcaaaa aagtgaatgg tcagaagttt gtgtacaagt     1500
ttgtctctta tccagagatt ttgaacatgg atccaatgac agtgggcagg attgagggtg     1560
actgtgaaag tttaaacttc agtgaagtca gcagcagttc caaagatgtg gagaatggag     1620
ggaaagataa accacctcag cctggtgcca agacctctag ccgcaatgac tacatacact     1680
ctggcttata ttcttcattt actctccaact cttgaactc ctccaatgta agcttttca      1740 aattgataaa gactgagaat ccagccgaga aactggcaga gaaaaatct cctcaggagc      1800 ccacaccatc tgtcatcaaa tttgtcacga caccttccaa aaagccaccg gttgaacctg     1860
```

```
ttgctgccac catttcaatt ggcccaagta tttctccatc ttcagaagaa actatccaag      1920
ctttggagac attggtttcc ccaaaactgc cttccctgga agcccaacc tctgcctcta       1980 acgtaatgac tgcttttgcc accacaccac ccatttcgtc catacccct ttgcaggaac       2040 ctcccagaac accttcacca ccactgagtt ctcacccaga catcgacaca gacattgatt      2100
cagtggcttc tcagccaatg gaacttccag agaatttgtc actggagcct aaagaccagg     2160
attcagtctt gctagaaaag gacaaagtaa ataattcatc aagatccaag aaacccaaag    2220
ggttagaact ggcacccacc cttgtgatca cgagcagtga tccaagccca ctgggaatac     2280
tgagcccatc tctccctaca gcttctctta caccagcatt ttttcacag acacccatca      2340 tactgactcc aagcccttg ctctccagta tccacttctg gagtactctc agtcctgttg      2400
ctcccctaag tccagccaga ctgcaaggtg ctaacacact tttccagttt ccttctgtac    2460
tgaacagtca tgggccattc actctgtctg ggctggatgg accttccacc cctggcccat     2520
tttccccaga cctacagaag acataaccta tgcacttgtg aatgagaga accgaggaac     2580 gaagaaacag acattcaaca tgattgcatt tgaagtgagc aattgatagt tctacaatgc   2640
tgataataga ctattgtgat ttttgccatt ccccattgaa aacatctttt taggattctc     2700
tttgaatagg actcaagttg gactatatgt ataaaaatgc cttaattgga gtctaaactc     2760
cacctccctc tgtctttcc ttttctttt ctttccttcc ttcttttct tttcctttt         2820 aaaaatattt tgagctttgt gctgaagaag tttttggtgg gctttagtga ctgtgctttg     2880
caaaagcaat taagaacaaa gttactcctt ctggctattg ggacccttg gccaggaaaa      2940 attatgctta gaatctatta tttaagaaa tatttgtgaa atgaaaaaa aaaaaaaaa        3000 aaaaaaaaa aaaaaaaaa aaaaaaaaa aaaa                                    3034
```

<210> SEQ ID NO 45  
<211> LENGTH: 3077  
<212> TYPE: DNA  
<213> ORGANISM: Homo sapiens

<400> SEQUENCE: 45

```
tttcttgtta aacaaacacc taatttattt cttggaggtt ttgttcagct gtcctaattt      60
atgactttac attccttctg gtgctaaact gctcaagtag cctcttgtat caagtgtgac      120
ctgattcctt aagaattta cttaatgaga acctctaagc tagaaactct tgctaggtgt      180
ttcatgcacc ttatttctt taatcattac aacaactcta agattgggtt ctctccacct     240
tataaatgat gactgtttta gagaggttaa ggttgcttaa aattggtgag ttagtgaggg    300
gtagagccac gaatggattt ctggtcgctg cctccatcgt cagggcaagc ttttcccacg    360
actccagcgc ttccatttgt cagtcccag gctagaaagc cacagtgcta atttagtatt      420
tatcaagcgt ttgtagtgtc ctgggatctg gcacttcgat gagaaagctg tgacggcccc    480
aacttctaac agcgagtggt aaggaggacg agggacacag gagggaggag actctcccca   540
aagcttagca ccaacagaag tggtccccg caggttgctc tgcgagcgcc acctcttccc      600
tccaaccgag gagaaagtgg cgcgcctttg aggagtccga ggtcccggcc caggcggcag    660
cttgggtcct ggcgggttcc ggacgggcgc tcagggacc tggaagcaac cgcaccgaac    720
gcgacggaga gcggcgagac gactccagga ggcgcccgag ctacatcccc cggccacacc   780
aaacccgggt ttgctggcag acgcggctca cgacacccct tagggtcgca gcccctcccc  840
cggaagtgac gtgtagcgac tacggcgtct gggagggacc caggagcagt cgggggtttt    900
```

```
gagagtggcg gcggccgcgg agggcctggc aggccccgcc gctgcaagga acgccccgaa    960
cgcgcgcgcc cggcgtgtag cggcccaag acccgcgccg ccgctgccgc gtgcgggggc   1020
ggggagggcg gggcgccagg agccgcggcg gcgggagatg cgggcggctg cgggcacccg   1080
gcgggctcgg cttggccgcc gccgccttct acggctccgc cgcgggggtc gcagcggctg   1140
ccgcgccgtc ctcgagtttc cagcgtgagg aggaggctga gggcggagag gcgcatcgtg   1200
ttcgaggcgg agaccgaggg ggagccccgc gcgcggcgtc gctcattgct atggacagtg   1260
ctatcaccct gtggcagttc cttcttcagc tcctgcagaa gcctcagaac aagcacatga   1320
tctgttggac ctctaatgat gggcagttta agcttttgca ggcagaagag gtggctcgtc   1380
tctgggggat tcgcaagaac aagcctaaca tgaattatga caaactcagc cgagccctca   1440
gatactatta tgtaaagaat atcatcaaaa aagtgaatgg tcagaagttt gtgtacaagt   1500
ttgtctctta tccagagatt ttgaacatgg atccaatgac agtgggcagg attgagggtg   1560
actgtgaaag tttaaacttc agtgaagtca gcagcagttc caaagatgtg gagaatggag   1620
ggaaagataa accacctcag cctggtgcca agacctctag ccgcaatgac tacatacact   1680
ctggcttata ttcttcattt actctcaact ctttgaactc ctccaatgta aagcttttca   1740
aattgataaa gactgagaat ccagccgaga aactggcaga gaaaaaatct cctcaggagc   1800
ccacaccatc tgtcatcaaa tttgtcacga caccttccaa aaagccaccg gttgaacctg   1860
ttgctgccac catttcaatt ggcccaagta tttctccatc ttcagaagaa actatccaag   1920 cttttggagac attggtttcc ccaaaactgc cttccctgga agccccaacc tctgcctcta   1980
acgtaatgac tgcttttgcc accacaccac ccatttcgtc catacccct ttgcaggaac   2040 ctcccagaac accttcacca ccactgagtt ctcacccaga catcgacaca gacattgatt   2100
cagtggcttc tcagccaatg gaacttccag agaatttgtc actggagcct aaagaccagg   2160
attcagtctt gctagaaaag gacaaagtaa ataattcatc aagatccaag aaacccaaag   2220
ggttagaact ggcacccacc cttgtgatca cgagcagtga tccaagccca ctgggaatac   2280
tgagcccatc tctccctaca gcttctctta caccagcatt tttttcacag gtagcttgct   2340 cgctcttttat ggtgtcacca ttgctttcat ttatttgccc ttttaagcaa atccagaatt   2400
tatacactca agtttgcttt ctgttactta ggtttgtctt agaaaggtta tgtgtgactg   2460
tcatgtgaaa gttaccccat ttctcatctt aattaggatt gctaaaatag aaagtttgga   2520
gtattttctt aaaaaattca ttgttctaca agtaaataaa tattttgatt tttctatttc   2580
ctcctaaaga aagtacacac actctctcgc tctctctcgg tcttataaaa ctcgttggtg   2640
tcttataaaa caaacagtga taatctcaag ttagaaaaca gtaggtcctg agaaccataa   2700
gaaaaatgac tggtgtgatg ttgagtaaca agttggtaca gttactttag ctatttatta   2760
acttgctcat ctcatagaac attttagtag attttcaca cacctcatta ttaaaaaaaa   2820
acaaacatgc tggtgtcttg gttacccatt attcctctgt acctgaattc aggttggttt   2880
ttctatttgg aaaagacttt ataaatgttg gcttaaaaag aggttgagca ccagaatctc   2940
agaatttacc accaaagaac tcatccatgt aaccaaaaac cacttgtacc cccaaaaact   3000
attgaaataa aaatttaaaa aattttaaaa aaaaaaaaaa aaaaaaaaaa aaaaaaaaaa   3060
aaaaaaaaaa aaaaaaa                                                3077
```

<210> SEQ ID NO 46
<211> LENGTH: 1443
<212> TYPE: DNA
<213> ORGANISM: Homo sapiens

<400> SEQUENCE: 46

```
gggggggtg gatgaggagg agccggagac gccgcggagg agaccggacc gaagacggac      60
cgtgccggga agagcaggcg ggtgaaaatg aaagccggct gtagcatcgt ggaaaagcca    120
gaaggaggtg gagggtatca gtttcctgac tgggcctaca aaacagagtc atccccaggc    180
tcccggcaga tccagctgtg gcacttcatc ctggagctgc tgcagaagga agagttccgc    240
catgtcatcg cctggcagca gggagagtac ggggaatttg tcatcaagga tccagatgag    300
gtggcccgcc tctggggccg caggaaatgc aaaccacaga tgaattatga caagctgagc    360
cgggccctca gatactatta caacaagagg atccttcata aaacaaaagg aaaagatttt    420
acctataaat ttaacttcaa caagctggtg atgcccaact acccattcat caacattcgg    480
tcaagtggta agatacaaac tcttttggta gggaattaat tttgaattga aagaatttt    540
taaaaatcca aatctaagac atggcatgtt taggaagatt ttagaaacac taaaataatg    600
tgatcctttg gattgcctca atgttcttac tcaagtcatc tcacttataa ggagagttat    660
aggctattca gtatcaagat agatttcttt ggtttatttg gttggttccc ttttctgcat    720
attgtttgta atctcctaga tactattacg ctatcttgtt tgggaatgat gtttcatagg    780
tttgtgatga tctttacgtt caggactcag ttttaacacc cagcccagtg gttctttcat    840
agatgggaac ctgtttctac aaacacttcc gattttctgt gaaactacca agctctccct    900
tatcaagtga atatcatcaa aaccacagca tccttgatca gagaagggg aggttcacat    960
gtttgcagtg aaaagcagtg tctttgatct gcaacagcaa atcctcagag aaaaagattc   1020
tggggttact tgaccttctc tcctgttaag tgcagtaggg cttcccctct tgactttcct   1080
ggttatagct ttccatcaca gctccccaca ttctctcttg atgttgaaag cagtctctca   1140
aaagactttg ttgttgtgtg gttttttgtt tgtgattttt ttccttatgc aaatcatact   1200
cctgcccaag aaaatacagt agttccccctt atctgagcag tatatgttct aagacccta   1260
gtagattcgc aaaccacaga tagtaccaaa ctccattcat atatatgatg tttttcttc   1320
ccttaaccccc actcatatgt atctgtgata acgtttaatt tataaattag gcacagtaag   1380
agattaatga caataataaa atagaaaaat tataaaaaaa aaaaaaaaa aaaaaaaaa     1440
aaa                                                                 1443
```

<210> SEQ ID NO 47
<211> LENGTH: 229
<212> TYPE: DNA
<213> ORGANISM: Homo sapiens

<400> SEQUENCE: 47

```
cccactagtt acccaccccca aactggatcc tacagccaag ctccaagtca atatagccaa    60
cagagcagca gctacgggca gcagaatccg tatcagatcc tgggcccgac cagcagtcgc   120
ctagccaacc ctggaagcgg gcagatccag ctgtggcaat tcctcctgga gctgctctcc   180
gacagcgcca acgccagctg tatcacctgg gagggaccaa acgggagt                 229
```

<210> SEQ ID NO 48
<211> LENGTH: 2319
<212> TYPE: DNA
<213> ORGANISM: Homo sapiens

<400> SEQUENCE: 48

```
cacaaggcta caggtgtctt tatttccact gcacgctggt gctgggagcg cctgccttct     60
```

| | |
|---|---|
| cttgccttga aagcctcctc tttggaccta gccaccgctg ccctcacggt aatgttggac | 120 |
| tcggtgacac acagcacctt cctgcctaat gcatccttct gcgatcccct gatgtcgtgg | 180 |
| actgatctgt tcagcaatga agagtactac cctgcctttg agcatcagac agcctgtgac | 240 |
| tcatactgga catcagtcca ccctgaatac tggactaagc gccatgtgtg ggagtggctc | 300 |
| cagttctgct gcgaccagta caagttggac accaattgca tctccttctg caacttcaac | 360 |
| atcagtggcc tgcagctgtg cagcatgaca caggaggagt cgtcgaggc agctggcctc | 420 |
| tgcggcgagt acctgtactt catcctccag aacatccgca cacaaggtta ctccttttt | 480 |
| aatgacgctg aagaaagcaa ggccaccatc aaagactatg ctgattccaa ctgcttgaaa | 540 |
| acaagtggca tcaaaagtca agactgtcac agtcatagta gaacaagcct ccaaagttct | 600 |
| catctatggg aatttgtacg agacctgctt ctatctcctg aagaaaactg tggcattctg | 660 |
| gaatgggaag atagggaaca aggaattttt cgggtggtta atcggaagc cctggcaaag | 720 |
| atgtggggac aaaggaagaa aaatgacaga atgacatatg aaaagttgag cagagccctg | 780 |
| agatactact ataaaacagg aattttggag cgggttgacc gaaggttagt gtacaaattt | 840 |
| ggaaaaatg cacacgggtg gcaggaagac aagctatgat ctgctccagg catcaagctc | 900 |
| attttatgga tttctgtctt ttaaaacaat cagattgcaa tagacattcg aaaggcttca | 960 |
| tttcttctc ttttttttt aacctgcaaa catgctgata aatttctcc acatctcagc | 1020 |
| ttacatttgg attcagagtt gttgtctacg gagggtgaga gcagaaactc ttaagaaatc | 1080 |
| ctttcttctc cctaagggga tgaggggatg atcttttgtg gtgtcttgat caaacttat | 1140 |
| tttcctagag ttgtggaatg acaacagccc atgccattga tgctgatcag agaaaaacta | 1200 |
| ttcaattctg ccattagaga cacatccaat gctcccatcc caaaggttca aaagttttca | 1260 |
| ataactgtg gcagctcacc aaagtgggg gaaagcatga ttagtttgca ggttatggta | 1320 |
| ggagagggtg agatataaga catacatact ttagatttta aattattaaa gtcaaaaatc | 1380 |
| catagaaaag tatccctttt ttttttttt gagacgggtt ctcactatgt tgcccagggc | 1440 |
| tggtcttgaa ctcctatgct caagtgatcc tcccacctcg gcctcccaaa gtactgtgat | 1500 |
| tacaagcgtg agccacggca cctgggcaga aaagtatctt aattaatgaa agagctaagc | 1560 |
| catcaagctg ggacttaatt ggatttaaca taggttcaca gaaagtttcc taaccagagc | 1620 |
| atcttttga ccactcagca aaacttccac agacatcctt ctggacttaa acacttaaca | 1680 |
| ttaaccacat tattaattgt tgctgagttt attcccccctt ctaactgatg gctggcatct | 1740 |
| gatatgcaga gttagtcaac agacactggc atcaattaca aaatcactgc tgtttctgtg | 1800 |
| attcaagctg tcaacacaat aaaatcgaaa ttcattgatt ccatctctgg tccagatgtt | 1860 |
| aaacgtttat aaaaccggaa atgtcctaac aactctgtaa tggcaaatta aattgtgtgt | 1920 |
| ctttttgtt ttgtctttct acctgatgtg tattcaagtg ctataacacg tatttccttg | 1980 |
| acaaaatag tgacagtgaa ttcacactaa taaatgttca taggttaaag tctgcactga | 2040 |
| cattttctca tcaatcactg gtatgtaagt tatcagtgac tgacagctag gtggactgcc | 2100 |
| cctaggactt ctgtttcacc agagcaggaa tcaagtggtg aggcactgaa tcgctgtaca | 2160 |
| ggctgaagac ctccttatta gagttgaact tcaaagtaac ttgttttaaa aaatgtgaat | 2220 |
| tactgtaaaa taatctatt tggattcatg tgttttccag gtggatatag tttgtaaaca | 2280 |
| atgtgaataa agtatttaac atgtaaaaaa aaaaaaaa | 2319 |

<210> SEQ ID NO 49
<211> LENGTH: 3617

<212> TYPE: DNA
<213> ORGANISM: Homo sapiens

<400> SEQUENCE: 49

```
acccgtggtg ccccatccct ataggagctg gtgagattgc agcctgctgc ctcccctcca    60
tcagccacag ctattggatt tcccacccag aatctttagg taaatgagat catgattctg   120
gaaggaggtg gtgtaatgaa tctcaacccc ggcaacaacc tccttcacca gccgccagcc   180
tggacagaca gctactccac gtgcaatgtt tccagtgggt tttttggagg ccagtggcat   240
gaaattcatc ctcagtactg gaccaagtac caggtgtggg agtggctcca gcacctcctg   300
gacaccaacc agctggatgc caattgtatc cctttccaag agttcgacat caacggcgag   360
cacctctgca gcatgagttt gcaggagttc acccgggcgg cagggacggc ggggcagctc   420
ctctacagca acttgcagca tctgaagtgg aacggccagt gcagtagtga cctgttccag   480
tccacacaca atgtcattgt caagactgaa caaactgagc cttccatcat gaacacctgg   540
aaagacgaga actatttata tgacaccaac tatggtagca cagtagattt gttggacagc   600
aaaactttct gccgggctca gatctccatg acaaccacca gtcaccttcc tgttgcagag   660
tcacctgata tgaaaaagga gcaagacccc cctgccaagt gccacaccaa aaagcacaac   720
ccgagaggga ctcacttatg ggaattcatc cgcgacatcc tcttgaaccc agacaagaac   780
ccaggattaa taaatgggga agaccgatct gagggcgtct tcaggttctt gaaatcagag   840
gcagtggctc agctatgggg taaaaagaag aacaacagca gcatgaccta tgaaaagctc   900
agccgagcta tgagatatta ctacaaaaga gaaattctgg agcgtgtgga tggacgaaga   960
ctggtatata aatttgggaa gaatgcccga ggatggagag aaaatgaaaa ctgaagctgc  1020
caatactttg gacacaaacc aaaacacaca ccaaataatc agaaacaaag aactcctgga  1080
cgtaaatatt tcaaagacta cttttctctg atatttatgt accatgaggg gaacaagaaa  1140
ctacttctaa cgggaagaag aaacactaca gtcgattaaa aaaattattt tgttacttcg  1200
aagtatgtcc tatatgggga aaaaacgtac acagttttct gtgaaatatg atgctgtatg  1260
tggttgtgat tttttttcac ctctattgtg aattctttt cactgcaaga gtaacaggat  1320
ttgtagcctt gtgcttcttg ctaagagaaa gaaaacaaa atcagagggc attaaatgtt  1380
ttgtatgtga catgatttag aaaaaggtga tgcatcctcc tcacataagc atccatatgg  1440
cttcgtcaag ggaggtgaac attgttgctg agttaaattc cagggtctca gatggttagg  1500
acaaagtgga tggatgccgg gaagtttaac ctgagcctta ggatccaatg agtggagaat  1560
ggggacttcc aaaacccaag gttggctata atctctgcat aaccacatga cttggaatgc  1620
ttaaatcagc aagaagaata atggtggggt ctttatactc attcaggaat ggtttatctg  1680
atgccagggc tgtcttcctt tctcccctttt ggatggttgg tgaaatactt taattgccct  1740
gtctgctcac ttctagctat ttaagagaga acccagcttg gttctttttt gctccaagtg  1800
cttaaaaata agttggaaaa aggagacggt ggtgtggaaa tggctgaaga gtttgctctt  1860
gtatccctat agtccaaggt ttctcaatct gcacaattga catttttggc cggagtgttc  1920
tttgtggtga gggctttcct gtgcattgta agatgttcag cagtatccac tcatggtctc  1980
taaccacttg acaccagaaa ccccccagct gtgataacgc aaaatgtctc tagacatcac  2040
caaatgttcc ctgggggtgg caaatttgcc cttgattgag aaccaccagt ttagctagtc  2100
aatatgagga tggtggttta ttctcagaag aaaaagatat gtaaggtctt ttagctcctt  2160
agagtgaagc aaaagcaaga cttcaacctc aacctatctt tatgttttaa atgttaggga  2220
```

| | |
|---|---|
| caataagttg aaatagctag aggagcttct tttcagaacc ccagatgaga gccaatgtca | 2280 |
| gataaagtaa gcatagtaat gtagcaggaa ctacaataga agacattttc actggaatta | 2340 |
| caaagcagaa ttaaaattat attgtagaag gaaacaccaa gaaaagaatt tccagggaaa | 2400 |
| atcctctttg caggtattaa ttcttataat tttttgtctt ttggattatc tgtttactgt | 2460 |
| ctcatctgaa ctgatcccag gtgaacggtt tattgcctag atttgtactc agaggaattt | 2520 |
| ttttttgtttt gttttgtctt ttaagaaagg aaagaaagga tgaaaaaaat aaacagaaaa | 2580 |
| ctcagctcag gcacaattgt caccaaggag ttaaaagctt cttcttcaat agaggaattg | 2640 |
| ttctgggggt cctggagact taccattgag ccatgcaatc tgggaagcac aggaataagt | 2700 |
| agacactttg aaaatggatt tgaatgttct catcccttt gcagcttttc ttttggctc | 2760 |
| tctcatgtcc ttggcttgct cctctattct acctctcttt ctccagcaat aatatgcaaa | 2820 |
| tgaagacatg tatccataag aaggagtgct cttcatcaac taatagagca cctaccacag | 2880 |
| tgtcataccct ggtagaggtg agcaattcat attcaaaggt tgcaaagtgt ttgtaatata | 2940 |
| ttcatgaggc tggaagtaag aagaattaaa aatttgtcct aattacaatg agaaccattc | 3000 |
| taggtagtga tcttggagca cacatgaata actttctgaa ggtgcaacca aatccatttt | 3060 |
| tatttctgcc tggcttggtc acctctgtaa aggtttaact tagtgttgtc aagtaacagt | 3120 |
| tactgaaaga gctgagaaaa agaacaatga acagcaacga tcttgactgt gcaactcaga | 3180 |
| cattcctgca gaaaagacat atgttgcttt acaagaaggc caagaactta tggggccttc | 3240 |
| ccagcatttg actgttcatt gcatagaatg aattaaatat ccagttactt gaatgggtat | 3300 |
| aacgcatgaa tatttgtgtg tctgtgtgtg tgtctgagtt gtgtgatttt attaggggca | 3360 |
| tctgccaatt ctctcactgt ggttccttct ctgactttgc ctgttcatca tctaaggagg | 3420 |
| ctagatcctt cgctgacttc accattcctc aaacctgtaa gttctcact tcttccaaat | 3480 |
| tggctttggc tctttctgca acctttccat tcaagagcaa tctttgctaa ggagtaagtg | 3540 |
| aatgtgaaga gtaccaacta caacaattct acagataatt agtggattgt gttgtttgtt | 3600 |
| gagagtgaag gtttctt | 3617 |

<210> SEQ ID NO 50
<211> LENGTH: 1894
<212> TYPE: DNA
<213> ORGANISM: Homo sapiens

<400> SEQUENCE: 50

| | |
|---|---|
| gtctgacttc ctcccagcac attcctgcac tctgccgtgt ccacactgcc ccacagaccc | 60 |
| agtcctccaa gcctgctgcc agctccctgc aagcccctca ggttgggcct tgccacggtg | 120 |
| ccagcaggca gccctgggct gggggtaggg gactccctac aggcacgcag ccctgagacc | 180 |
| tcagagggcc acccttgag ggtggccagg cccccagtgg ccaacctgag tgctgcctct | 240 |
| gccaccagcc ctgctggccc ctggttccgc tggcccccca gatgcctggc tgagacacgc | 300 |
| cagtggcctc agctgcccac acctcttccc ggcccctgaa gttggcactg cagcagacag | 360 |
| ctccctgggc accaggcagc taacagacac agccgccagc ccaaacagca gcggcatggg | 420 |
| cagcgccagc ccgggtctga gcagcgtatc ccccagccac ctcctgctgc ccccgacac | 480 |
| ggtgtcgcgg acaggcttgg agaaggcggc agcggggca gtgggtctcg agagacggga | 540 |
| ctggagtccc agtccacccg ccacgccgca gcagggcctg tccgccttct acctctccta | 600 |
| cttttgacatg ctgtaccctg aggacagcag ctgggcagcc aaggccctg gggccagcag | 660 |
| tcgggaggag ccacctgagg agcctgagca gtgcccggtc attgacagcc aagccccagc | 720 |

```
gggcagcctg gacttggtgc ccggcgggct gaccttggag gagcactcgc tggagcaggt      780
gcagtccatg gtggtgggcg aagtgctcaa ggacatcgag acggcctgca agctgctcaa      840
catcaccgca gatcccatgg actggagccc cagcaatgtg cagaagtggc tcctgtggac      900
agagcaccaa taccggctgc cccccatggg caaggccttc caggagctgg cgggcaagga      960
gctgtgcgcc atgtcggagg agcagttccg ccagcgctcg ccctgggtg gggatgtgct      1020 gcacgcccac ctggacatct ggaagtcagc ggcctggatg aaagagcgga cttcacctgg     1080
ggcgattcac tactgtgcct cgaccagtga ggagagctgg accgacagcg aggtggactc     1140
atcatgctcc gggcagccca tccacctgtg gcagttcctc aaggagttgc tactcaagcc     1200
ccacagctat ggccgcttca ttaggtggct caacaaggag aagggcatct tcaaaattga     1260
ggactcagcc caggtggccc ggctgtgggg catccgcaag aaccgtcccg ccatgaacta     1320
cgacaagctg agccgctcca tccgccagta ttacaagaag gcatcatcc ggaagccaga      1380 catctcccag cgcctcgtct accagttcgt gcacccatc tgagtgcctg cccagggcc       1440 tgaaacccgc cctcaggggc ctctctcctg cctgccctgc ctcagccagg ccctgagatg     1500
ggggaaaacg ggcagtctgc tctgctgctc tgaccttcca gagcccaagg tcagggaggg     1560
gcaaccaact gccccagggg gatatgggtc ctctggggcc ttcgggacca tggggcaggg    1620
gtgcttcctc ctcaggccca gctgctcccc tggaggacag agggagacag gctgctccc    1680 caacacctgc ctctgacccc agcatttcca gagcagagcc tacagaaggg cagtgactcg     1740
acaaaggcca caggcagtcc aggcctctct ctgctccatc cccctgcctc ccattctgca    1800
ccacacctgg catggtgcag ggagacatct gcaccctga gttgggcagc caggagtgcc    1860
cccgggaatg gataataaag atactagaga actg                                1894

<210> SEQ ID NO 51
<211> LENGTH: 2180
<212> TYPE: DNA
<213> ORGANISM: Homo sapiens

<400> SEQUENCE: 51
gggcggaaaa gcctgtttac acagactgca caccgcctgg ggaataatgc agtaaaggaa       60
gtgagccggc tcggcctgac tgctccaact tcctgctctc acacacacca gaggggaaaa      120 aaaagagga gcgagagaaa gaaaaaaagg gggaaaatc aggatctcat tacaagagcc        180
acagaccgtc tgcagacgcc tgtcagcatg gaaagtcggg ggctttcgcc cgggtcctcc       240
tagaaattcc ccccgaagaa gactccccca catctgggta tggagagtgc aatcacgctg       300
tggcagttcc tgttgcagtt gctgctggat cagaaacatg agcatttgat ctgctggacc       360
tcgaacgatg gtgaattcaa gctcctcaaa gcagaagaag tggccaagct gtggggactc      420
cgaaaaaaca aaacaaatat gaactatgat aagctgagca gagccctgcg atactattat      480
gacaagaaca tcatcaagaa ggtgatcggg cagaagtttg tgtacaagtt tgtctctttc      540
ccggagatcc tgaagatgga tcctcacgcg gtggagatca gccgggagag ccttctgctg      600
caggacagcg actgcaaggc gtctccggag ggccgcgagg cccacaaaca cggcctggcc     660
gccctcagaa gcacgagccg caacgaatac atccactcag gcctgtactc gtccttcacc      720
attaattccc tgcagaaccc accagacgcc ttcaaggcca tcaagacgga gaagctggag      780
gagccgcccg aagacagccc cccgtggaa gaagtcagga ctgtgatcag gtttgtgacc       840
aataaaaccg acaagcacgt caccaggccg gtggtgtccc tgccttccac gtcagaggct      900
```

```
gcggcggcgt ccgccttcct ggcctcgtcc gtctcggcca agatctcctc tttaatgttg      960
ccaaacgctg ccagtatttc atccgcctca cccttctcat ctcggtcccc gtccctgtcc     1020
cccaactcac ccctcccttc tgaacacaga agcctcttcc tggaggccgc ctgccatgac     1080
tccgattccc tggagcccTT gaacctgtca tcgggctcca agaccaagtc tccatctctt     1140
cccccaaagg ccaaaaaacc caaaggcttg gaaatctcag cgccccgct ggtgctctcc      1200 ggcaccgaca tcggctccat cgccctcaac agcccagccc tccctcgggg atccctcacc     1260
ccagccttct tcaccgcaca gacaccaaat ggattgcttc tgactccgag tccactgctc     1320
tccagcatac atttctggag cagccttagt ccagttgctc cgctgagtcc tgccaggctg     1380
caagggccaa gcacgctgtt ccagttcccc acactgctta atggccacat gccagtgcca     1440
atccccagtc tggacagagc tgcttctcca gtactgcttt cttcaaactc tcagaaatcc     1500
tgatgacgtc tggccacaat taaggactca ttaactgatg aaacaaattt gtccccacgg     1560
gctagtttac ctgtgtcgtg agaaggacat tgtgaaactc ttgttaattt ggtttgcact     1620
tttcataaca tggatagtct agattttatgt tagcatttta aaaactgttt ttgatatatt    1680
caagtatata tgaaaatctg tttggcatta agtgaatttt aatgttttg ttttatatc      1740 cttttagctc ttaagtgttg aacactgttg acagtgaaga acttttctta atggttttca    1800
gtataactaa taaggatgtg aagcttttt ctctttagtt ctgagtatgc taaactgtgt     1860
gcttatatag actataacca gttgtgcctt cctttgcatt taatgtaaat gaatgattta    1920
tatatttttt agtattaaga ggaaatgttt gaaagatgaa aattagtatc aaacagctct    1980
ctagtagaat ttcattattt ttcaccagtg ggcaatatga aagcatatat cacgttttgt    2040
tttactttca attgtataag aattgcctta gaacctcttt tgaactgaaa ttcagtaaat    2100
gtccaagtaa tgttttata ataaactaag ccatatttag acaataaaca tcgaaaaaaa     2160
aaaaaaaaaa aaaaaaaa                                                   2180
```

<210> SEQ ID NO 52
<211> LENGTH: 3171
<212> TYPE: DNA
<213> ORGANISM: Homo sapiens

<400> SEQUENCE: 52

```
gttgccagct gcggcggccg ccacagccac agccgccgcc gccgccgccg ccgcccctgc       60
ccctgccgcc cctgcccctg ccgttaggtg gtggggtttc tcagcccggc ggcgggaggc      120
gggccggcct cggcttcctg tcggaggacg cgcaaggatc cgggcgtcgg agtgtgtgcg      180
agtgcgtgag tgtgtgtcgg tcgcacggcg tgtgtctccg gccgcgggtt ccgcctcctc      240
ccctgccgcc gctgctcacg gtgtaagtca atgtgaagca gcagctccag ccccgggata      300
aacatggcga cgtctctgca tgagggaccc acgaaccagc tggatctgct catccgggcc      360
gtggaagcat cagttcacag cagtaatgca cactgtacag ataagacaat tgaagctgct      420
gaagccctgc ttcatatgga atctcctacc tgcttgaggg attcaagaag tcctgtggaa      480
gtgtttgttc ctccttgtgt atcaactcca gaattcatcc atgctgctat gaggccagat      540
gtcattacag aaactgtagt ggaggtgtca actgaagagt ctgaacccat ggatacctct      600
cctattccaa catcaccaga tagccatgaa ccaatgaaaa agaaaaaagt tggccgtaaa      660
ccaaagaccc agcaatcacc aatttccaat gggtctcctg agttaggtat aaagaagaaa      720
ccaagagaag gaaaaggaaa cacaacctat ttgtgggagt ttcttttaga tctacttcaa      780
gataaaaata cttgtcccag gtatattaaa tggactcaga gagaaaagg catattcaag      840
```

```
ctggtggatt caaaggctgt ctctaagctt tggggaaagc ataagaacaa accagacatg    900
aactatgaaa ccatgggacg agctttgaga tactactacc aaagggggaat tcttgcaaag   960
gttgaaggac agaggcttgt atatcagttc aaggatatgc cgaaaaacat agtggtcata  1020
gatgatgaca aaagtgaaac ctgtaatgaa gatttagcag gaactactga tgaaaaatca  1080
ttagaacgag tgtcactgtc tgcagaaagt ctcctgaaag cagcatcctc tgttcgcagt  1140
ggaaaaaatt catcccctat aaactgctcc agagcagaga agggtgtagc tagagttgtg  1200
aatatcactt cccctgggca cgatgcttca tccaggtctc ctactaccac tgcatctgtg  1260
tcagcaacag cagctccaag gacagttcgt gtggcaatgc aggtacctgt tgtaatgaca  1320
tcattgggtc agaaaatttc aactgtggca gttcagtcag ttaatgcagg tgcaccatta  1380
ataaccagca ctagtccaac aacagcgacc tctccaaagg tagtcattca gacaatccct  1440
actgtgatgc cagcttctac tgaaaatgga gacaaaatca ccatgcagcc tgccaaaatt  1500
attaccatcc cagctacaca gcttgcacag tgtcaactgc agacaaagtc aaatctgact  1560
ggatcaggaa gcattaacat tgttggaacc ccattggctg tgagagcact taccccctgtt  1620
tcaatagccc atggtacacc tgtaatgaga ctatcaatgc ctactcagca ggcatctggc  1680
cagactcctc ctcgagttat cagtgcagtc ataaaggggc cagaggttaa atcggaagca  1740
gtggcaaaaa agcaagaaca tgatgtgaaa actttgcagc tagtagaaga aaaaccagca  1800
gatggaaata agacagtgac ccacgtagtg gttgtcagtg cgccttcagc tattgccctt  1860
cctgtaacta tgaaaacaga aggactagtg acatgtgaga ataaaaatag cagctccacc  1920
atggacttca ggctgttagt ggcagtactg acataaacat ttgcaaggga agtcatcaag  1980
aaaagtcaaa gaagacttta aaacatttttt aatgcatata caaaaacaat cagacttact  2040
ggaaataaat tacctatccc atgtttcagt gggaaatgaa ctacatattg agatgctgac  2100
agaaaactgc ctcttacagt aggaaacaac tgaacccatc aataagaaaa aggatcgaaa  2160
gggaccaagc agctcactac gatatcaagt tacactaaga cttggaacac taacattctg  2220
taagaggtta tatagttttc agtgggaggg gttgggatgg gtaatctcat tgttacatat  2280
agcaattttt gatgcatttt tatgcatac cagcaattat tactgtgttc gcacagttct  2340
cacttaactg gtgctatgtg aagactctgc taatataggt attttagaat gtgaattgaa  2400
gaatggatcc caaaaacttc agaaagagga tagcaaaaaa agatctagtg cgattttata  2460
tatatatata tatatatata catacatata tatatcat atagcttaag ctgatttaaa  2520
acaaaggcct tagactaatt ttcgattttc tttcttgaaa taagctaatg gcttgtttgt  2580
gtaaagcttt tttattaaaa gaaaaatttt aaaaatcttg tacctagcac agtattgtta  2640
tagaatatac atgtaacatt ttatatggta gtttaagtct gtcagtttct taattgtgga  2700
caaattaaca gttggctctg gccttttgct gtaacatgcc tgtgtcactc acttagcctt  2760
ggcatttgtg cagacatacc attttcagtt ctgctgtcac ttggaagttc aggctcagca  2820
tgaattttttg gcaggtagct ctaatacctg gagttttctt tgtttttttt tcttttttttt  2880
agttgaagtt tatgagggaa ataccagtgt tcagttttga actataatag tttgtatatt  2940
caacatttga agtatattct attttgttgt actcttgttt caaagtgtat tcaagtaggt  3000
tttctgaaat atagaaatga aatttatctt ctgttttggt ctctggtgat attttaaaca  3060
atatttaaaa gtcagtatag aagtgtttta gttaggaagt gataaaacat ctctcttctc  3120
cttcccaact actgcatgaa gaaattctac ttccattata ttaatatttg g            3171
```

<210> SEQ ID NO 53
<211> LENGTH: 3218
<212> TYPE: DNA
<213> ORGANISM: Homo sapiens

<400> SEQUENCE: 53

| | | | | | |
|---|---|---|---|---|---|
| aaaatagtga | aggatgctta | gactacttaa | catacaaact | gctttctggt | taatcatctt | 60 |
| tagaagactg | gatttctgga | tatctactcc | actccatctc | tattgacttt | taaaacatga | 120 |
| taatgcaaac | ctataacact | ggcaaccatc | agtgaacctt | taatttcatt | gattaatagc | 180 |
| gtttgaagct | tcctcaggga | ataacaatga | catcagcagt | ggttgacagt | ggaggtacta | 240 |
| ttttggagct | ttccagcaat | ggagtagaaa | atcaagagga | aagtgaaaag | gtttctgaat | 300 |
| atccagcagt | gattgtggag | ccagttccaa | gtgccagatt | agagcagggc | tatgcagccc | 360 |
| aggttctggt | ttatgatgat | gagacttata | tgatgcaaga | tgtggcagaa | gaacaagaag | 420 |
| ttgagaccga | gaatgtggaa | acagtggaag | catcagttca | cagcagtaat | gcacactgta | 480 |
| cagataagac | aattgaagct | gctgaagccc | tgcttcatat | ggaatctcct | acctgcttga | 540 |
| gggattcaag | aagtcctgaa | ttcatccatg | ctgctatgag | gccagatgtc | attacagaaa | 600 |
| ctgtagtgga | ggtgtcaact | gaagagtctg | aacccatgga | tacctctcct | attccaacat | 660 |
| caccagatag | ccatgaacca | atgaaaaaga | aaaagttggg | ccgtaaacca | agacccagc | 720 |
| aatcaccaat | ttccaatggg | tctcctgagt | taggtataaa | gaagaaacca | agagaaggaa | 780 |
| aaggaaacac | aacctatttg | tgggagtttc | ttttagatct | acttcaagat | aaaaatactt | 840 |
| gtcccaggta | tattaaatgg | actcagagag | aaaaggcat | attcaagctg | gtggattcaa | 900 |
| aggctgtctc | taagctttgg | ggaaagcata | agaacaaacc | agacatgaac | tatgaaacca | 960 |
| tgggacgagc | tttgagatac | tactaccaaa | ggggaattct | tgcaaaggtt | gaaggacaga | 1020 |
| ggcttgtata | tcagttcaag | gatatgccga | aaaacatagt | ggtcatagat | gatgacaaaa | 1080 |
| gtgaaacctg | taatgaagat | ttagcaggaa | ctactgatga | aaaatcatta | gaacgagtgt | 1140 |
| cactgtctgc | agaaagtctc | ctgaaagcag | catcctctgt | tcgcagtgga | aaaaattcat | 1200 |
| cccctataaa | ctgctccaga | gcagagaagg | gtgtagctag | agttgtgaat | atcacttccc | 1260 |
| ctgggcacga | tgcttcatcc | aggtctccta | ctaccactgc | atctgtgtca | gcaacagcag | 1320 |
| ctccaaggac | agttcgtgtg | gcaatgcagg | tacctgttgt | aatgacatca | ttgggtcaga | 1380 |
| aaatttcaac | tgtggcagtt | cagtcagtta | atgcaggtgc | accattaata | accagcacta | 1440 |
| gtccaacaac | agcgacctct | ccaaaggtag | tcattcagac | aatccctact | gtgatgccag | 1500 |
| cttctactga | aaatggagac | aaaatcacca | tgcagcctgc | caaaattatt | accatcccag | 1560 |
| ctacacagct | tgcacagtgt | caactgcaga | caaagtcaaa | tctgactgga | tcaggaagca | 1620 |
| ttaacattgt | tggaaccca | ttggctgtga | gagcacttac | ccctgtttca | atagcccatg | 1680 |
| gtacacctgt | aatgagacta | tcaatgccta | ctcagcaggc | atctggccag | actcctcctc | 1740 |
| gagttatcag | tgcagtcata | aaggggccag | aggttaaatc | ggaagcagtg | gcaaaaaagc | 1800 |
| aagaacatga | tgtgaaaact | ttgcagctag | tagaagaaaa | accagcagat | ggaaataaga | 1860 |
| cagtgaccca | cgtagtggtt | gtcagtgcgc | cttcagctat | tgcccttcct | gtaactatga | 1920 |
| aaacagaagg | actagtgaca | tgtgagaaat | aaaatagcag | ctccaccatg | gacttcaggc | 1980 |
| tgttagtggc | agtactgaca | taaacatttg | caagggaagt | catcaagaaa | agtcaaagaa | 2040 |
| gactttaaaa | cattttttaat | gcatatacaa | aaacaatcag | acttactgga | aataaattac | 2100 |
| ctatcccatg | tttcagtggg | aaatgaacta | catattgaga | tgctgacaga | aaactgcctc | 2160 |

```
ttacagtagg aaacaactga acccatcaat aagaaaaagg atcgaaaggg accaagcagc    2220
tcactacgat atcaagttac actaagactt ggaacactaa cattctgtaa gaggttatat    2280
agttttcagt gggaggggtt gggatgggta atctcattgt tacatatagc aattttttgat   2340 gcattttata tgcataccag caattattac tgtgttcgca cagttctcac ttaactggtg    2400
ctatgtgaag actctgctaa tataggtatt ttagaatgtg aattgaagaa tggatcccaa    2460
aaacttcaga aagaggatag caaaaaaaga tctagtgcga ttttatatat atatatatat    2520
atatatacat acatatatat atatcatata gcttaagctg atttaaaaca aaggccttag    2580
actaattttc gattttcttt cttgaaataa gctaatggct tgtttgtgta aagctttttt    2640
attaaaagaa aaattttaaa aatcttgtac ctagcacagt attgttatag aatatacatg    2700
taacatttta tatggtagtt taagtctgtc agtttcttaa ttgtggacaa attaacagtt    2760
ggctctggcc ttttgctgta acatgcctgt gtcactcact tagccttggc atttgtgcag    2820
acataccatt ttcagttctg ctgtcacttg gaagttcagg ctcagcatga attttttggca   2880 ggtagctcta atacctggag ttttctttgt tttttttttct tttttttagt tgaagtttat    2940
gagggaaata ccagtgttca gttttgaact ataatagttt gtatattcaa catttgaagt    3000
atattctatt ttgttgtact cttgtttcaa agtgtattca agtaggtttt ctgaaatata    3060
gaaatgaaat ttatcttctg ttttggtctc tggtgatatt ttaaacaata tttaaaagtc    3120
agtatagaag tgttttagtt aggaagtgat aaaacatctc tcttctcctt cccaactact    3180
gcatgaagaa attctacttc cattatatta atatttgg                            3218
```

<210> SEQ ID NO 54
<211> LENGTH: 1901
<212> TYPE: DNA
<213> ORGANISM: Homo sapiens

<400> SEQUENCE: 54

```
gcggcgagtg gagcgggagc cgactggaag aagggctcta gggaggggc tgtggctgct      60 ggggtccgag gtggggccgg gtacaccagc cccatcactg tttgcagaga gtcagggagg    120
cggaaaagac acgcgctcta ggctcccatc agggcacatg gcccgggccc atccccgcg     180 cgtctccccg gctgcggggc gcggggggct gccgggtgcg cttggctgtg gcgcggcgcg    240
ttggagactt tattgcgatg ggacgataag aggggcgggg gcgggtcct ggggggccgag    300 gcggcagcgc tttaattaaa acggaaattg cggccccggg ccgcgcgggg gccggagggt    360
tccaagcggc cccttagctg gaagcgtttc tccaggaccc ccccgcaacc ccgccacgc     420 ccgggctgcc ccctcccgcc aggccctgcc ggacccggcg ccgtcttctc ctccttgtca    480
cccgcggtcg cttcgggcgg ggatcggtgc caccgagcgc aaagcctgcc tcgccccct    540 tccccgtccc cccatctcc caccgcccag tcccggcgg cgatgagaca gagcggcgcc     600
tcccagcccc tgctgatcaa catgtacctg ccagatcccg tcgagacgg tctcttcaag    660 gacgggaaga acccgagctg ggggccgctg agccccgcgg ttcagaaagg cagcggacag    720
atccagctgt ggcagtttct gctggagctg ctggctgacc gcgcgaacgc cggctgcatc    780
gcgtgggagg gcggtcacgg cgagttcaag ctcacgggacc cggacgaggt ggcgcggcg    840 tggggcgagc gcaagagcaa gcccaacatg aactacgaca agctgagccg cgccctgcgc    900
tactactacg acaagaacat catgagcaag gtgcatggca agcgctacgc ctaccgcttc    960
gacttccagg gcctggcgca ggcctgccag ccgccgcccg cgcacgctca tgccgccgcc   1020
```

```
gcagctgctg ccgccgccgc ggccgcccag gacggcgcgc tctacaagct gcccgccggc    1080
ctcgccccgc tgcccttccc cggcctctcc aaactcaacc tcatggccgc ctcggccggg    1140
gtcgcgcccg ccggcttctc ctactggccg ggcccgggcc ccgccgccac cgctgccgcc    1200
gccaccgccg cgctctaccc cagtcccagc ttgcagcccc cgcccgggcc cttcggggcc    1260
gtggccgcag cctcgcactt ggggggccat taccactaga cggggcggtc gggtgcctgc    1320
ggcctcgccc gcacgcctag agtctcgccc gatcccatcg gcatcccggg gagggcccgg    1380
gagcctccgt caaccgtcct ctaatccaga gtttactcca cctgccgcac ttagcagggg    1440
gacgggaccg aagctccctc aatccttgtc tggtactaga tttgctcctg tcccaccccg    1500
cagtcccctg aggagggcga tgtgcgccct ctttcacttt ttttcttcta ggtctccagg    1560
tcccggaggg gatttgtgga cctctcttgt ctccccacca ctccagtgca tttccgcctg    1620
gctcctagaa gccccattca atatcactac tctttaacga gtgccaaatc ttttcccact    1680
tttgctcttc cccaaggaac tgctcccacc tcagcacgtg gaggcctctc acggtcctcc    1740
ttcctgggac ctgagcaggt ttggtgaaag ccaccgtcct ccgtgacaca cggccccctt    1800
cctcctgtcc ccacactccc aggagaaact cccggtgtgt ttctgaccct ttcagcccca    1860
ttaaagctcc tgagctctca aaaaaaaaaa aaaaaaaaa a                          1901

<210> SEQ ID NO 55
<211> LENGTH: 21
<212> TYPE: DNA
<213> ORGANISM: Homo sapiens

<400> SEQUENCE: 55
taggcgcgag ctaagcagga g                                                21

<210> SEQ ID NO 56
<211> LENGTH: 25
<212> TYPE: DNA
<213> ORGANISM: Homo sapiens

<400> SEQUENCE: 56
gtaggcacac tcaaacaacg actgg                                            25

<210> SEQ ID NO 57
<211> LENGTH: 19
<212> TYPE: DNA
<213> ORGANISM: Homo sapiens

<400> SEQUENCE: 57
cgcgagctaa gcaggaggc                                                   19

<210> SEQ ID NO 58
<211> LENGTH: 22
<212> TYPE: DNA
<213> ORGANISM: Homo sapiens

<400> SEQUENCE: 58
caggccatga aaagccaaac tt                                               22

<210> SEQ ID NO 59
<211> LENGTH: 49
<212> TYPE: DNA
<213> ORGANISM: Homo sapiens

<400> SEQUENCE: 59
aaaaaaaaaa aaaaaaaaaa aaaaaaaaa tttcucgauu cguccuccg                   49
```

<210> SEQ ID NO 60
<211> LENGTH: 51
<212> TYPE: DNA
<213> ORGANISM: Homo sapiens

<400> SEQUENCE: 60
aaaaaaaaaa aaaaaaaaaa aaaaaaaaaa tttauccgcg cucgauucgu c    51

<210> SEQ ID NO 61
<211> LENGTH: 23
<212> TYPE: DNA
<213> ORGANISM: Homo sapiens

<400> SEQUENCE: 61
gagggcgagg ggcggggagc gcc    23

<210> SEQ ID NO 62
<211> LENGTH: 31
<212> TYPE: DNA
<213> ORGANISM: Homo sapiens

<400> SEQUENCE: 62
cctatcatta ctcgatgctg ttgataacag c    31

<210> SEQ ID NO 63
<211> LENGTH: 43
<212> TYPE: DNA
<213> ORGANISM: Homo sapiens

<400> SEQUENCE: 63
aatttaatac gactcactat agggagaaac tttcagcctg ata    43

<210> SEQ ID NO 64
<211> LENGTH: 51
<212> TYPE: DNA
<213> ORGANISM: Homo sapiens

<400> SEQUENCE: 64
aatttaatac gactcactat agggagactc tgtgagtcat ttgtcttgct t    51

<210> SEQ ID NO 65
<211> LENGTH: 47
<212> TYPE: DNA
<213> ORGANISM: Homo sapiens

<400> SEQUENCE: 65
aatttaatac gactcactat agggagagca cactcaaaca acgactg    47

<210> SEQ ID NO 66
<211> LENGTH: 23
<212> TYPE: DNA
<213> ORGANISM: Homo sapiens

<400> SEQUENCE: 66
gcgcggcagc ucagguaccu gac    23

<210> SEQ ID NO 67
<211> LENGTH: 26
<212> TYPE: DNA
<213> ORGANISM: Homo sapiens

<400> SEQUENCE: 67

```
gcuuugaacu cacucaggua ccugac                                           26

<210> SEQ ID NO 68
<211> LENGTH: 27
<212> TYPE: DNA
<213> ORGANISM: Homo sapiens

<400> SEQUENCE: 68
gagcgcggca ggaagccuua ucaguug                                          27

<210> SEQ ID NO 69
<211> LENGTH: 28
<212> TYPE: DNA
<213> ORGANISM: Homo sapiens

<400> SEQUENCE: 69
gagcgcggca gguuauucca ggaucuuu                                         28

<210> SEQ ID NO 70
<211> LENGTH: 17
<212> TYPE: DNA
<213> ORGANISM: Homo sapiens

<400> SEQUENCE: 70
cgcggcagga agccuua                                                     17

<210> SEQ ID NO 71
<211> LENGTH: 22
<212> TYPE: DNA
<213> ORGANISM: Homo sapiens

<400> SEQUENCE: 71
tccgtaggca cactcaaaca ac                                               22

<210> SEQ ID NO 72
<211> LENGTH: 18
<212> TYPE: DNA
<213> ORGANISM: Homo sapiens

<400> SEQUENCE: 72
cagttgtgag tgaggacc                                                    18

<210> SEQ ID NO 73
<211> LENGTH: 72
<212> TYPE: DNA
<213> ORGANISM: Homo sapiens

<400> SEQUENCE: 73
ggggtgcagc ttttattttc ccaaatactt cagtatatcc tgaagctacg caaagaatta     60
caactaggcc ag                                                          72

<210> SEQ ID NO 74
<211> LENGTH: 40
<212> TYPE: PRT
<213> ORGANISM: Homo sapiens

<400> SEQUENCE: 74

Met Ala Ser Thr Ile Lys Glu Ala Leu Ser Val Val Ser Glu Asp Gln
  1               5                  10                  15

Ser Leu Phe Glu Cys Ala Tyr Gly Thr Pro His Leu Ala Lys Thr Glu
                 20                  25                  30

Met Thr Ala Ser Ser Ser Ser Asp
```

```
                35                  40

<210> SEQ ID NO 75
<211> LENGTH: 5
<212> TYPE: PRT
<213> ORGANISM: Homo sapiens

<400> SEQUENCE: 75

Ser Ser Ser Ser Asp
1               5

<210> SEQ ID NO 76
<211> LENGTH: 40
<212> TYPE: PRT
<213> ORGANISM: Homo sapiens

<400> SEQUENCE: 76

Tyr Gly Gln Thr Ser Lys Met Ser Pro Arg Val Pro Gln Gln Asp Trp
1               5                   10                  15

Leu Ser Gln Pro Pro Ala Arg Val Thr Ile Lys Met Glu Cys Asn Pro
            20                  25                  30

Ser Gln Val Asn Gly Ser Arg Asn
        35                  40

<210> SEQ ID NO 77
<211> LENGTH: 13
<212> TYPE: PRT
<213> ORGANISM: Homo sapiens

<400> SEQUENCE: 77

Val Pro Gln Gln Asp Trp Leu Ser Gln Pro Pro Ala Arg
1               5                   10

<210> SEQ ID NO 78
<211> LENGTH: 13
<212> TYPE: PRT
<213> ORGANISM: Homo sapiens

<400> SEQUENCE: 78

Val Pro Gln Gln Asp Trp Leu Ser Gln Pro Pro Ala Arg
1               5                   10

<210> SEQ ID NO 79
<211> LENGTH: 13
<212> TYPE: PRT
<213> ORGANISM: Homo sapiens

<400> SEQUENCE: 79

Val Pro Gln Gln Asp Trp Leu Ser Gln Pro Pro Ala Arg
1               5                   10

<210> SEQ ID NO 80
<211> LENGTH: 13
<212> TYPE: PRT
<213> ORGANISM: Homo sapiens

<400> SEQUENCE: 80

Val Pro Gln Gln Asp Trp Leu Ser Gln Pro Pro Ala Arg
1               5                   10

<210> SEQ ID NO 81
<211> LENGTH: 21
<212> TYPE: PRT
<213> ORGANISM: Homo sapiens
```

```
<400> SEQUENCE: 81

Tyr Gly Gln Thr Ser Lys Met Ser Val Pro Gln Gln Asp Trp Leu Ser
1               5                   10                  15

Gln Pro Pro Ala Arg
            20

<210> SEQ ID NO 82
<211> LENGTH: 13
<212> TYPE: PRT
<213> ORGANISM: Homo sapiens

<400> SEQUENCE: 82

Val Pro Gln Gln Asp Trp Leu Ser Gln Pro Pro Ala Arg
1               5                   10

<210> SEQ ID NO 83
<211> LENGTH: 13
<212> TYPE: PRT
<213> ORGANISM: Homo sapiens

<400> SEQUENCE: 83

Val Pro Gln Gln Asp Trp Leu Ser Gln Pro Pro Ala Arg
1               5                   10

<210> SEQ ID NO 84
<211> LENGTH: 13
<212> TYPE: PRT
<213> ORGANISM: Homo sapiens

<400> SEQUENCE: 84

Val Pro Gln Gln Asp Trp Leu Ser Gln Pro Pro Ala Arg
1               5                   10

<210> SEQ ID NO 85
<211> LENGTH: 25
<212> TYPE: PRT
<213> ORGANISM: Homo sapiens

<400> SEQUENCE: 85

Val Pro Gln Gln Asp Trp Leu Ser Gln Pro Pro Ala Arg Met Glu Cys
1               5                   10                  15

Asn Pro Ser Gln Val Asn Gly Ser Arg
            20                  25

<210> SEQ ID NO 86
<211> LENGTH: 13
<212> TYPE: PRT
<213> ORGANISM: Homo sapiens

<400> SEQUENCE: 86

Val Pro Gln Gln Asp Trp Leu Ser Gln Pro Pro Ala Arg
1               5                   10

<210> SEQ ID NO 87
<211> LENGTH: 13
<212> TYPE: PRT
<213> ORGANISM: Homo sapiens

<400> SEQUENCE: 87

Val Pro Gln Gln Asp Trp Leu Ser Gln Pro Pro Ala Arg
1               5                   10
```

-continued

<210> SEQ ID NO 88
<211> LENGTH: 40
<212> TYPE: PRT
<213> ORGANISM: Homo sapiens

<400> SEQUENCE: 88

Ser Pro Asp Glu Cys Ser Val Ala Lys Gly Gly Lys Met Val Gly Ser
1               5                   10                  15

Pro Asp Thr Val Gly Met Asn Tyr Gly Ser Tyr Met Glu Glu Lys His
            20                  25                  30

Met Pro Pro Pro Asn Met Thr Thr
        35                  40

<210> SEQ ID NO 89
<211> LENGTH: 9
<212> TYPE: PRT
<213> ORGANISM: Homo sapiens

<400> SEQUENCE: 89

His Met Pro Pro Pro Asn Met Thr Thr
1               5

<210> SEQ ID NO 90
<211> LENGTH: 9
<212> TYPE: PRT
<213> ORGANISM: Homo sapiens

<400> SEQUENCE: 90

His Met Pro Pro Pro Asn Met Thr Thr
1               5

<210> SEQ ID NO 91
<211> LENGTH: 9
<212> TYPE: PRT
<213> ORGANISM: Homo sapiens

<400> SEQUENCE: 91

His Met Pro Pro Pro Asn Met Thr Thr
1               5

<210> SEQ ID NO 92
<211> LENGTH: 12
<212> TYPE: PRT
<213> ORGANISM: Homo sapiens

<400> SEQUENCE: 92

Asn Tyr Gly Ser Tyr Met Glu Glu Lys His Met Pro
1               5                   10

<210> SEQ ID NO 93
<211> LENGTH: 28
<212> TYPE: PRT
<213> ORGANISM: Homo sapiens

<400> SEQUENCE: 93

Met Val Gly Ser Pro Asp Thr Val Gly Met Asn Tyr Gly Ser Tyr Met
1               5                   10                  15

Glu Glu Lys His Met Pro Pro Pro Asn Met Thr Thr
            20                  25

<210> SEQ ID NO 94
<211> LENGTH: 9
<212> TYPE: PRT
<213> ORGANISM: Homo sapiens

```
<400> SEQUENCE: 94

His Met Pro Pro Pro Asn Met Thr Thr
1               5

<210> SEQ ID NO 95
<211> LENGTH: 9
<212> TYPE: PRT
<213> ORGANISM: Homo sapiens

<400> SEQUENCE: 95

His Met Pro Pro Pro Asn Met Thr Thr
1               5

<210> SEQ ID NO 96
<211> LENGTH: 28
<212> TYPE: PRT
<213> ORGANISM: Homo sapiens

<400> SEQUENCE: 96

Met Val Gly Ser Pro Asp Thr Val Gly Met Asn Tyr Gly Ser Tyr Met
1               5                   10                  15

Glu Glu Lys His Met Pro Pro Pro Asn Met Thr Thr
            20                  25

<210> SEQ ID NO 97
<211> LENGTH: 28
<212> TYPE: PRT
<213> ORGANISM: Homo sapiens

<400> SEQUENCE: 97

Met Val Gly Ser Pro Asp Thr Val Gly Met Asn Tyr Gly Ser Tyr Met
1               5                   10                  15

Glu Glu Lys His Met Pro Pro Pro Asn Met Thr Thr
            20                  25

<210> SEQ ID NO 98
<211> LENGTH: 40
<212> TYPE: PRT
<213> ORGANISM: Homo sapiens

<400> SEQUENCE: 98

Asn Glu Arg Arg Val Ile Val Pro Ala Asp Pro Thr Leu Trp Ser Thr
1               5                   10                  15

Asp His Val Arg Gln Trp Leu Glu Trp Ala Val Lys Glu Tyr Gly Leu
            20                  25                  30

Pro Asp Val Asn Ile Leu Leu Phe
        35                  40

<210> SEQ ID NO 99
<211> LENGTH: 39
<212> TYPE: PRT
<213> ORGANISM: Homo sapiens

<400> SEQUENCE: 99

Asn Glu Arg Val Ile Val Pro Ala Asp Pro Thr Leu Trp Ser Thr Asp
1               5                   10                  15

His Val Arg Gln Trp Leu Glu Trp Ala Val Lys Glu Tyr Gly Leu Pro
            20                  25                  30

Asp Val Asn Ile Leu Leu Phe
        35
```

-continued

<210> SEQ ID NO 100
<211> LENGTH: 15
<212> TYPE: PRT
<213> ORGANISM: Homo sapiens

<400> SEQUENCE: 100

Asn Glu Arg Glu Tyr Gly Leu Pro Asp Val Asn Ile Leu Leu Phe
1               5                   10                  15

<210> SEQ ID NO 101
<211> LENGTH: 3
<212> TYPE: PRT
<213> ORGANISM: Homo sapiens

<400> SEQUENCE: 101

Asn Glu Arg
1

<210> SEQ ID NO 102
<211> LENGTH: 27
<212> TYPE: PRT
<213> ORGANISM: Homo sapiens

<400> SEQUENCE: 102

Asn Glu Arg Val Ile Val Pro Ala Asp Pro Thr Leu Trp Ser Thr Asp
1               5                   10                  15

His Val Arg Gln Trp Leu Glu Trp Ala Val Lys
            20                  25

<210> SEQ ID NO 103
<211> LENGTH: 32
<212> TYPE: PRT
<213> ORGANISM: Homo sapiens

<400> SEQUENCE: 103

Asn Glu Arg Arg Val Ile Val Pro Ala Asp Pro Thr Leu Trp Ser Thr
1               5                   10                  15

Asp His Val Arg Glu Tyr Gly Leu Pro Asp Val Asn Ile Leu Leu Phe
            20                  25                  30

<210> SEQ ID NO 104
<211> LENGTH: 39
<212> TYPE: PRT
<213> ORGANISM: Homo sapiens

<400> SEQUENCE: 104

Asn Glu Arg Val Ile Val Pro Ala Asp Pro Thr Leu Trp Ser Thr Asp
1               5                   10                  15

His Val Arg Gln Trp Leu Glu Trp Ala Val Lys Glu Tyr Gly Leu Pro
            20                  25                  30

Asp Val Asn Ile Leu Leu Phe
        35

<210> SEQ ID NO 105
<211> LENGTH: 40
<212> TYPE: PRT
<213> ORGANISM: Homo sapiens

<400> SEQUENCE: 105

Asn Glu Arg Arg Val Ile Val Pro Ala Asp Pro Thr Leu Trp Ser Thr
1               5                   10                  15

Asp His Val Arg Gln Trp Leu Glu Trp Ala Val Lys Glu Tyr Gly Leu

```
                20                  25                  30

Pro Asp Val Asn Ile Leu Leu Phe
        35                  40

<210> SEQ ID NO 106
<211> LENGTH: 20
<212> TYPE: PRT
<213> ORGANISM: Homo sapiens

<400> SEQUENCE: 106

Asn Glu Arg Arg Val Ile Val Pro Ala Asp Pro Thr Leu Trp Ser Thr
1               5                   10                  15

Asp His Val Arg
            20

<210> SEQ ID NO 107
<211> LENGTH: 12
<212> TYPE: PRT
<213> ORGANISM: Homo sapiens

<400> SEQUENCE: 107

Glu Tyr Gly Leu Pro Asp Val Asn Ile Leu Leu Phe
1               5                   10

<210> SEQ ID NO 108
<211> LENGTH: 40
<212> TYPE: PRT
<213> ORGANISM: Homo sapiens

<400> SEQUENCE: 108

Gln Asn Ile Asp Gly Lys Glu Leu Cys Lys Met Thr Lys Asp Asp Phe
1               5                   10                  15

Gln Arg Leu Thr Pro Ser Tyr Asn Ala Asp Ile Leu Leu Ser His Leu
            20                  25                  30

His Tyr Leu Arg Glu Thr Pro Leu
        35                  40

<210> SEQ ID NO 109
<211> LENGTH: 28
<212> TYPE: PRT
<213> ORGANISM: Homo sapiens

<400> SEQUENCE: 109

Gln Asn Ile Asp Gly Lys Leu Thr Pro Ser Tyr Asn Ala Asp Ile Leu
1               5                   10                  15

Leu Ser His Leu His Tyr Leu Arg Glu Thr Pro Leu
            20                  25

<210> SEQ ID NO 110
<211> LENGTH: 4
<212> TYPE: PRT
<213> ORGANISM: Homo sapiens

<400> SEQUENCE: 110

Glu Thr Pro Leu
1

<210> SEQ ID NO 111
<211> LENGTH: 10
<212> TYPE: PRT
<213> ORGANISM: Homo sapiens

<400> SEQUENCE: 111
```

Gln Asn Ile Asp Gly Lys Glu Thr Pro Leu
1               5                   10

<210> SEQ ID NO 112
<211> LENGTH: 4
<212> TYPE: PRT
<213> ORGANISM: Homo sapiens

<400> SEQUENCE: 112

Glu Thr Pro Leu
1

<210> SEQ ID NO 113
<211> LENGTH: 4
<212> TYPE: PRT
<213> ORGANISM: Homo sapiens

<400> SEQUENCE: 113

Glu Thr Pro Leu
1

<210> SEQ ID NO 114
<211> LENGTH: 28
<212> TYPE: PRT
<213> ORGANISM: Homo sapiens

<400> SEQUENCE: 114

Gln Asn Ile Asp Gly Lys Leu Thr Pro Ser Tyr Asn Ala Asp Ile Leu
1               5                   10                  15

Leu Ser His Leu His Tyr Leu Arg Glu Thr Pro Leu
            20                  25

<210> SEQ ID NO 115
<211> LENGTH: 4
<212> TYPE: PRT
<213> ORGANISM: Homo sapiens

<400> SEQUENCE: 115

Glu Thr Pro Leu
1

<210> SEQ ID NO 116
<211> LENGTH: 28
<212> TYPE: PRT
<213> ORGANISM: Homo sapiens

<400> SEQUENCE: 116

Gln Asn Ile Asp Gly Lys Leu Thr Pro Ser Tyr Asn Ala Asp Ile Leu
1               5                   10                  15

Leu Ser His Leu His Tyr Leu Arg Glu Thr Pro Leu
            20                  25

<210> SEQ ID NO 117
<211> LENGTH: 28
<212> TYPE: PRT
<213> ORGANISM: Homo sapiens

<400> SEQUENCE: 117

Gln Asn Ile Asp Gly Lys Leu Thr Pro Ser Tyr Asn Ala Asp Ile Leu
1               5                   10                  15

Leu Ser His Leu His Tyr Leu Arg Glu Thr Pro Leu
            20                  25

```
<210> SEQ ID NO 118
<211> LENGTH: 22
<212> TYPE: PRT
<213> ORGANISM: Homo sapiens

<400> SEQUENCE: 118

Leu Thr Pro Ser Tyr Asn Ala Asp Ile Leu Leu Ser His Leu His Tyr
1               5                   10                  15

Leu Arg Glu Thr Pro Leu
            20

<210> SEQ ID NO 119
<211> LENGTH: 6
<212> TYPE: PRT
<213> ORGANISM: Homo sapiens

<400> SEQUENCE: 119

Gln Asn Ile Asp Gly Lys
1               5

<210> SEQ ID NO 120
<211> LENGTH: 20
<212> TYPE: PRT
<213> ORGANISM: Homo sapiens

<400> SEQUENCE: 120

Pro Ser Tyr Asn Ala Asp Ile Leu Leu Ser His Leu His Tyr Leu Arg
1               5                   10                  15

Glu Thr Pro Leu
            20

<210> SEQ ID NO 121
<211> LENGTH: 40
<212> TYPE: PRT
<213> ORGANISM: Homo sapiens

<400> SEQUENCE: 121

Pro His Leu Thr Ser Asp Asp Val Asp Lys Ala Leu Gln Asn Ser Pro
1               5                   10                  15

Arg Leu Met His Ala Arg Asn Thr Gly Gly Ala Ala Phe Ile Phe Pro
            20                  25                  30

Asn Thr Ser Val Tyr Pro Glu Ala
            35                  40

<210> SEQ ID NO 122
<211> LENGTH: 9
<212> TYPE: PRT
<213> ORGANISM: Homo sapiens

<400> SEQUENCE: 122

Pro Arg Leu Met His Ala Arg Asn Thr
1               5

<210> SEQ ID NO 123
<211> LENGTH: 10
<212> TYPE: PRT
<213> ORGANISM: Homo sapiens

<400> SEQUENCE: 123

Pro His Leu Thr Ser Asp Asp Val Asp Lys
1               5                   10
```

```
<210> SEQ ID NO 124
<211> LENGTH: 17
<212> TYPE: PRT
<213> ORGANISM: Homo sapiens

<400> SEQUENCE: 124

Pro His Leu Thr Ser Asp Asp Val Asp Lys Ala Leu Gln Asn Ser Pro
1               5                   10                  15

Arg

<210> SEQ ID NO 125
<211> LENGTH: 17
<212> TYPE: PRT
<213> ORGANISM: Homo sapiens

<400> SEQUENCE: 125

Pro His Leu Thr Ser Asp Asp Val Asp Lys Ala Leu Gln Asn Ser Pro
1               5                   10                  15

Arg

<210> SEQ ID NO 126
<211> LENGTH: 17
<212> TYPE: PRT
<213> ORGANISM: Homo sapiens

<400> SEQUENCE: 126

Pro His Leu Thr Ser Asp Asp Val Asp Lys Ala Leu Gln Asn Ser Pro
1               5                   10                  15

Arg

<210> SEQ ID NO 127
<211> LENGTH: 17
<212> TYPE: PRT
<213> ORGANISM: Homo sapiens

<400> SEQUENCE: 127

Pro His Leu Thr Ser Asp Asp Val Asp Lys Ala Leu Gln Asn Ser Pro
1               5                   10                  15

Arg

<210> SEQ ID NO 128
<211> LENGTH: 10
<212> TYPE: PRT
<213> ORGANISM: Homo sapiens

<400> SEQUENCE: 128

Pro His Leu Thr Ser Asp Asp Val Asp Lys
1               5                   10

<210> SEQ ID NO 129
<211> LENGTH: 17
<212> TYPE: PRT
<213> ORGANISM: Homo sapiens

<400> SEQUENCE: 129

Pro His Leu Thr Ser Asp Asp Val Asp Lys Ala Leu Gln Asn Ser Pro
1               5                   10                  15

Arg

<210> SEQ ID NO 130
<211> LENGTH: 17
<212> TYPE: PRT
```

-continued

<213> ORGANISM: Homo sapiens

<400> SEQUENCE: 130

Pro His Leu Thr Ser Asp Asp Val Asp Lys Ala Leu Gln Asn Ser Pro
1               5                   10                  15
Arg

<210> SEQ ID NO 131
<211> LENGTH: 17
<212> TYPE: PRT
<213> ORGANISM: Homo sapiens

<400> SEQUENCE: 131

Pro His Leu Thr Ser Asp Asp Val Asp Lys Ala Leu Gln Asn Ser Pro
1               5                   10                  15
Arg

<210> SEQ ID NO 132
<211> LENGTH: 3
<212> TYPE: PRT
<213> ORGANISM: Homo sapiens

<400> SEQUENCE: 132

Arg Asn Thr
1

<210> SEQ ID NO 133
<211> LENGTH: 17
<212> TYPE: PRT
<213> ORGANISM: Homo sapiens

<400> SEQUENCE: 133

Pro His Leu Thr Ser Asp Asp Val Asp Lys Ala Leu Gln Asn Ser Pro
1               5                   10                  15
Arg

<210> SEQ ID NO 134
<211> LENGTH: 18
<212> TYPE: PRT
<213> ORGANISM: Homo sapiens

<400> SEQUENCE: 134

Pro His Leu Thr Ser Asp Asp Val Asp Lys Ala Leu Gln Asn Ser Pro
1               5                   10                  15
Arg Leu

<210> SEQ ID NO 135
<211> LENGTH: 40
<212> TYPE: PRT
<213> ORGANISM: Homo sapiens

<400> SEQUENCE: 135

Thr Gln Arg Ile Thr Thr Arg Pro Asp Leu Pro Tyr Glu Pro Pro Arg
1               5                   10                  15
Arg Ser Ala Trp Thr Gly His Gly His Pro Thr Pro Gln Ser Lys Ala
            20                  25                  30
Ala Gln Pro Ser Pro Ser Thr Val
        35                  40

<210> SEQ ID NO 136
<211> LENGTH: 8

```
<212> TYPE: PRT
<213> ORGANISM: Homo sapiens

<400> SEQUENCE: 136

Asp Leu Pro Tyr Glu Pro Pro Arg
1               5

<210> SEQ ID NO 137
<211> LENGTH: 23
<212> TYPE: PRT
<213> ORGANISM: Homo sapiens

<400> SEQUENCE: 137

Ser Ala Trp Thr Gly His Gly His Pro Thr Pro Gln Ser Lys Ala Ala
1               5                   10                  15

Gln Pro Ser Pro Ser Thr Val
            20

<210> SEQ ID NO 138
<211> LENGTH: 7
<212> TYPE: PRT
<213> ORGANISM: Homo sapiens

<400> SEQUENCE: 138

Pro Tyr Glu Pro Pro Arg Arg
1               5

<210> SEQ ID NO 139
<211> LENGTH: 23
<212> TYPE: PRT
<213> ORGANISM: Homo sapiens

<400> SEQUENCE: 139

Ser Ala Trp Thr Gly His Gly His Pro Thr Pro Gln Ser Lys Ala Ala
1               5                   10                  15

Gln Pro Ser Pro Ser Thr Val
            20

<210> SEQ ID NO 140
<211> LENGTH: 23
<212> TYPE: PRT
<213> ORGANISM: Homo sapiens

<400> SEQUENCE: 140

Ser Ala Trp Thr Gly His Gly His Pro Thr Pro Gln Ser Lys Ala Ala
1               5                   10                  15

Gln Pro Ser Pro Ser Thr Val
            20

<210> SEQ ID NO 141
<211> LENGTH: 30
<212> TYPE: PRT
<213> ORGANISM: Homo sapiens

<400> SEQUENCE: 141

Pro Tyr Glu Pro Pro Arg Arg Ser Ala Trp Thr Gly His Gly His Pro
1               5                   10                  15

Thr Pro Gln Ser Lys Ala Ala Gln Pro Ser Pro Ser Thr Val
            20                  25                  30

<210> SEQ ID NO 142
<211> LENGTH: 23
<212> TYPE: PRT
```

```
<213> ORGANISM: Homo sapiens

<400> SEQUENCE: 142

Ser Ala Trp Thr Gly His Gly His Pro Thr Pro Gln Ser Lys Ala Ala
1               5                   10                  15

Gln Pro Ser Pro Ser Thr Val
            20

<210> SEQ ID NO 143
<211> LENGTH: 23
<212> TYPE: PRT
<213> ORGANISM: Homo sapiens

<400> SEQUENCE: 143

Ser Ala Trp Thr Gly His Gly His Pro Thr Pro Gln Ser Lys Ala Ala
1               5                   10                  15

Gln Pro Ser Pro Ser Thr Val
            20

<210> SEQ ID NO 144
<211> LENGTH: 9
<212> TYPE: PRT
<213> ORGANISM: Homo sapiens

<400> SEQUENCE: 144

Asp Leu Pro Tyr Glu Pro Pro Arg Arg
1               5

<210> SEQ ID NO 145
<211> LENGTH: 30
<212> TYPE: PRT
<213> ORGANISM: Homo sapiens

<400> SEQUENCE: 145

Pro Tyr Glu Pro Pro Arg Arg Ser Ala Trp Thr Gly His Gly His Pro
1               5                   10                  15

Thr Pro Gln Ser Lys Ala Ala Gln Pro Ser Pro Ser Thr Val
            20                  25                  30

<210> SEQ ID NO 146
<211> LENGTH: 32
<212> TYPE: PRT
<213> ORGANISM: Homo sapiens

<400> SEQUENCE: 146

Asp Leu Pro Tyr Glu Pro Pro Arg Arg Ser Ala Trp Thr Gly His Gly
1               5                   10                  15

His Pro Thr Pro Gln Ser Lys Ala Ala Gln Pro Ser Pro Ser Thr Val
            20                  25                  30

<210> SEQ ID NO 147
<211> LENGTH: 9
<212> TYPE: PRT
<213> ORGANISM: Homo sapiens

<400> SEQUENCE: 147

Asp Leu Pro Tyr Glu Pro Pro Arg Arg
1               5

<210> SEQ ID NO 148
<211> LENGTH: 32
<212> TYPE: PRT
<213> ORGANISM: Homo sapiens
```

<400> SEQUENCE: 148

Asp Leu Pro Tyr Glu Pro Pro Arg Arg Ser Ala Trp Thr Gly His Gly
1               5                   10                  15

His Pro Thr Pro Gln Ser Lys Ala Ala Gln Pro Ser Pro Ser Thr Val
            20                  25                  30

<210> SEQ ID NO 149
<211> LENGTH: 9
<212> TYPE: PRT
<213> ORGANISM: Homo sapiens

<400> SEQUENCE: 149

Ala Ala Gln Pro Ser Pro Ser Thr Val
1               5

<210> SEQ ID NO 150
<211> LENGTH: 23
<212> TYPE: PRT
<213> ORGANISM: Homo sapiens

<400> SEQUENCE: 150

Ser Ala Trp Thr Gly His Gly His Pro Thr Pro Gln Ser Lys Ala Ala
1               5                   10                  15

Gln Pro Ser Pro Ser Thr Val
            20

<210> SEQ ID NO 151
<211> LENGTH: 32
<212> TYPE: PRT
<213> ORGANISM: Homo sapiens

<400> SEQUENCE: 151

Asp Leu Pro Tyr Glu Pro Pro Arg Arg Ser Ala Trp Thr Gly His Gly
1               5                   10                  15

His Pro Thr Pro Gln Ser Lys Ala Ala Gln Pro Ser Pro Ser Thr Val
            20                  25                  30

<210> SEQ ID NO 152
<211> LENGTH: 40
<212> TYPE: PRT
<213> ORGANISM: Homo sapiens

<400> SEQUENCE: 152

Pro Lys Thr Glu Asp Gln Arg Pro Gln Leu Asp Pro Tyr Gln Ile Leu
1               5                   10                  15

Gly Pro Thr Ser Ser Arg Leu Ala Asn Pro Gly Ser Gly Gln Ile Gln
            20                  25                  30

Leu Trp Gln Phe Leu Leu Glu Leu
        35                  40

<210> SEQ ID NO 153
<211> LENGTH: 2
<212> TYPE: PRT
<213> ORGANISM: Homo sapiens

<400> SEQUENCE: 153

Pro Lys
1

<210> SEQ ID NO 154
<211> LENGTH: 20

```
<212> TYPE: PRT
<213> ORGANISM: Homo sapiens

<400> SEQUENCE: 154

Thr Glu Asp Gln Arg Pro Gln Leu Asp Pro Tyr Gln Ile Leu Gly Pro
1               5                   10                  15

Thr Ser Ser Arg
            20

<210> SEQ ID NO 155
<211> LENGTH: 22
<212> TYPE: PRT
<213> ORGANISM: Homo sapiens

<400> SEQUENCE: 155

Pro Lys Thr Glu Asp Gln Arg Pro Gln Leu Asp Pro Tyr Gln Ile Leu
1               5                   10                  15

Gly Pro Thr Ser Ser Arg
            20

<210> SEQ ID NO 156
<211> LENGTH: 22
<212> TYPE: PRT
<213> ORGANISM: Homo sapiens

<400> SEQUENCE: 156

Pro Lys Thr Glu Asp Gln Arg Pro Gln Leu Asp Pro Tyr Gln Ile Leu
1               5                   10                  15

Gly Pro Thr Ser Ser Arg
            20

<210> SEQ ID NO 157
<211> LENGTH: 22
<212> TYPE: PRT
<213> ORGANISM: Homo sapiens

<400> SEQUENCE: 157

Pro Lys Thr Glu Asp Gln Arg Pro Gln Leu Asp Pro Tyr Gln Ile Leu
1               5                   10                  15

Gly Pro Thr Ser Ser Arg
            20

<210> SEQ ID NO 158
<211> LENGTH: 22
<212> TYPE: PRT
<213> ORGANISM: Homo sapiens

<400> SEQUENCE: 158

Pro Lys Thr Glu Asp Gln Arg Pro Gln Leu Asp Pro Tyr Gln Ile Leu
1               5                   10                  15

Gly Pro Thr Ser Ser Arg
            20

<210> SEQ ID NO 159
<211> LENGTH: 22
<212> TYPE: PRT
<213> ORGANISM: Homo sapiens

<400> SEQUENCE: 159

Pro Lys Thr Glu Asp Gln Arg Pro Gln Leu Asp Pro Tyr Gln Ile Leu
1               5                   10                  15

Gly Pro Thr Ser Ser Arg
```

-continued

```
<210> SEQ ID NO 160
<211> LENGTH: 20
<212> TYPE: PRT
<213> ORGANISM: Homo sapiens

<400> SEQUENCE: 160

Thr Glu Asp Gln Arg Pro Gln Leu Asp Pro Tyr Gln Ile Leu Gly Pro
1               5                   10                  15

Thr Ser Ser Arg
            20

<210> SEQ ID NO 161
<211> LENGTH: 22
<212> TYPE: PRT
<213> ORGANISM: Homo sapiens

<400> SEQUENCE: 161

Pro Lys Thr Glu Asp Gln Arg Pro Gln Leu Asp Pro Tyr Gln Ile Leu
1               5                   10                  15

Gly Pro Thr Ser Ser Arg
            20

<210> SEQ ID NO 162
<211> LENGTH: 22
<212> TYPE: PRT
<213> ORGANISM: Homo sapiens

<400> SEQUENCE: 162

Pro Lys Thr Glu Asp Gln Arg Pro Gln Leu Asp Pro Tyr Gln Ile Leu
1               5                   10                  15

Gly Pro Thr Ser Ser Arg
            20

<210> SEQ ID NO 163
<211> LENGTH: 22
<212> TYPE: PRT
<213> ORGANISM: Homo sapiens

<400> SEQUENCE: 163

Pro Lys Thr Glu Asp Gln Arg Pro Gln Leu Asp Pro Tyr Gln Ile Leu
1               5                   10                  15

Gly Pro Thr Ser Ser Arg
            20

<210> SEQ ID NO 164
<211> LENGTH: 2
<212> TYPE: PRT
<213> ORGANISM: Homo sapiens

<400> SEQUENCE: 164

Pro Lys
1

<210> SEQ ID NO 165
<211> LENGTH: 22
<212> TYPE: PRT
<213> ORGANISM: Homo sapiens

<400> SEQUENCE: 165

Pro Lys Thr Glu Asp Gln Arg Pro Gln Leu Asp Pro Tyr Gln Ile Leu
1               5                   10                  15
```

Gly Pro Thr Ser Ser Arg
            20

<210> SEQ ID NO 166
<211> LENGTH: 22
<212> TYPE: PRT
<213> ORGANISM: Homo sapiens

<400> SEQUENCE: 166

Pro Lys Thr Glu Asp Gln Arg Pro Gln Leu Asp Pro Tyr Gln Ile Leu
1               5                   10                  15

Gly Pro Thr Ser Ser Arg
            20

<210> SEQ ID NO 167
<211> LENGTH: 2
<212> TYPE: PRT
<213> ORGANISM: Homo sapiens

<400> SEQUENCE: 167

Pro Lys
1

<210> SEQ ID NO 168
<211> LENGTH: 40
<212> TYPE: PRT
<213> ORGANISM: Homo sapiens

<400> SEQUENCE: 168

Leu Ser Asp Ser Ser Asn Ser Ser Cys Ile Thr Trp Glu Gly Thr Asn
1               5                   10                  15

Gly Glu Phe Lys Met Thr Asp Pro Asp Glu Val Ala Arg Arg Trp Gly
            20                  25                  30

Glu Arg Lys Ser Lys Pro Asn Met
        35                  40

<210> SEQ ID NO 169
<211> LENGTH: 9
<212> TYPE: PRT
<213> ORGANISM: Homo sapiens

<400> SEQUENCE: 169

Met Thr Asp Pro Asp Glu Val Ala Arg
1               5

<210> SEQ ID NO 170
<211> LENGTH: 9
<212> TYPE: PRT
<213> ORGANISM: Homo sapiens

<400> SEQUENCE: 170

Met Thr Asp Pro Asp Glu Val Ala Arg
1               5

<210> SEQ ID NO 171
<211> LENGTH: 9
<212> TYPE: PRT
<213> ORGANISM: Homo sapiens

<400> SEQUENCE: 171

Met Thr Asp Pro Asp Glu Val Ala Arg
1               5

```
<210> SEQ ID NO 172
<211> LENGTH: 9
<212> TYPE: PRT
<213> ORGANISM: Homo sapiens

<400> SEQUENCE: 172

Met Thr Asp Pro Asp Glu Val Ala Arg
1               5

<210> SEQ ID NO 173
<211> LENGTH: 9
<212> TYPE: PRT
<213> ORGANISM: Homo sapiens

<400> SEQUENCE: 173

Met Thr Asp Pro Asp Glu Val Ala Arg
1               5

<210> SEQ ID NO 174
<211> LENGTH: 10
<212> TYPE: PRT
<213> ORGANISM: Homo sapiens

<400> SEQUENCE: 174

Met Thr Asp Pro Asp Glu Val Ala Arg Arg
1               5                   10

<210> SEQ ID NO 175
<211> LENGTH: 15
<212> TYPE: PRT
<213> ORGANISM: Homo sapiens

<400> SEQUENCE: 175

Thr Asp Pro Asp Glu Val Ala Arg Arg Lys Ser Lys Pro Asn Met
1               5                   10                  15

<210> SEQ ID NO 176
<211> LENGTH: 9
<212> TYPE: PRT
<213> ORGANISM: Homo sapiens

<400> SEQUENCE: 176

Met Thr Asp Pro Asp Glu Val Ala Arg
1               5

<210> SEQ ID NO 177
<211> LENGTH: 6
<212> TYPE: PRT
<213> ORGANISM: Homo sapiens

<400> SEQUENCE: 177

Lys Ser Lys Pro Asn Met
1               5

<210> SEQ ID NO 178
<211> LENGTH: 40
<212> TYPE: PRT
<213> ORGANISM: Homo sapiens

<400> SEQUENCE: 178

Asn Tyr Asp Lys Leu Ser Arg Ala Leu Arg Tyr Tyr Tyr Asp Lys Asn
1               5                   10                  15

Ile Met Thr Lys Val His Gly Lys Arg Tyr Ala Tyr Lys Phe Asp Phe
            20                  25                  30
```

His Gly Ile Ala Gln Ala Leu Gln
        35                  40

<210> SEQ ID NO 179
<211> LENGTH: 11
<212> TYPE: PRT
<213> ORGANISM: Homo sapiens

<400> SEQUENCE: 179

Phe Asp Phe His Gly Ile Ala Gln Ala Leu Gln
1               5                   10

<210> SEQ ID NO 180
<211> LENGTH: 11
<212> TYPE: PRT
<213> ORGANISM: Homo sapiens

<400> SEQUENCE: 180

Phe Asp Phe His Gly Ile Ala Gln Ala Leu Gln
1               5                   10

<210> SEQ ID NO 181
<211> LENGTH: 11
<212> TYPE: PRT
<213> ORGANISM: Homo sapiens

<400> SEQUENCE: 181

Phe Asp Phe His Gly Ile Ala Gln Ala Leu Gln
1               5                   10

<210> SEQ ID NO 182
<211> LENGTH: 11
<212> TYPE: PRT
<213> ORGANISM: Homo sapiens

<400> SEQUENCE: 182

Phe Asp Phe His Gly Ile Ala Gln Ala Leu Gln
1               5                   10

<210> SEQ ID NO 183
<211> LENGTH: 25
<212> TYPE: PRT
<213> ORGANISM: Homo sapiens

<400> SEQUENCE: 183

Tyr Tyr Tyr Asp Lys Asn Ile Met Thr Lys Tyr Ala Tyr Lys Phe Asp
1               5                   10                  15

Phe His Gly Ile Ala Gln Ala Leu Gln
            20                  25

<210> SEQ ID NO 184
<211> LENGTH: 7
<212> TYPE: PRT
<213> ORGANISM: Homo sapiens

<400> SEQUENCE: 184

Asn Tyr Asp Lys Leu Ser Arg
1               5

<210> SEQ ID NO 185
<211> LENGTH: 17
<212> TYPE: PRT
<213> ORGANISM: Homo sapiens

<400> SEQUENCE: 185

Asn Tyr Asp Lys Leu Ser Arg Tyr Tyr Asp Lys Asn Ile Met Thr
1               5                   10                  15

Lys

<210> SEQ ID NO 186
<211> LENGTH: 40
<212> TYPE: PRT
<213> ORGANISM: Homo sapiens

<400> SEQUENCE: 186

Pro His Pro Pro Glu Ser Ser Leu Tyr Lys Tyr Pro Ser Asp Leu Pro
1               5                   10                  15

Tyr Met Gly Ser Tyr His Ala His Pro Gln Lys Met Asn Phe Val Ala
            20                  25                  30

Pro His Pro Pro Ala Leu Pro Val
            35                  40

<210> SEQ ID NO 187
<211> LENGTH: 10
<212> TYPE: PRT
<213> ORGANISM: Homo sapiens

<400> SEQUENCE: 187

Pro His Pro Pro Glu Ser Ser Leu Tyr Lys
1               5                   10

<210> SEQ ID NO 188
<211> LENGTH: 24
<212> TYPE: PRT
<213> ORGANISM: Homo sapiens

<400> SEQUENCE: 188

Pro His Pro Pro Glu Ser Ser Leu Tyr Lys Tyr Pro Ser Asp Leu Pro
1               5                   10                  15

Tyr Met Gly Ser Tyr His Ala His
            20

<210> SEQ ID NO 189
<211> LENGTH: 27
<212> TYPE: PRT
<213> ORGANISM: Homo sapiens

<400> SEQUENCE: 189

Pro His Pro Pro Glu Ser Ser Leu Tyr Lys Tyr Pro Ser Asp Leu Pro
1               5                   10                  15

Tyr Met Gly Ser Tyr His Ala His Pro Gln Lys
            20                  25

<210> SEQ ID NO 190
<211> LENGTH: 27
<212> TYPE: PRT
<213> ORGANISM: Homo sapiens

<400> SEQUENCE: 190

Pro His Pro Pro Glu Ser Ser Leu Tyr Lys Tyr Pro Ser Asp Leu Pro
1               5                   10                  15

Tyr Met Gly Ser Tyr His Ala His Pro Gln Lys
            20                  25

<210> SEQ ID NO 191

<211> LENGTH: 17
<212> TYPE: PRT
<213> ORGANISM: Homo sapiens

<400> SEQUENCE: 191

Tyr Pro Ser Asp Leu Pro Tyr Met Gly Ser Tyr His Ala His Pro Gln
1               5                   10                  15

Lys

<210> SEQ ID NO 192
<211> LENGTH: 27
<212> TYPE: PRT
<213> ORGANISM: Homo sapiens

<400> SEQUENCE: 192

Pro His Pro Pro Glu Ser Ser Leu Tyr Lys Tyr Pro Ser Asp Leu Pro
1               5                   10                  15

Tyr Met Gly Ser Tyr His Ala His Pro Gln Lys
            20                  25

<210> SEQ ID NO 193
<211> LENGTH: 39
<212> TYPE: PRT
<213> ORGANISM: Homo sapiens

<400> SEQUENCE: 193

Thr Ser Ser Ser Phe Phe Ala Ala Pro Asn Pro Tyr Trp Asn Ser Pro
1               5                   10                  15

Thr Gly Gly Ile Tyr Pro Asn Thr Arg Leu Pro Thr Ser His Met Pro
            20                  25                  30

Ser His Leu Gly Thr Tyr Tyr
        35

<210> SEQ ID NO 194
<211> LENGTH: 5
<212> TYPE: PRT
<213> ORGANISM: Homo sapiens

<400> SEQUENCE: 194

Asn Ser Pro Thr Gly
1               5

<210> SEQ ID NO 195
<211> LENGTH: 11
<212> TYPE: PRT
<213> ORGANISM: Homo sapiens

<400> SEQUENCE: 195

Ser Pro Thr Gly Gly Ile Tyr Pro Asn Thr Arg
1               5                   10

<210> SEQ ID NO 196
<211> LENGTH: 24
<212> TYPE: PRT
<213> ORGANISM: Homo sapiens

<400> SEQUENCE: 196

Gly Gly Ala Ala Phe Ile Phe Pro Asn Thr Ser Val Tyr Pro Glu Ala
1               5                   10                  15

Thr Gln Arg Ile Thr Thr Arg Pro
            20

<210> SEQ ID NO 197
<211> LENGTH: 10
<212> TYPE: PRT
<213> ORGANISM: Homo sapiens

<400> SEQUENCE: 197

Val Pro Gln Gln Asp Trp Leu Ser Gln Pro
1               5                   10

<210> SEQ ID NO 198
<211> LENGTH: 10
<212> TYPE: PRT
<213> ORGANISM: Homo sapiens

<400> SEQUENCE: 198

Val Pro Gln Gln Asp Trp Leu Ser Gln Pro
1               5                   10

<210> SEQ ID NO 199
<211> LENGTH: 12
<212> TYPE: PRT
<213> ORGANISM: Homo sapiens

<400> SEQUENCE: 199

Met Ile Gln Thr Val Pro Asp Pro Ala Ala His Ile
1               5                   10

<210> SEQ ID NO 200
<211> LENGTH: 55
<212> TYPE: PRT
<213> ORGANISM: Homo sapiens

<400> SEQUENCE: 200

Met Ala Ser Thr Ile Lys Glu Ala Leu Ser Val Val Ser Glu Asp Gln
1               5                   10                  15

Ser Leu Phe Glu Cys Ala Tyr Gly Thr Pro His Leu Ala Lys Thr Glu
                20                  25                  30

Met Thr Ala Tyr Gly Gln Thr Ser Lys Met Ser Pro Arg Val Pro Gln
            35                  40                  45

Gln Asp Trp Leu Ser Gln Pro
        50                  55

<210> SEQ ID NO 201
<211> LENGTH: 12
<212> TYPE: PRT
<213> ORGANISM: Homo sapiens

<400> SEQUENCE: 201

Met Ile Gln Thr Val Pro Asp Pro Ala Ala His Ile
1               5                   10

<210> SEQ ID NO 202
<211> LENGTH: 23
<212> TYPE: DNA
<213> ORGANISM: Homo sapiens

<400> SEQUENCE: 202
gctgcagact tggccaaatg gac                                    23

<210> SEQ ID NO 203
<211> LENGTH: 23
<212> TYPE: DNA
<213> ORGANISM: Homo sapiens

<400> SEQUENCE: 203
tcaccaccga cagagcctcc tta                                    23

<210> SEQ ID NO 204
<211> LENGTH: 26
<212> TYPE: DNA
<213> ORGANISM: Homo sapiens

<400> SEQUENCE: 204
accacatgaa tggatccagg gagtct                                 26

<210> SEQ ID NO 205
<211> LENGTH: 24
<212> TYPE: DNA
<213> ORGANISM: Homo sapiens

<400> SEQUENCE: 205
accagcttgc tgcatttgct aacg                                   24

<210> SEQ ID NO 206
<211> LENGTH: 20
<212> TYPE: DNA
<213> ORGANISM: Homo sapiens

<400> SEQUENCE: 206
ctccgcgcca ccaccctcta                                        20

<210> SEQ ID NO 207
<211> LENGTH: 24
<212> TYPE: DNA
<213> ORGANISM: Homo sapiens

<400> SEQUENCE: 207
ggccagcagt gaactttccc tgag                                   24

<210> SEQ ID NO 208
<211> LENGTH: 23
<212> TYPE: DNA
<213> ORGANISM: Homo sapiens

<400> SEQUENCE: 208
ctcctcccaa catgaccacc aac                                    23

<210> SEQ ID NO 209
<211> LENGTH: 22
<212> TYPE: DNA
<213> ORGANISM: Homo sapiens

<400> SEQUENCE: 209
gtctgcgggg acgatgactc tc                                     22

<210> SEQ ID NO 210
<211> LENGTH: 23
<212> TYPE: DNA
<213> ORGANISM: Homo sapiens

<400> SEQUENCE: 210
catgtgaggc aatggctgga gtg                                    23

<210> SEQ ID NO 211
<211> LENGTH: 26
<212> TYPE: DNA
<213> ORGANISM: Homo sapiens

```
<400> SEQUENCE: 211
ccatgttctg gaaaaaggat gtgtcg                                          26

<210> SEQ ID NO 212
<211> LENGTH: 21
<212> TYPE: DNA
<213> ORGANISM: Homo sapiens

<400> SEQUENCE: 212
ccttggaggg gcacaaacga t                                               21

<210> SEQ ID NO 213
<211> LENGTH: 22
<212> TYPE: DNA
<213> ORGANISM: Homo sapiens

<400> SEQUENCE: 213
ggtcgggccc aggatctgat ac                                              22

<210> SEQ ID NO 214
<211> LENGTH: 21
<212> TYPE: DNA
<213> ORGANISM: Homo sapiens

<400> SEQUENCE: 214
cgccaacgcc agctgtatca c                                               21

<210> SEQ ID NO 215
<211> LENGTH: 19
<212> TYPE: DNA
<213> ORGANISM: Homo sapiens

<400> SEQUENCE: 215
agcgcctggc cacctcatc                                                  19

<210> SEQ ID NO 216
<211> LENGTH: 30
<212> TYPE: DNA
<213> ORGANISM: Homo sapiens

<400> SEQUENCE: 216
atgtttttat gaccaaagca gtttcttgtc                                      30

<210> SEQ ID NO 217
<211> LENGTH: 27
<212> TYPE: DNA
<213> ORGANISM: Homo sapiens

<400> SEQUENCE: 217
atgacgggtt aagtccatga ttctgtg                                         27

<210> SEQ ID NO 218
<211> LENGTH: 21
<212> TYPE: DNA
<213> ORGANISM: Homo sapiens

<400> SEQUENCE: 218
cgaaagctgc tcaaccatct c                                               21

<210> SEQ ID NO 219
<211> LENGTH: 22
<212> TYPE: DNA
```

```
<213> ORGANISM: Homo sapiens

<400> SEQUENCE: 219
taactgagga cgctggtctt ca                                    22

<210> SEQ ID NO 220
<211> LENGTH: 15
<212> TYPE: DNA
<213> ORGANISM: Homo sapiens

<400> SEQUENCE: 220
ccacagtgcc caaaa                                            15

<210> SEQ ID NO 221

<400> SEQUENCE: 221

000

<210> SEQ ID NO 222
<211> LENGTH: 25
<212> TYPE: DNA
<213> ORGANISM: Homo sapiens

<400> SEQUENCE: 222
cggcaaaaga tatgcttaca aattt                                 25

<210> SEQ ID NO 223
<211> LENGTH: 19
<212> TYPE: DNA
<213> ORGANISM: Homo sapiens

<400> SEQUENCE: 223
gacgactcgg tcggatgtg                                        19

<210> SEQ ID NO 224
<211> LENGTH: 14
<212> TYPE: DNA
<213> ORGANISM: Homo sapiens

<400> SEQUENCE: 224
cacggcattg ccca                                             14

<210> SEQ ID NO 225
<211> LENGTH: 17
<212> TYPE: DNA
<213> ORGANISM: Homo sapiens

<400> SEQUENCE: 225
cgcggcagga agcctta                                          17

<210> SEQ ID NO 226
<211> LENGTH: 22
<212> TYPE: DNA
<213> ORGANISM: Homo sapiens

<400> SEQUENCE: 226
tccgtaggca cactcaaaca ac                                    22

<210> SEQ ID NO 227
<211> LENGTH: 18
<212> TYPE: DNA
<213> ORGANISM: Homo sapiens
```

```
<400> SEQUENCE: 227
cagttgtgag tgaggacc                                                      18

<210> SEQ ID NO 228
<211> LENGTH: 25
<212> TYPE: DNA
<213> ORGANISM: Homo sapiens

<400> SEQUENCE: 228
gctcgctccg atactattat gagaa                                              25

<210> SEQ ID NO 229
<211> LENGTH: 25
<212> TYPE: DNA
<213> ORGANISM: Homo sapiens

<400> SEQUENCE: 229
cacacacaaa cttgtacacg taacg                                              25

<210> SEQ ID NO 230
<211> LENGTH: 16
<212> TYPE: DNA
<213> ORGANISM: Homo sapiens

<400> SEQUENCE: 230
accagccacc ttctgc                                                        16

<210> SEQ ID NO 231
<211> LENGTH: 25
<212> TYPE: DNA
<213> ORGANISM: Homo sapiens

<400> SEQUENCE: 231
ggtcgaggca tggaatttaa actga                                              25

<210> SEQ ID NO 232
<211> LENGTH: 22
<212> TYPE: DNA
<213> ORGANISM: Homo sapiens

<400> SEQUENCE: 232
gctggcctgt ttttctgaat gc                                                 22

<210> SEQ ID NO 233
<211> LENGTH: 15
<212> TYPE: DNA
<213> ORGANISM: Homo sapiens

<400> SEQUENCE: 233
tcgggccacc tcttc                                                         15

<210> SEQ ID NO 234
<211> LENGTH: 12
<212> TYPE: PRT
<213> ORGANISM: Homo sapiens

<400> SEQUENCE: 234

Met Ile Gln Thr Val Pro Asp Pro Ala Ala His Ile
 1               5                  10

<210> SEQ ID NO 235
<211> LENGTH: 23
<212> TYPE: PRT
```

```
<213> ORGANISM: Homo sapiens

<400> SEQUENCE: 235

Ser Ala Trp Thr Gly His Gly His Pro Thr Pro Gln Ser Lys Ala Ala
1               5                   10                  15

Gln Pro Ser Pro Ser Thr Val
            20

<210> SEQ ID NO 236
<211> LENGTH: 42
<212> TYPE: PRT
<213> ORGANISM: Homo sapiens
<220> FEATURE:
<221> NAME/KEY: NON_CONS
<222> LOCATION: (18)..(19)

<400> SEQUENCE: 236

Met Ile Gln Thr Val Pro Asp Pro Ala Ala Ser His Ile Lys Glu Ala
1               5                   10                  15

Leu Ser Gly Gly Ala Ala Phe Ile Phe Pro Asn Thr Ser Val Tyr Pro
            20                  25                  30

Glu Ala Thr Gln Arg Ile Thr Thr Arg Pro
        35                  40

<210> SEQ ID NO 237
<211> LENGTH: 18
<212> TYPE: PRT
<213> ORGANISM: Homo sapiens

<400> SEQUENCE: 237

Met Ile Gln Thr Val Pro Asp Pro Ala Ala Ser His Ile Lys Glu Ala
1               5                   10                  15

Leu Ser

<210> SEQ ID NO 238
<211> LENGTH: 42
<212> TYPE: PRT
<213> ORGANISM: Homo sapiens
<220> FEATURE:
<221> NAME/KEY: NON_CONS
<222> LOCATION: (10)..(11)
<220> FEATURE:
<221> NAME/KEY: NON_CONS
<222> LOCATION: (14)..(15)
<220> FEATURE:
<221> NAME/KEY: NON_CONS
<222> LOCATION: (18)..(19)

<400> SEQUENCE: 238

Met Ala Ser Thr Ile Lys Glu Ala Leu Ser Met Thr Ala Ser Met Ser
1               5                   10                  15

Pro Arg Gly Gly Ala Ala Phe Ile Phe Pro Asn Thr Ser Val Tyr Pro
            20                  25                  30

Glu Ala Thr Gln Arg Ile Thr Thr Arg Pro
        35                  40

<210> SEQ ID NO 239
<211> LENGTH: 18
<212> TYPE: PRT
<213> ORGANISM: Homo sapiens
<220> FEATURE:
<221> NAME/KEY: NON_CONS
<222> LOCATION: (10)..(11)
<220> FEATURE:
<221> NAME/KEY: NON_CONS
```

<222> LOCATION: (14)..(15)

<400> SEQUENCE: 239

| | | | | | | | | | | | | | | |
|---|---|---|---|---|---|---|---|---|---|---|---|---|---|---|
| Met | Ala | Ser | Thr | Ile | Lys | Glu | Ala | Leu | Ser | Met | Thr | Ala | Ser | Met | Ser |
| 1 | | | | 5 | | | | | 10 | | | | | 15 | |
| Pro | Arg | | | | | | | | | | | | | | |

<210> SEQ ID NO 240
<211> LENGTH: 479
<212> TYPE: PRT
<213> ORGANISM: Homo sapiens

<400> SEQUENCE: 240

| | | | | | | | | | | | | | | |
|---|---|---|---|---|---|---|---|---|---|---|---|---|---|---|
| Met | Ala | Ser | Thr | Ile | Lys | Glu | Ala | Leu | Ser | Val | Val | Ser | Glu | Asp | Gln |
| 1 | | | | 5 | | | | | 10 | | | | | 15 | |
| Ser | Leu | Phe | Glu | Cys | Ala | Tyr | Gly | Thr | Pro | His | Leu | Ala | Lys | Thr | Glu |
| | | | 20 | | | | | 25 | | | | | 30 | | |
| Met | Thr | Ala | Ser | Ser | Ser | Asp | Tyr | Gly | Gln | Thr | Ser | Lys | Met | Ser | |
| | | 35 | | | | | 40 | | | | | 45 | | | |
| Pro | Arg | Val | Pro | Gln | Gln | Asp | Trp | Leu | Ser | Gln | Pro | Pro | Ala | Arg | Val |
| 50 | | | | | 55 | | | | | 60 | | | | | |
| Thr | Ile | Lys | Met | Glu | Cys | Asn | Pro | Ser | Gln | Val | Asn | Gly | Ser | Arg | Asn |
| 65 | | | | | 70 | | | | | 75 | | | | | 80 |
| Ser | Pro | Asp | Glu | Cys | Ser | Val | Ala | Lys | Gly | Gly | Lys | Met | Val | Gly | Ser |
| | | | | 85 | | | | | 90 | | | | | 95 | |
| Pro | Asp | Thr | Val | Gly | Met | Asn | Tyr | Gly | Ser | Tyr | Met | Glu | Glu | Lys | His |
| | | | 100 | | | | | 105 | | | | | 110 | | |
| Met | Pro | Pro | Pro | Asn | Met | Thr | Thr | Asn | Glu | Arg | Arg | Val | Ile | Val | Pro |
| | | 115 | | | | | 120 | | | | | 125 | | | |
| Ala | Asp | Pro | Thr | Leu | Trp | Ser | Thr | Asp | His | Val | Arg | Gln | Trp | Leu | Glu |
| 130 | | | | | 135 | | | | | 140 | | | | | |
| Trp | Ala | Val | Lys | Glu | Tyr | Gly | Leu | Pro | Asp | Val | Asn | Ile | Leu | Leu | Phe |
| 145 | | | | | 150 | | | | | 155 | | | | | 160 |
| Gln | Asn | Ile | Asp | Gly | Lys | Glu | Leu | Cys | Lys | Met | Thr | Lys | Asp | Asp | Phe |
| | | | | 165 | | | | | 170 | | | | | 175 | |
| Gln | Arg | Leu | Thr | Pro | Ser | Tyr | Asn | Ala | Asp | Ile | Leu | Leu | Ser | His | Leu |
| | | | 180 | | | | | 185 | | | | | 190 | | |
| His | Tyr | Leu | Arg | Glu | Thr | Pro | Leu | Pro | His | Leu | Thr | Ser | Asp | Asp | Val |
| | | | | 195 | | | | | 200 | | | | | 205 | |
| Asp | Lys | Ala | Leu | Gln | Asn | Ser | Pro | Arg | Leu | Met | His | Ala | Arg | Asn | Thr |
| | 210 | | | | | 215 | | | | | 220 | | | | |
| Gly | Gly | Ala | Ala | Phe | Ile | Phe | Pro | Asn | Thr | Ser | Val | Tyr | Pro | Glu | Ala |
| 225 | | | | | 230 | | | | | 235 | | | | | 240 |
| Thr | Gln | Arg | Ile | Thr | Thr | Arg | Pro | Asp | Leu | Pro | Tyr | Glu | Pro | Pro | Arg |
| | | | | 245 | | | | | 250 | | | | | 255 | |
| Arg | Ser | Ala | Trp | Thr | Gly | His | Gly | His | Pro | Thr | Pro | Gln | Ser | Lys | Ala |
| | | | 260 | | | | | 265 | | | | | 270 | | |
| Ala | Gln | Pro | Ser | Pro | Ser | Thr | Val | Pro | Lys | Thr | Glu | Asp | Gln | Arg | Pro |
| | 275 | | | | | 280 | | | | | 285 | | | | |
| Gln | Leu | Asp | Pro | Tyr | Gln | Ile | Leu | Gly | Pro | Thr | Ser | Ser | Arg | Leu | Ala |
| | 290 | | | | | 295 | | | | | 300 | | | | |
| Asn | Pro | Gly | Ser | Gly | Gln | Ile | Gln | Leu | Trp | Gln | Phe | Leu | Leu | Glu | Leu |
| 305 | | | | | 310 | | | | | 315 | | | | | 320 |
| Leu | Ser | Asp | Ser | Ser | Asn | Ser | Ser | Cys | Ile | Thr | Trp | Glu | Gly | Thr | Asn |
| | | | | 325 | | | | | 330 | | | | | 335 | |

```
Gly Glu Phe Lys Met Thr Asp Pro Asp Glu Val Ala Arg Arg Trp Gly
            340                 345                 350
Glu Arg Lys Ser Lys Pro Asn Met Asn Tyr Asp Lys Leu Ser Arg Ala
            355                 360                 365
Leu Arg Tyr Tyr Tyr Asp Lys Asn Ile Met Thr Lys Val His Gly Lys
370                 375                 380
Arg Tyr Ala Tyr Lys Phe Asp Phe His Gly Ile Ala Gln Ala Leu Gln
385                 390                 395                 400
Pro His Pro Pro Glu Ser Ser Leu Tyr Lys Tyr Pro Ser Asp Leu Pro
                405                 410                 415
Tyr Met Gly Ser Tyr His Ala His Pro Gln Lys Met Asn Phe Val Ala
                420                 425                 430
Pro His Pro Pro Ala Leu Pro Val Thr Ser Ser Ser Phe Phe Ala Ala
                435                 440                 445
Pro Asn Pro Tyr Trp Asn Ser Pro Thr Gly Gly Ile Tyr Pro Asn Thr
            450                 455                 460
Arg Leu Pro Thr Ser His Met Pro Ser His Leu Gly Thr Tyr Tyr
465                 470                 475

<210> SEQ ID NO 241
<211> LENGTH: 13
<212> TYPE: PRT
<213> ORGANISM: Homo sapiens

<400> SEQUENCE: 241

Gly Ala Ala Phe Ile Phe Pro Asn Thr Ser Val Tyr Pro
1               5                   10

<210> SEQ ID NO 242
<211> LENGTH: 477
<212> TYPE: PRT
<213> ORGANISM: Homo sapiens

<400> SEQUENCE: 242

Met Asp Gly Phe Tyr Asp Gln Gln Val Pro Tyr Met Val Thr Asn Ser
1               5                   10                  15
Gln Arg Gly Arg Asn Cys Asn Glu Lys Pro Thr Asn Val Arg Lys Arg
            20                  25                  30
Lys Phe Ile Asn Arg Asp Leu Ala His Asp Ser Glu Glu Leu Phe Gln
            35                  40                  45
Asp Leu Ser Gln Leu Gln Glu Thr Trp Leu Ala Glu Ala Gln Val Pro
        50                  55                  60
Asp Asn Asp Glu Gln Phe Val Pro Asp Tyr Gln Ala Glu Ser Leu Ala
65                  70                  75                  80
Phe His Gly Leu Pro Leu Lys Ile Lys Lys Glu Pro His Ser Pro Cys
                85                  90                  95
Ser Glu Ile Ser Ser Ala Cys Ser Gln Glu Gln Pro Phe Lys Phe Ser
                100                 105                 110
Tyr Gly Glu Lys Cys Leu Tyr Asn Val Ser Ala Tyr Asp Gln Lys Pro
            115                 120                 125
Gln Val Gly Met Arg Pro Ser Asn Pro Pro Thr Pro Ser Ser Thr Pro
            130                 135                 140
Val Ser Pro Leu His His Ala Ser Pro Asn Ser Thr His Thr Pro Lys
145                 150                 155                 160
Pro Asp Arg Ala Phe Pro Ala His Leu Pro Pro Ser Gln Ser Ile Pro
                165                 170                 175
```

-continued

```
Asp Ser Ser Tyr Pro Met Asp His Arg Phe Arg Arg Gln Leu Ser Glu
            180                 185                 190

Pro Cys Asn Ser Phe Pro Pro Leu Pro Thr Met Pro Arg Glu Gly Arg
            195                 200                 205

Pro Met Tyr Gln Arg Gln Met Ser Glu Pro Asn Ile Pro Phe Pro Pro
            210                 215                 220

Gln Gly Phe Lys Gln Glu Tyr His Asp Pro Val Tyr Glu His Asn Thr
225                 230                 235                 240

Met Val Gly Ser Ala Ala Ser Gln Ser Phe Pro Pro Leu Met Ile
                245                 250                 255

Lys Gln Glu Pro Arg Asp Phe Ala Tyr Asp Ser Glu Val Pro Ser Cys
            260                 265                 270

His Ser Ile Tyr Met Arg Gln Glu Gly Phe Leu Ala His Pro Ser Arg
            275                 280                 285

Thr Glu Gly Cys Met Phe Glu Lys Gly Pro Arg Gln Phe Tyr Asp Asp
            290                 295                 300

Thr Cys Val Val Pro Glu Lys Phe Asp Gly Asp Ile Lys Gln Glu Pro
305                 310                 315                 320

Gly Met Tyr Arg Glu Gly Pro Thr Tyr Gln Arg Arg Gly Ser Leu Gln
            325                 330                 335

Leu Trp Gln Phe Leu Val Ala Leu Leu Asp Asp Pro Ser Asn Ser His
            340                 345                 350

Phe Ile Ala Trp Thr Gly Arg Gly Met Glu Phe Lys Leu Ile Glu Pro
            355                 360                 365

Glu Glu Val Ala Arg Arg Trp Gly Ile Gln Lys Asn Arg Pro Ala Met
            370                 375                 380

Asn Tyr Asp Lys Leu Ser Arg Ser Leu Arg Tyr Tyr Tyr Glu Lys Gly
385                 390                 395                 400

Ile Met Gln Lys Val Ala Gly Glu Arg Tyr Val Tyr Lys Phe Val Cys
            405                 410                 415

Asp Pro Glu Ala Leu Phe Ser Met Ala Phe Pro Asp Asn Gln Arg Pro
            420                 425                 430

Leu Leu Lys Thr Asp Met Glu Arg His Ile Asn Glu Glu Asp Thr Val
            435                 440                 445

Pro Leu Ser His Phe Asp Glu Ser Met Ala Tyr Met Pro Glu Gly Gly
            450                 455                 460

Cys Cys Asn Pro His Pro Tyr Asn Glu Gly Tyr Val Tyr
465                 470                 475

<210> SEQ ID NO 243
<211> LENGTH: 14
<212> TYPE: PRT
<213> ORGANISM: Homo sapiens

<400> SEQUENCE: 243

Pro His Ser Pro Cys Ser Glu Ile Ser Ser Ala Cys Ser Gln
1               5                   10

<210> SEQ ID NO 244
<211> LENGTH: 13
<212> TYPE: PRT
<213> ORGANISM: Homo sapiens

<400> SEQUENCE: 244

Thr Pro Ser Ser Thr Pro Val Ser Pro Leu His His Ala
1               5                   10
```

<210> SEQ ID NO 245
<211> LENGTH: 16
<212> TYPE: PRT
<213> ORGANISM: Homo sapiens

<400> SEQUENCE: 245

Arg Ala Phe Pro Ala His Leu Pro Pro Ser Gln Ser Ile Pro Asp Ser
1               5                   10                  15

<210> SEQ ID NO 246
<211> LENGTH: 452
<212> TYPE: PRT
<213> ORGANISM: Homo sapiens

<400> SEQUENCE: 246

Met Asp Gly Thr Ile Lys Glu Ala Leu Ser Val Val Ser Asp Asp Gln
1               5                   10                  15

Ser Leu Phe Asp Ser Ala Tyr Gly Ala Ala His Leu Pro Lys Ala
            20                  25                  30

Asp Met Thr Ala Ser Gly Ser Pro Asp Tyr Gly Gln Pro His Lys Ile
            35                  40                  45

Asn Pro Leu Pro Pro Gln Gln Glu Trp Ile Asn Gln Pro Val Arg Val
        50                  55                  60

Asn Val Lys Arg Glu Tyr Asp His Met Asn Gly Ser Arg Glu Ser Pro
65                  70                  75                  80

Val Asp Cys Ser Val Ser Lys Cys Ser Lys Leu Val Gly Gly Gly Glu
                85                  90                  95

Ser Asn Pro Met Asn Tyr Asn Ser Tyr Met Asp Glu Lys Asn Gly Pro
            100                 105                 110

Pro Pro Pro Asn Met Thr Thr Asn Glu Arg Arg Val Ile Val Pro Ala
        115                 120                 125

Asp Pro Thr Leu Trp Thr Gln Glu His Val Arg Gln Trp Leu Glu Trp
    130                 135                 140

Ala Ile Lys Glu Tyr Ser Leu Met Glu Ile Asp Thr Ser Phe Phe Gln
145                 150                 155                 160

Asn Met Asp Gly Lys Glu Leu Cys Lys Met Asn Lys Glu Asp Phe Leu
                165                 170                 175

Arg Ala Thr Thr Leu Tyr Asn Thr Glu Val Leu Leu Ser His Leu Ser
            180                 185                 190

Tyr Leu Arg Glu Ser Ser Leu Leu Ala Tyr Asn Thr Thr Ser His Thr
        195                 200                 205

Asp Gln Ser Ser Arg Leu Ser Val Lys Glu Asp Pro Ser Tyr Asp Ser
    210                 215                 220

Val Arg Arg Gly Ala Trp Gly Asn Asn Met Asn Ser Gly Leu Asn Lys
225                 230                 235                 240

Ser Pro Pro Leu Gly Gly Ala Gln Thr Ile Ser Lys Asn Thr Glu Gln
                245                 250                 255

Arg Pro Gln Pro Asp Pro Tyr Gln Ile Leu Gly Pro Thr Ser Ser Arg
            260                 265                 270

Leu Ala Asn Pro Gly Ser Gly Gln Ile Gln Leu Trp Gln Phe Leu Leu
        275                 280                 285

Glu Leu Leu Ser Asp Ser Ala Asn Ala Ser Cys Ile Thr Trp Glu Gly
    290                 295                 300

Thr Asn Gly Glu Phe Lys Met Thr Asp Pro Asp Glu Val Ala Arg Arg
305                 310                 315                 320

```
Trp Gly Glu Arg Lys Ser Lys Pro Asn Met Asn Tyr Asp Lys Leu Ser
            325                 330                 335

Arg Ala Leu Arg Tyr Tyr Asp Lys Asn Ile Met Thr Lys Val His
            340                 345                 350

Gly Lys Arg Tyr Ala Tyr Lys Phe Asp Phe His Gly Ile Ala Gln Ala
            355                 360                 365

Leu Gln Pro His Pro Thr Glu Ser Ser Met Tyr Lys Tyr Pro Ser Asp
    370                 375                 380

Ile Ser Tyr Met Pro Ser Tyr His Ala His Gln Gln Lys Val Asn Phe
385                 390                 395                 400

Val Pro Pro His Pro Ser Ser Met Pro Val Thr Ser Ser Ser Phe Phe
                405                 410                 415

Gly Ala Ala Ser Gln Tyr Trp Thr Ser Pro Thr Gly Gly Ile Tyr Pro
            420                 425                 430

Asn Pro Asn Val Pro Arg His Pro Asn Thr His Val Pro Ser His Leu
            435                 440                 445

Gly Ser Tyr Tyr
    450

<210> SEQ ID NO 247
<211> LENGTH: 14
<212> TYPE: PRT
<213> ORGANISM: Homo sapiens

<400> SEQUENCE: 247

Ser Leu Phe Asp Ser Ala Tyr Gly Ala Ala His Leu Pro
1               5                   10

<210> SEQ ID NO 248
<211> LENGTH: 18
<212> TYPE: PRT
<213> ORGANISM: Homo sapiens

<400> SEQUENCE: 248

His Lys Ile Asn Pro Leu Pro Pro Gln Ile Asn Gln Pro Val Arg Val
1               5                   10                  15

Asn Val

<210> SEQ ID NO 249
<211> LENGTH: 17
<212> TYPE: PRT
<213> ORGANISM: Homo sapiens

<400> SEQUENCE: 249

Arg Glu Ser Pro Val Asp Cys Ser Val Ser Lys Cys Ser Lys Leu Val
1               5                   10                  15

Gly

<210> SEQ ID NO 250
<211> LENGTH: 7
<212> TYPE: PRT
<213> ORGANISM: Homo sapiens

<400> SEQUENCE: 250

Thr Gln Glu His Val Arg Gln
1               5

<210> SEQ ID NO 251
<211> LENGTH: 8
```

```
<212> TYPE: PRT
<213> ORGANISM: Homo sapiens

<400> SEQUENCE: 251

Ser Ser Arg Leu Ser Val Lys Glu
1               5

<210> SEQ ID NO 252
<211> LENGTH: 9
<212> TYPE: PRT
<213> ORGANISM: Homo sapiens

<400> SEQUENCE: 252

Pro Asn Thr His Val Pro Ser His Leu
1               5

<210> SEQ ID NO 253
<211> LENGTH: 484
<212> TYPE: PRT
<213> ORGANISM: Homo sapiens

<400> SEQUENCE: 253

Met Glu Arg Arg Met Lys Ala Gly Tyr Leu Asp Gln Gln Val Pro Tyr
1               5                   10                  15

Thr Phe Ser Ser Lys Ser Pro Gly Asn Gly Ser Leu Arg Glu Ala Leu
            20                  25                  30

Ile Gly Pro Leu Gly Lys Leu Met Asp Pro Gly Ser Leu Pro Pro Leu
        35                  40                  45

Asp Ser Glu Asp Leu Phe Gln Asp Leu Ser His Phe Gln Glu Thr Trp
    50                  55                  60

Leu Ala Glu Ala Gln Val Pro Asp Ser Asp Glu Gln Phe Val Pro Asp
65                  70                  75                  80

Phe His Ser Glu Asn Leu Ala Phe His Ser Pro Thr Thr Arg Ile Lys
                85                  90                  95

Lys Glu Pro Gln Ser Pro Arg Thr Asp Pro Ala Leu Ser Cys Ser Arg
            100                 105                 110

Lys Pro Pro Leu Pro Tyr His His Gly Glu Gln Cys Leu Tyr Ser Ser
        115                 120                 125

Ala Tyr Asp Pro Pro Arg Gln Ile Ala Ile Lys Ser Pro Ala Pro Gly
    130                 135                 140

Ala Leu Gly Gln Ser Pro Leu Gln Pro Phe Pro Arg Ala Glu Gln Arg
145                 150                 155                 160

Asn Phe Leu Arg Ser Ser Gly Thr Ser Gln Pro His Pro Gly His Gly
                165                 170                 175

Tyr Leu Gly Glu His Ser Ser Val Phe Gln Gln Pro Leu Asp Ile Cys
            180                 185                 190

His Ser Phe Thr Ser Gln Gly Gly Arg Glu Pro Leu Pro Ala Pro
        195                 200                 205

Tyr Gln His Gln Leu Ser Glu Pro Cys Pro Pro Tyr Pro Gln Gln Ser
    210                 215                 220

Phe Lys Gln Glu Tyr His Asp Pro Leu Tyr Glu Gln Ala Gly Gln Pro
225                 230                 235                 240

Ala Val Asp Gln Gly Gly Val Asn Gly His Arg Tyr Pro Gly Ala Gly
                245                 250                 255

Val Val Ile Lys Gln Glu Gln Thr Asp Phe Ala Tyr Asp Ser Asp Val
            260                 265                 270

Thr Gly Cys Ala Ser Met Tyr Leu His Thr Glu Gly Phe Ser Gly Pro
```

-continued

```
            275                 280                 285
Ser Pro Gly Asp Gly Ala Met Gly Tyr Gly Tyr Glu Lys Pro Leu Arg
290                 295                 300

Pro Phe Pro Asp Asp Val Cys Val Val Pro Glu Lys Phe Glu Gly Asp
305                 310                 315                 320

Ile Lys Gln Glu Gly Val Gly Ala Phe Arg Glu Gly Pro Pro Tyr Gln
                325                 330                 335

Arg Arg Gly Ala Leu Gln Leu Trp Gln Phe Leu Val Ala Leu Leu Asp
            340                 345                 350

Asp Pro Thr Asn Ala His Phe Ile Ala Trp Thr Gly Arg Gly Met Glu
        355                 360                 365

Phe Lys Leu Ile Glu Pro Glu Glu Val Ala Arg Leu Trp Gly Ile Gln
    370                 375                 380

Lys Asn Arg Pro Ala Met Asn Tyr Asp Lys Leu Ser Arg Ser Leu Arg
385                 390                 395                 400

Tyr Tyr Tyr Glu Lys Gly Ile Met Gln Lys Val Ala Gly Glu Arg Tyr
                405                 410                 415

Val Tyr Lys Phe Val Cys Glu Pro Glu Ala Leu Phe Ser Leu Ala Phe
            420                 425                 430

Pro Asp Asn Gln Arg Pro Ala Leu Lys Ala Glu Phe Asp Arg Pro Val
        435                 440                 445

Ser Glu Glu Asp Thr Val Pro Leu Ser His Leu Asp Glu Ser Pro Ala
450                 455                 460

Tyr Leu Pro Glu Leu Ala Gly Pro Ala Gln Pro Phe Gly Pro Lys Gly
465                 470                 475                 480

Gly Tyr Ser Tyr

<210> SEQ ID NO 254
<211> LENGTH: 12
<212> TYPE: PRT
<213> ORGANISM: Homo sapiens

<400> SEQUENCE: 254

Gly Tyr Leu Asp Gln Gln Val Pro Tyr Thr Phe Ser
1               5                   10

<210> SEQ ID NO 255
<211> LENGTH: 11
<212> TYPE: PRT
<213> ORGANISM: Homo sapiens

<400> SEQUENCE: 255

Leu Arg Glu Ala Leu Ile Gly Pro Leu Gly Lys
1               5                   10

<210> SEQ ID NO 256
<211> LENGTH: 7
<212> TYPE: PRT
<213> ORGANISM: Homo sapiens

<400> SEQUENCE: 256

Leu Phe Gln Asp Leu Ser His
1               5

<210> SEQ ID NO 257
<211> LENGTH: 7
<212> TYPE: PRT
<213> ORGANISM: Homo sapiens
```

<400> SEQUENCE: 257

Ser Glu Asn Leu Ala Phe His
1               5

<210> SEQ ID NO 258
<211> LENGTH: 7
<212> TYPE: PRT
<213> ORGANISM: Homo sapiens

<400> SEQUENCE: 258

Thr Asp Pro Ala Leu Ser Cys
1               5

<210> SEQ ID NO 259
<211> LENGTH: 20
<212> TYPE: PRT
<213> ORGANISM: Homo sapiens

<400> SEQUENCE: 259

Ser Arg Lys Pro Pro Leu Pro Tyr His His Gly Glu Gln Cys Leu Tyr
1               5                   10                  15

Ser Ser Ala Tyr
            20

<210> SEQ ID NO 260
<211> LENGTH: 25
<212> TYPE: PRT
<213> ORGANISM: Homo sapiens

<400> SEQUENCE: 260

Asp Pro Pro Arg Gln Ile Ala Ile Lys Ser Pro Ala Pro Gly Ala Leu
1               5                   10                  15

Gly Gln Ser Pro Leu Gln Pro Phe Pro
            20                  25

<210> SEQ ID NO 261
<211> LENGTH: 21
<212> TYPE: PRT
<213> ORGANISM: Homo sapiens

<400> SEQUENCE: 261

Ser Gln Pro His Pro Gly His Tyr Leu Gly Glu His Ser Ser Val Phe
1               5                   10                  15

Gln Gln Pro Leu Asp
            20

<210> SEQ ID NO 262
<211> LENGTH: 5
<212> TYPE: PRT
<213> ORGANISM: Homo sapiens

<400> SEQUENCE: 262

Ile Cys His Ser Phe
1               5

<210> SEQ ID NO 263
<211> LENGTH: 21
<212> TYPE: PRT
<213> ORGANISM: Homo sapiens

<400> SEQUENCE: 263

Glu Pro Leu Pro Ala Pro Tyr Gln His Gln Leu Ser Glu Pro Cys Pro
1               5                   10                  15

-continued

Pro Tyr Pro Gln Gln
            20

<210> SEQ ID NO 264
<211> LENGTH: 15
<212> TYPE: PRT
<213> ORGANISM: Homo sapiens

<400> SEQUENCE: 264

Tyr His Asp Pro Leu Tyr Glu Gln Gly Gln Pro Ala Val Asp Gln
1               5                   10                  15

<210> SEQ ID NO 265
<211> LENGTH: 10
<212> TYPE: PRT
<213> ORGANISM: Homo sapiens

<400> SEQUENCE: 265

Arg Tyr Pro Gly Ala Gly Val Val Ile Lys
1               5                   10

<210> SEQ ID NO 266
<211> LENGTH: 12
<212> TYPE: PRT
<213> ORGANISM: Homo sapiens

<400> SEQUENCE: 266

Tyr Asp Ser Asp Val Thr Gly Cys Ala Ser Met Tyr
1               5                   10

<210> SEQ ID NO 267
<211> LENGTH: 12
<212> TYPE: PRT
<213> ORGANISM: Homo sapiens

<400> SEQUENCE: 267

Tyr Glu Lys Pro Leu Arg Pro Phe Pro Asp Asp Val
1               5                   10

<210> SEQ ID NO 268
<211> LENGTH: 5
<212> TYPE: PRT
<213> ORGANISM: Homo sapiens

<400> SEQUENCE: 268

Cys Val Val Pro Glu
1               5

<210> SEQ ID NO 269
<211> LENGTH: 71
<212> TYPE: DNA
<213> ORGANISM: Homo sapiens

<400> SEQUENCE: 269
cgcgagctaa gcaggaggcg gaggcggagg cggagggcga ggggcgggga gcgccgcctg      60
gagcgcggca g                                                          71

<210> SEQ ID NO 270
<211> LENGTH: 142
<212> TYPE: DNA
<213> ORGANISM: Homo sapiens

<400> SEQUENCE: 270

```
cgcgagctaa gcaggaggcg gaggcggagg cggagggcga ggggcgggga gcgccgcctg    60
gagcgcggca ggtcatattg aacattccag atacctatca ttactcgatg ctgttgataa   120
cagcaagatg gctttgaact ca                                            142
```

<210> SEQ ID NO 271
<211> LENGTH: 365
<212> TYPE: DNA
<213> ORGANISM: Homo sapiens

<400> SEQUENCE: 271

```
cgcgagctaa gcaggaggcg gaggcggagg cggagggcga ggggcgggga gcgccgcctg    60
gagcgcggca ggtcatattg aacattccag atacctatca ttactcgatg ctgttgataa   120
cagcaagatg gctttgaact cagggtcacc accagctatt ggaccttact atgaaaacca   180
tggataccaa ccggaaaaacc cctatcccgc acagcccact gtggtcccca ctgtctacga   240
ggtgcatccg gctcagtact acccgtcccc cgtgccccag tacgcccga gggtcctgac    300 gcaggcttcc aaccccgtcg tctgcacgca gcccaaatcc ccatccggga cagtgtgcac   360
ctcaa                                                               365
```

<210> SEQ ID NO 272
<211> LENGTH: 452
<212> TYPE: DNA
<213> ORGANISM: Homo sapiens

<400> SEQUENCE: 272

```
cgcgagctaa gcaggaggcg gaggcggagg cggagggcga ggggcgggga gcgccgcctg    60
gagcgcggca ggtcatattg aacattccag atacctatca ttactcgatg ctgttgataa   120
cagcaagatg gctttgaact cagggtcacc accagctatt ggaccttact atgaaaacca   180
tggataccaa ccggaaaaacc cctatcccgc acagcccact gtggtcccca ctgtctacga   240
ggtgcatccg gctcagtact acccgtcccc cgtgccccag tacgcccga gggtcctgac    300 gcaggcttcc aaccccgtcg tctgcacgca gcccaaatcc ccatccggga cagtgtgcac   360
ctcaaagact aagaaagcac tgtgcatcac cttgaccctg ggaccttcc tcgtgggagc    420 tgcgctggcc gctggcctac tctggaagtt ca                                 452
```

<210> SEQ ID NO 273
<211> LENGTH: 572
<212> TYPE: DNA
<213> ORGANISM: Homo sapiens

<400> SEQUENCE: 273

```
cgcgagctaa gcaggaggcg gaggcggagg cggagggcga ggggcgggga gcgccgcctg    60
gagcgcggca ggtcatattg aacattccag atacctatca ttactcgatg ctgttgataa   120
cagcaagatg gctttgaact cagggtcacc accagctatt ggaccttact atgaaaacca   180
tggataccaa ccggaaaaacc cctatcccgc acagcccact gtggtcccca ctgtctacga   240
ggtgcatccg gctcagtact acccgtcccc cgtgccccag tacgcccga gggtcctgac    300 gcaggcttcc aaccccgtcg tctgcacgca gcccaaatcc ccatccggga cagtgtgcac   360
ctcaaagact aagaaagcac tgtgcatcac cttgaccctg ggaccttcc tcgtgggagc    420 tgcgctggcc gctggcctac tctggaagtt catgggcagc aagtgctcca actctgggat   480
agagtgcgac tcctcaggta cctgcatcaa cccctctaac tggtgtgatg gcgtgtcaca   540
ctgccccggc ggggaggacg agaatcggtg tg                                 572
```

<210> SEQ ID NO 274
<211> LENGTH: 67
<212> TYPE: DNA
<213> ORGANISM: Homo sapiens

<400> SEQUENCE: 274

```
ctttgataaa taagtttgta agaggagcct cagcatcgta aagagctttt ctccccgctt      60
ctcgcag                                                                67
```

<210> SEQ ID NO 275
<211> LENGTH: 33
<212> TYPE: DNA
<213> ORGANISM: Homo sapiens

<400> SEQUENCE: 275

```
atcgtaaaga gcttttctcc ccgcttctcg cag                                   33
```

<210> SEQ ID NO 276
<211> LENGTH: 102
<212> TYPE: DNA
<213> ORGANISM: Homo sapiens

<400> SEQUENCE: 276

```
gttattccag gatctttgga gacccgagga aagccgtgtt gaccaaaagc aagacaaatg      60
actcacagag aaaaaagatg gcagaaccaa gggcaactaa ag                        102
```

<210> SEQ ID NO 277
<211> LENGTH: 86
<212> TYPE: DNA
<213> ORGANISM: Homo sapiens

<400> SEQUENCE: 277

```
ccgtcaggtt ctgaacagct ggtagatggg ctggcttact gaaggacatg attcagactg      60
tcccggaccc agcagctcat atcaag                                           86
```

<210> SEQ ID NO 278
<211> LENGTH: 218
<212> TYPE: DNA
<213> ORGANISM: Homo sapiens

<400> SEQUENCE: 278

```
gaagccttat cagttgtgag tgaggaccag tcgttgtttg agtgtgccta cggaacgcca      60
cacctggcta agacagagat gaccgcgtcc tcctccagcg actatggaca gacttccaag     120
atgagcccac gcgtccctca gcaggattgg ctgtctcaac ccccagccag ggtcaccatc     180
aaaatggaat gtaacccctag ccaggtgaat ggctcaag                            218
```

<210> SEQ ID NO 279
<211> LENGTH: 152
<212> TYPE: DNA
<213> ORGANISM: Homo sapiens

<400> SEQUENCE: 279

```
gaactctcct gatgaatgca gtgtggccaa aggcgggaag atggtgggca gcccagacac      60
cgttgggatg aactacggca gctacatgga ggagaagcac atgccacccc caaacatgac     120
cacgaacgag cgcagagtta tcgtgccagc ag                                   152
```

<210> SEQ ID NO 280

```
<211> LENGTH: 204
<212> TYPE: DNA
<213> ORGANISM: Homo sapiens

<400> SEQUENCE: 280
atcctacgct atggagtaca gaccatgtgc ggcagtggct ggagtgggcg gtgaaagaat      60
atggccttcc agacgtcaac atcttgttat tccagaacat cgatgggaag gaactgtgca     120
agatgaccaa ggacgacttc cagaggctca cccccagcta caacgccgac atccttctct     180
cacatctcca ctacctcaga gaga                                            204

<210> SEQ ID NO 281
<211> LENGTH: 81
<212> TYPE: DNA
<213> ORGANISM: Homo sapiens

<400> SEQUENCE: 281
ctcctcttcc acatttgact tcagatgatg ttgataaagc cttacaaaac tctccacggt      60
taatgcatgc tagaaacaca g                                                81

<210> SEQ ID NO 282
<211> LENGTH: 72
<212> TYPE: DNA
<213> ORGANISM: Homo sapiens

<400> SEQUENCE: 282
ggggtgcagc ttttattttc ccaaatactt cagtatatcc tgaagctacg caaagaatta      60
caactaggcc ag                                                          72

<210> SEQ ID NO 283
<211> LENGTH: 69
<212> TYPE: DNA
<213> ORGANISM: Homo sapiens

<400> SEQUENCE: 283
atttaccata tgagcccccc aggagatcag cctggaccgg tcacggccac cccacgcccc      60
agtcgaaag                                                              69

<210> SEQ ID NO 284
<211> LENGTH: 57
<212> TYPE: DNA
<213> ORGANISM: Homo sapiens

<400> SEQUENCE: 284
ctgctcaacc atctccttcc acagtgccca aaactgaaga ccagcgtcct cagttag         57

<210> SEQ ID NO 285
<211> LENGTH: 48
<212> TYPE: DNA
<213> ORGANISM: Homo sapiens

<400> SEQUENCE: 285
atccttatca gattcttgga ccaacaagta gccgccttgc aaatccag                   48

<210> SEQ ID NO 286
<211> LENGTH: 521
<212> TYPE: DNA
<213> ORGANISM: Homo sapiens

<400> SEQUENCE: 286
gcagtggcca gatccagctt tggcagttcc tcctggagct cctgtcggac agctccaact      60
```

```
ccagctgcat cacctgggaa ggcaccaacg gggagttcaa gatgacggat cccgacgagg    120
tggcccggcg ctggggagag cggaagagca aacccaacat gaactacgat aagctcagcc    180
gcgccctccg ttactactat gacaagaaca tcatgaccaa ggtccatggg aagcgctacg    240
cctacaagtt cgacttccac gggatcgccc aggcccctcca gccccacccc ccggagtcat    300
ctctgtacaa gtacccctca gacctcccgt acatgggctc ctatcacgcc cacccacaga    360
agatgaactt tgtggcgccc caccctccag cccctccccgt gacatcttcc agttttttg    420 ctgccccaaa cccatactgg aattcaccaa ctgggggtat ataccccaac actaggctcc    480
ccaccagcca tatgccttct catctgggca cttactacta a                        521

<210> SEQ ID NO 287
<211> LENGTH: 54
<212> TYPE: DNA
<213> ORGANISM: Homo sapiens

<400> SEQUENCE: 287
ctcaggtacc tgacaatgat gagcagtttg taccagacta tcaggctgaa agtt          54

<210> SEQ ID NO 288
<211> LENGTH: 130
<212> TYPE: DNA
<213> ORGANISM: Homo sapiens

<400> SEQUENCE: 288
tggcttttca tggcctgcca ctgaaaatca agaaagaacc ccacagtcca tgttcagaaa    60
tcagctctgc ctgcagtcaa gaacagccct ttaaattcag ctatggagaa aagtgcctgt   120
acaatgtcag                                                          130

<210> SEQ ID NO 289
<211> LENGTH: 189
<212> TYPE: DNA
<213> ORGANISM: Homo sapiens

<400> SEQUENCE: 289
tgcctatgat cagaagccac aagtgggaat gaggccctcc aaccccccca caccatccag    60
cacgccagtg tccccactgc atcatgcatc tccaaactca actcatacac cgaaacctga   120
ccgggccttc ccagctcacc tccctccatc gcagtccata ccagatagca gctacccccat   180 ggaccacag                                                           189

<210> SEQ ID NO 290
<211> LENGTH: 248
<212> TYPE: DNA
<213> ORGANISM: Homo sapiens

<400> SEQUENCE: 290
atttcgccgc cagctttctg aaccctgtaa ctcctttcct cctttgccga cgatgccaag    60
ggaaggacgt cctatgtacc aacgccagat gtctgagcca acatcccct tcccaccaca   120 aggctttaag caggagtacc acgacccagt gtatgaacac aacaccatgg ttggcagtgc   180
ggccagccaa agctttcccc ctcctctgat gattaaacag gaacccagag attttgcata   240
tgactcag                                                            248

<210> SEQ ID NO 291
<211> LENGTH: 69
<212> TYPE: DNA
```

<213> ORGANISM: Homo sapiens

<400> SEQUENCE: 291
aagtgcctag ctgccactcc atttatatga ggcaagaagg cttcctggct catcccagca    60
gaacagaag                                                            69

<210> SEQ ID NO 292
<211> LENGTH: 69
<212> TYPE: DNA
<213> ORGANISM: Homo sapiens

<400> SEQUENCE: 292
gctgtatgtt tgaaaagggc cccaggcagt tttatgatga cacctgtgtt gtcccagaaa    60
aattcgatg                                                            69

<210> SEQ ID NO 293
<211> LENGTH: 170
<212> TYPE: DNA
<213> ORGANISM: Homo sapiens

<400> SEQUENCE: 293
gagacatcaa acaagagcca ggaatgtatc gggaaggacc cacataccaa cggcgaggat    60
cacttcagct ctggcagttt tggtagctc ttctggatga cccttcaaat tctcatttta    120
ttgcctggac tggtcgaggc atggaattta aactgattga gcctgaagag              170

<210> SEQ ID NO 294
<211> LENGTH: 102
<212> TYPE: DNA
<213> ORGANISM: Homo sapiens

<400> SEQUENCE: 294
gtggcccgac gttggggcat tcagaaaaac aggccagcta tgaactatga taaacttagc    60
cgttcactcc gctattacta tgagaaagga attatgcaaa ag                       102

<210> SEQ ID NO 295
<211> LENGTH: 222
<212> TYPE: DNA
<213> ORGANISM: Homo sapiens

<400> SEQUENCE: 295
gtggctggag agagatatgt ctacaagttt gtgtgtgatc cagaagccct tttctccatg    60
gcctttccag ataatcagcg tccactgctg aagacagaca tggaacgtca catcaacgag    120
gaggacacag tgcctctttc tcactttgat gagagcatgg cctacatgcc ggaagggggc    180
tgctgcaacc cccacccta caacgaaggc tacgtgtatt aa                        222

<210> SEQ ID NO 296
<211> LENGTH: 93
<212> TYPE: DNA
<213> ORGANISM: Homo sapiens

<400> SEQUENCE: 296
aaatcgcccg gaaatgggag cttgcgcgaa gcgctgatcg gcccgctggg gaagctcatg    60
gacccgggct ccctgccgcc ctcgactctg aag                                 93

<210> SEQ ID NO 297
<211> LENGTH: 48
<212> TYPE: DNA
<213> ORGANISM: Homo sapiens

```
<400> SEQUENCE: 297
atctcttcca ggatctaagt cacttccagg agacgtggct cgctgaag                48

<210> SEQ ID NO 298
<211> LENGTH: 54
<212> TYPE: DNA
<213> ORGANISM: Homo sapiens

<400> SEQUENCE: 298
ctcaggtacc agacagtgat gagcagtttg ttcctgattt ccattcagaa aacc          54

<210> SEQ ID NO 299
<211> LENGTH: 127
<212> TYPE: DNA
<213> ORGANISM: Homo sapiens

<400> SEQUENCE: 299
tagctttcca cagccccacc accaggatca agaaggagcc ccagagtccc cgcacagacc    60
cggccctgtc ctgcagcagg aagccgccac tcccctacca ccatggcgag cagtgccttt   120
actccag                                                            127

<210> SEQ ID NO 300
<211> LENGTH: 162
<212> TYPE: DNA
<213> ORGANISM: Homo sapiens

<400> SEQUENCE: 300
tgcctatgac ccccccagac aaatcgccat caagtcccct gccctggtg ccctttggaca    60 gtcgccccta cagcccttc cccgggcaga gcaacggaat ttcctgagat cctctggcac    120
ctcccagccc caccctggcc atgggtacct cggggaacat ag                      162

<210> SEQ ID NO 301
<211> LENGTH: 266
<212> TYPE: DNA
<213> ORGANISM: Homo sapiens

<400> SEQUENCE: 301
ctccgtcttc cagcagcccc tggacatttg ccactccttc acatctcagg gaggggccg     60 ggaacccctc ccagcccct accaacacca gctgtcggag ccctgccac cctatcccca    120 gcagagcttt aagcaagaat accatgatcc cctgtatgaa caggcgggcc agccagccgt   180
ggaccagggt ggggtcaatg gcacaggta cccaggggcg ggggtggtga tcaaacagga   240
acagacggac ttcgcctacg actcag                                       266

<210> SEQ ID NO 302
<211> LENGTH: 75
<212> TYPE: DNA
<213> ORGANISM: Homo sapiens

<400> SEQUENCE: 302
gtgtcaccgg gtgcgcatca atgtacctcc acacagaggg cttctctggg ccctctccag    60
gtgacggggc catgg                                                    75

<210> SEQ ID NO 303
<211> LENGTH: 69
<212> TYPE: DNA
<213> ORGANISM: Homo sapiens
```

```
<400> SEQUENCE: 303
gctatggcta tgagaaacct ctgcgaccat tcccagatga tgtctgcgtt gtccctgaga      60
aatttgaag                                                             69

<210> SEQ ID NO 304
<211> LENGTH: 173
<212> TYPE: DNA
<213> ORGANISM: Homo sapiens

<400> SEQUENCE: 304
gagacatcaa gcaggaaggg gtcggtgcat ttcgagaggg gccgccctac cagcgccggg      60
gtgccctgca gctgtggcaa tttctggtgg ccttgctgga tgacccaaca aatgcccatt     120
tcattgcctg gacgggccgg ggaatggagt tcaagctcat tgagcctgag gag           173

<210> SEQ ID NO 305
<211> LENGTH: 102
<212> TYPE: DNA
<213> ORGANISM: Homo sapiens

<400> SEQUENCE: 305
gtcgccaggc tctggggcat ccagaagaac cggccagcca tgaattacga caagctgagc      60
cgctcgctcc gatactatta tgagaaaggc atcatgcaga ag                        102

<210> SEQ ID NO 306
<211> LENGTH: 225
<212> TYPE: DNA
<213> ORGANISM: Homo sapiens

<400> SEQUENCE: 306
gtggctggtg agcgttacgt gtacaagttt gtgtgtgagc ccgaggccct cttctctttg      60
gccttcccgg acaatcagcg tccagctctc aaggctgagt ttgaccggcc tgtcagtgag     120
gaggacacag tccctttgtc ccacttggat gagagcccg cctacctccc agagctggct     180
ggccccgccc agccatttgg ccccaagggt ggctactctt actag                    225

<210> SEQ ID NO 307
<211> LENGTH: 3226
<212> TYPE: DNA
<213> ORGANISM: Homo sapiens

<400> SEQUENCE: 307
cgcgagctaa gcaggaggcg gaggcggagg cggagggcga ggggcgggga gcgccgcctg      60
gagcgcggca ggtcatattg aacattccag ataccatca ttactcgatg ctgttgataa     120
cagcaagatg gctttgaact cagggtcacc accagctatt ggaccttact atgaaaacca     180
tggataccaa ccggaaaacc cctatcccgc acagcccact gtggtcccca ctgtctacga     240
ggtgcatccg gctcagtact acccgtcccc cgtgccccag tacgccccga ggtcctgac     300 gcaggcttcc aaccccgtcg tctgcacgca gcccaaatcc ccatccggga cagtgtgcac     360
ctcaaagact aagaaagcac tgtgcatcac cttgaccctg gggaccttcc tcgtgggagc     420
tgcgctggcc gctggcctac tctggaagtt catgggcagc aagtgctcca actctgggat     480
agagtgcgac tcctcaggta cctgcatcaa cccctctaac tggtgtgatg gcgtgtcaca     540
ctgccccggc ggggaggacg agaatcggtg tgttcgcctc tacggaccaa acttcatcct     600
tcagatgtac tcatctcaga ggaagtcctg gcacccgtgt gccaagacg actggaacga     660 gaactacggg cgggcggcct gcagggacat gggctataag aataatttt actctagcca     720
```

```
aggaatagtg gatgacagcg gatccaccag ctttatgaaa ctgaacacaa gtgccggcaa    780
tgtcgatatc tataaaaaac tgtaccacag tgatgcctgt tcttcaaaag cagtggtttc    840
tttacgctgt atagcctgcg gggtcaactt gaactcaagc cgccagagca ggatcgtggg    900
cggtgagagc gcgctcccgg gggcctggcc ctggcaggtc agcctgcacg tccagaacgt    960
ccacgtgtgc ggaggctcca tcatcacccc cgagtggatc gtgacagccg cccactgcgt   1020
ggaaaaacct cttaacaatc catggcattg gacggcattt gcggggattt tgagacaatc   1080
tttcatgttc tatggagccg gataccaagt agaaaagtg atttctcatc caaattatga    1140
ctccaagacc aagaacaatg acattgcgct gatgaagctg cagaagcctc tgactttcaa   1200
cgacctagtg aaaccagtgt gtctgcccaa cccaggcatg atgctgcagc cagaacagct   1260
ctgctggatt tccgggtggg gggccaccga ggagaaaggg aagacctcag aagtgctgaa   1320
cgctgccaag gtgcttctca ttgagacaca gagatgcaac agcagatatg tctatgacaa   1380
cctgatcaca ccagccatga tctgtgccgg cttcctgcag gggaacgtcg attcttgcca   1440
gggtgacagt ggagggcctc tggtcacttc gaagaacaat atctggtggc tgatagggga   1500
tacaagctgg ggttctggct gtgccaaagc ttacagacca ggagtgtacg gaatgtgat    1560
ggtattcacg gactggattt atcgacaaat gagggcagac ggctaatcca catggtcttc   1620
gtccttgacg tcgtttttaca agaaaacaat ggggctggtt ttgcttcccc gtgcatgatt   1680
tactcttaga gatgattcag aggtcacttc atttttatta aacagtgaac ttgtctggct   1740
ttggcactct ctgccattct gtgcaggctg cagtggctcc cctgcccagc ctgctctccc   1800
taaccccttg tccgcaaggg gtgatggccg gctggttgtg ggcactggcg gtcaagtgtg   1860
gaggagaggg gtggaggctg ccccattgag atcttcctgc tgagtccttt ccaggggcca   1920
attttggatg agcatggagc tgtcacctct cagctgctgg atgacttgag atgaaaaagg   1980
agagacatgg aaagggagac agccaggtgg cacctgcagc ggctgccctc tggggccact   2040
tggtagtgtc cccagcctac ctctccacaa ggggattttg ctgatgggtt cttagagcct   2100
tagcagccct ggatggtggc cagaaataaa gggaccagcc cttcatgggt ggtgacgtgg   2160
tagtcacttg taagggaac agaaacattt ttgttcttat ggggtgagaa tatagacagt    2220
gcccttggtg cgagggaagc aattgaaaag gaacttgccc tgagcactcc tggtgcaggt   2280
ctccacctgc acattgggtg gggctcctgg gagggagact cagccttcct cctcatcctc   2340
cctgaccctg ctcctagcac cctggagagt gcacatgccc cttggtcctg cagggcgcc    2400
aagtctggca ccatgttggc ctcttcaggc ctgctagtca ctggaaattg aggtccatgg   2460
gggaaatcaa ggatgctcag tttaaggtac actgtttcca tgttatgttt ctacacattg   2520
ctacctcagt gctcctggaa acttagcttt tgatgtctcc aagtagtcca ccttcattta   2580
actctttgaa actgtatcac ctttgccaag taagagtggt ggcctatttc agctgctttg   2640
acaaaatgac tggctcctga cttaacgttc tataaatgaa tgtgctgaag caaagtgccc   2700
atggtggcgg cgaagaagag aaagatgtgt tttgttttgg actctctgtg gtcccttcca   2760
atgctgtggg tttccaacca ggggaagggt ccctttttgca ttgccaagtg ccataaccat   2820
gagcactact ctaccatggt tctgcctcct ggccaagcag gctggtttgc aagaatgaaa   2880
tgaatgattc tacagctagg acttaacctt gaaatggaaa gtcttgcaat cccatttgca   2940
ggatccgtct gtgcacatgc ctctgtagag agcagcattc ccaggaccct tggaaacagt   3000
tggcactgta aggtgcttgc tccccaagac acatcctaaa aggtgttgta atggtgaaaa   3060
```

```
cgtcttcctt ctttattgcc ccttcttatt tatgtgaaca actgtttgtc tttttttgta    3120
tcttttttaa actgtaaagt tcaattgtga aaatgaatat catgcaaata aattatgcga    3180
tttttttttc aaagcaaaaa aaaaaaaaaa aaaaaaaaaa aaaaaa                   3226
```